US011198734B2

(12) United States Patent
Micklem et al.

(10) Patent No.: US 11,198,734 B2
(45) Date of Patent: Dec. 14, 2021

(54) ANTI-AXL ANTAGONISTIC ANTIBODIES

(71) Applicants: BERGEN TEKNOLOGIOVERFØRING ASA, Bergen (NO); BERGENBIO ASA, Bergen (NO)

(72) Inventors: David Robert Micklem, Bergen (NO); Sergej Kiprijanov, Oslo (NO); James Bradley Lorens, Bønes (NO); Lavina Ahmed, Bergen (NO); Linn Nilsson, Bergen (NO); Tone Sandal, Bergen (NO)

(73) Assignees: Bergen Teknologioverføring AS, Bergen (NO); BerGenBio ASA, Bergen (NO)

( * ) Notice: Subject to any disclaimer, the term of this patent is extended or adjusted under 35 U.S.C. 154(b) by 398 days.

(21) Appl. No.: 16/098,933

(22) PCT Filed: Jun. 21, 2017

(86) PCT No.: PCT/EP2017/065313
§ 371 (c)(1),
(2) Date: Nov. 5, 2018

(87) PCT Pub. No.: WO2017/220695
PCT Pub. Date: Dec. 28, 2017

(65) Prior Publication Data
US 2021/0171643 A1 Jun. 10, 2021

(30) Foreign Application Priority Data
Jun. 22, 2016 (GB) .................................... 1610902

(51) Int. Cl.
C07K 16/28 (2006.01)
A61K 47/68 (2017.01)
A61P 35/00 (2006.01)
A61K 45/06 (2006.01)
A61K 39/00 (2006.01)

(52) U.S. Cl.
CPC .......... C07K 16/2863 (2013.01); A61K 45/06 (2013.01); A61K 47/6801 (2017.08); A61P 35/00 (2018.01); A61K 2039/505 (2013.01)

(58) Field of Classification Search
CPC ................................................. C07K 16/2863
See application file for complete search history.

(56) References Cited

U.S. PATENT DOCUMENTS

| 9,975,953 B2 | 5/2018 | Micklem et al. |
| 9,975,954 B2 | 5/2018 | Micklem et al. |
| 9,986,723 B2 | 6/2018 | Wilkie et al. |
| 2010/0330095 A1 | 12/2010 | Hettmann et al. |
| 2013/0243753 A1 | 9/2013 | Pei et al. |
| 2015/0037323 A1 | 2/2015 | Wirtz et al. |
| 2017/0107290 A1 | 4/2017 | Micklem et al. |
| 2017/0129957 A1 | 5/2017 | Micklem et al. |
| 2017/0349658 A1 | 12/2017 | Micklem et al. |

FOREIGN PATENT DOCUMENTS

| EP | 2228392 A1 | 9/2010 | |
| EP | 2267454 A2 | 12/2010 | |
| EP | 2431393 A1 | 3/2012 | |
| EP | 2589609 A1 | 5/2013 | |
| EP | 2853544 A1 | 4/2015 | |
| WO | 2009062690 A1 | 5/2009 | |
| WO | 2010/130751 A1 | 11/2010 | |
| WO | 2011014457 A1 | 2/2011 | |
| WO | 2011159980 A1 | 12/2011 | |
| WO | 2012175691 A1 | 12/2012 | |
| WO | 2012175692 A1 | 12/2012 | |
| WO | 2013/064684 A1 | 5/2013 | |
| WO | 2013064685 A1 | 5/2013 | |
| WO | 2014068139 A2 | 5/2014 | |
| WO | WO-2014068139 A1 * | 5/2014 | ............. A61P 35/00 |
| WO | 2014/174111 A1 | 10/2014 | |
| WO | 2015193428 A1 | 12/2015 | |
| WO | 2015193430 A1 | 12/2015 | |
| WO | 2016091891 A1 | 6/2016 | |
| WO | 2016097370 A2 | 6/2016 | |

OTHER PUBLICATIONS

Kim, et al. Biomol Ther (Seoul) 2015; 23(6): 493-509 (Year: 2015).*
Safdari, et al. Biotechnology and Genetic Engineering Reviews, 29:2 176-186 (Year: 2013).*
Kunik, et al., PLoS Comput Biol Feb. 2012; 8(2) (Year: 2012).*
Cheung, et al. FEBS Letters 588 (2014) 288-297 (Year: 2014).*
Sela-Culang, et al., Frontiers in Immunology 2013 Vol. 4 Article 302 (Year: 2013).*
UKIPO Search Report issued in GB1610902.7, dated Mar. 17, 2017, 4 pages.
International Search Report and Written Opinion issued in PCT/EP2017/065313, dated Sep. 26, 2017, 17 pages.
International Search Report and Written Opinion issued in PCT Application No. PCT/EP2015/063704, dated Oct. 8, 2015, 12 pages.
UKIPO Search Report issued in GB1410825.2 dated Mar. 17, 2015; 5 pages.
UKIPO Search Report issued in GB1410826.0 dated Mar. 30, 2015; 6 pages.
"Mus Musculus Isolate 26 Immunoglobulin V Kappa Light Chain mRNA, Partial CDS," NCBI Accession No. GU563184; 1 page, 2010.

(Continued)

Primary Examiner — Julie Wu
Assistant Examiner — John L Van Druff
(74) Attorney, Agent, or Firm — McNeill Baur PLLC

(57) ABSTRACT

The present disclosure relates to antibodies that specifically bind a novel epitope on the Axl protein. Also disclosed are methods for the production and use of the anti-Axl antibodies.

31 Claims, 24 Drawing Sheets
Specification includes a Sequence Listing.

(56) References Cited

OTHER PUBLICATIONS

International Preliminary Report on Patentability and Written Opinion issued in PCT/EP2015/063700, dated Dec. 20, 2016; 8 pages.
International Preliminary Report on Patentability and Written Opinion issued in PCT/EP2015/063704, dated Dec. 20, 2016, 8 pages.
Rudikoff et al., "Somatic Diversification of Immunoglobulins," Proc. Natl. Acad. Sci USA, vol. 81, pp. 2162-2166; Apr. 1984.
Ye et al., "An Anti-Axl Monocolnal Antibody Attenuates Xenograft Tumor Growth and Enhances the Effect of Multiple Anticancer Therapies," Oncogene 29, pp. 5254-5264; 2010.
Leconet et al., "Preclinical validation of AXL receptor as a target for antibody-based pancreatic cancer immunotherapy," Oncogene, 33:5405-14, 2014.
Ben-Batalla, et al., "Axl, a prognostic and therapeutic target in acute myeloid leukemia mediates paracrine crosstalk of leukemia cells with bone marrow stroma," Blood, 122(14):2443-2452.
International Search Report and Written Opinion issued in application PCT/EP2015/080654, dated Jun. 16, 2016, 21 pages.
Li, Y. et al., "Axl as a potential therapeutic target in cancer: role of Axl in tumor growth, metastasis and angiogenesis," Oncogene 28: 3442-3455 (2009).
Zhang, Y. X., et al. "AXL is a potential target for therapeutic intervention in breast cancer progression," Cancer Res 38(6): 1905-1915(2008).
Zhang, P. et al., "Challenges of glycosylation analysis and control: an integrated approach to producing optimal and consistent therapeutic drugs," Drug Discovery Today 21(5): 740-765 (2016).

* cited by examiner

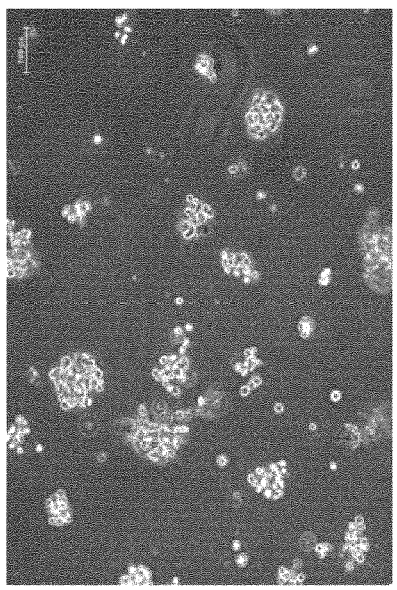
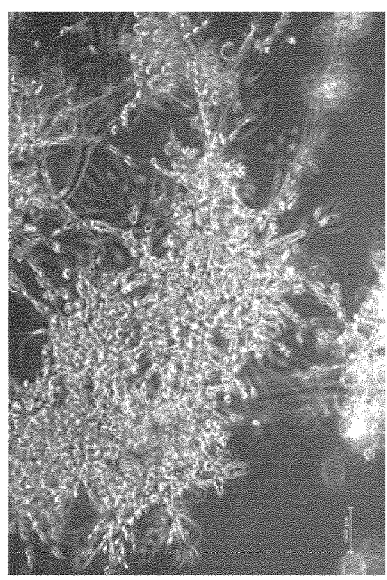
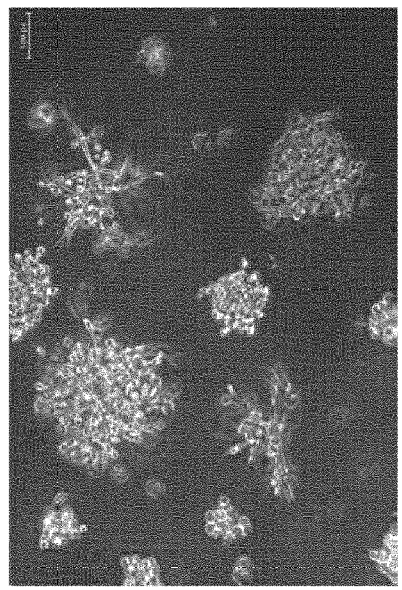
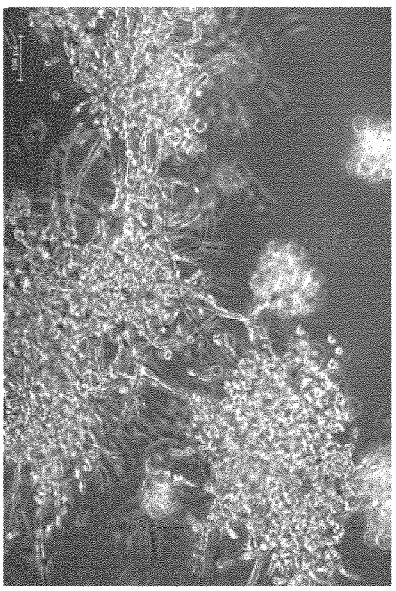
FIGURE 6

IgG control
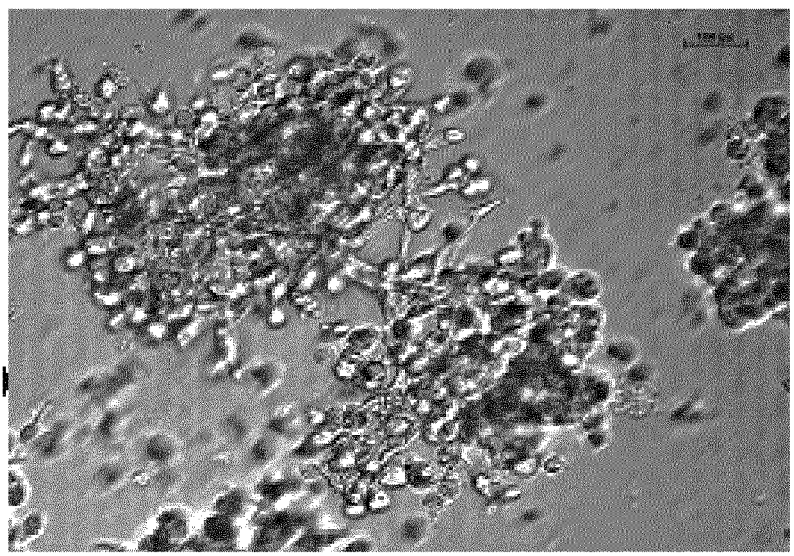
10G5
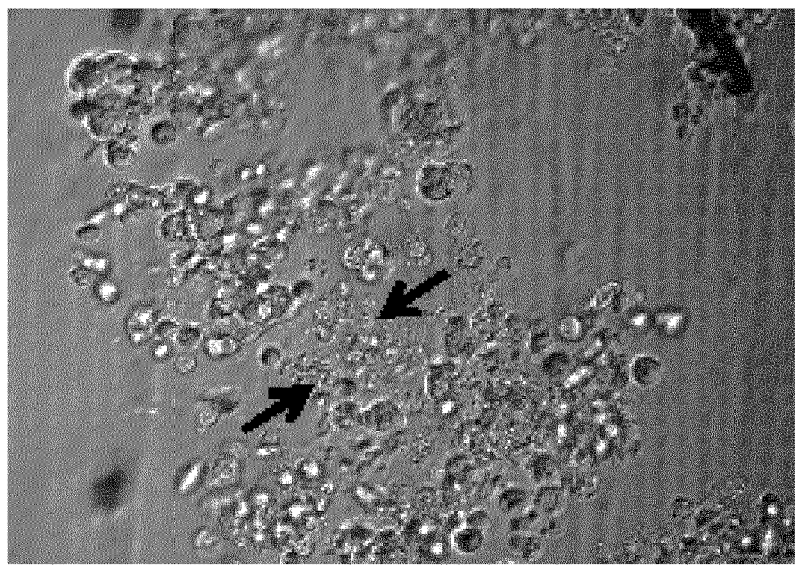
FIGURE 7

Antibody → humanised 10G5

VH(GH1)
EVQLVQSGAGLVQPGGSVRLSCAAS<u>GYSFTDFYIN</u>WVRQAPGKGLEWIA<u>RIFPGGDNTYY
NEKFKG</u>RFTLSADTSSSTAYLQLNSLRAEDTAVYYCAR<u>RGLYYAMDY</u>WGQGTLVTVSS

VH(GH2)
EVQLVESGGGLVQPGGSLRLSCAAS<u>GYSFTDFYIN</u>WVRQAPGKGLEWVA<u>RIFPGGDNTYY
NEKFKG</u>RFTLSADTSKSTAYLQMNSLRAEDTAVYYCAR<u>RGLYYAMDY</u>WGQGTLVTVSS

VL(GL1)
DIQMTQSPSSLSASVGDRVTITC<u>RSSQSLVHSNGIPYLH</u>WYQQKPGKAPKLLIY<u>RVSNRFS</u>
GVPSRFSGSGSGTDFTLTISSLQPEDFATYYC<u>SQGTHVPPT</u>FGQGTKVEIK

VL(GL2)
DIQMTQSPSSLSASVGDRVTITC<u>RSSQSLVHSNGIPYLH</u>WYQQKPGKAPKLLIY<u>RVSNRFS</u>
GVPSRFSGSRSGTDFTLTISSLQPEDFATYYC<u>SQGTHVPPT</u>FGQGTKVEIK

FIGURE 10

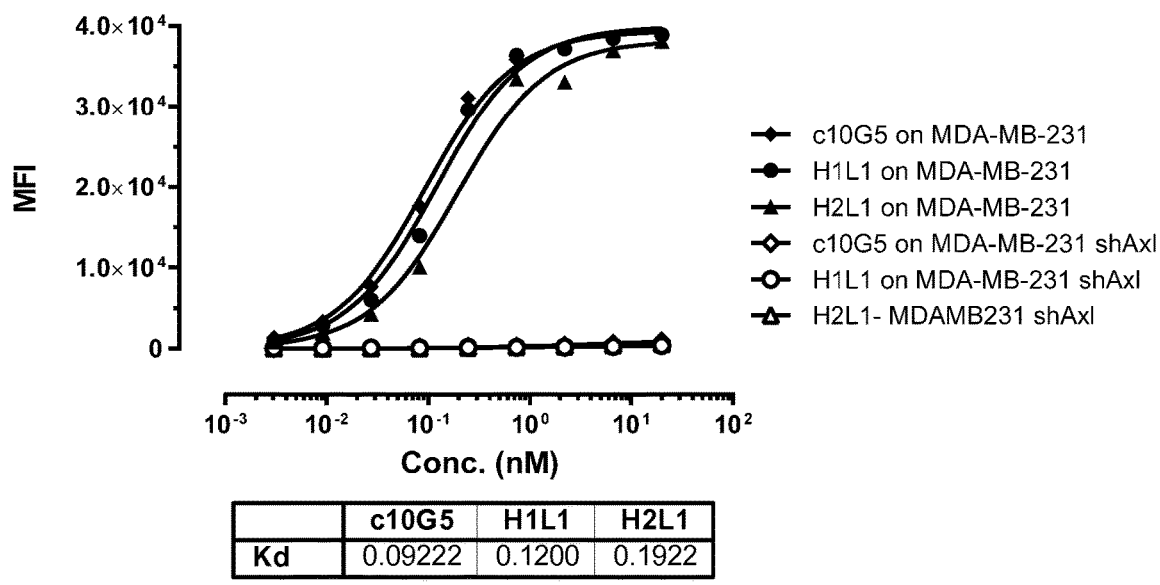
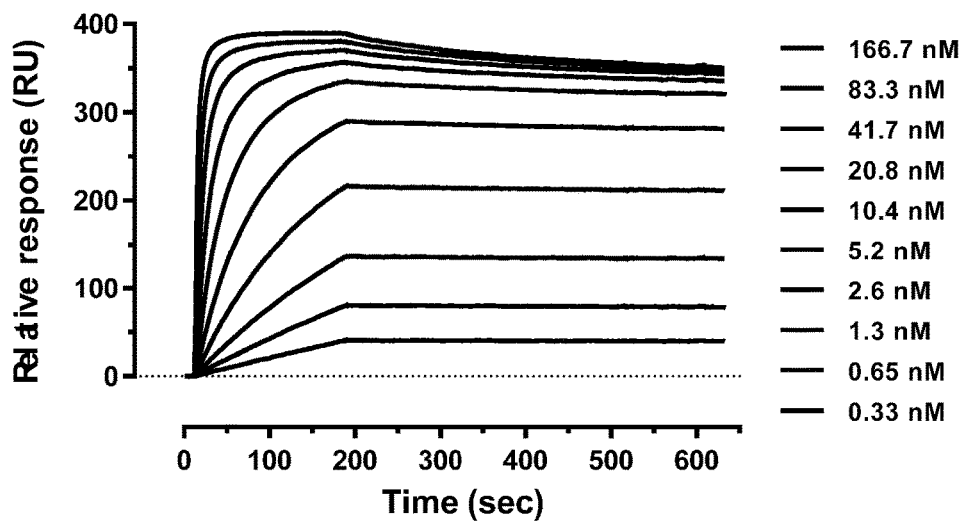
FIGURE 19

SEQUENCE LISTING

```
<160> NUMBER OF SEQ ID NOS: 35

<210> SEQ ID NO 1
<211> LENGTH: 118
<212> TYPE: PRT
<213> ORGANISM: Artificial Sequence
<220> FEATURE:
<223> OTHER INFORMATION: hu10G5 VH(GH1)

<400> SEQUENCE: 1

Glu Val Gln Leu Val Gln Ser Gly Ala Gly Leu Val Gln Pro Gly Gly
1               5                   10                  15

Ser Val Arg Leu Ser Cys Ala Ala Ser Gly Tyr Ser Phe Thr Asp Phe
            20                  25                  30

Tyr Ile Asn Trp Val Arg Gln Ala Pro Gly Lys Gly Leu Glu Trp Ile
        35                  40                  45

Ala Arg Ile Phe Pro Gly Gly Asp Asn Thr Tyr Tyr Asn Glu Lys Phe
    50                  55                  60

Lys Gly Arg Phe Thr Leu Ser Ala Asp Thr Ser Ser Ser Thr Ala Tyr
65                  70                  75                  80

Leu Gln Leu Asn Ser Leu Arg Ala Glu Asp Thr Ala Val Tyr Tyr Cys
                85                  90                  95
```

Ala Arg Arg Gly Leu Tyr Tyr Ala Met Asp Tyr Trp Gly Gln Gly Thr
            100                 105                 110

Leu Val Thr Val Ser Ser
        115

<210> SEQ ID NO 2
<211> LENGTH: 118
<212> TYPE: PRT
<213> ORGANISM: Artificial Sequence
<220> FEATURE:
<223> OTHER INFORMATION: hu10G5 VH(GH2)

<400> SEQUENCE: 2

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Ser Phe Thr Asp Phe
            20                  25                  30

Tyr Ile Asn Trp Val Arg Gln Ala Pro Gly Lys Gly Leu Glu Trp Val
        35                  40                  45

Ala Arg Ile Phe Pro Gly Gly Asp Asn Thr Tyr Tyr Asn Glu Lys Phe
    50                  55                  60

Lys Gly Arg Phe Thr Leu Ser Ala Asp Thr Ser Lys Ser Thr Ala Tyr
65                  70                  75                  80

Leu Gln Met Asn Ser Leu Arg Ala Glu Asp Thr Ala Val Tyr Tyr Cys
                85                  90                  95

Ala Arg Arg Gly Leu Tyr Tyr Ala Met Asp Tyr Trp Gly Gln Gly Thr
            100                 105                 110

Leu Val Thr Val Ser Ser
        115

<210> SEQ ID NO 3
<211> LENGTH: 112
<212> TYPE: PRT
<213> ORGANISM: Artificial Sequence
<220> FEATURE:
<223> OTHER INFORMATION: hu10G5 VL(GL1)

<400> SEQUENCE: 3

Asp Ile Gln Met Thr Gln Ser Pro Ser Ser Leu Ser Ala Ser Val Gly
1               5                   10                  15

Asp Arg Val Thr Ile Thr Cys Arg Ser Ser Gln Ser Leu Val His Ser
            20                  25                  30

Asn Gly Ile Pro Tyr Leu His Trp Tyr Gln Gln Lys Pro Gly Lys Ala
        35                  40                  45

Pro Lys Leu Leu Ile Tyr Arg Val Ser Asn Arg Phe Ser Gly Val Pro
    50                  55                  60

Ser Arg Phe Ser Gly Ser Gly Ser Gly Thr Asp Phe Thr Leu Thr Ile
65                  70                  75                  80

Ser Ser Leu Gln Pro Glu Asp Phe Ala Thr Tyr Tyr Cys Ser Gln Gly
                85                  90                  95

Thr His Val Pro Pro Thr Phe Gly Gln Gly Thr Lys Val Glu Ile Lys
            100                 105                 110

<210> SEQ ID NO 4
<211> LENGTH: 112
<212> TYPE: PRT
<213> ORGANISM: Artificial Sequence
<220> FEATURE:
<223> OTHER INFORMATION: hu10G5 VL(GL2)

<400> SEQUENCE: 4

Asp Ile Gln Met Thr Gln Ser Pro Ser Ser Leu Ser Ala Ser Val Gly
1               5                   10                  15

Asp Arg Val Thr Ile Thr Cys Arg Ser Ser Gln Ser Leu Val His Ser
            20                  25                  30

Asn Gly Ile Pro Tyr Leu His Trp Tyr Gln Gln Lys Pro Gly Lys Ala
        35                  40                  45

Pro Lys Leu Leu Ile Tyr Arg Val Ser Asn Arg Phe Ser Gly Val Pro
    50                  55                  60

Ser Arg Phe Ser Gly Ser Arg Ser Gly Thr Asp Phe Thr Leu Thr Ile
65              70                  75                  80

Ser Ser Leu Gln Pro Glu Asp Phe Ala Thr Tyr Tyr Cys Ser Gln Gly
                85                  90                  95

Thr His Val Pro Pro Thr Phe Gly Gln Gly Thr Lys Val Glu Ile Lys
            100                 105                 110

<210> SEQ ID NO 5
<211> LENGTH: 330
<212> TYPE: PRT
<213> ORGANISM: Artificial Sequence
<220> FEATURE:
<223> OTHER INFORMATION: example heavy chain constant region

<400> SEQUENCE: 5

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65              70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145             150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225             230                 235                 240

Met Thr Lys Asn Gln Val Ser Leu Thr Cys Leu Val Lys Gly Phe Tyr

```
            245                 250                 255
Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
            290                 295                 300

Val Phe Ser Cys Ser Val Met His Glu Ala Leu His Asn His Tyr Thr
305             310                 315                 320

Gln Lys Ser Leu Ser Leu Ser Pro Gly Lys
            325                 330

<210> SEQ ID NO 6
<211> LENGTH: 448
<212> TYPE: PRT
<213> ORGANISM: Artificial Sequence
<220> FEATURE:
<223> OTHER INFORMATION: 10G5 GH1 Heavy chain

<400> SEQUENCE: 6

Glu Val Gln Leu Val Gln Ser Gly Ala Gly Leu Val Gln Pro Gly Gly
1               5                   10                  15

Ser Val Arg Leu Ser Cys Ala Ala Ser Gly Tyr Ser Phe Thr Asp Phe
            20                  25                  30

Tyr Ile Asn Trp Val Arg Gln Ala Pro Gly Lys Gly Leu Glu Trp Ile
            35                  40                  45

Ala Arg Ile Phe Pro Gly Gly Asp Asn Thr Tyr Tyr Asn Glu Lys Phe
50              55                  60

Lys Gly Arg Phe Thr Leu Ser Ala Asp Thr Ser Ser Ser Thr Ala Tyr
65              70                  75                  80

Leu Gln Leu Asn Ser Leu Arg Ala Glu Asp Thr Ala Val Tyr Tyr Cys
            85                  90                  95

Ala Arg Arg Gly Leu Tyr Tyr Ala Met Asp Tyr Trp Gly Gln Gly Thr
            100                 105                 110

Leu Val Thr Val Ser Ser Ala Ser Thr Lys Gly Pro Ser Val Phe Pro
            115                 120                 125

Leu Ala Pro Ser Ser Lys Ser Thr Ser Gly Gly Thr Ala Ala Leu Gly
            130                 135                 140

Cys Leu Val Lys Asp Tyr Phe Pro Glu Pro Val Thr Val Ser Trp Asn
145             150                 155                 160

Ser Gly Ala Leu Thr Ser Gly Val His Thr Phe Pro Ala Val Leu Gln
            165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
            195                 200                 205

Asn Thr Lys Val Asp Lys Lys Val Glu Pro Lys Ser Cys Asp Lys Thr
            210                 215                 220

His Thr Cys Pro Pro Cys Pro Ala Pro Glu Leu Leu Gly Gly Pro Ser
225             230                 235                 240

Val Phe Leu Phe Pro Pro Lys Pro Lys Asp Thr Leu Met Ile Ser Arg
            245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
```

```
                275                 280                 285
Lys Thr Lys Pro Arg Glu Glu Gln Tyr Asn Ser Thr Tyr Arg Val Val
    290                 295                 300
Ser Val Leu Thr Val Leu His Gln Asp Trp Leu Asn Gly Lys Glu Tyr
305                 310                 315                 320
Lys Cys Lys Val Ser Asn Lys Ala Leu Pro Ala Pro Ile Glu Lys Thr
                325                 330                 335
Ile Ser Lys Ala Lys Gly Gln Pro Arg Glu Pro Gln Val Tyr Thr Leu
            340                 345                 350
Pro Pro Ser Arg Glu Glu Met Thr Lys Asn Gln Val Ser Leu Thr Cys
                355                 360                 365
Leu Val Lys Gly Phe Tyr Pro Ser Asp Ile Ala Val Glu Trp Glu Ser
        370                 375                 380
Asn Gly Gln Pro Glu Asn Asn Tyr Lys Thr Thr Pro Pro Val Leu Asp
385                 390                 395                 400
Ser Asp Gly Ser Phe Phe Leu Tyr Ser Lys Leu Thr Val Asp Lys Ser
                405                 410                 415
Arg Trp Gln Gln Gly Asn Val Phe Ser Cys Ser Val Met His Glu Ala
            420                 425                 430
Leu His Asn His Tyr Thr Gln Lys Ser Leu Ser Leu Ser Pro Gly Lys
        435                 440                 445

<210> SEQ ID NO 7
<211> LENGTH: 448
<212> TYPE: PRT
<213> ORGANISM: Artificial Sequence
<220> FEATURE:
<223> OTHER INFORMATION: 10G5 GH2 Heavy chain

<400> SEQUENCE: 7

Glu Val Gln Leu Val Glu Ser Gly Gly Gly Leu Val Gln Pro Gly Gly
1               5                   10                  15
Ser Leu Arg Leu Ser Cys Ala Ala Ser Gly Tyr Ser Phe Thr Asp Phe
            20                  25                  30
Tyr Ile Asn Trp Val Arg Gln Ala Pro Gly Lys Gly Leu Glu Trp Val
        35                  40                  45
Ala Arg Ile Phe Pro Gly Gly Asp Asn Thr Tyr Tyr Asn Glu Lys Phe
    50                  55                  60
Lys Gly Arg Phe Thr Leu Ser Ala Asp Thr Ser Lys Ser Thr Ala Tyr
65                  70                  75                  80
Leu Gln Met Asn Ser Leu Arg Ala Glu Asp Thr Ala Val Tyr Tyr Cys
                85                  90                  95
Ala Arg Arg Gly Leu Tyr Tyr Ala Met Asp Tyr Trp Gly Gln Gly Thr
            100                 105                 110
Leu Val Thr Val Ser Ser Ala Ser Thr Lys Gly Pro Ser Val Phe Pro
        115                 120                 125
Leu Ala Pro Ser Ser Lys Ser Thr Ser Gly Gly Thr Ala Ala Leu Gly
    130                 135                 140
Cys Leu Val Lys Asp Tyr Phe Pro Glu Pro Val Thr Val Ser Trp Asn
145                 150                 155                 160
Ser Gly Ala Leu Thr Ser Gly Val His Thr Phe Pro Ala Val Leu Gln
                165                 170                 175
Ser Ser Gly Leu Tyr Ser Leu Ser Ser Val Val Thr Val Pro Ser Ser
            180                 185                 190
Ser Leu Gly Thr Gln Thr Tyr Ile Cys Asn Val Asn His Lys Pro Ser
```

```
            195                 200                 205
Asn Thr Lys Val Asp Lys Lys Val Glu Pro Lys Ser Cys Asp Lys Thr
210                 215                 220
His Thr Cys Pro Pro Cys Pro Ala Pro Glu Leu Leu Gly Gly Pro Ser
225                 230                 235                 240
Val Phe Leu Phe Pro Pro Lys Pro Lys Asp Thr Leu Met Ile Ser Arg
                245                 250                 255
Thr Pro Glu Val Thr Cys Val Val Val Asp Val Ser His Glu Asp Pro
                260                 265                 270
Glu Val Lys Phe Asn Trp Tyr Val Asp Gly Val Glu Val His Asn Ala
                275                 280                 285
Lys Thr Lys Pro Arg Glu Glu Gln Tyr Asn Ser Thr Tyr Arg Val Val
290                 295                 300
Ser Val Leu Thr Val Leu His Gln Asp Trp Leu Asn Gly Lys Glu Tyr
305                 310                 315                 320
Lys Cys Lys Val Ser Asn Lys Ala Leu Pro Ala Pro Ile Glu Lys Thr
                325                 330                 335
Ile Ser Lys Ala Lys Gly Gln Pro Arg Glu Pro Gln Val Tyr Thr Leu
                340                 345                 350
Pro Pro Ser Arg Glu Glu Met Thr Lys Asn Gln Val Ser Leu Thr Cys
                355                 360                 365
Leu Val Lys Gly Phe Tyr Pro Ser Asp Ile Ala Val Glu Trp Glu Ser
                370                 375                 380
Asn Gly Gln Pro Glu Asn Asn Tyr Lys Thr Thr Pro Pro Val Leu Asp
385                 390                 395                 400
Ser Asp Gly Ser Phe Phe Leu Tyr Ser Lys Leu Thr Val Asp Lys Ser
                405                 410                 415
Arg Trp Gln Gln Gly Asn Val Phe Ser Cys Ser Val Met His Glu Ala
                420                 425                 430
Leu His Asn His Tyr Thr Gln Lys Ser Leu Ser Leu Ser Pro Gly Lys
                435                 440                 445

<210> SEQ ID NO 8
<211> LENGTH: 107
<212> TYPE: PRT
<213> ORGANISM: Artificial Sequence
<220> FEATURE:
<223> OTHER INFORMATION: example light chain constant region

<400> SEQUENCE: 8

Arg Thr Val Ala Ala Pro Ser Val Phe Ile Phe Pro Pro Ser Asp Glu
1               5                   10                  15
Gln Leu Lys Ser Gly Thr Ala Ser Val Val Cys Leu Leu Asn Asn Phe
                20                  25                  30
Tyr Pro Arg Glu Ala Lys Val Gln Trp Lys Val Asp Asn Ala Leu Gln
            35                  40                  45
Ser Gly Asn Ser Gln Glu Ser Val Thr Glu Gln Asp Ser Lys Asp Ser
        50                  55                  60
Thr Tyr Ser Leu Ser Ser Thr Leu Thr Leu Ser Lys Ala Asp Tyr Glu
65              70                  75                  80
Lys His Lys Val Tyr Ala Cys Glu Val Thr His Gln Gly Leu Ser Ser
                85                  90                  95
Pro Val Thr Lys Ser Phe Asn Arg Gly Glu Cys
                100                 105
```

-continued

```
<210> SEQ ID NO 9
<211> LENGTH: 219
<212> TYPE: PRT
<213> ORGANISM: Artificial Sequence
<220> FEATURE:
<223> OTHER INFORMATION: 10G5 GL1 Light chain

<400> SEQUENCE: 9

Asp Ile Gln Met Thr Gln Ser Pro Ser Ser Leu Ser Ala Ser Val Gly
1               5                   10                  15

Asp Arg Val Thr Ile Thr Cys Arg Ser Ser Gln Ser Leu Val His Ser
            20                  25                  30

Asn Gly Ile Pro Tyr Leu His Trp Tyr Gln Gln Lys Pro Gly Lys Ala
        35                  40                  45

Pro Lys Leu Leu Ile Tyr Arg Val Ser Asn Arg Phe Ser Gly Val Pro
    50                  55                  60

Ser Arg Phe Ser Gly Ser Gly Ser Gly Thr Asp Phe Thr Leu Thr Ile
65                  70                  75                  80

Ser Ser Leu Gln Pro Glu Asp Phe Ala Thr Tyr Tyr Cys Ser Gln Gly
                85                  90                  95

Thr His Val Pro Pro Thr Phe Gly Gln Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 10
<211> LENGTH: 219
<212> TYPE: PRT
<213> ORGANISM: Artificial Sequence
<220> FEATURE:
<223> OTHER INFORMATION: 10G5 GL2 Light chain

<400> SEQUENCE: 10

Asp Ile Gln Met Thr Gln Ser Pro Ser Ser Leu Ser Ala Ser Val Gly
1               5                   10                  15

Asp Arg Val Thr Ile Thr Cys Arg Ser Ser Gln Ser Leu Val His Ser
            20                  25                  30

Asn Gly Ile Pro Tyr Leu His Trp Tyr Gln Gln Lys Pro Gly Lys Ala
        35                  40                  45

Pro Lys Leu Leu Ile Tyr Arg Val Ser Asn Arg Phe Ser Gly Val Pro
    50                  55                  60

Ser Arg Phe Ser Gly Ser Arg Ser Gly Thr Asp Phe Thr Leu Thr Ile
65                  70                  75                  80

Ser Ser Leu Gln Pro Glu Asp Phe Ala Thr Tyr Tyr Cys Ser Gln Gly
                85                  90                  95
```

```
Thr His Val Pro Pro Thr Phe Gly Gln Gly Thr Lys Val Glu Ile Lys
             100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215
```

```
<210> SEQ ID NO 11
<211> LENGTH: 354
<212> TYPE: DNA
<213> ORGANISM: Artificial Sequence
<220> FEATURE:
<223> OTHER INFORMATION: hu10G5 VH(GH1) nucleic acid

<400> SEQUENCE: 11
gaggtgcagc tggtccagtc cggagctgga ctggtgcagc caggcggatc tgtcagactg      60
agttgcgccg cttccggcta cagcttcacc gactttttata tcaactgggt cagacaggcc    120
cccggcaagg gtctggagtg gatcgctcgc attttccctg ggggtgacaa cacatactac    180
aacgaaaagt tcaaaggcag gttcaccctg tccgccgata cttccagctc taccgcatac    240
ctgcaactga actccctgag ggcagaagac acagccgtgt actattgtgc caggcgggc    300 ctgtactatg ctatggatta ttggggccag ggaaccctgg tgacagtctc gagc          354
```

```
<210> SEQ ID NO 12
<211> LENGTH: 354
<212> TYPE: DNA
<213> ORGANISM: Artificial Sequence
<220> FEATURE:
<223> OTHER INFORMATION: hu10G5 VH(GH2) nucleic acid

<400> SEQUENCE: 12
gaggtgcagc tggtggaatc cggcggaggg ctggtgcagc caggtggcag cctgagactg      60
tcttgcgccg cttcaggata ctccttcacc gactttttata tcaactgggt cagacaggcc    120
cccggcaagg gcctggagtg ggtcgctcgc attttccctg agggggacaa cacatactac    180
aacgaaaagt tcaaaggcag gttcaccctg agtgctgata cttctaaaag taccgcatac    240
ctgcaaatga atagcctgag ggcagaggac acagccgtgt actattgtgc caggcggggc    300
ctgtactatg ctatggatta ttgggggacag gggaccctgg tgacagtctc gagc         354
```

```
<210> SEQ ID NO 13
<211> LENGTH: 336
<212> TYPE: DNA
<213> ORGANISM: Artificial Sequence
<220> FEATURE:
<223> OTHER INFORMATION: hu10G5 VL(GL1) nucleic acid

<400> SEQUENCE: 13
gacatccaga tgacacagtc tccctccagc ctgagcgcct ctgtgggaga tagagtcacc       60
```

```
atcacatgca ggtctagtca gagcctggtg cactctaacg gcatccccta cctgcattgg    120
tatcagcaga agccagggaa agctcccaag ctgctgatct acagagtcag taatcggttc    180
tctggtgtcc cttcgaggtt tagtggctca ggctccggga cagacttcac tctgaccatt    240
tcatccctgc aaccgagga ttttgcaact tactattgta gccagggcac acacgtgccc     300
cctactttcg gtcagggcac caaagtcgaa attaag                              336
```

<210> SEQ ID NO 14
<211> LENGTH: 336
<212> TYPE: DNA
<213> ORGANISM: Artificial Sequence
<220> FEATURE:
<223> OTHER INFORMATION: hu10G5 VL(GL2) nucleic acid
<400> SEQUENCE: 14

```
gacatccaga tgacacagtc tccctccagc ctgagcgcct ctgtgggcga tcgagtcacc     60
atcacatgca ggtctagtca gagcctggtg cactctaacg gcattcctta cctgcattgg    120
tatcagcaga agccaggaaa agctcccaag ctgctgatct acagagtcag taatcggttc    180
tctggcgtgc cctccaggtt ctccgggtca cgctccggaa cagacttcac tctgaccatt    240
tcatccctgc aaccagagga ttttgcaact tactattgta gccagggaac acacgtgccc    300
cctactttcg gccagggaac caaagtcgaa attaag                              336
```

<210> SEQ ID NO 15
<211> LENGTH: 990
<212> TYPE: DNA
<213> ORGANISM: Artificial Sequence
<220> FEATURE:
<223> OTHER INFORMATION: example heavy chain constant region nucleic
      acid <400> SEQUENCE: 15

```
gctagcacaa agggccctag tgtgtttcct ctggctccct cttccaaatc cacttctggt     60
ggcactgctg ctctgggatg cctggtgaag gattactttc ctgaacctgt gactgtctca    120
tggaactctg gtgctctgac ttctggtgtc cacacttttc ctgctgtgct gcagtctagt    180
ggactgtact ctctgtcatc tgtggtcact gtgccctctt catctctggg aacccagacc    240
tacatttgta atgtgaacca caaaccatcc aacactaaag tggacaaaaa agtggaaccc    300
aaatcctgtg acaaaaccca cacctgccca ccttgtcctg ccctgaact gctgggagga    360 ccttctgtgt ttctgttccc ccccaaacca aaggataccc tgatgatctc tagaacccct    420
gaggtgacat gtgtggtggt ggatgtgtct catgaggacc ctgaggtcaa attcaactgg    480
tacgtggatg gagtggaagt ccacaatgcc aaaaccaagc ctagagagga cagtacaat    540 tcaacctaca gagtggtcag tgtgctgact gtgctgcatc aggattggct gaatggcaag    600
gaatacaagt gtaaagtctc aaacaaggcc ctgcctgctc aattgagaa acaatctca     660 aaggccaagg gacagcctag ggaacccag gtctacaccc tgccaccttc aagagaggaa    720
atgaccaaaa accaggtgtc cctgacatgc ctggtcaaag gcttctaccc ttctgacatt    780
gctgtggagt gggagtcaaa tggacagcct gagaacaact acaaaacaac cccccctgtg    840
ctggattctg atggctcttt ctttctgtac tccaaactga ctgtggacaa gtctagatgg    900
cagcagggga atgtcttttc ttgctctgtc atgcatgagg ctctgcataa ccactacact    960
cagaaatccc tgtctctgtc tcccgggaaa                                     990
```

<210> SEQ ID NO 16
<211> LENGTH: 1344
<212> TYPE: DNA
<213> ORGANISM: Artificial Sequence
<220> FEATURE:
<223> OTHER INFORMATION: 10G5 GH1 Heavy chain nucleic acid

<400> SEQUENCE: 16

```
gaggtgcagc tggtccagtc cggagctgga ctggtgcagc aggcggatc tgtcagactg      60
agttgcgccg cttccggcta cagcttcacc gactttata tcaactgggt cagacaggcc    120
cccggcaagg gtctggagtg gatcgctcgc attttccctg ggggtgacaa cacatactac    180
aacgaaaagt tcaaaggcag gttcaccctg tccgccgata cttccagctc taccgcatac    240
ctgcaactga actccctgag ggcagaagac acagccgtgt actattgtgc caggcggggc    300
ctgtactatg ctatggatta ttggggccag ggaaccctgg tgacagtctc gagcgctagc    360
acaaagggcc ctagtgtgtt tcctctggct ccctcttcca aatccacttc tggtggcact    420
gctgctctgg gatgcctggt gaaggattac tttcctgaac tgtgactgt ctcatggaac    480
tctggtgctc tgacttctgg tgtccacact ttccctgctg tgctgcagtc tagtggactg    540
tactctctgt catctgtggt cactgtgccc tcttcatctc tgggaaccca gacctacatt    600
tgtaatgtga accacaaacc atccaacact aaagtggaca aaaagtgga acccaaatcc    660
tgtgacaaaa cccacacctg cccaccttgt cctgccctg aactgctggg aggaccttct    720
gtgtttctgt tccccccaa accaaggat accctgatga tctctagaac ccctgaggtg    780
acatgtgtgg tggtggatgt gtctcatgag accctgaagg tcaaattcaa ctggtacgtg    840
gatggagtgg aagtccacaa tgccaaaacc aagcctagag aggaacagta caattcaacc    900
tacagagtgg tcagtgtgct gactgtgctg catcaggatt ggctgaatgg caaggaatac    960
aagtgtaaag tctcaaacaa ggccctgcct gctccaattg agaaaacaat ctcaaaggcc   1020
aagggacagc ctagggaacc ccaggtctac accctgccac cttcaagaga ggaaatgacc   1080
aaaaaccagg tgtccctgac atgcctggtc aaaggcttct acccttctga cattgctgtg   1140
gagtgggagt caaatggaca gcctgagaac aactacaaaa caaccccccc tgtgctggat   1200
tctgatggct ctttctttct gtactccaaa ctgactgtgg acaagtctag atggcagcag   1260
gggaatgtct tttcttgctc tgtcatgcat gaggctctgc ataaccacta cactcagaaa   1320
tccctgtctc tgtctcccgg gaaa                                          1344
```

<210> SEQ ID NO 17
<211> LENGTH: 1344
<212> TYPE: DNA
<213> ORGANISM: Artificial Sequence
<220> FEATURE:
<223> OTHER INFORMATION: 10G5 GH2 Heavy chain nucleic acid

<400> SEQUENCE: 17

```
gaggtgcagc tggtggaatc cggcggaggg ctggtgcagc aggtggcag cctgagactg      60
tcttgcgccg cttcaggata tcccttcacc gactttata tcaactgggt cagacaggcc    120
cccggcaagg gcctggagtg ggtcgctcgc attttccctg agggggacaa cacatactac    180
aacgaaaagt tcaaaggcag gttcaccctg agtgctgata cttctaaaag taccgcatac    240
ctgcaaatga atagcctgag ggcagaggac acagccgtgt actattgtgc caggcggggc    300
ctgtactatg ctatggatta ttggggacag ggaccctgg tgacagtctc gagcgctagc    360
acaaagggcc ctagtgtgtt tcctctggct ccctcttcca aatccacttc tggtggcact    420
```

| | |
|---|---|
| gctgctctgg gatgcctggt gaaggattac tttcctgaac ctgtgactgt ctcatggaac | 480 |
| tctggtgctc tgacttctgg tgtccacact ttccctgctg tgctgcagtc tagtggactg | 540 |
| tactctctgt catctgtggt cactgtgccc tcttcatctc tgggaaccca gacctacatt | 600 |
| tgtaatgtga accacaaacc atccaacact aaagtggaca aaaagtgga acccaaatcc | 660 |
| tgtgacaaaa cccacacctg cccaccttgt cctgcccctg aactgctggg aggaccttct | 720 |
| gtgtttctgt tccccccaa accaaaggat accctgatga tctctagaac ccctgaggtg | 780 |
| acatgtgtgg tggtggatgt gtctcatgag gaccctgagg tcaaattcaa ctggtacgtg | 840 |
| gatggagtgg aagtccacaa tgccaaaacc aagcctagag aggaacagta caattcaacc | 900 |
| tacagagtgg tcagtgtgct gactgtgctg catcaggatt ggctgaatgg caaggaatac | 960 |
| aagtgtaaag tctcaaacaa ggccctgcct gctccaattg agaaaacaat ctcaaaggcc | 1020 |
| aagggacagc ctagggaacc ccaggtctac accctgccac cttcaagaga ggaaatgacc | 1080 |
| aaaaaccagg tgtccctgac atgcctggtc aaaggcttct acccttctga cattgctgtg | 1140 |
| gagtgggagt caaatggaca gcctgagaac aactacaaaa caaccccccc tgtgctggat | 1200 |
| tctgatggct ctttctttct gtactccaaa ctgactgtgg acaagtctag atggcagcag | 1260 |
| gggaatgtct tttcttgctc tgtcatgcat gaggctctgc ataaccacta cactcagaaa | 1320 |
| tccctgtctc tgtctcccgg gaaa | 1344 |

<210> SEQ ID NO 18
<211> LENGTH: 321
<212> TYPE: DNA
<213> ORGANISM: Artificial Sequence
<220> FEATURE:
<223> OTHER INFORMATION: light chain constant region nucleic acid

<400> SEQUENCE: 18

| | |
|---|---|
| cgtacggtcg cggcgccttc tgtgttcatt ttcccccat ctgatgaaca gctgaaatct | 60 |
| ggcactgctt ctgtggtctg tctgctgaac aacttctacc ctagagaggc caaagtccag | 120 |
| tggaaagtgg acaatgctct gcagagtggg aattcccagg aatctgtcac tgagcaggac | 180 |
| tctaaggata gcacatactc cctgtcctct actctgacac tgagcaaggc tgattacgag | 240 |
| aaacacaaag tgtacgcctg tgaagtcaca catcaggggc tgtctagtcc tgtgaccaaa | 300 |
| tccttcaata ggggagagtg c | 321 |

<210> SEQ ID NO 19
<211> LENGTH: 657
<212> TYPE: DNA
<213> ORGANISM: Artificial Sequence
<220> FEATURE:
<223> OTHER INFORMATION: 10G5 GL1 Light chain nucleic acid

<400> SEQUENCE: 19

| | |
|---|---|
| gacatccaga tgacacagtc tccctccagc ctgagcgcct ctgtgggaga tagagtcacc | 60 |
| atcacatgca ggtctagtca gagcctggtg cactctaacg gcatccccta cctgcattgg | 120 |
| tatcagcaga agccagggaa agctcccaag ctgctgatct acagagtcag taatcggttc | 180 |
| tctggtgtcc cttcgaggtt tagtggctca ggctccggga cagacttcac tctgaccatt | 240 |
| tcatccctgc aaccagagga ttttgcaact tactattgta gccagggcac acacgtgccc | 300 |
| cctactttcg gtcagggcac caaagtcgaa attaagcgta cggtcgcggc gccttctgtg | 360 |
| ttcattttcc cccatctga tgaacagctg aaatctggca ctgcttctgt ggtctgtctg | 420 |
| ctgaacaact tctaccctag agaggccaaa gtccagtgga aagtggacaa tgctctgcag | 480 |

```
agtgggaatt cccaggaatc tgtcactgag caggactcta aggatagcac atactccctg    540
tcctctactc tgacactgag caaggctgat tacgagaaac acaaagtgta cgcctgtgaa    600
gtcacacatc aggggctgtc tagtcctgtg accaaatcct tcaataggggg agagtgc      657
```

<210> SEQ ID NO 20
<211> LENGTH: 657
<212> TYPE: DNA
<213> ORGANISM: Artificial Sequence
<220> FEATURE:
<223> OTHER INFORMATION: 10G5 GL2 Light chain nucleic acid

<400> SEQUENCE: 20

```
gacatccaga tgacacagtc tccctccagc ctgagcgcct ctgtgggcga tcgagtcacc     60
atcacatgca ggtctagtca gagcctggtg cactctaacg gcattcctta cctgcattgg    120
tatcagcaga agccaggaaa agctcccaag ctgctgatct acagagtcag taatcggttc    180
tctggcgtgc cctccaggtt ctccgggtca cgctccggaa cagacttcac tctgaccatt    240
tcatccctgc aaccagagga ttttgcaact tactattgta gccagggaac acacgtgccc    300
cctactttcg gccagggaac caaagtcgaa attaagcgta cggtcgcggc gccttctgtg    360 ttcatttcc ccccatctga tgaacagctg aaatctggca ctgcttctgt ggtctgtctg    420
ctgaacaact ctaccctag agaggccaaa gtccagtgga agtggacaa tgctctgcag    480 agtgggaatt cccaggaatc tgtcactgag caggactcta aggatagcac atactccctg    540
tcctctactc tgacactgag caaggctgat tacgagaaac acaaagtgta cgcctgtgaa    600
gtcacacatc aggggctgtc tagtcctgtg accaaatcct tcaataggggg agagtgc      657
```

<210> SEQ ID NO 21
<211> LENGTH: 626
<212> TYPE: PRT
<213> ORGANISM: Homo sapiens
<220> FEATURE:
<221> NAME/KEY: MISC_FEATURE
<222> LOCATION: (1)..(626)
<223> OTHER INFORMATION: Homo sapiens Axl

<400> SEQUENCE: 21

```
Met Gly Ile Gln Ala Gly Glu Pro Asp Pro Glu Glu Pro Leu Thr
1               5                   10                  15

Ser Gln Ala Ser Val Pro Pro His Gln Leu Arg Leu Gly Ser Leu His
                20                  25                  30

Pro His Thr Pro Tyr His Ile Arg Val Ala Cys Thr Ser Ser Gln Gly
            35                  40                  45

Pro Ser Ser Trp Thr His Trp Leu Pro Val Glu Thr Pro Glu Gly Val
        50                  55                  60

Pro Leu Gly Pro Pro Glu Asn Ile Ser Ala Thr Arg Asn Gly Ser Gln
65                  70                  75                  80

Ala Phe Val His Trp Gln Glu Pro Arg Ala Pro Leu Gln Gly Thr Leu
                85                  90                  95

Leu Gly Tyr Arg Leu Ala Tyr Gln Gly Gln Asp Thr Pro Glu Val Leu
            100                 105                 110

Met Asp Ile Gly Leu Arg Gln Glu Val Thr Leu Glu Leu Gln Gly Asp
        115                 120                 125

Gly Ser Val Ser Asn Leu Thr Val Cys Val Ala Ala Tyr Thr Ala Ala
    130                 135                 140

Gly Asp Gly Pro Trp Ser Leu Pro Val Pro Leu Glu Ala Trp Arg Pro
```

-continued

```
            145                 150                 155                 160
        Gly Gln Ala Gln Pro Val His Gln Leu Val Lys Glu Pro Ser Thr Pro
                        165                 170                 175
        Ala Phe Ser Trp Pro Trp Tyr Val Leu Leu Gly Ala Val Val Ala
                        180                 185                 190
        Ala Ala Cys Val Leu Ile Leu Ala Leu Phe Leu Val His Arg Arg Lys
                        195                 200                 205
        Lys Glu Thr Arg Tyr Gly Glu Val Phe Glu Pro Thr Val Glu Arg Gly
                210                 215                 220
        Glu Leu Val Val Arg Tyr Arg Val Arg Lys Ser Tyr Ser Arg Arg Thr
        225                 230                 235                 240
        Thr Glu Ala Thr Leu Asn Ser Leu Gly Ile Ser Glu Glu Leu Lys Glu
                        245                 250                 255
        Lys Leu Arg Asp Val Met Val Asp Arg His Lys Val Ala Leu Gly Lys
                        260                 265                 270
        Thr Leu Gly Glu Gly Glu Phe Gly Ala Val Met Glu Gly Gln Leu Asn
                        275                 280                 285
        Gln Asp Asp Ser Ile Leu Lys Val Ala Val Lys Thr Met Lys Ile Ala
                290                 295                 300
        Ile Cys Thr Arg Ser Glu Leu Glu Asp Phe Leu Ser Glu Ala Val Cys
        305                 310                 315                 320
        Met Lys Glu Phe Asp His Pro Asn Val Met Arg Leu Ile Gly Val Cys
                        325                 330                 335
        Phe Gln Gly Ser Glu Arg Glu Ser Phe Pro Ala Pro Val Val Ile Leu
                        340                 345                 350
        Pro Phe Met Lys His Gly Asp Leu His Ser Phe Leu Leu Tyr Ser Arg
                        355                 360                 365
        Leu Gly Asp Gln Pro Val Tyr Leu Pro Thr Gln Met Leu Val Lys Phe
                370                 375                 380
        Met Ala Asp Ile Ala Ser Gly Met Glu Tyr Leu Ser Thr Lys Arg Phe
        385                 390                 395                 400
        Ile His Arg Asp Leu Ala Ala Arg Asn Cys Met Leu Asn Glu Asn Met
                        405                 410                 415
        Ser Val Cys Val Ala Asp Phe Gly Leu Ser Lys Lys Ile Tyr Asn Gly
                        420                 425                 430
        Asp Tyr Tyr Arg Gln Gly Arg Ile Ala Lys Met Pro Val Lys Trp Ile
                        435                 440                 445
        Ala Ile Glu Ser Leu Ala Asp Arg Val Tyr Thr Ser Lys Ser Asp Val
                450                 455                 460
        Trp Ser Phe Gly Val Thr Met Trp Glu Ile Ala Thr Arg Gly Gln Thr
        465                 470                 475                 480
        Pro Tyr Pro Gly Val Glu Asn Ser Glu Ile Tyr Asp Tyr Leu Arg Gln
                        485                 490                 495
        Gly Asn Arg Leu Lys Gln Pro Ala Asp Cys Leu Asp Gly Leu Tyr Ala
                        500                 505                 510
        Leu Met Ser Arg Cys Trp Glu Leu Asn Pro Gln Asp Arg Pro Ser Phe
                        515                 520                 525
        Thr Glu Leu Arg Glu Asp Leu Glu Asn Thr Leu Lys Ala Leu Pro Pro
                530                 535                 540
        Ala Gln Glu Pro Asp Glu Ile Leu Tyr Val Asn Met Asp Glu Gly Gly
        545                 550                 555                 560
        Gly Tyr Pro Glu Pro Pro Gly Ala Ala Gly Gly Ala Asp Pro Pro Thr
                        565                 570                 575
```

```
Gln Pro Asp Pro Lys Asp Ser Cys Ser Cys Leu Thr Ala Ala Glu Val
            580                 585                 590

His Pro Ala Gly Arg Tyr Val Leu Cys Pro Ser Thr Pro Ser Pro
            595                 600                 605

Ala Gln Pro Ala Asp Arg Gly Ser Pro Ala Ala Pro Gly Gln Glu Asp
        610                 615                 620

Gly Ala
625

<210> SEQ ID NO 22
<211> LENGTH: 879
<212> TYPE: PRT
<213> ORGANISM: Mus musculus
<220> FEATURE:
<221> NAME/KEY: MISC_FEATURE
<222> LOCATION: (1)..(879)
<223> OTHER INFORMATION: Mus musculus Axl

<400> SEQUENCE: 22

Met Gly Arg Val Pro Leu Ala Trp Trp Leu Ala Leu Cys Cys Trp Gly
1               5                   10                  15

Cys Ala Ala His Lys Asp Thr Gln Thr Glu Ala Gly Ser Pro Phe Val
            20                  25                  30

Gly Asn Pro Gly Asn Ile Thr Gly Ala Arg Gly Leu Thr Gly Thr Leu
        35                  40                  45

Arg Cys Glu Leu Gln Val Gln Gly Glu Pro Pro Glu Val Val Trp Leu
    50                  55                  60

Arg Asp Gly Gln Ile Leu Glu Leu Ala Asp Asn Thr Gln Thr Gln Val
65                  70                  75                  80

Pro Leu Gly Glu Asp Trp Gln Asp Glu Trp Lys Val Val Ser Gln Leu
                85                  90                  95

Arg Ile Ser Ala Leu Gln Leu Ser Asp Ala Gly Glu Tyr Gln Cys Met
            100                 105                 110

Val His Leu Glu Gly Arg Thr Phe Val Ser Gln Pro Gly Phe Val Gly
        115                 120                 125

Leu Glu Gly Leu Pro Tyr Phe Leu Glu Glu Pro Glu Asp Lys Ala Val
    130                 135                 140

Pro Ala Asn Thr Pro Phe Asn Leu Ser Cys Gln Ala Gln Gly Pro Pro
145                 150                 155                 160

Glu Pro Val Thr Leu Leu Trp Leu Gln Asp Ala Val Pro Leu Ala Pro
                165                 170                 175

Val Thr Gly His Ser Ser Gln His Ser Leu Gln Thr Pro Gly Leu Asn
            180                 185                 190

Lys Thr Ser Ser Phe Ser Cys Glu Ala His Asn Ala Lys Gly Val Thr
        195                 200                 205

Thr Ser Arg Thr Ala Thr Ile Thr Val Leu Pro Gln Arg Pro His His
    210                 215                 220

Leu His Val Val Ser Arg Gln Pro Thr Glu Leu Glu Val Ala Trp Thr
225                 230                 235                 240

Pro Gly Leu Ser Gly Ile Tyr Pro Leu Thr His Cys Asn Leu Gln Ala
                245                 250                 255

Val Leu Ser Asp Asp Gly Val Gly Ile Trp Leu Gly Lys Ser Asp Pro
            260                 265                 270

Pro Glu Asp Pro Leu Thr Leu Gln Val Ser Val Pro Pro His Gln Leu
        275                 280                 285
```

```
Arg Leu Glu Lys Leu Leu Pro His Thr Pro Tyr His Ile Arg Ile Ser
    290                 295                 300

Cys Ser Ser Ser Gln Gly Pro Ser Pro Trp Thr His Trp Leu Pro Val
305                 310                 315                 320

Glu Thr Thr Glu Gly Val Pro Leu Gly Pro Pro Glu Asn Val Ser Ala
                325                 330                 335

Met Arg Asn Gly Ser Gln Val Leu Val Arg Trp Gln Glu Pro Arg Val
            340                 345                 350

Pro Leu Gln Gly Thr Leu Leu Gly Tyr Arg Leu Ala Tyr Arg Gly Gln
        355                 360                 365

Asp Thr Pro Glu Val Leu Met Asp Ile Gly Leu Thr Arg Glu Val Thr
    370                 375                 380

Leu Glu Leu Arg Gly Asp Arg Pro Val Ala Asn Leu Thr Val Ser Val
385                 390                 395                 400

Thr Ala Tyr Thr Ser Ala Gly Asp Gly Pro Trp Ser Leu Pro Val Pro
                405                 410                 415

Leu Glu Pro Trp Arg Pro Val Ser Glu Pro Pro Arg Ala Phe Ser
            420                 425                 430

Trp Pro Trp Trp Tyr Val Leu Leu Gly Ala Leu Val Ala Ala Ala Cys
        435                 440                 445

Val Leu Ile Leu Ala Leu Phe Leu Val His Arg Arg Lys Lys Glu Thr
    450                 455                 460

Arg Tyr Gly Glu Val Phe Glu Pro Thr Val Glu Arg Gly Glu Leu Val
465                 470                 475                 480

Val Arg Tyr Arg Val Arg Lys Ser Tyr Ser Arg Arg Thr Thr Glu Ala
                485                 490                 495

Thr Leu Asn Ser Leu Gly Ile Ser Glu Glu Leu Lys Glu Lys Leu Arg
            500                 505                 510

Asp Val Met Val Asp Arg His Lys Val Ala Leu Gly Lys Thr Leu Gly
        515                 520                 525

Glu Gly Glu Phe Gly Ala Val Met Glu Gly Gln Leu Asn Gln Asp Asp
    530                 535                 540

Ser Ile Leu Lys Val Ala Val Lys Thr Met Lys Ile Ala Ile Cys Thr
545                 550                 555                 560

Arg Ser Glu Leu Glu Asp Phe Leu Ser Glu Ala Val Cys Met Lys Glu
                565                 570                 575

Phe Asp His Pro Asn Val Met Arg Leu Ile Gly Val Cys Phe Gln Gly
            580                 585                 590

Ser Asp Arg Glu Gly Phe Pro Glu Pro Val Val Ile Leu Pro Phe Met
        595                 600                 605

Lys His Gly Asp Leu His Ser Phe Leu Leu Tyr Ser Arg Leu Gly Asp
    610                 615                 620

Gln Pro Val Phe Leu Pro Thr Gln Met Leu Val Lys Phe Met Ala Asp
625                 630                 635                 640

Ile Ala Ser Gly Met Glu Tyr Leu Ser Thr Lys Arg Phe Ile His Arg
                645                 650                 655

Asp Leu Ala Ala Arg Asn Cys Met Leu Asn Glu Asn Met Ser Val Cys
            660                 665                 670

Val Ala Asp Phe Gly Leu Ser Lys Lys Ile Tyr Asn Gly Asp Tyr Tyr
        675                 680                 685

Arg Gln Gly Arg Ile Ala Lys Met Pro Val Lys Trp Ile Ala Ile Glu
    690                 695                 700

Ser Leu Ala Asp Arg Val Tyr Thr Ser Lys Ser Asp Val Trp Ser Phe
```

```
                705                 710                 715                 720
Gly Val Thr Met Trp Glu Ile Ala Thr Arg Gly Gln Thr Pro Tyr Pro
                    725                 730                 735
Gly Val Glu Asn Ser Glu Ile Tyr Asp Tyr Leu Arg Gln Gly Asn Arg
                    740                 745                 750
Leu Lys Gln Pro Val Asp Cys Leu Asp Gly Leu Tyr Ala Leu Met Ser
                    755                 760                 765
Arg Cys Trp Glu Leu Asn Pro Arg Asp Arg Pro Ser Phe Ala Glu Leu
                    770                 775                 780
Arg Glu Asp Leu Glu Asn Thr Leu Lys Ala Leu Pro Pro Ala Gln Glu
785                 790                 795                 800
Pro Asp Glu Ile Leu Tyr Val Asn Met Asp Glu Gly Gly Ser His Leu
                    805                 810                 815
Glu Pro Arg Gly Ala Ala Gly Gly Ala Asp Pro Pro Thr Gln Pro Asp
                    820                 825                 830
Pro Lys Asp Ser Cys Ser Cys Leu Thr Ala Ala Asp Val His Ser Ala
                    835                 840                 845
Gly Arg Tyr Val Leu Cys Pro Ser Thr Ala Pro Gly Pro Thr Leu Ser
                    850                 855                 860
Ala Asp Arg Gly Cys Pro Ala Pro Pro Gly Gln Glu Asp Gly Ala
865                 870                 875

<210> SEQ ID NO 23
<211> LENGTH: 890
<212> TYPE: PRT
<213> ORGANISM: Homo sapiens
<220> FEATURE:
<221> NAME/KEY: MISC_FEATURE
<222> LOCATION: (1)..(890)
<223> OTHER INFORMATION: Homo sapiens Tyro3

<400> SEQUENCE: 23

Met Ala Leu Arg Arg Ser Met Gly Arg Pro Gly Leu Pro Pro Leu Pro
1               5                   10                  15
Leu Pro Pro Pro Arg Leu Gly Leu Leu Ala Ala Leu Ala Ser
                    20                  25                  30
Leu Leu Leu Pro Glu Ser Ala Ala Ala Gly Leu Lys Leu Met Gly Ala
                35                  40                  45
Pro Val Lys Leu Thr Val Ser Gln Gly Gln Pro Val Lys Leu Asn Cys
                50                  55                  60
Ser Val Glu Gly Met Glu Glu Pro Asp Ile Gln Trp Val Lys Asp Gly
65                  70                  75                  80
Ala Val Val Gln Asn Leu Asp Gln Leu Tyr Ile Pro Val Ser Glu Gln
                    85                  90                  95
His Trp Ile Gly Phe Leu Ser Leu Lys Ser Val Glu Arg Ser Asp Ala
                    100                 105                 110
Gly Arg Tyr Trp Cys Gln Val Glu Asp Gly Gly Glu Thr Glu Ile Ser
                    115                 120                 125
Gln Pro Val Trp Leu Thr Val Glu Gly Val Pro Phe Phe Thr Val Glu
                130                 135                 140
Pro Lys Asp Leu Ala Val Pro Pro Asn Ala Pro Phe Gln Leu Ser Cys
145                 150                 155                 160
Glu Ala Val Gly Pro Pro Glu Pro Val Thr Ile Val Trp Trp Arg Gly
                    165                 170                 175
Thr Thr Lys Ile Gly Gly Pro Ala Pro Ser Pro Ser Val Leu Asn Val
                    180                 185                 190
```

```
Thr Gly Val Thr Gln Ser Thr Met Phe Ser Cys Glu Ala His Asn Leu
        195                 200                 205
Lys Gly Leu Ala Ser Ser Arg Thr Ala Thr Val His Leu Gln Ala Leu
        210                 215                 220
Pro Ala Ala Pro Phe Asn Ile Thr Val Thr Lys Leu Ser Ser Ser Asn
225                 230                 235                 240
Ala Ser Val Ala Trp Met Pro Gly Ala Asp Gly Arg Ala Leu Leu Gln
                245                 250                 255
Ser Cys Thr Val Gln Val Thr Gln Ala Pro Gly Gly Trp Glu Val Leu
                260                 265                 270
Ala Val Val Pro Val Pro Phe Thr Cys Leu Leu Arg Asp Leu
        275                 280                 285
Val Pro Ala Thr Asn Tyr Ser Leu Arg Val Arg Cys Ala Asn Ala Leu
        290                 295                 300
Gly Pro Ser Pro Tyr Ala Asp Trp Val Pro Phe Gln Thr Lys Gly Leu
305                 310                 315                 320
Ala Pro Ala Ser Ala Pro Gln Asn Leu His Ala Ile Arg Thr Asp Ser
                325                 330                 335
Gly Leu Ile Leu Glu Trp Glu Glu Val Ile Pro Glu Ala Pro Leu Glu
                340                 345                 350
Gly Pro Leu Gly Pro Tyr Lys Leu Ser Trp Val Gln Asp Asn Gly Thr
                355                 360                 365
Gln Asp Glu Leu Thr Val Glu Gly Thr Arg Ala Asn Leu Thr Gly Trp
        370                 375                 380
Asp Pro Gln Lys Asp Leu Ile Val Arg Val Cys Val Ser Asn Ala Val
385                 390                 395                 400
Gly Cys Gly Pro Trp Ser Gln Pro Leu Val Val Ser Ser His Asp Arg
                405                 410                 415
Ala Gly Gln Gln Gly Pro Pro His Ser Arg Thr Ser Trp Val Pro Val
                420                 425                 430
Val Leu Gly Val Leu Thr Ala Leu Val Thr Ala Ala Leu Ala Leu
        435                 440                 445
Ile Leu Leu Arg Lys Arg Lys Glu Thr Arg Phe Gly Gln Ala Phe
        450                 455                 460
Asp Ser Val Met Ala Arg Gly Glu Pro Ala Val His Phe Arg Ala Ala
465                 470                 475                 480
Arg Ser Phe Asn Arg Glu Arg Pro Glu Arg Ile Glu Ala Thr Leu Asp
                485                 490                 495
Ser Leu Gly Ile Ser Asp Glu Leu Lys Glu Lys Leu Glu Asp Val Leu
                500                 505                 510
Ile Pro Glu Gln Gln Phe Thr Leu Gly Arg Met Leu Gly Lys Gly Glu
        515                 520                 525
Phe Gly Ser Val Arg Glu Ala Gln Leu Lys Gln Glu Asp Gly Ser Phe
        530                 535                 540
Val Lys Val Ala Val Lys Met Leu Lys Ala Asp Ile Ile Ala Ser Ser
545                 550                 555                 560
Asp Ile Glu Glu Phe Leu Arg Glu Ala Ala Cys Met Lys Glu Phe Asp
                565                 570                 575
His Pro His Val Ala Lys Leu Val Gly Val Ser Leu Arg Ser Arg Ala
                580                 585                 590
Lys Gly Arg Leu Pro Ile Pro Met Val Ile Leu Pro Phe Met Lys His
        595                 600                 605
```

```
Gly Asp Leu His Ala Phe Leu Leu Ala Ser Arg Ile Gly Glu Asn Pro
        610                 615                 620

Phe Asn Leu Pro Leu Gln Thr Leu Ile Arg Phe Met Val Asp Ile Ala
625                 630                 635                 640

Cys Gly Met Glu Tyr Leu Ser Ser Arg Asn Phe Ile His Arg Asp Leu
                645                 650                 655

Ala Ala Arg Asn Cys Met Leu Ala Glu Asp Met Thr Val Cys Val Ala
                660                 665                 670

Asp Phe Gly Leu Ser Arg Lys Ile Tyr Ser Gly Asp Tyr Tyr Arg Gln
            675                 680                 685

Gly Cys Ala Ser Lys Leu Pro Val Lys Trp Leu Ala Leu Glu Ser Leu
        690                 695                 700

Ala Asp Asn Leu Tyr Thr Val Gln Ser Asp Val Trp Ala Phe Gly Val
705                 710                 715                 720

Thr Met Trp Glu Ile Met Thr Arg Gly Gln Thr Pro Tyr Ala Gly Ile
                725                 730                 735

Glu Asn Ala Glu Ile Tyr Asn Tyr Leu Ile Gly Gly Asn Arg Leu Lys
                740                 745                 750

Gln Pro Pro Glu Cys Met Glu Asp Val Tyr Asp Leu Met Tyr Gln Cys
            755                 760                 765

Trp Ser Ala Asp Pro Lys Gln Arg Pro Ser Phe Thr Cys Leu Arg Met
770                 775                 780

Glu Leu Glu Asn Ile Leu Gly Gln Leu Ser Val Leu Ser Ala Ser Gln
785                 790                 795                 800

Asp Pro Leu Tyr Ile Asn Ile Glu Arg Ala Glu Glu Pro Thr Ala Gly
                805                 810                 815

Gly Ser Leu Glu Leu Pro Gly Arg Asp Gln Pro Tyr Ser Gly Ala Gly
            820                 825                 830

Asp Gly Ser Gly Met Gly Ala Val Gly Gly Thr Pro Ser Asp Cys Arg
        835                 840                 845

Tyr Ile Leu Thr Pro Gly Gly Leu Ala Glu Gln Pro Gly Gln Ala Glu
            850                 855                 860

His Gln Pro Glu Ser Pro Leu Asn Glu Thr Gln Arg Leu Leu Leu Leu
865                 870                 875                 880

Gln Gln Gly Leu Leu Pro His Ser Ser Cys
                885                 890

<210> SEQ ID NO 24
<211> LENGTH: 999
<212> TYPE: PRT
<213> ORGANISM: Homo sapiens
<220> FEATURE:
<221> NAME/KEY: MISC_FEATURE
<222> LOCATION: (1)..(999)
<223> OTHER INFORMATION: Homo sapiens Mer

<400> SEQUENCE: 24

Met Gly Pro Ala Pro Leu Pro Leu Leu Leu Gly Leu Phe Leu Pro Ala
1               5                   10                  15

Leu Trp Arg Arg Ala Ile Thr Glu Ala Arg Glu Glu Ala Lys Pro Tyr
                20                  25                  30

Pro Leu Phe Pro Gly Pro Phe Pro Gly Ser Leu Gln Thr Asp His Thr
            35                  40                  45

Pro Leu Leu Ser Leu Pro His Ala Ser Gly Tyr Gln Pro Ala Leu Met
        50                  55                  60

Phe Ser Pro Thr Gln Pro Gly Arg Pro His Thr Gly Asn Val Ala Ile
```

-continued

```
            65                  70                  75                  80

Pro Gln Val Thr Ser Val Glu Ser Lys Pro Leu Pro Pro Leu Ala Phe
                    85                  90                  95

Lys His Thr Val Gly His Ile Ile Leu Ser Glu His Lys Gly Val Lys
                    100                 105                 110

Phe Asn Cys Ser Ile Ser Val Pro Asn Ile Tyr Gln Asp Thr Thr Ile
                    115                 120                 125

Ser Trp Trp Lys Asp Gly Lys Glu Leu Leu Gly Ala His His Ala Ile
            130                 135                 140

Thr Gln Phe Tyr Pro Asp Asp Glu Val Thr Ala Ile Ile Ala Ser Phe
145                 150                 155                 160

Ser Ile Thr Ser Val Gln Arg Ser Asp Asn Gly Ser Tyr Ile Cys Lys
                    165                 170                 175

Met Lys Ile Asn Asn Glu Glu Ile Val Ser Asp Pro Ile Tyr Ile Glu
            180                 185                 190

Val Gln Gly Leu Pro His Phe Thr Lys Gln Pro Glu Ser Met Asn Val
            195                 200                 205

Thr Arg Asn Thr Ala Phe Asn Leu Thr Cys Gln Ala Val Gly Pro Pro
            210                 215                 220

Glu Pro Val Asn Ile Phe Trp Val Gln Asn Ser Ser Arg Val Asn Glu
225                 230                 235                 240

Gln Pro Glu Lys Ser Pro Ser Val Leu Thr Val Pro Gly Leu Thr Glu
                    245                 250                 255

Met Ala Val Phe Ser Cys Glu Ala His Asn Asp Lys Gly Leu Thr Val
            260                 265                 270

Ser Lys Gly Val Gln Ile Asn Ile Lys Ala Ile Pro Ser Pro Pro Thr
            275                 280                 285

Glu Val Ser Ile Arg Asn Ser Thr Ala His Ser Ile Leu Ile Ser Trp
            290                 295                 300

Val Pro Gly Phe Asp Gly Tyr Ser Pro Phe Arg Asn Cys Ser Ile Gln
305                 310                 315                 320

Val Lys Glu Ala Asp Pro Leu Ser Asn Gly Ser Val Met Ile Phe Asn
                    325                 330                 335

Thr Ser Ala Leu Pro His Leu Tyr Gln Ile Lys Gln Leu Gln Ala Leu
                    340                 345                 350

Ala Asn Tyr Ser Ile Gly Val Ser Cys Met Asn Glu Ile Gly Trp Ser
                    355                 360                 365

Ala Val Ser Pro Trp Ile Leu Ala Ser Thr Thr Glu Gly Ala Pro Ser
            370                 375                 380

Val Ala Pro Leu Asn Val Thr Val Phe Leu Asn Glu Ser Ser Asp Asn
385                 390                 395                 400

Val Asp Ile Arg Trp Met Lys Pro Pro Thr Lys Gln Gln Asp Gly Glu
                    405                 410                 415

Leu Val Gly Tyr Arg Ile Ser His Val Trp Gln Ser Ala Gly Ile Ser
                    420                 425                 430

Lys Glu Leu Leu Glu Glu Val Gly Gln Asn Gly Ser Arg Ala Arg Ile
            435                 440                 445

Ser Val Gln Val His Asn Ala Thr Cys Thr Val Arg Ile Ala Ala Val
            450                 455                 460

Thr Arg Gly Gly Val Gly Pro Phe Ser Asp Pro Val Lys Ile Phe Ile
465                 470                 475                 480

Pro Ala His Gly Trp Val Asp Tyr Ala Pro Ser Ser Thr Pro Ala Pro
                    485                 490                 495
```

Gly Asn Ala Asp Pro Val Leu Ile Ile Phe Gly Cys Phe Cys Gly Phe
                500                 505                 510

Ile Leu Ile Gly Leu Ile Leu Tyr Ile Ser Leu Ala Ile Arg Lys Arg
    515                 520                 525

Val Gln Glu Thr Lys Phe Gly Asn Ala Phe Thr Glu Glu Asp Ser Glu
530                 535                 540

Leu Val Val Asn Tyr Ile Ala Lys Lys Ser Phe Cys Arg Arg Ala Ile
545                 550                 555                 560

Glu Leu Thr Leu His Ser Leu Gly Val Ser Glu Leu Gln Asn Lys
                565                 570                 575

Leu Glu Asp Val Val Ile Asp Arg Asn Leu Leu Ile Leu Gly Lys Ile
                580                 585                 590

Leu Gly Glu Gly Glu Phe Gly Ser Val Met Glu Gly Asn Leu Lys Gln
                595                 600                 605

Glu Asp Gly Thr Ser Leu Lys Val Ala Val Lys Thr Met Lys Leu Asp
    610                 615                 620

Asn Ser Ser Gln Arg Glu Ile Glu Glu Phe Leu Ser Glu Ala Ala Cys
625                 630                 635                 640

Met Lys Asp Phe Ser His Pro Asn Val Ile Arg Leu Leu Gly Val Cys
                645                 650                 655

Ile Glu Met Ser Ser Gln Gly Ile Pro Lys Pro Met Val Ile Leu Pro
                660                 665                 670

Phe Met Lys Tyr Gly Asp Leu His Thr Tyr Leu Leu Tyr Ser Arg Leu
                675                 680                 685

Glu Thr Gly Pro Lys His Ile Pro Leu Gln Thr Leu Leu Lys Phe Met
    690                 695                 700

Val Asp Ile Ala Leu Gly Met Glu Tyr Leu Ser Asn Arg Asn Phe Leu
705                 710                 715                 720

His Arg Asp Leu Ala Ala Arg Asn Cys Met Leu Arg Asp Asp Met Thr
                725                 730                 735

Val Cys Val Ala Asp Phe Gly Leu Ser Lys Lys Ile Tyr Ser Gly Asp
                740                 745                 750

Tyr Tyr Arg Gln Gly Arg Ile Ala Lys Met Pro Val Lys Trp Ile Ala
    755                 760                 765

Ile Glu Ser Leu Ala Asp Arg Val Tyr Thr Ser Lys Ser Asp Val Trp
770                 775                 780

Ala Phe Gly Val Thr Met Trp Glu Ile Ala Thr Arg Gly Met Thr Pro
785                 790                 795                 800

Tyr Pro Gly Val Gln Asn His Glu Met Tyr Asp Tyr Leu Leu His Gly
                805                 810                 815

His Arg Leu Lys Gln Pro Glu Asp Cys Leu Asp Glu Leu Tyr Glu Ile
                820                 825                 830

Met Tyr Ser Cys Trp Arg Thr Asp Pro Leu Asp Arg Pro Thr Phe Ser
    835                 840                 845

Val Leu Arg Leu Gln Leu Glu Lys Leu Leu Glu Ser Leu Pro Asp Val
                850                 855                 860

Arg Asn Gln Ala Asp Val Ile Tyr Val Asn Thr Gln Leu Leu Glu Ser
865                 870                 875                 880

Ser Glu Gly Leu Ala Gln Gly Ser Thr Leu Ala Pro Leu Asp Leu Asn
                885                 890                 895

Ile Asp Pro Asp Ser Ile Ile Ala Ser Cys Thr Pro Arg Ala Ala Ile
                900                 905                 910

```
Ser Val Val Thr Ala Glu Val His Asp Ser Lys Pro His Glu Gly Arg
            915                 920                 925

Tyr Ile Leu Asn Gly Gly Ser Glu Glu Trp Glu Asp Leu Thr Ser Ala
            930                 935                 940

Pro Ser Ala Ala Val Thr Ala Glu Lys Asn Ser Val Leu Pro Gly Glu
945                 950                 955                 960

Arg Leu Val Arg Asn Gly Val Ser Trp Ser His Ser Ser Met Leu Pro
            965                 970                 975

Leu Gly Ser Ser Leu Pro Asp Glu Leu Leu Phe Ala Asp Ser Ser
            980                 985                 990

Glu Gly Ser Glu Val Leu Met
            995

<210> SEQ ID NO 25
<211> LENGTH: 465
<212> TYPE: PRT
<213> ORGANISM: Homo sapiens
<220> FEATURE:
<221> NAME/KEY: MISC_FEATURE
<222> LOCATION: (1)..(465)
<223> OTHER INFORMATION: Homo sapiens Akt3

<400> SEQUENCE: 25

Met Ser Asp Val Thr Ile Val Lys Glu Gly Trp Val Gln Lys Arg Gly
1               5                   10                  15

Glu Tyr Ile Lys Asn Trp Arg Pro Arg Tyr Phe Leu Leu Lys Thr Asp
            20                  25                  30

Gly Ser Phe Ile Gly Tyr Lys Glu Lys Pro Gln Asp Val Asp Leu Pro
        35                  40                  45

Tyr Pro Leu Asn Asn Phe Ser Val Ala Lys Cys Gln Leu Met Lys Thr
50                  55                  60

Glu Arg Pro Lys Pro Asn Thr Phe Ile Ile Arg Cys Leu Gln Trp Thr
65                  70                  75                  80

Thr Val Ile Glu Arg Thr Phe His Val Asp Thr Pro Glu Glu Arg Glu
            85                  90                  95

Glu Trp Thr Glu Ala Ile Gln Ala Val Ala Asp Arg Leu Gln Arg Gln
        100                 105                 110

Glu Glu Glu Arg Met Asn Cys Ser Pro Thr Ser Gln Ile Asp Asn Ile
    115                 120                 125

Gly Glu Glu Glu Met Asp Ala Ser Thr Thr His His Lys Arg Lys Thr
130                 135                 140

Met Asn Asp Phe Asp Tyr Leu Lys Leu Leu Gly Lys Gly Thr Phe Gly
145                 150                 155                 160

Lys Val Ile Leu Val Arg Glu Lys Ala Ser Gly Lys Tyr Tyr Ala Met
            165                 170                 175

Lys Ile Leu Lys Lys Glu Val Ile Ile Ala Lys Asp Glu Val Ala His
        180                 185                 190

Thr Leu Thr Glu Ser Arg Val Leu Lys Asn Thr Arg His Pro Phe Leu
    195                 200                 205

Thr Ser Leu Lys Tyr Ser Phe Gln Thr Lys Asp Arg Leu Cys Phe Val
210                 215                 220

Met Glu Tyr Val Asn Gly Gly Glu Leu Phe His Leu Ser Arg Glu
225                 230                 235                 240

Arg Val Phe Ser Glu Asp Arg Thr Arg Phe Tyr Gly Ala Glu Ile Val
            245                 250                 255

Ser Ala Leu Asp Tyr Leu His Ser Gly Lys Ile Val Tyr Arg Asp Leu
```

```
                260                 265                 270
Lys Leu Glu Asn Leu Met Leu Asp Lys Asp Gly His Ile Lys Ile Thr
            275                 280                 285
Asp Phe Gly Leu Cys Lys Glu Gly Ile Thr Asp Ala Ala Thr Met Lys
        290                 295                 300
Thr Phe Cys Gly Thr Pro Glu Tyr Leu Ala Pro Glu Val Leu Glu Asp
305                 310                 315                 320
Asn Asp Tyr Gly Arg Ala Val Asp Trp Trp Gly Leu Gly Val Val Met
                325                 330                 335
Tyr Glu Met Met Cys Gly Arg Leu Pro Phe Tyr Asn Gln Asp His Glu
            340                 345                 350
Lys Leu Phe Glu Leu Ile Leu Met Glu Asp Ile Lys Phe Pro Arg Thr
        355                 360                 365
Leu Ser Ser Asp Ala Lys Ser Leu Leu Ser Gly Leu Leu Ile Lys Asp
    370                 375                 380
Pro Asn Lys Arg Leu Gly Gly Gly Pro Asp Asp Ala Lys Glu Ile Met
385                 390                 395                 400
Arg His Ser Phe Phe Ser Gly Val Asn Trp Gln Asp Val Tyr Asp Lys
                405                 410                 415
Lys Leu Val Pro Pro Phe Lys Pro Gln Val Thr Ser Glu Thr Asp Thr
            420                 425                 430
Arg Tyr Phe Asp Glu Glu Phe Thr Ala Gln Thr Ile Thr Ile Thr Pro
        435                 440                 445
Pro Glu Lys Cys Gln Gln Ser Asp Cys Gly Met Leu Gly Asn Trp Lys
    450                 455                 460
Lys
465

<210> SEQ ID NO 26
<211> LENGTH: 678
<212> TYPE: PRT
<213> ORGANISM: Homo sapiens
<220> FEATURE:
<221> NAME/KEY: MISC_FEATURE
<222> LOCATION: (1)..(678)
<223> OTHER INFORMATION: Homo sapiens Gas6

<400> SEQUENCE: 26

Met Ala Pro Ser Leu Ser Pro Gly Pro Ala Ala Leu Arg Arg Ala Pro
1               5                   10                  15
Gln Leu Leu Leu Leu Leu Leu Ala Ala Glu Cys Ala Leu Ala Ala Leu
            20                  25                  30
Leu Pro Ala Arg Glu Ala Thr Gln Phe Leu Arg Pro Arg Gln Arg Arg
        35                  40                  45
Ala Phe Gln Val Phe Glu Glu Ala Lys Gln Gly His Leu Glu Arg Glu
    50                  55                  60
Cys Val Glu Glu Leu Cys Ser Arg Glu Glu Ala Arg Glu Val Phe Glu
65                  70                  75                  80
Asn Asp Pro Glu Thr Asp Tyr Phe Tyr Pro Arg Tyr Leu Asp Cys Ile
                85                  90                  95
Asn Lys Tyr Gly Ser Pro Tyr Thr Lys Asn Ser Gly Phe Ala Thr Cys
            100                 105                 110
Val Gln Asn Leu Pro Asp Gln Cys Thr Pro Asn Pro Cys Asp Arg Lys
        115                 120                 125
Gly Thr Gln Ala Cys Gln Asp Leu Met Gly Asn Phe Phe Cys Leu Cys
    130                 135                 140
```

-continued

```
Lys Ala Gly Trp Gly Gly Arg Leu Cys Asp Lys Asp Val Asn Glu Cys
145                 150                 155                 160

Ser Gln Glu Asn Gly Gly Cys Leu Gln Ile Cys His Asn Lys Pro Gly
                165                 170                 175

Ser Phe His Cys Ser Cys His Ser Gly Phe Glu Leu Ser Ser Asp Gly
            180                 185                 190

Arg Thr Cys Gln Asp Ile Asp Glu Cys Ala Asp Ser Glu Ala Cys Gly
            195                 200                 205

Glu Ala Arg Cys Lys Asn Leu Pro Gly Ser Tyr Ser Cys Leu Cys Asp
210                 215                 220

Glu Gly Phe Ala Tyr Ser Ser Gln Glu Lys Ala Cys Arg Asp Val Asp
225                 230                 235                 240

Glu Cys Leu Gln Gly Arg Cys Glu Gln Val Cys Val Asn Ser Pro Gly
                245                 250                 255

Ser Tyr Thr Cys His Cys Asp Gly Arg Gly Gly Leu Lys Leu Ser Gln
            260                 265                 270

Asp Met Asp Thr Cys Glu Asp Ile Leu Pro Cys Val Pro Phe Ser Val
            275                 280                 285

Ala Lys Ser Val Lys Ser Leu Tyr Leu Gly Arg Met Phe Ser Gly Thr
290                 295                 300

Pro Val Ile Arg Leu Arg Phe Lys Arg Leu Gln Pro Thr Arg Leu Val
305                 310                 315                 320

Ala Glu Phe Asp Phe Arg Thr Phe Asp Pro Glu Gly Ile Leu Leu Phe
                325                 330                 335

Ala Gly Gly His Gln Asp Ser Thr Trp Ile Val Leu Ala Leu Arg Ala
            340                 345                 350

Gly Arg Leu Glu Leu Gln Leu Arg Tyr Asn Gly Val Gly Arg Val Thr
            355                 360                 365

Ser Ser Gly Pro Val Ile Asn His Gly Met Trp Gln Thr Ile Ser Val
370                 375                 380

Glu Glu Leu Ala Arg Asn Leu Val Ile Lys Val Asn Arg Asp Ala Val
385                 390                 395                 400

Met Lys Ile Ala Val Ala Gly Asp Leu Phe Gln Pro Glu Arg Gly Leu
                405                 410                 415

Tyr His Leu Asn Leu Thr Val Gly Gly Ile Pro Phe His Glu Lys Asp
            420                 425                 430

Leu Val Gln Pro Ile Asn Pro Arg Leu Asp Gly Cys Met Arg Ser Trp
            435                 440                 445

Asn Trp Leu Asn Gly Glu Asp Thr Thr Ile Gln Glu Thr Val Lys Val
450                 455                 460

Asn Thr Arg Met Gln Cys Phe Ser Val Thr Glu Arg Gly Ser Phe Tyr
465                 470                 475                 480

Pro Gly Ser Gly Phe Ala Phe Tyr Ser Leu Asp Tyr Met Arg Thr Pro
                485                 490                 495

Leu Asp Val Gly Thr Glu Ser Thr Trp Glu Val Glu Val Val Ala His
            500                 505                 510

Ile Arg Pro Ala Ala Asp Thr Gly Val Leu Phe Ala Leu Trp Ala Pro
            515                 520                 525

Asp Leu Arg Ala Val Pro Leu Ser Val Ala Leu Val Asp Tyr His Ser
530                 535                 540

Thr Lys Lys Leu Lys Lys Gln Leu Val Val Leu Ala Val Glu His Thr
545                 550                 555                 560
```

```
Ala Leu Ala Leu Met Glu Ile Lys Val Cys Asp Gly Gln Glu His Val
            565                 570                 575

Val Thr Val Ser Leu Arg Asp Gly Glu Ala Thr Leu Glu Val Asp Gly
        580                 585                 590

Thr Arg Gly Gln Ser Glu Val Ser Ala Ala Gln Leu Gln Glu Arg Leu
            595                 600                 605

Ala Val Leu Glu Arg His Leu Arg Ser Pro Val Leu Thr Phe Ala Gly
610                 615                 620

Gly Leu Pro Asp Val Pro Val Thr Ser Ala Pro Val Thr Ala Phe Tyr
625                 630                 635                 640

Arg Gly Cys Met Thr Leu Glu Val Asn Arg Arg Leu Leu Asp Leu Asp
            645                 650                 655

Glu Ala Ala Tyr Lys His Ser Asp Ile Thr Ala His Ser Cys Pro Pro
            660                 665                 670

Val Glu Pro Ala Ala Ala
            675

<210> SEQ ID NO 27
<211> LENGTH: 894
<212> TYPE: PRT
<213> ORGANISM: Macaca fascicularis
<220> FEATURE:
<221> NAME/KEY: MISC_FEATURE
<222> LOCATION: (1)..(894)
<223> OTHER INFORMATION: Macaca fascicularis Axl

<400> SEQUENCE: 27

Met Ala Trp Arg Cys Pro Arg Met Gly Arg Val Pro Leu Ala Trp Cys
1               5                   10                  15

Leu Ala Leu Cys Gly Trp Val Cys Met Ala Pro Arg Gly Thr Gln Ala
            20                  25                  30

Glu Glu Ser Pro Phe Val Gly Asn Pro Gly Asn Ile Thr Gly Ala Arg
        35                  40                  45

Gly Leu Thr Gly Thr Leu Arg Cys Gln Leu Gln Val Gln Gly Glu Pro
    50                  55                  60

Pro Glu Val His Trp Leu Arg Asp Gly Gln Ile Leu Glu Leu Ala Asp
65                  70                  75                  80

Ser Thr Gln Thr Gln Val Pro Leu Gly Glu Asp Glu Gln Asp Asp Trp
                85                  90                  95

Ile Val Val Ser Gln Leu Arg Ile Ala Ser Leu Gln Leu Ser Asp Ala
            100                 105                 110

Gly Gln Tyr Gln Cys Leu Val Phe Leu Gly His Gln Asn Phe Val Ser
        115                 120                 125

Gln Pro Gly Tyr Val Gly Leu Glu Gly Leu Pro Tyr Phe Leu Glu Glu
    130                 135                 140

Pro Glu Asp Arg Thr Val Ala Ala Asn Thr Pro Phe Asn Leu Ser Cys
145                 150                 155                 160

Gln Ala Gln Gly Pro Pro Glu Pro Val Asp Leu Leu Trp Leu Gln Asp
                165                 170                 175

Ala Val Pro Leu Ala Thr Ala Pro Gly His Gly Pro Gln Arg Asn Leu
            180                 185                 190

His Val Pro Gly Leu Asn Lys Thr Ser Ser Phe Ser Cys Glu Ala His
        195                 200                 205

Asn Ala Lys Gly Val Thr Thr Ser Arg Thr Ala Thr Ile Thr Val Leu
    210                 215                 220

Pro Gln Gln Pro Arg Asn Leu His Leu Val Ser Arg Gln Pro Thr Glu
```

```
                225                 230                 235                 240

Leu Glu Val Ala Trp Thr Pro Gly Leu Ser Gly Ile Tyr Pro Leu Thr
                    245                 250                 255

His Cys Thr Leu Gln Ala Val Leu Ser Asp Asp Gly Met Gly Ile Gln
                    260                 265                 270

Ala Gly Glu Pro Asp Pro Pro Glu Pro Leu Thr Leu Gln Ala Ser
            275                 280                 285

Val Pro Pro His Gln Leu Arg Leu Gly Ser Leu His Pro His Thr Pro
        290                 295                 300

Tyr His Ile Arg Val Ala Cys Thr Ser Ser Gln Gly Pro Ser Ser Trp
305                 310                 315                 320

Thr His Trp Leu Pro Val Glu Thr Pro Glu Gly Val Pro Leu Gly Pro
                        325                 330                 335

Pro Glu Asn Ile Ser Ala Thr Arg Asn Gly Ser Gln Ala Phe Val His
                340                 345                 350

Trp Gln Glu Pro Arg Ala Pro Leu Gln Gly Thr Leu Leu Gly Tyr Arg
                355                 360                 365

Leu Ala Tyr Gln Gly Gln Asp Thr Pro Glu Val Leu Met Asp Ile Gly
        370                 375                 380

Leu Arg Gln Glu Val Thr Leu Glu Leu Gln Gly Asp Gly Ser Val Ser
385                 390                 395                 400

Asn Leu Thr Val Cys Val Ala Ala Tyr Thr Ala Ala Gly Asp Gly Pro
                        405                 410                 415

Trp Ser Leu Pro Val Pro Leu Glu Ala Trp Arg Pro Gly Gln Ala Gln
                420                 425                 430

Pro Val His Gln Leu Val Lys Glu Thr Ser Ala Pro Ala Phe Ser Trp
                435                 440                 445

Pro Trp Trp Tyr Ile Leu Leu Gly Ala Val Val Ala Ala Ala Cys Val
                450                 455                 460

Leu Ile Leu Ala Leu Phe Leu Val His Arg Arg Lys Lys Glu Thr Arg
465                 470                 475                 480

Tyr Gly Glu Val Phe Glu Pro Thr Val Glu Arg Gly Glu Leu Val Val
                        485                 490                 495

Arg Tyr Arg Val Arg Lys Ser Tyr Ser Arg Arg Thr Thr Glu Ala Thr
                500                 505                 510

Leu Asn Ser Leu Gly Ile Ser Glu Glu Leu Lys Glu Lys Leu Arg Asp
                515                 520                 525

Val Met Val Asp Arg His Lys Val Ala Leu Gly Lys Thr Leu Gly Glu
        530                 535                 540

Gly Glu Phe Gly Ala Val Met Glu Gly Gln Leu Asn Gln Asp Asp Ser
545                 550                 555                 560

Ile Leu Lys Val Ala Val Lys Thr Met Lys Ile Ala Ile Cys Thr Arg
                            565                 570                 575

Ser Glu Leu Glu Asp Phe Leu Ser Glu Ala Val Cys Met Lys Glu Phe
                580                 585                 590

Asp His Pro Asn Val Met Arg Leu Ile Gly Val Cys Phe Gln Gly Ser
                595                 600                 605

Glu Arg Glu Ser Phe Pro Ala Pro Val Val Ile Leu Pro Phe Met Lys
        610                 615                 620

His Gly Asp Leu His Ser Phe Leu Leu Tyr Ser Arg Leu Gly Asp Gln
625                 630                 635                 640

Pro Val Tyr Leu Pro Thr Gln Met Leu Val Lys Phe Met Ala Asp Ile
                        645                 650                 655
```

```
Ala Ser Gly Met Glu Tyr Leu Ser Thr Lys Arg Phe Ile His Arg Asp
            660                 665                 670

Leu Ala Ala Arg Asn Cys Met Leu Asn Glu Asn Met Ser Val Cys Val
            675                 680                 685

Ala Asp Phe Gly Leu Ser Lys Lys Ile Tyr Asn Gly Asp Tyr Tyr Arg
            690                 695                 700

Gln Gly Arg Ile Ala Lys Met Pro Val Lys Trp Ile Ala Ile Glu Ser
705                 710                 715                 720

Leu Ala Asp Arg Val Tyr Thr Ser Lys Ser Asp Val Trp Ser Phe Gly
                725                 730                 735

Val Thr Met Trp Glu Ile Ala Thr Arg Gly Gln Thr Pro Tyr Pro Gly
            740                 745                 750

Val Glu Asn Ser Glu Ile Tyr Asp Tyr Leu Arg Gln Gly Asn Arg Leu
            755                 760                 765

Lys Gln Pro Ala Asp Cys Leu Asp Gly Leu Tyr Ala Leu Met Ser Arg
            770                 775                 780

Cys Trp Glu Leu Asn Pro Gln Asp Arg Pro Ser Phe Thr Glu Leu Arg
785                 790                 795                 800

Glu Asp Leu Glu Asn Thr Leu Lys Ala Leu Pro Pro Ala Gln Glu Pro
                805                 810                 815

Asp Glu Ile Leu Tyr Val Asn Met Asp Glu Gly Gly Gly Tyr Pro Glu
            820                 825                 830

Pro Pro Gly Ala Ala Gly Gly Ala Asp Pro Pro Thr Gln Leu Asp Pro
            835                 840                 845

Lys Asp Ser Cys Ser Cys Leu Thr Ser Ala Glu Val His Pro Ala Gly
            850                 855                 860

Arg Tyr Val Leu Cys Pro Ser Thr Ala Pro Ser Pro Ala Gln Pro Ala
865                 870                 875                 880

Asp Arg Gly Ser Pro Ala Ala Pro Gly Gln Glu Asp Gly Ala
                885                 890

<210> SEQ ID NO 28
<211> LENGTH: 118
<212> TYPE: PRT
<213> ORGANISM: Mus musculus
<220> FEATURE:
<221> NAME/KEY: MISC_FEATURE
<222> LOCATION: (1)..(118)
<223> OTHER INFORMATION: Mus musculus 10G5 VH domain

<400> SEQUENCE: 28

Gln Val Gln Leu Gln Gln Ser Gly Ala Glu Leu Val Arg Pro Gly Ala
1               5                   10                  15

Ser Val Lys Leu Ser Cys Lys Ala Ser Gly Tyr Ser Phe Thr Asp Phe
            20                  25                  30

Tyr Ile Asn Trp Val Arg Gln Arg Pro Gly Gln Gly Leu Glu Trp Ile
        35                  40                  45

Ala Arg Ile Phe Pro Gly Gly Asp Asn Thr Tyr Tyr Asn Glu Lys Phe
    50                  55                  60

Lys Gly Lys Ala Thr Leu Thr Ala Glu Glu Ser Ser Ser Thr Ala Tyr
65                  70                  75                  80

Ile Gln Leu Ser Ser Leu Thr Ser Glu Asp Ser Ala Val Tyr Phe Cys
                85                  90                  95

Ala Arg Arg Gly Leu Tyr Tyr Ala Met Asp Tyr Trp Gly Gln Gly Ile
            100                 105                 110
```

Ser Val Thr Val Ser Ser
        115

<210> SEQ ID NO 29
<211> LENGTH: 112
<212> TYPE: PRT
<213> ORGANISM: Mus musculus
<220> FEATURE:
<221> NAME/KEY: MISC_FEATURE
<222> LOCATION: (1)..(112)
<223> OTHER INFORMATION: Mus musculus 10G5 VL domain

<400> SEQUENCE: 29

Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Ser Leu Val His Ser
            20                  25                  30

Asn Gly Ile Pro Tyr Leu His Trp Tyr Leu Gln Lys Pro Gly Gln Ser
        35                  40                  45

Pro Lys Leu Leu Ile Tyr Arg Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser Gln Gly
                85                  90                  95

Thr His Val Pro Pro Thr Phe Gly Gly Gly Thr Lys Leu Glu Ile Lys
            100                 105                 110

<210> SEQ ID NO 30
<211> LENGTH: 10
<212> TYPE: PRT
<213> ORGANISM: Artificial Sequence
<220> FEATURE:
<223> OTHER INFORMATION: 10G5 VH CDR1

<400> SEQUENCE: 30

Gly Tyr Ser Phe Thr Asp Phe Tyr Ile Asn
1               5                   10

<210> SEQ ID NO 31
<211> LENGTH: 17
<212> TYPE: PRT
<213> ORGANISM: Artificial Sequence
<220> FEATURE:
<223> OTHER INFORMATION: 10G5 VH CDR2

<400> SEQUENCE: 31

Arg Ile Phe Pro Gly Gly Asp Asn Thr Tyr Tyr Asn Glu Lys Phe Lys
1               5                   10                  15

Gly

<210> SEQ ID NO 32
<211> LENGTH: 9
<212> TYPE: PRT
<213> ORGANISM: Artificial Sequence
<220> FEATURE:
<223> OTHER INFORMATION: 10G5 VH CDR3

<400> SEQUENCE: 32

Arg Gly Leu Tyr Tyr Ala Met Asp Tyr
1               5

<210> SEQ ID NO 33

```
<211> LENGTH: 16
<212> TYPE: PRT
<213> ORGANISM: Artificial Sequence
<220> FEATURE:
<223> OTHER INFORMATION: 10G5 VL CDR1

<400> SEQUENCE: 33

Arg Ser Ser Gln Ser Leu Val His Ser Asn Gly Ile Pro Tyr Leu His
1               5                   10                  15

<210> SEQ ID NO 34
<211> LENGTH: 7
<212> TYPE: PRT
<213> ORGANISM: Artificial Sequence
<220> FEATURE:
<223> OTHER INFORMATION: 10G5 VL CDR2

<400> SEQUENCE: 34

Arg Val Ser Asn Arg Phe Ser
1               5

<210> SEQ ID NO 35
<211> LENGTH: 9
<212> TYPE: PRT
<213> ORGANISM: Artificial Sequence
<220> FEATURE:
<223> OTHER INFORMATION: 10G5 VL CDR3

<400> SEQUENCE: 35

Ser Gln Gly Thr His Val Pro Pro Thr
1               5
```

ANTI-AXL ANTAGONISTIC ANTIBODIES

CROSS-REFERENCE TO THE RELATED APPLICATIONS

This application is a national phase entry pursuant to 35 U.S.C. § 371 of International Application No. PCT/EP2017/065313, filed Jun. 21, 2017, which claims the benefit of priority of GB Application No. 1610902.7, filed Jun. 22, 2016, each of which is incorporated by reference herein in its entirety for any purpose.

The present disclosure relates to antibodies that specifically bind to the Axl protein. Also disclosed are methods for the production and use of the anti-Axl antibodies.

BACKGROUND

Axl is a member of the TAM (Tyro3-Axl-Mer) receptor tyrosine kinases (RTK) that share the vitamin K-dependent ligand Gas6 (growth arrest-specific 6). TAM family RTKs regulate a diverse range of cellular responses including cell survival, proliferation, autophagy, migration, angiogenesis, platelet aggregation, and natural killer cell differentiation. Axl is expressed in many embryonic tissues and is thought to be involved in mesenchymal and neural development, with expression in adult tissues largely restricted to smooth muscle cells (MGI Gene Expression Database; www.informatics.jax.org). Axl activation is linked to several signal transduction pathways, including Akt, MAP kinases, NF-κB, STAT, and others.

Originally identified as a transforming gene from a patient with chronic myelogenous leukaemia, Axl has since been associated with various high-grade cancers and correlated with poor prognosis.

Axl receptor overexpression has been detected in a wide range of solid tumours and myeloid leukaemia (Linger et al, Adv Cancer Res. 100: 35, 2008; Linger et al, Expert Opin Ther Targets. 14:1073, 2010).

Axl expression correlates with malignant progression and is an independent predictor of poor patient overall survival in several malignancies including pancreatic (Song et al, Cancer. 117:734, 2011), prostate (Paccez et al, Oncogene. 32:698, 2013), lung (Ishikawa et al. Ann Surg Oncol. 2012; Zhang et al, Nat Genet. 44:852, 2012), breast (Gjerdrum, Proc natl Acad Sci USA 107:1124, 2010), colon cancer (Yuen et al, PLoS One, 8:e54211, 2013) and acute myeloid leukaemia (AML) (Ben-Batalla et al, Blood 122:2443, 2013).

Axl signal transduction is activated by a protein ligand (Gas6) secreted by tumour associated macrophages (Loges et al, Blood. 115:2264, 2010) or autocrine mechanisms (Gjerdrum, Proc natl Acad Sci USA 107:1124, 2010), that drives receptor dimerization, autophosphorylation and downstream signalling, such as via PI3 kinase (PI3K)-AKT, particularly AKT and mitogen-activated protein kinase (MAPK) pathways (Korshunov, Clinical Science. 122:361, 2012). Heterodimerization with other tyrosine kinase receptors, e.g. epidermal growth factor receptor (EGFR), is also reported to occur (Linger et al, Expert Opin Ther Targets. 14:1073, 2010; Meyer et al Science Signalling 6:ra66, 2013).

Aberrant activation of Axl in tumour cells is widely associated with acquired drug resistance to targeted therapeutics in vitro and in vivo (Zhang et al. Nat Genet. 44: 852, 2012; Byers et al. Clin Cancer Res. 19: 279, 2013). Axl-targeting agents block tumour formation, metastasis and reverse drug resistance (e.g. to erlotinib) by reversing EMT/CSC characteristics in several experimental cancer models, including triple negative breast cancer, hormone resistant prostate cancer and adenocarcinoma of the lung (Holland et al Cancer Res 70:1544, 2010; Gjerdrum, Proc natl Acad Sci USA 107:1124, 2010; Zhang et al. Nat Genet. 44: 852, 2012; Paccez et al, Oncogene. 32:698, 2013).

Other applications relating to Axl and anti-Axl antibodies include EP2267454A2 [Diagnosis and prevention of cancer cell invasion measuring . . . Axl—Max Planck]; WO2009063965 [anti Axl—Chugai Pharmaceutical]; WO2011159980A1 [anti-Axl—Genentech], WO2011014457A1 [combination treatments Axl and VEGF antagonists—Genentech], Oncogene (2009) 28, 3442-3455, Oncogene (2010) 29, 5254-5264 [anti-Axl—Genentech]; WO2012-175691A1 [Anti Axl 20G7-D9—INSERM], WO2012-175692A1 [Anti Axl 3E3-E8—INSERM], Oncogene 33, 5405-5414 (20 Nov. 2014, doi:10.1038/onc.2013.487); WO2009/062690A1 [anti Axl—U3 Pharma] and WO2010/130751A1 [humanised anti Axl—U3 Pharma].

The anti-Axl antibodies described in the above documents have diverse properties. For example, Oncogene (2009) 28, 3442-3455 describes three anti-Axl antibodies from Genentech designated 3G9, 8B5, and 12A11; the authors report that whilst all three antibodies induce downregulation of Axl expression, only 3G9 and 8B5 block ligand binding to the Axl receptor (see ibid., page 3453, right column, top). A later paper by many of the same authors (Oncogene (2010) 29, 5254-5264) reports that an antibody which blocks ligand binding (YW327.652) is able to attenuate MDA-MB-231 xenograft tumor growth and enhance the effect of anti-vEGF treatment, whilst the 12A11 antibody is not (see ibid., FIG. 4).

In another example, the 'D9' and 'E8' antibodies described in Oncogene 33, 5405-5414 (20 Nov. 2014, doi: 10.1038/onc.2013.487) are reported to inhibit phosphorylation of AXL and of its downstream target AKT without affecting growth arrest-specific factor 6 (GAS6) binding (see ibid., abstract). The same authors also describe the D4 antibody in WO2016/091891 (see SEQ ID Nos 1 & 2 of that publication).

In a final example, the 11B7 antibody described in WO 2009062690 A1 is not reported to inhibit the binding of the GAS6 ligand to the receptor Axl.

In view of the role of Axl in tumourigenesis, it is desirable to identify further antibodies with advantageous properties that specifically bind Axl. The present disclosure concerns such antibodies.

Figure 1:
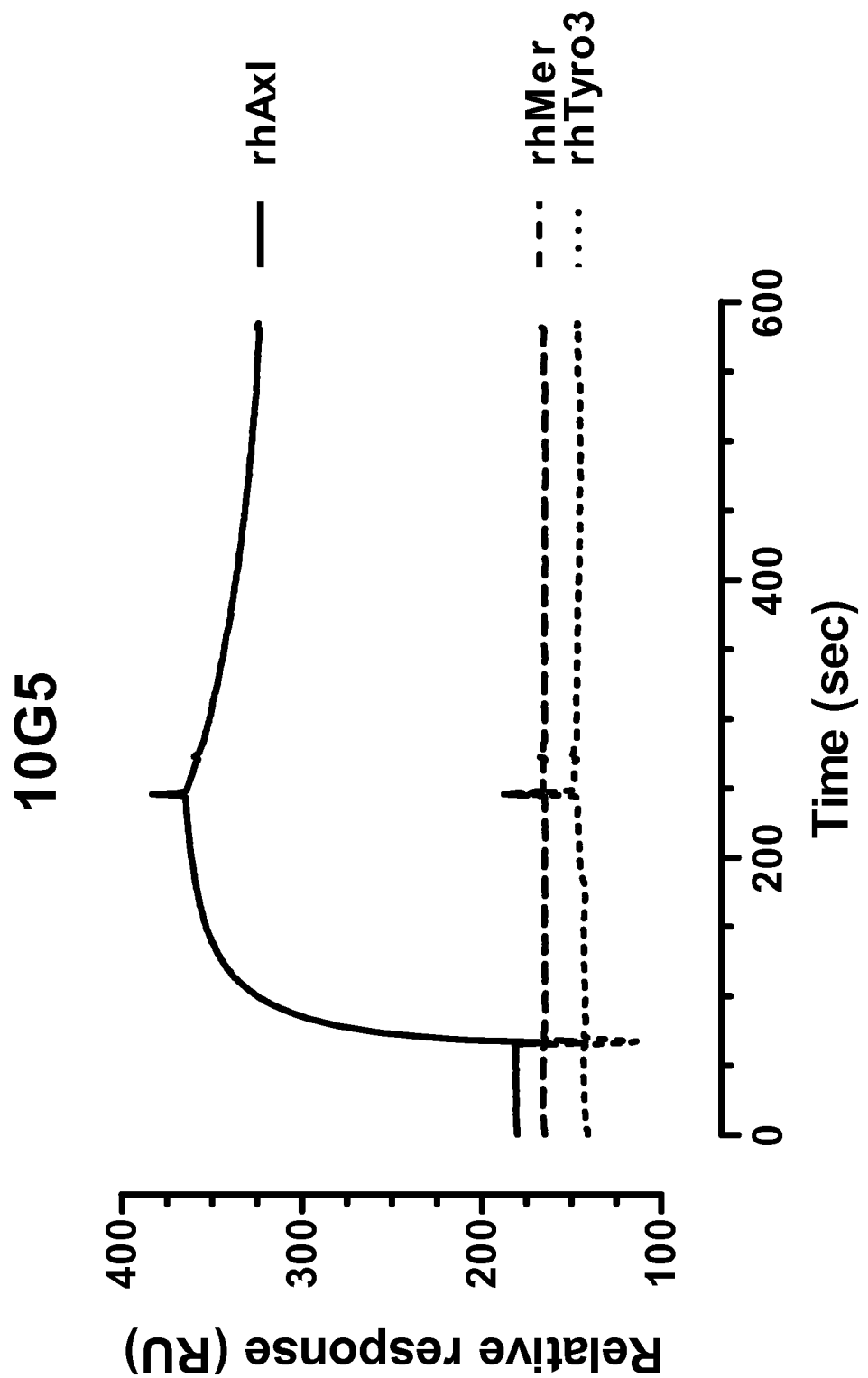
FIG. 1

Overlay plots of sensograms from the binding analyses showing interactions of chimeric MAb 10G5 with recombinant human (rh) Axl, rhMer and rhTyro3. The curves after subtraction of blank surface signals are shown.

FIG. 2

Biacore analyses of ligands (murine MAb 10G5 and rmGas6) interacting with a sensor chip CM5 coated with rhAxl, recombinant murine (rm) Axl and rhTyro3. The curves after subtraction of blank surface signals are shown.

FIG. 3

Biacore analyses of ligands (murine MAb 10G5) interacting with a sensor chip CM5 coated with recombinant human Axl (rhAxl) and Axl antigen from cynomolgus monkey (cyno-Axl). The curves after subtraction of blank surface signals are shown.

FIG. 4

Kinetic analysis of murine MAb 10G5 interacting with rhAxl immobilized on the surface of the Biacore sensor chip. Overlay plots of sensograms for different antibody concentrations (0.3-166.7 nM for murine 10G5) are shown. The precise kinetic analysis was performed using BIA evaluation software and curve fitting according to 1:1 Langmuir binding model. The affinity constants (kinetic and steady state) as well as the calculated half-live of antigen binding at 25° C. are shown in Table 1, below.

TABLE 1

| MAb | On-rate ($k_{on}$; $M^{-1}s^{-1}$) | Off-rate ($k_{off}$; $s^{-1}$) | $K_D$ (M) | Half-life ($t_{1/2}$; min) |
|---|---|---|---|---|
| murine 10G5 | $8.29 \times 10^5$ | $4.39 \times 10^{-4}$ | $5.30 \times 10^{-10}$ | 26.32 min |

FIG. 5

Analysis of the competition between murine MAb 10G5 (1st sample) and anti-Axl MAb MAB154 (R&D Systems), murine antibody 10G5, rhGas6 and rmGas6 (2nd samples) using Biacore 3000. The overlay plot of sensograms using different 2nd samples is shown. Start points of injections of the 1st sample (murine 10G5) and the 2nd sample are indicated with arrows.

FIG. 6

The effect of anti-Axl antibodies on the development on three-dimensional (3D) organotypic tumour masses. Highly aggressive human mammary carcinoma cells MDA-MB-231 were treated with either control IgG (shown in the middle upper panel) or anti-Axl MAbs (lower panels) while growing in the presence of extracellular matrix, thus creating 3D organotypic models. As positive control, MDA-MB-231 cells with knocked-down Axl expression are shown.

FIG. 7

Effect of anti-Axl antibody murine 10G5 on established 3D organotypic tumour masses. The developed 9-days old stellate-shaped 3D organoid masses of human mammary carcinoma cells (MDA-MB-231) were treated with either control IgG or anti-Axl antibody murine 10G5 for 72 hours. Images were captured using bright field; arrows indicate apoptotic, degrading stellate-shaped cells.

FIG. 8

Western blot analysis illustrating effect of treatment with either antibodies of multikinase inhibitor Foretinib on Axl receptor expression. Highly aggressive human mammary carcinoma cells MDA-MB-231 were treated with either antibodies (irrelevant IgG control and anti-Axl MAbs murine 10G5 and MAb #3) or Foretinib for 24 hrs before loading on SDS-PAA gel. The levels of actin protein were used as loading controls.

FIG. 9

Western blot analysis illustrating inhibition of Gas6-mediated Axl signalling in the presence of mouse monoclonal antibody murine 10G5. Phosphorylation of Akt on Ser$^{473}$ was used as surrogate readout for Axl activity. M, molecular weight markers. Immunoblots of total cell lysates were probed with anti-phospho-Akt (Ser$^{473}$), or anti-GAPDH (glyceraldehyde 3-phosphate dehydrogenase) as loading control.

FIG. 10

Amino acid sequences of the humanised VH and VL domains derived from anti-Axl monoclonal antibody 10G5. The CDR regions of the heavy and light chains are underlined.

FIG. 11

Dose-dependent binding of the chimeric variant of antibody 10G5 (c10G5) to Axl-positive cells. Different concentrations of chimeric antibody was tested in flow cytometry for binding to triple-negative breast cancer cell line MDA-MB-231. The bound chimeric antibody was detected with APC-conjugated donkey F(ab')$_2$ fragments specific for either mouse IgG (H+L), 1:500 dilution, or human IgG (H+L), 1:300 dilution, respectively (both from Jackson ImmunoResearch). The cell staining was measured using Accuri C6 flow cytometer (BD Biosciences). MFI, geometric mean fluorescence intensity.

FIG. 12

Overlay plots of sensograms from the Biacore binding analyses showing interactions of the chimeric antibody c10G5 and its murine counterpart with recombinant human (rh) Axl. The curves after subtraction of blank surface signals are shown.

FIG. 13

Kinetic analysis of chimeric antibody c10G5 interacting with rhAxl immobilized on the surface of the Biacore sensor chip. Overlay plots of sensograms for different antibody concentrations (0.3-166.7 nM for c10G5) are shown. The precise kinetic analysis was performed using BIA evaluation software and curve fitting according to 1:1 Langmuir binding model. The affinity constants (kinetic and steady state) as well as the calculated half-live of antigen binding at 25° C. are shown in Table 2, below.

TABLE 2

| MAb | On-rate ($k_{on}$; $M^{-1}s^{-1}$) | Off-rate ($k_{off}$; $s^{-1}$) | $K_D$ (M) | Half-life ($t_{1/2}$; min) |
|---|---|---|---|---|
| c10G5 | $1.64 \times 10^6$ | $1.69 \times 10^{-4}$ | $1.03 \times 10^{-10}$ | 68.36 min |

FIG. 14

Inhibition of A549 xenograft tumour growth by chimeric antibody 10G5. The antibody was administered intraperitoneally at 20 mg/kg, twice a week, starting when the mean tumour size reached 100 mm$^3$. Tumour growth curves for the groups treated with either vehicle (sterile PBS) or chimeric 10G5 are shown. Error bars represent standard error of the mean (SEM). Statistical analysis was performed using two-way ANOVA. **, P<0.01.

FIG. 15

Inhibition of Mv4-11 xenograft tumour growth by the chimeric antibody 10G5. The antibody was administered intraperitoneally at 30 mg/kg, twice a week, starting when the mean tumour size reached 200 mm$^3$. Tumour growth curves for the groups treated with either vehicle (sterile PBS) or chimeric 10G5 are shown. Error bars represent standard error of the mean (SEM). Statistical analysis was performed using two-way ANOVA. *, P<0.05; , P<0.01; **, P<0.0001.

FIG. 16

Data from Example 16. The antibody Glymax-c10G5 significantly attenuated growth of A549 tumours compared with the c10G5 (P<0.0001, as determined by two-way ANOVA). The significant difference in activity of wt and defucosylated versions of the chimeric 10G5 indicates importance of antibody-dependent cellular cytotoxicity (ADCC) in inhibition of tumor growth.

FIG. 17

Data from Example 17. The hu10G5 H2L1 antibody significantly attenuated growth of A549 tumours compared with the control (P<0.051, as determined by two-way ANOVA); around 25% inhibition was observed after two weeks of treatment.

FIG. 18

Data from Example 18. The hu10G5 (H1L1-GLYMAXX) antibody showed moderate anti-tumor activity, similar to the anti-tumor effect of the Anti-EGFR therapeutic antibody cetuximab (Erbitux). Combination of both antibodies resulted in significant tumor growth retardation (P<0.0001; as determined by two-way ANOVA) when compared to isotype control treated animals. The combined effect was also significant when compared to the groups treated with either hu10G5 (H1L1-GLYMAXX) or Erbitux alone (P<0.05; as determined by two-way ANOVA).

FIG. 19

Dose-dependent binding of the humanized antibody 10G5 (c10G5) to Axl-positive cells (FIG. 19A). Kinetic analysis of humanised antibody interacting with rhAxl immobilized on the surface of the Biacore sensor chip (FIG. 19B). Experimental details are given in Example 19.

FIG. 20

Tumour cell killing using antibody-Saporin conjugates. Comparison of chimeric 10G5 and two humanized 10G5 variants. Experimental details are given in Example 20.

FIG. 21

Overlay plots showing binding competition between MAbs c10G5 or YW327.6S2-var as first samples and the MAb YW327.6S2-var as a second sample, by Biacore assays (FIG. 21A).

FIG. 21B shows the results of competition when YW327.6S2-var was injected as a first sample followed by injection of the MAbs YW327.6S2-var or c10G5 as the second samples.

FIG. 22

Activation of Axl by Gas6 or cross-linking antibodies leads to phosphorylation of Akt. Stimulation of Axl signaling by cross-linking with chimeric 1H12 produces stronger activation of Akt than stimulation with recombinant Axl ligand Gas6 (a). Stimulation of Axl signalling by cross-linking with mAb 1H12 can be inhibited with BGB324 (b).

FIG. 23

Inhibition of fibrotic markers by anti-Axl antibodies 10G5 and YW327.6S2var. Each bar chart reports on the x-axis the relative mRNA expression of the titled marker. On the y-axis is shown the antibodies incubated with the LX2 cell population prior to mRNA quantification: 1H12=clustering anti-Axl antibody leading to Axl autophosphorylation and activation; 10G5=BerGenBio anti-Axl as described herein; YW327.6S2var=Genentech anti-Axl as referenced herein.

FIG. 24

A plot showing the tumor growth of individual tumors in mice treated with either GlymaxX-c10G5) and the variant of anti-Axl human antibody from Genentech (YW327.6S2var), as described in Example 22.

The disclosure includes the combination of the cases and preferred features described except where such a combination is clearly impermissible or expressly avoided.

The section headings used herein are for organizational purposes only and are not to be construed as limiting the subject matter described.

Cases and embodiments of the present disclosure will now be illustrated, by way of example, with reference to the accompanying figures. Further cases and embodiments will be apparent to those skilled in the art. All documents mentioned in this text are incorporated herein by reference.

Throughout this specification, including the claims which follow, unless the context requires otherwise, the word "comprise," and variations such as "comprises" and "comprising," will be understood to imply the inclusion of a stated integer or step or group of integers or steps but not the exclusion of any other integer or step or group of integers or steps.

It must be noted that, as used in the specification and the appended claims, the singular forms "a," "an," and "the" include plural referents unless the context clearly dictates otherwise. Ranges may be expressed herein as from "about" one particular value, and/or to "about" another particular value. When such a range is expressed, another embodiment includes from the one particular value and/or to the other particular value. Similarly, when values are expressed as approximations, by the use of the antecedent "about," it will be understood that the particular value forms another embodiment.

DISCLOSURE OF THE INVENTION

This invention provides humanised antibodies that bind to Axl protein and inhibits the binding of Axl to its ligand Gas6. The antibodies preferably also downregulate Axl expression, inhibit Axl receptor signalling, and/or inhibit tumour growth.

Disclosed herein are specific examples of such humanised antibodies that bind Axl and inhibit the binding of Axl to its ligand Gas6. These antibodies comprise a variable heavy (VH) and variable light (VL) domain selected from the GH1, GH2, GL1, and GL2 domains disclosed herein. In a first embodiment the antibody comprises GH1 and GL1. In a second embodiment the antibody comprises GH2 and GL1. In a third embodiment the antibody comprises GH1 and GL2. In a fourth embodiment the antibody comprises GH2 and GL2.

Preferably the antibody inhibits the binding of Axl to its ligand Gas6. Even more preferably, the antibody also downregulates Axl expression, inhibits Axl receptor signalling, and/or inhibits tumour growth.

Antibodies having the same CDRs and binding specificity as the antibodies described herein are described in WO2016/097370. However, antibodies comprising the specific VH and VL sequences described herein have been found to have improved properties relative to the murine and chimeric antibodies exemplified in WO2016/097370. Specifically, the antibodies described herein advantageously have increased binding affinity and cell killing activity as compared to the murine and chimeric antibodies exemplified in WO2016/097370.

These improved properties are surprising, since the antibodies disclosed herein and those of WO2016/097370 share identical CDR sequences and, if anything, transfer of the murine CDRs out of their native framework and into a human framework could be expected to diminish the antibody's binding properties.

Furthermore, the comparison of the humanised 10G5 anti-Axl antibodies disclosed herein to a number of prior art anti-Axl antibodies has highlighted a number of advantages of the humanised 10G5 antibodies, including:

the 10G5 antibodies bind a novel Axl epitope, allowing for their use in combination with prior art antibodies
  as noted above, the 10G5 inhibits the binding of Axl to its ligand Gas6; of the tested prior art antibodies, only YW327.652 shared this property
  incubation with 10G5 inhibits Axl activation, as measured by levels of Axl auto-phosphorylation; in contrast, incubation with YW327.6S2 increases levels of Axl activation In a fibrotic disease model, incubation with 10G5 inhibited Axl activation and the expression of fibrosis markers; in contrast, incubation with the YW327.6S2var antibody led to increased expression levels of fibrosis markers 10G5 has lower cross-reactivity than YW327.6S2 (YW327.6S2 cross-reacts with murine Axl, whereas 10G5 does not); this allows separation of antibody effects on tumour vs. host cells in in vivo models 10G5 has similar efficacy to YW327.6S2 in a murine xenograft cancer model, despite having no effect on the murine host cells; in a human subject 10G5 would also target host cells, with additional treatment effects These advantages are discussed in more detail below, with experimental details given in examples 21 and 22.

SEQUENCES

The following sequences are disclosed herein (see 'SEQUENCES' section below for full sequence):

| | | |
|---|---|---|
| SEQ ID NO. 1 | → | humanised 10G5 VH domain GH1, amino acid |
| SEQ ID NO. 2 | → | humanised 10G5 VH domain GH2, amino acid |
| SEQ ID NO. 3 | → | humanised 10G5 VL domain GL1, amino acid |
| SEQ ID NO. 4 | → | humanised 10G5 VL domain GL2, amino acid |
| SEQ ID NO. 5 | → | example heavy chain constant region, amino acid |
| SEQ ID NO. 6 | → | 10G5 GH1 Heavy chain, amino acid |
| SEQ ID NO. 7 | → | 10G5 GH2 Heavy chain, amino acid |
| SEQ ID NO. 8 | → | heavy light constant region, amino acid |
| SEQ ID NO. 9 | → | 10G5 GL1 Light chain, amino acid |
| SEQ ID NO. 10 | → | 10G5 GL2 Light chain, amino acid |
| SEQ ID NO. 11 | → | humanised 10G5 VH domain GH1, nucleic acid |
| SEQ ID NO. 12 | → | humanised 10G5 VH domain GH2, nucleic acid |
| SEQ ID NO. 13 | → | humanised 10G5 VL domain GL1, nucleic acid |
| SEQ ID NO. 14 | → | humanised 10G5 VL domain GL2, nucleic acid |
| SEQ ID NO. 15 | → | example heavy chain constant region, nucleic acid |
| SEQ ID NO. 16 | → | 10G5 GH1 Heavy chain, nucleic acid |
| SEQ ID NO. 17 | → | 10G5 GH2 Heavy chain, nucleic acid |
| SEQ ID NO. 18 | → | heavy light constant region, nucleic acid |
| SEQ ID NO. 19 | → | 10G5 GL1 Light chain, nucleic acid |
| SEQ ID NO. 20 | → | 10G5 GL2 Light chain, nucleic acid |
| SEQ ID NO. 21 | → | Human Axl encoding amino acid sequence |
| SEQ ID NO. 22 | → | Murine Axl encoding amino acid sequence |
| SEQ ID NO. 23 | → | Human Tyro3 encoding amino acid sequence |
| SEQ ID NO. 24 | → | Human Mer encoding amino acid sequence |
| SEQ ID NO. 25 | → | Human Akt3 encoding amino acid sequence |
| SEQ ID NO. 26 | → | Human Gas6 encoding amino acid sequence |
| SEQ ID NO. 27 | → | 'Cyno-Axl' encoding amino acid sequence |
| SEQ ID NO. 28 | → | murine 10G5 VH domain |
| SEQ ID NO. 29 | → | murine 10G5 VL domain |
| SEQ ID NO. 30 | → | 10G5 VH CDR1 |
| SEQ ID NO. 31 | → | 10G5 VH CDR2 |
| SEQ ID NO. 32 | → | 10G5 VH CDR3 |
| SEQ ID NO. 33 | → | 10G5 VL CDR1 |
| SEQ ID NO. 34 | → | 10G5 VL CDR2 |
| SEQ ID NO. 35 | → | 10G5 VL CDR3 |

In one aspect of the invention there is provided an antibody that binds Axl and that comprises:
an antibody VH domain selected from the group consisting of the humanised 10G5 VH domain GH1 (SEQ ID NO: 1), the humanised 10G5 VH domain GH2 (SEQ ID NO: 2), and a VH domain comprising a VH CDR3 with the amino acid sequence of SEQ ID NO: 32 and optionally one or more VH CDR's with an amino acid sequence selected from SEQ ID NO: 31 and SEQ ID NO: 30; and/or
an antibody VL domain selected from the group consisting of the humanised 10G5 VL domain GL1 (SEQ ID NO: 3), the humanised 10G5 VL domain GL2 (SEQ ID NO: 4), and a VL domain comprising one or more VL CDR's with an amino acid sequence selected from SEQ ID NO: 33, SEQ ID NO: 34 and SEQ ID NO: 35.

For example, the antibody may comprise an antibody VH domain comprising the VH CDR's with the amino acid sequences of SEQ ID NO: 30, SEQ ID NO: 31 and SEQ ID NO: 32. The antibody may further comprise an antibody VL domain comprising the VL CDR's with the amino acid sequences of SEQ ID NO: 33, SEQ ID NO: 34 and SEQ ID NO: 35.

In some embodiments the antibody comprises: (i) an antibody VH domain comprising the VH CDR's with the amino acid sequences of SEQ ID NO: 30, SEQ ID NO: 31 and SEQ ID NO: 32, and (ii) an antibody VL domain comprising the VL CDR's with the amino acid sequences of SEQ ID NO: 33, SEQ ID NO: 34 and SEQ ID NO: 35.

In one aspect, the present invention provides an isolated antibody that binds Axl and that comprises the 10G5 VH(GH1) domain (SEQ ID NO: 1) or the 10G5 VH(GH2) domain (SEQ ID NO: 2). Preferably the bound Axl is human Axl.

In some embodiments the VH(GH1) domain (SEQ ID NO: 1) or the 10G5 VH(GH2) domain (SEQ ID NO: 2) is paired with the 10G5 VL(GL1) domain (SEQ ID NO: 3), so that an antibody antigen binding site is formed comprising a 10G5 VH and VL domain.

In some embodiments the VH(GH1) domain (SEQ ID NO: 1) or the 10G5 VH(GH2) domain (SEQ ID NO: 2) is paired with the 10G5 VL(GL2) domain (SEQ ID NO: 4), so that an antibody antigen binding site is formed comprising a 10G5 VH and VL domain.

In some embodiments the antibody comprises the VH(GH1) domain (SEQ ID NO: 1) and the 10G5 VL(GL1) domain (SEQ ID NO: 3). In some embodiments the antibody comprises the VH(GH1) domain (SEQ ID NO: 1) and the 10G5 VL(GL2) domain (SEQ ID NO: 4).

In preferred embodiments the antibody comprises the VH(GH2) domain (SEQ ID NO: 2) and the 10G5 VL(GL1) domain (SEQ ID NO: 3). In some embodiments the antibody comprises the VH(GH2) domain (SEQ ID NO: 2) and the 10G5 VL(GL2) domain (SEQ ID NO: 4).

In other embodiments, the 10G5 VH(GH1) domain (SEQ ID NO: 1) or the 10G5 VH(GH2) domain (SEQ ID NO: 2) is paired with a VL domain other than the 10G5 VL; light-chain promiscuity is well established in the art.

In some embodiments the antibody further comprises a heavy chain constant region. In some embodiments the heavy chain constant region has the sequence set out in SEQ ID NO: 5.

Accordingly, in some embodiments the present invention provides an isolated antibody that binds Axl and that comprises the 10G5 GH1 Heavy chain (SEQ ID NO: 6) or the 10G5 GH2 Heavy chain (SEQ ID NO: 7).

In some embodiments the antibody further comprises a light chain constant region. In some embodiments the light chain constant region has the sequence set out in SEQ ID NO: 8.

Accordingly, in some embodiments the present invention provides an isolated antibody that binds Axl and that comprises the 10G5 GL1 Light chain (SEQ ID NO: 9) or the 10G5 GL2 Light chain (SEQ ID NO: 10).

In some embodiments the 10G5 GH1 Heavy chain (SEQ ID NO: 6) or the 10G5 GH2 Heavy chain (SEQ ID NO: 7) is paired with the 10G5 GL1 Light chain (SEQ ID NO: 9), so that an antibody antigen binding site is formed comprising a 10G5 VH and VL domain.

In some embodiments the 10G5 GH1 Heavy chain (SEQ ID NO: 6) or the 10G5 GH2 Heavy chain (SEQ ID NO: 7) is paired with the 10G5 GL2 Light chain (SEQ ID NO: 10), so that an antibody antigen binding site is formed comprising a 10G5 VH and VL domain.

In preferred embodiments the antibody comprises the 10G5 GH2 Heavy chain (SEQ ID NO: 7) and the 10G5 GL1 Light chain (SEQ ID NO: 9). In another embodiment the antibody comprises the 10G5 GH2 Heavy chain (SEQ ID NO: 7) and the 10G5 GL2 Light chain (SEQ ID NO: 10).

In some embodiments the antibody comprises the 10G5 GH1 Heavy chain (SEQ ID NO: 6) and the 10G5 GL1 Light chain (SEQ ID NO: 9). In another embodiment the antibody comprises the 10G5 GH1 Heavy chain (SEQ ID NO: 6) and the 10G5 GL2 Light chain (SEQ ID NO: 10).

Preferably the antibody competes for binding to human Axl with an Axl binding domain of an antibody comprising the 10G5 VH domain (SEQ ID NO: 12) and the 10G5 VL domain (SEQ ID NO: 13).

Preferably the antibody binds to the epitope bound by the antibody obtainable from the hybridoma WR-10G5-E5, as described in WO2016/097370.

Preferably the antibody inhibits the binding of Axl to its ligand Gas6. Even more preferably, the antibody also down-regulates Axl expression, inhibits Axl receptor signalling, and/or inhibits tumour growth.

In addition to antibody sequences, an antibody according to the present invention may comprise other amino acids, e.g. forming a peptide or polypeptide, such as a folded domain, or to impart to the molecule another functional characteristic in addition to ability to bind antigen.

Antibodies of the invention may carry a detectable label, or may be conjugated to a toxin (such as a cytotoxin), enzyme, or an organic moiety (e.g. via a peptidyl bond or linker).

Those skilled in the art are aware of numerous approaches to chemically conjugating molecules to proteins. In one embodiment of the present invention, the antibody can be conjugated to a detectable, fluorescent label, e.g. fluorescein isothiocyanate (FITC), or to a reporter enzyme such as horseradish peroxidase (HRP)

In a preferred embodiment, the antibody is conjugated to a cytotoxic drug with a formation of the antibody-drug conjugate (ADC). When the antibody is for pharmaceutical use, the bond linking the antibody and drug is preferably stable in circulation (for example, blood circulation) but labile once the conjugate is sequestered intracellularly. Thus, the antibody conjugated as an immunoconjugate may be used in a method of treatment of, for example, cancer.

In further aspects, the invention provides an isolated nucleic acid that comprises a sequence encoding an antibody, VH domain and/or VL domain according to the present invention, and methods of preparing an antibody, a VH domain and/or a VL domain of the invention, that comprise expressing said nucleic acid under conditions to bring about production of said antibody, VH domain and/or VL domain, and recovering it.

Antibodies according to the invention may be used in a method of treatment or diagnosis of the human or animal body, such as a method of treatment (that may include prophylactic treatment) of a disease or disorder in a human patient that comprises administering to said patient an effective amount of an antibody of the invention, or a conjugate, or drug-conjugate thereof. Conditions treatable in accordance with the present invention include those discussed elsewhere herein.

Antibodies according to the invention may be used in a method of imaging, for example, to determine the presence or location of cells to which the antibody binds.

In a further aspect, the present invention provides a diagnostic kit comprising an antibody according to the invention and one or more reagents to determine binding of the antibody to the antigen.

A further aspect of the present invention provides nucleic acid, generally isolated, encoding an antibody VH variable domain (SEQ ID NO: 1), an antibody VH variable domain (SEQ ID NO: 2), an antibody VL variable domain (SEQ ID NO: 3), and/or an antibody VL variable domain (SEQ ID NO: 4) disclosed herein. Examples of such nucleic acids are disclosed herein, as set out in the explanation of sequence identifiers spanning pages 8 and 9 of the specification (see above). For example, the nucleic acid having the sequence set out in SEQ ID NO: 11 encodes an antibody VH variable domain having the sequence set out in SEQ ID NO: 1; the nucleic acid having the sequence set out in SEQ ID NO: 12 encodes an antibody VH variable domain having the sequence set out in SEQ ID NO: 2; and so on.

A further aspect provides a host cell transformed with nucleic acid of the invention.

A yet further aspect provides a method of production of an antibody VH variable domain, the method including causing expression from encoding nucleic acid. Such a method may comprise culturing host cells under conditions for production of said antibody VH variable domain.

Analogous methods for production of VL variable domains and antibodies comprising a VH and/or VL domain are provided as further aspects of the present invention.

A method of production may comprise a step of isolation and/or purification of the product.

A method of production may comprise formulating the product into a composition including at least one additional component, such as a pharmaceutically acceptable excipient.

These and other aspects of the invention are described in further detail below.

Properties of the Humanised 10G5 Antibody

High Affinity for Axl

The humanised 10G5 antibody described herein binds to human Axl with high affinity. As shown in Table 3, the humanised antibody H1L1 has a $K_D$ that is at least 30% lower than the chimeric antibody comprising the VH of SEQ ID NO: 12 and the VL of SEQ ID NO: 13. Similarly, the humanised antibody H2L1 has a $K_D$ that is at least 50% lower than the chimeric antibody comprising the VH of SEQ ID NO: 12 and the VL of SEQ ID NO: 13.

Accordingly, the humanised 10G5 antibodies and variant thereof that are described herein bind Axl with high affinity; preferably human Axl is bound with high affinity. In some embodiments, an antibody binds to Axl (or human Axl) with a $K_D$ at least 15% lower than a chimeric antibody comprising the VH of SEQ ID NO: 12 and the VL of SEQ ID NO: 13, such as at least 20%, at least 25%, at least 30%, at least 35%, at least 40%, at least 45%, or at least 50% lower than the chimeric antibody comprising the VH of SEQ ID NO: 12 and the VL of SEQ ID NO: 13. In some embodiments, an antibody binds to Axl (or human Axl) with a $K_D$ no greater than $10^{-6}$ M, such as no greater than $5 \times 10^{-7}$ M, no greater than $10^{-7}$ M, no greater than $5 \times 10^{-8}$ M, no greater than $10^{-8}$ M, no greater than $5 \times 10^{-9}$ M, no greater than $10^{-9}$ M, no greater than $6 \times 10^{-10}$ M, no greater than $5 \times 10^{-10}$ M, no greater than $1.1 \times 10^{-10}$ M, no greater than $10^{-10}$ M, no greater than $5 \times 10^{-11}$ M, no greater than $10^{-11}$ M, no greater than $5 \times 10^{-12}$ M, no greater than $6 \times 10^{-12}$ M, no greater than $10^{-12}$ M, no greater than $5 \times 10^{-13}$ M, no greater than $10^{-13}$ M, no greater than $5 \times 10^{-14}$ M, no greater than $10^{-14}$ M, no greater than $5 \times 10^{-15}$ M, or no greater than $10^{-15}$ M.

In some embodiments, an antibody binds to Axl (or human Axl) with a $K_D$ from $10^{-8}$ M to $10^{-10}$ M, from $10^{-10}$ M to $10^{-12}$, from $10^{-12}$ M to $10^{-14}$, or from $10^{-14}$ M to $10^{-16}$.

The $K_D$ may be determined and calculated as set out in Example 19.

High Cell Killing Activity

The humanised 10G5 antibody described herein have high cell activity, as demonstrated by their low $EC_{50}$ values. As shown in Table 4, the humanised antibody H1L1 has an $EC_{50}$ that is at least 35% lower than the chimeric antibody comprising the VH of SEQ ID NO: 12 and the VL of SEQ ID NO: 13. Similarly, the humanised antibody H2L1 has a $EC_{50}$ that is at least 50% lower than the chimeric antibody comprising the VH of SEQ ID NO: 12 and the VL of SEQ ID NO: 13.

Accordingly, the humanised 10G5 antibodies and variant thereof that are described herein bind Axl with high affinity; preferably human Axl is bound with high affinity. In some embodiments, an antibody has an $EC_{50}$ at least 15% lower than a chimeric antibody comprising the VH of SEQ ID NO: 12 and the VL of SEQ ID NO: 13, such as at least 20%, at least 25%, at least 30%, at least 35%, at least 40%, at least 45%, or at least 50% lower than the chimeric antibody comprising the VH of SEQ ID NO: 12 and the VL of SEQ ID NO: 13.

The $EC_{50}$ may be determined and calculated as set out in Example 20.

Specific Binding

Generally, the terms 'specific' and 'specifically binds' may be used to refer to the situation in which an antibody will not show any significant binding to molecules other than its specific binding partner(s). For example, an antibody that 'specifically binds' human Axl would not show any significant binding for murine Axl.

The term is also applicable where e.g. an antibody is specific for a particular epitope that is carried by a number of antigens, in which case an antibody that 'specifically binds' an epitope will be able to bind to all of the various antigens that carry the recognised epitope.

Typically, specificity may be determined by means of a binding assay such as ELISA employing a panel of antigens.

The 10G5 antibodies described herein bind to human Axl with high specificity. That is, the 10G5 antibodies 'specifically bind' human Axl. This is demonstrated in the examples, where it is shown that:

(1) In Example 2, 10G5 show no significant binding to recombinant antigens derived from hMer and hTyro3, the other members of the human TAM receptor tyrosine kinase family;

(2) In Example 3, 10G5 bind strongly to human Axl, but show no binding to murine Axl (this is in contrast to murine Axl ligand, murine Gas 6, that binds strongly to both murine and human Axl, as well as (more weakly) binding human Tyro3);

(3) In Example 4, 10G5 bind strongly to Axl from the cynomolgus monkey (*Macaca fascicularis*).

This specificity advantageously allows for the separation of antibody effects on human tumour cells vs. murine host cells in murine xenograft in vivo models.

Accordingly, the antibodies described herein preferably specifically bind primate Axl. In some embodiments the antibodies described herein specifically bind human and monkey (such as *Macaca fascicularis*) Axl. In one embodiment the antibodies specifically bind only human Axl.

In some embodiments of the present invention, the antibodies described herein show no significant binding to human Tyro3 and/or human Mer. In some embodiments the antibodies described herein show no significant binding to murine Axl. In some embodiments the antibodies described herein show no significant binding to any of human Tyro3, human Mer, or murine Axl.

Whether an antibody shows "no significant binding" to an antigen can be readily determined by the skilled person using, for example, the techniques described in Examples 2 and 3. In some embodiments, an antibody is deemed to show "no significant binding" to a particular antigen if it binds the antigen with a $K_D$ greater than $10^{-3}$ M, such as greater than $10^{-2}$ M, greater than $10^{-1}$ M, or greater than 1 M. The $K_D$ may be determined and calculated as set out in Example 5.

Inhibition of Axl/Gas6 Binding

The 10G5 antibodies described herein inhibit the binding of Axl to its ligand Gas6.

Figure 5:
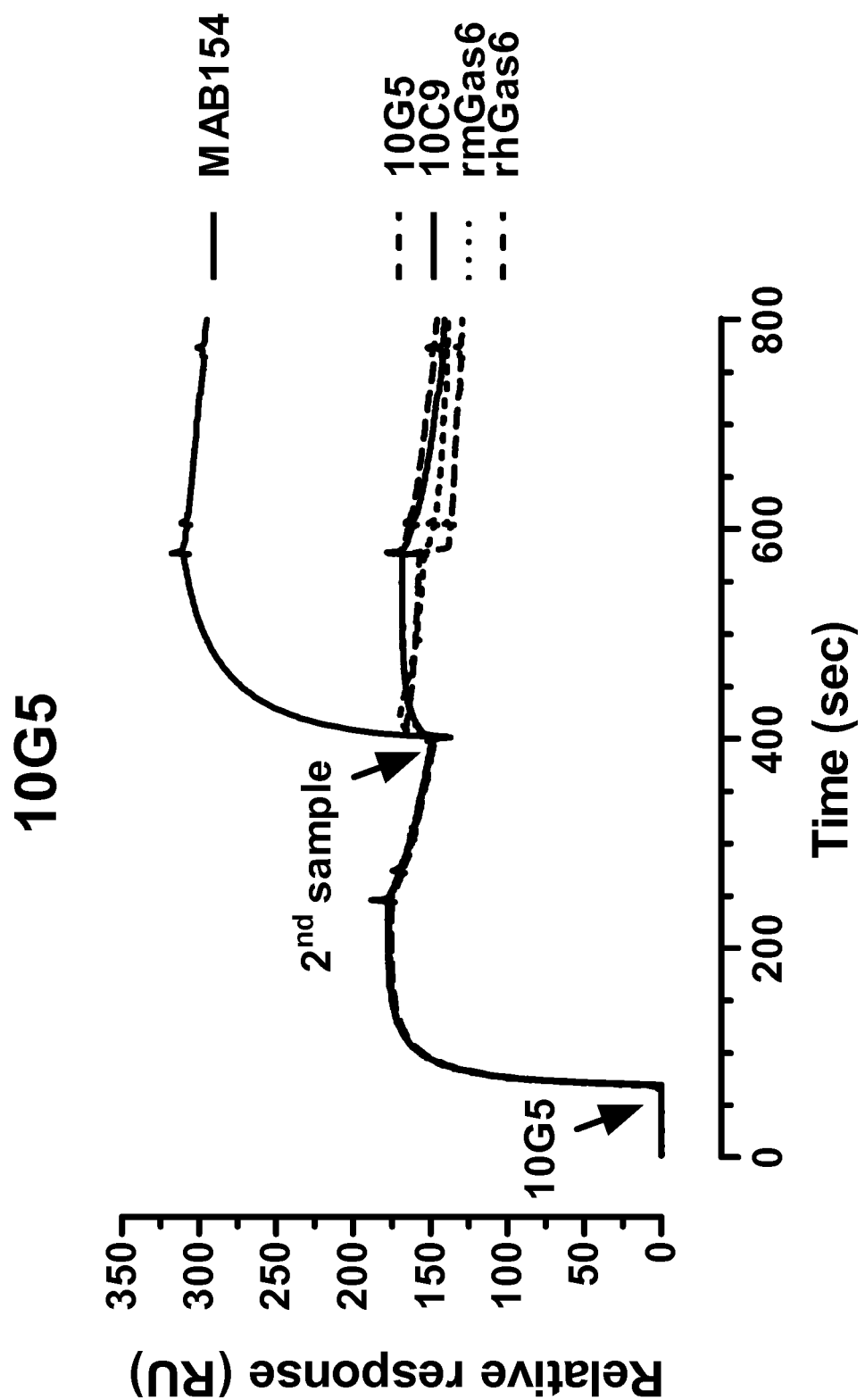

FIG. 5 shows the results of the competitive binding assay described in Example 6. The results show that immobilised rhAxl saturated with 10G5 cannot be bound by subsequently added 10G5, rhGas6 (a known ligand of rhAxl), or rmGas6. This indicates that the areas of the Axl molecule bound by 10G5 and Gas6 are in close proximity to one another. In contrast, the binding of 10G5 did no inhibit the binding of the MAB154 anti-Axl antibody, indicating that 10G5 and MAB154 bind to distinct parts of the Axl molecule.

Accordingly, in preferred embodiments the antibodies described herein inhibit the binding of Axl to Gas6 (for example, rhAxl to rhGas6). That is, preferably the antibodies described herein compete with human Gas 6 for binding to human Axl. Most preferably, inhibition of Axl/Gas 6 binding is such that no significant binding of Gas6 can be observed to an Axl sample saturated with the antibody (for example, no more than 1% of the binding observed to an Axl sample that has not been previously exposed to the antibody). Inhibition of Gas 6 binding may be assessed using the competitive binding assay described in Example 6.

Inhibition of Axl Receptor Expression

The antibodies of the invention lead to a significant reduction in the expression of Axl.

Figure 8:
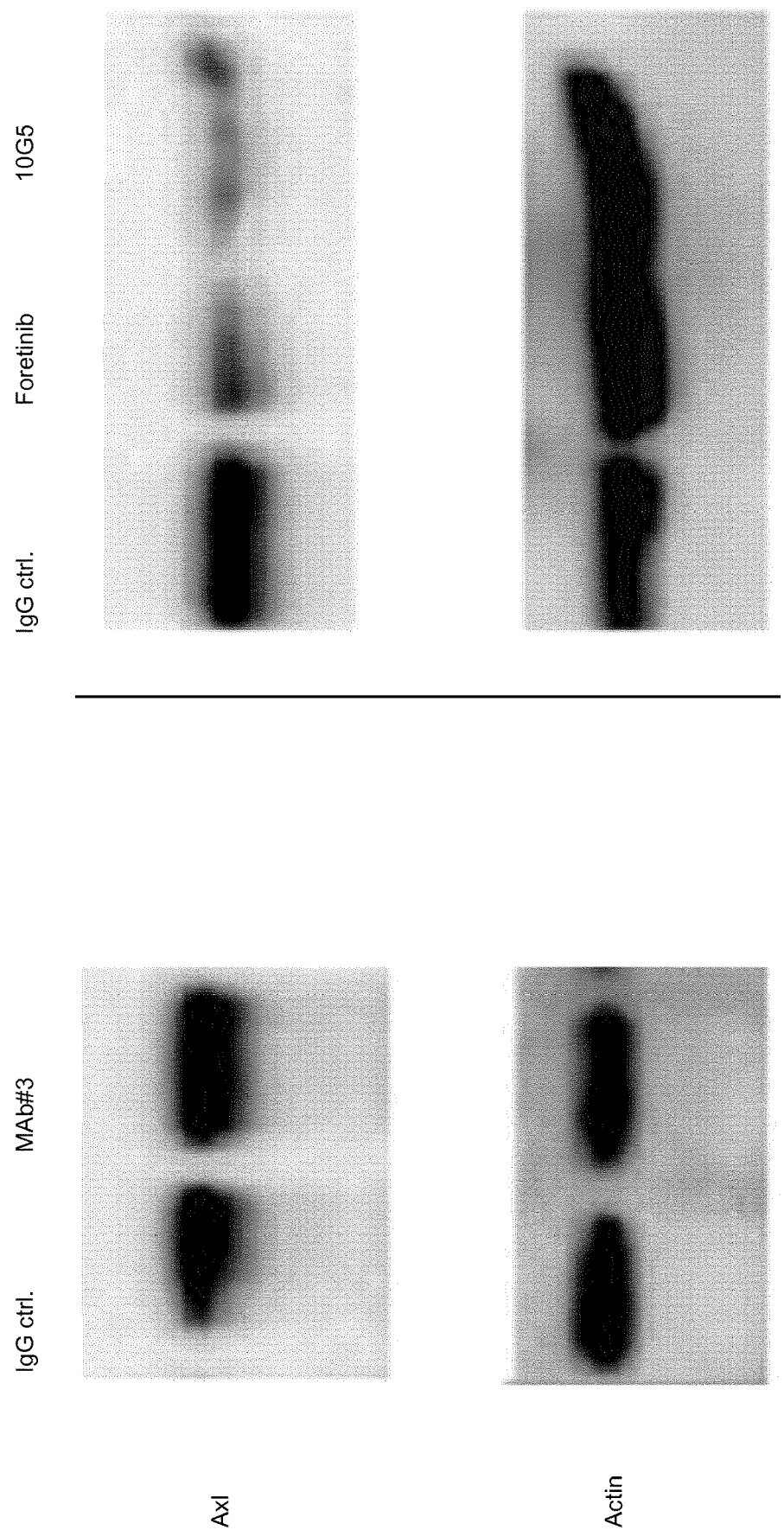

FIG. 8 shows the results of the Western Blot analyses described in Example 9, in which MBA-MD-231 cells are incubated overnight with one of a range of antibodies and then tested for Axl expression. The results show that incubation with 10G5 leads to a significant reduction in the amount of Axl receptor protein present in the cell, indicating that binding of the 10G5 antibody downregulates the expression of the Axl receptor.

Accordingly, in preferred embodiments the antibodies of the invention downregulate expression of the Axl receptor.

In some embodiments, the antibody of the invention reduces Axl receptor expression to less than 80% of the level observed in an otherwise identically treated sample that is not contacted with to the antibody. In some embodiments, the antibody of the invention reduces Axl receptor expression to less than 70%, less than 60%, less than 50%, less than 40%, less than 30%, less than 20%, or less than 10% of the level observed in an otherwise identically treated sample that is not contacted with the antibody. The level of Axl receptor expression may be assessed using the assay described in Example 9; a number of methods for accurately quantifying bands on Western blots are known in the art—see, for example, Taylor et al. Mol Biotechnol. 2013; 55(3): 217-226.

In some embodiments down-regulation of Axl receptor expression occurs rapidly; for example, in some embodiments a reduction of Axl receptor expression to less than 80% of the level observed in an otherwise identically treated sample that is not contacted with the antibody is observed within 12 hours of contacting the sample with the antibody, for example within 12 hours, within 6 hours, within 3 hours, or within 1 hour of contacting the sample with the antibody.

In some embodiments, the antibody causes persistent downregulation of Axl receptor expression. For example, in some embodiments the level of Axl receptor expression in a sample contacted with the antibody remains below 50% of the level observed in an otherwise identically treated sample that is not contacted with the antibody for at least 6 hours following contacting the sample with the antibody, such as at least 12 hours, at least 24 hours, at least 48 hours, or at least 96 hours.

Without wishing to be bound by theory, it is believed the observed down-regulation of Axl expression is caused by the antibody/Axl receptor complex being internalised and degraded by the cell. Internalisation of the antibody is highly advantageous for applications where it is desirable to get the antibody, or a molecule linked to the antibody, into a target cell. For example, where the target is a cancerous cell and the antibody is linked to a cytotoxic drug.

Accordingly, in preferred embodiments the antibodies of the invention increases the rate of Axl receptor internalization.

In some embodiments, the antibody of the invention increases the rate of Axl receptor internalization to at least 110% of the level observed in an otherwise identically treated sample that is not contacted with the antibody. In some embodiments, the antibody of the invention increases the rate of Axl receptor internalization to at least 120%, at least 130%, at least 140%, at least 150%, at least 160%, at least 170%, at least 180%, at least 190%, at least 200%, at least 500%, at least 1000% of the level observed in an otherwise identically treated sample that is not contacted with the antibody.

The level of Axl receptor internalization may be assessed using any one of the receptor internalisation assay known in the art; for example, the method described in Koenig et al. Methods in Molecular Biology Volume 259, 2004, pp 249-273.

Inhibition of Axl Activation

The antibodies of the invention lead to a significant reduction in Axl activation, as assessed by levels of Axl autophosphorylation.

Example 22 shows that lysates from cells stimulated with Gas6 in the presence of either H2L1 preparation or BGB324 gave pAXL readings (0.040, 0.055, 0.045) which were significantly lower than that of the Gas6 stimulated control cells (0.077); H2L1-Evitria and BGB324 were particularly low, with reading comparable to the starved control (0.44).

In contrast, the pAxl results indicate that the YW327.6S2var antibody strongly activates Axl auto-phosphorylation, with YW327.6S2var alone giving a pAxl reading of 0.092-higher than the Gas6 stimulated control cells (0.077).

Accordingly, in preferred embodiments the antibodies of the invention inhibit Axl autophosphorylation following stimulation by Gas6. The level of Axl autophosphorylation resulting from Gas6 stimulation following incubation with the antibody may be no more than 50%, 55%, 60%, 65%, 70%, 75%, 80%, 85%, or no more than 90% of the level of a control not incubated with an anti-Axl antibody prior to Gas6 stimulation. The level of Axl autophosphorylation may be assessed as described in Example 22.

Inhibition of Axl Receptor Signalling

Consistent with the observations that the antibodies of the invention (1) inhibit the binding of the Axl receptor to natural ligands such as Gas6, and (2) downregulate the expression of the Axl receptor, the antibodies of the invention inhibit ligand-induced signalling downstream of the Axl receptor. This is demonstrated in FIG. 9, where it can be seen that the presence of the 10G5 antibody significantly reduces the degree to which Akt's Serine 473 is phosphorylated on addition of the Axl ligand Gas6.

Accordingly, in preferred embodiments the antibodies of the invention inhibit Axl activity. The inhibited activity may be constitutive Axl activity.

In some embodiments the antibodies of the invention inhibit Axl downstream signalling, for example the phosphorylation of Akt at Serine 473. In some embodiments, the phosphorylation of Akt at Serine 473 in a sample contacted with the antibody of the invention is less than 80% of the level observed in an otherwise identically treated sample that is not contacted with the antibody. In some embodiments, the phosphorylation of Akt at Serine 473 in a sample contacted with the antibody of the invention is less than 70%, less than 60%, less than 50%, less than 40%, less than 30%, less than 20%, or less than 10% of the level observed in an otherwise identically treated sample that is not contacted with the antibody. The level of phosphorylation of Akt at Serine 473 may be assessed using the assay described in Example 10; a number of methods for accurately quantifying bands on Western blots are known in the art—see, for example, Taylor et al. Mol Biotechnol. 2013; 55(3): 217-226.

By virtue of inhibiting Axl receptor signalling, the antibodies of the invention are also expected to influence a range of processes in which Axl-receptor signalling plays a role.

For example, it is known that Axl-receptor signalling stimulates Gas6 dependent cell proliferation and inhibits cell-death, thus supporting tumour growth. It is also known that Axl-receptor signalling stimulates Epithelial-Mesenchymal transition (EMT) and thus promotes tumour metastases.

Accordingly, in some embodiments, the antibodies of the invention promotes cell death, for example by apoptosis. Preferably the cell is a tumour cell, such as a circulating tumour cell or a metastatic cell. For example, in some embodiments, the antibody of the invention increases the rate of cell-death to at least 110% of the level observed in an otherwise identically treated sample that is not contacted with the antibody. In some embodiments, the antibody of the invention increases the rate of cell death to at least 120%, at least 130%, at least 140%, at least 150%, at least 160%, at least 170%, at least 180%, at least 190%, at least 200%, at least 500%, at least 1000% of the level observed in an otherwise identically treated sample that is not exposed to the antibody. The rate of ell death may be measured by, for example BrdU incorporation assay, MTT, [$^3$H]-thymidine incorporation (e.g., TopCount assay (PerkinElmer)), cell viability assays (e.g., CellTiter-Glo (Promega)), DNA fragmentation assays, caspase activation assays, tryptan blue exclusion, chromatin morphology assays and the like.

In some embodiments, the antibodies of the invention inhibit Axl downstream signalling. In some embodiments, the antibodies of the invention inhibit Gas6 dependent cell proliferation.

In some embodiments, the antibodies of the invention inhibit inflammatory cytokine expression from tumour-associated macrophages.

Inhibition of Fibrotic Disorders

Consistent with the demonstrated property of 10G5 in reducing Axl activation, expression, and receptor signalling, 10G5 has also been demonstrated to reduce the expression of inflammatory and fibrosis markers in a fibrotic disease model.

The advantageous effects on fibrosis markers are not a general feature of anti-Axl antibodies, as demonstrated in Example 22 where 10G5 is compared to YW327.6S2, the other anti-Axl antibody shown to inhibit Gas6 binding to Axl.

In example 22, cells treated with 10G5 prior to Axl activation consistently exhibited expression levels for all four assayed markers which were similar to unstimulated control cells. In contrast, following pre-treatment with the YW327.6S2var antibody, raised expression levels were observed for all four assayed markers after Axl stimulation.

Accordingly, in preferred embodiments the antibodies of the invention are used in the treatment of fibrotic disorders. In some embodiments, the antibodies of the invention inhibit or reduce the expression of fibrotic markers such as alpha-SMA, Col1A1, MCP1 and/or TGF-beta. In some embodiments, the antibodies of the invention inhibit or reduce the expression of fibrotic markers alpha-SMA, Col1A1, MCP1 and TGF-beta.

Inhibition of Tumour Growth

Figure 14:
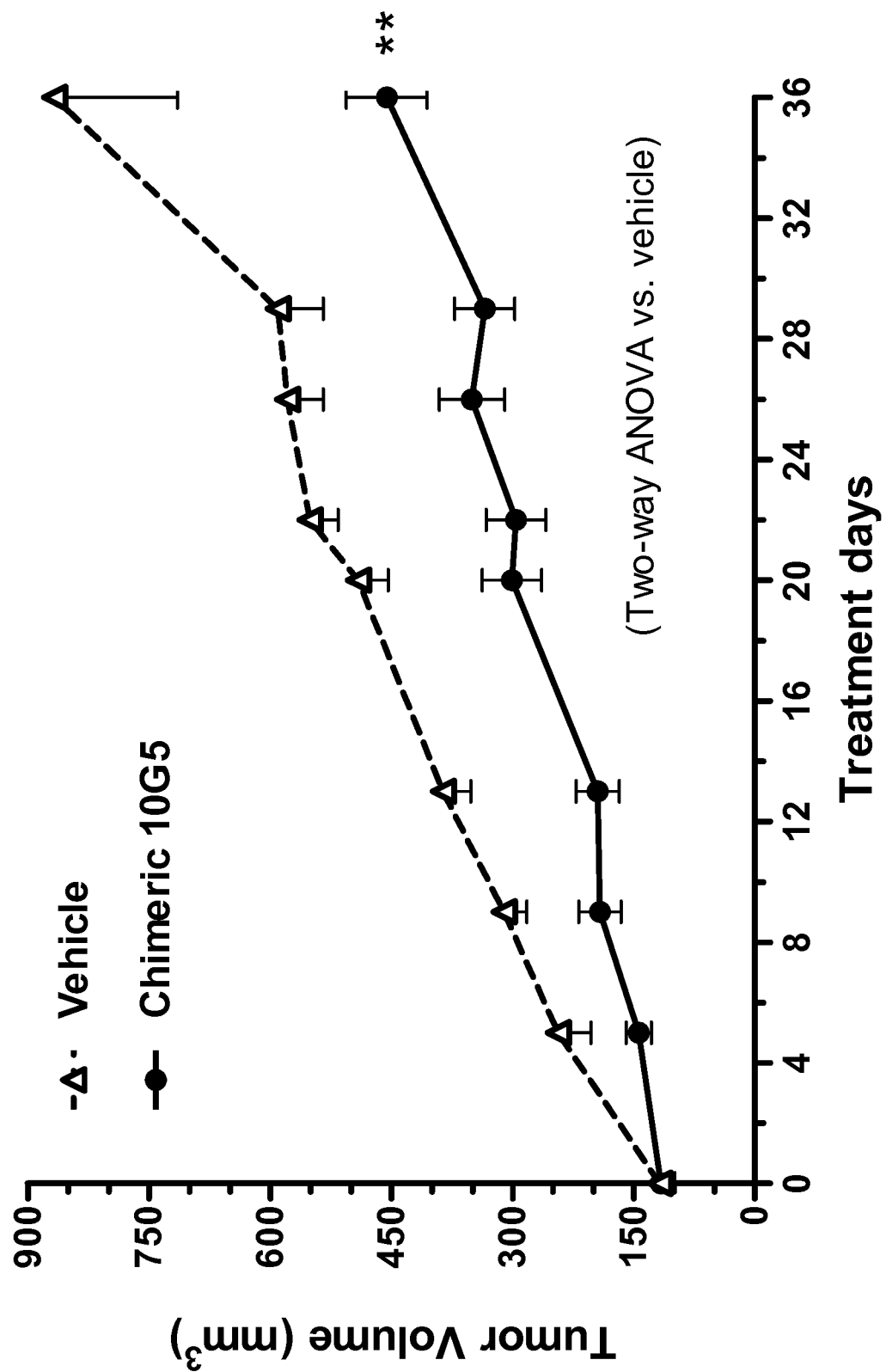
Figure 15:
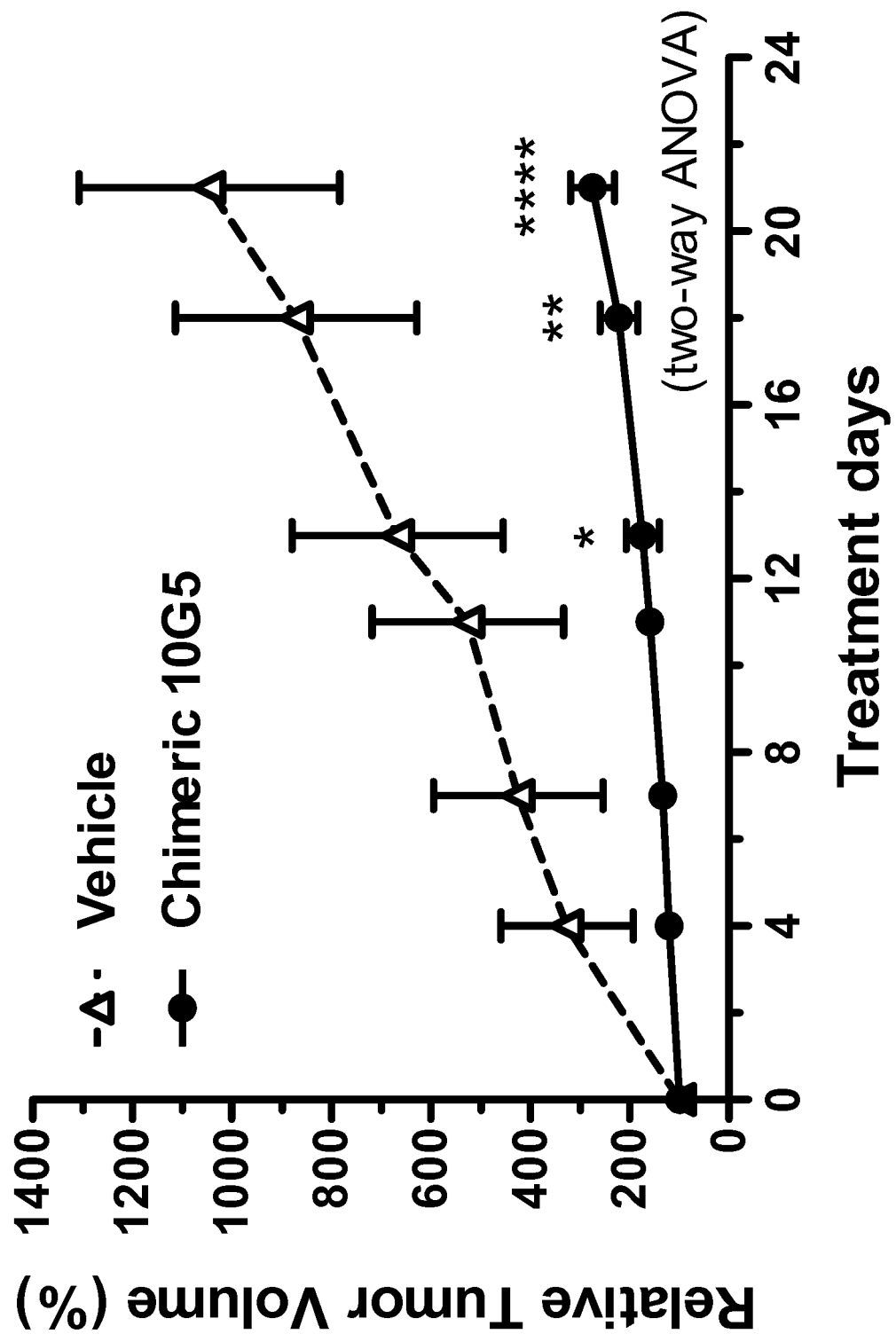

Consistent with the role of Axl and the EMT pathway in tumour growth, the antibodies of the invention reduce the rate of growth of both haematological and non-heamatological tumours; this is demonstrated by the data shown in FIGS. 14 and 15, as obtained through the methods described in Examples 14 and 15.

In addition, in Example 22 it is shown that chimeric 10G5 has similar efficacy to YW327.6S2 in a mouse xenograft NSCLC model, despite YW327.6S2 being active against both human tumour and host murine cells and 10G5 being active only against human tumour cells.

Accordingly, in preferred embodiments the antibodies of the invention inhibit tumour growth and/or metastasis by, for example, modulating tumour stromal function.

In some embodiments the antibodies of the invention inhibit tumour growth by at least 10% compared to a control tumour. That is, the volume of the antibody treated tumour is no more than 90% of the volume of the control tumour. For example, in some embodiments the antibodies of the invention inhibit tumour growth by at least 20% compared to a control tumour, such as at least 30%, at least 40%, at least 50%, at least 60%, at least 70%, at least 80%, or at least 90%.

In some embodiments, the effect of the antibody on tumour growth is assayed as described in example 14. In some embodiments, the effect of the antibody on tumour growth is assayed as described in example 15.

Definitions

Antibody

This term describes an immunoglobulin whether natural or partly or wholly synthetically produced. The term also covers any polypeptide or protein comprising an antibody antigen-binding domain. Antibody fragments that comprise an antibody antigen-binding domain include whole antibodies (for example an IgG antibody comprising VH, CH1, CH2, CH3, VL, and CL domains in the canonical arrangement), or fragments of whole antibodies that retain their binding activity for a target antigen. Such fragments include Fv (fragment variable), Fab (fragment antibody binding) and F(ab')$_2$ fragments, as well as single-chain Fv antibodies (scFv), dsFv, minibodies, diabodies, single-chain diabodies, tandem scFv, TandAb, bi-body, tri-body, kappa(lambda) body, BiTE, DVD-Ig, SIP, SMIP, or DART. Furthermore, the antibodies and fragments thereof may be humanised antibodies, for example as described in EP239400A. For example: monoclonal and polyclonal antibodies, recombinant antibodies, proteolytic and recombinant fragments of antibodies (Fab, Fv, scFv, diabodies), single-domain antibodies (VHH, sdAb, nanobodies, IgNAR, VNAR), and proteins unrelated to antibodies, that have been engineered to have antibody-like specific binding (antibody mimetics), such as the following, but not limited to:

| Name | Based on: |
| --- | --- |
| Adnectins/ Monobodies | 10th type III domain of human fibronectin (10Fn3), 10 kDa |
| Affibodies | Protein A, Z domain, 6 kDa) |
| Affilins | Human y-crystallin/human ubiquitin (10-20 kDa) |
| Affitins | Sac7d (from Sulfolobus acidocaldarius), 7 kDa |
| Anticalins | Lipocalins, 20 kDa |
| Avimers | Domains of various membrane receptors, 9-18 kDa |
| DARPins | Ankyrin repeat motif, 14 kDa |
| Evibody | Cytotoxic T-Lymphocyte Antigen 4 (CTLA-4), 15 kDa |
| Fynomers | Fyn, SH3 domain, 7 kDa |
| Kunitz domain peptides | Various protease inhibitors, 6 kDa |

An antibody may comprise all or apportion of an antibody heavy chain constant region and/or an antibody light chain constant region.

It is possible to take monoclonal and other antibodies and use techniques of recombinant DNA technology to produce engineered antibodies or chimeric molecules, that retain the specificity of the original antibody. Such techniques may involve ligation of DNA fragments encoding the immunoglobulin variable regions, or the complementarity determining regions (CDRs), of an antibody with genes coding for the immunoglobulin constant regions, or the constant regions plus framework regions, of a different immunoglobulin. See, for instance, EP-A-184187, GB 2188638A or EP-A-239400. A hybridoma or other cell producing an antibody may be subject to genetic mutation or other changes, that may or may not alter the binding specificity of antibodies produced.

As antibodies can be modified in a number of ways, the term "antibody molecule" should be construed as covering any polypeptide or other molecule having an antibody-derived antigen-binding domain with the required specificity. Thus, this term covers antibody fragments and derivatives, including any polypeptide comprising an immunoglobulin binding domain, whether natural or wholly or partially synthetic. Chimeric molecules comprising an immunoglobulin binding domain, or equivalent, fused to another polypeptide are therefore included. Cloning and expression of chimeric antibodies are described in EP-A-0120694 and EP-A-0125023.

It has been shown that fragments of a whole antibody can perform the function of binding antigens. Examples of binding fragments are (i) the Fab fragment consisting of VL, VH, CL and CH1 domains; (ii) the Fd fragment consisting of the VH and CH1 domains; (iii) the Fv fragment consisting of the VL and VH domains of a single antibody; (iv) the dAb fragment (Ward, E. S. et al., Nature 341, 544-546 (1989)) that consists of a VH domain; (v) isolated CDR regions; (vi) F(ab')2 fragments, a bivalent fragment comprising two linked Fab fragments; (vii) single chain Fv molecules (scFv), wherein a VH domain and a VL domain are linked by a peptide linker that allows the two domains to associate to form an antigen binding site (Bird et al, Science, 242, 423-426, 1988; Huston et al, PNAS USA, 85, 5879-5883, 1988); (viii) bispecific single chain Fv dimers (PCT/US92/09965) and (ix) "diabodies", multivalent or multispecific fragments constructed by gene fusion (WO94/13804; P. Holliger et al, Proc. Natl. Acad. Sci. USA 90, 6444-6448, 1993). Fv, scFv or diabody molecules may be stabilised by the incorporation of disulphide bridges linking the VH and VL domains (Y. Reiter et al, Nature Biotech, 14, 1239-1245, 1996). Minibodies comprising a scFv joined to a CH3 domain may also be made (S. Hu et al, Cancer Res., 56, 3055-3061, 1996).

The antibody may be bispecific or multispecific. Where bispecific antibodies are to be used, these may be conventional bispecific antibodies, that can be manufactured in a variety of ways (Holliger, P. and Winter G. Current Opinion Biotechnol. 4, 446-449 (1993)), e.g. prepared chemically or from hybrid hybridomas, or may be any of the bispecific antibody fragments mentioned above. Diabodies and scFv can be constructed without an Fc region, using only variable domains, potentially reducing the side effects, such as those due to the antibody effector functions, or human-anti-mouse antibody (HAMA) response in case of using antibodies of murine origin.

Bispecific diabodies, as opposed to bispecific whole antibodies, may also be particularly useful because they can be readily constructed and expressed in bacteria (e.g. *Escherichia coli*). Diabodies (and many other polypeptides such as antibody fragments) of appropriate binding specificities can be readily selected using phage display (WO94/13804) from the antibody libraries. If one arm of the diabody is to be kept constant, for instance, with a specificity directed against Axl, then a library can be made where the other arm is varied and an antibody of appropriate specificity selected. Bispecific whole antibodies may be made by "knobs-into-holes" engineering (J. B. B. Ridgeway et al, Protein Eng., 9, 616-621, 1996).

Sample

As used herein, a "sample" may be a single cell or a population of cells. The cell(s) may be normal, healthy cell(s) or may be tumour cells, such as circulating tumour cells.

The sample may be in vivo, ex vivo, or in vitro. For example, the sample may be an in vivo tumour mass, or an in vitro cell population.

Antigen Binding Domain

This describes the part of an antibody molecule that comprises the area that recognizes and specifically binds to and is complementary part or all of an antigen. Where an antigen is large, an antibody may only bind to a particular part of the antigen, which part is termed an epitope. An antigen binding domain may be provided by one or more antibody variable domains (e.g. a so-called Fd antibody fragment consisting of a VH domain). Preferably, an antigen binding domain comprises an antibody light chain variable region (VL) and an antibody heavy chain variable region (VH).

Specific Proteins

Human Axl

As used herein, 'human Axl' refers to the Axl member of the human TAM family of receptor tyrosine kinases. Human Axl occurs in the following isoforms:

| Axl Isoform | mRNA:NCBI reference | Polypeptide:NCBI reference |
| --- | --- | --- |
| A | NM_001278599.1, GI:520260398, record update date: Nov. 28, 2014 12:30 AM | NP_001265528.1, GI:520260399, record update date: Nov. 28, 2014 12:30 AM |
| B | NM_001699.5, GI:520260376, record update date: Nov 28, 2014 12:30 AM | NP_001690.2 GI:21536468, record update date: Nov 28, 2014 12:30 AM |
| C | NM_021913.4, GI:520260356, record update date: Nov. 28, 2014 12:30 AM | NP_068713.2, GI:21536466, record update date: Nov. 28, 2014 12:30 AM (SEQ ID NO. 21) |

In some embodiments, the human Axl polypeptide corresponds to Isoform "A", shown above.

In some embodiments, the human Axl polypeptide corresponds to Isoform "B", shown above.

In preferred embodiments, the human Axl polypeptide corresponds to Isoform "C", shown above.

Murine Axl

As used herein, 'murine Axl' refers to the Axl member of the murine TAM family of receptor tyrosine kinases. Murine Axl occurs in the following isoforms:

| Axl Isoform | mRNA: NCBI reference | Polypeptide: NCBI reference |
| --- | --- | --- |
| A | NM_001190974.1, GI: 300794859, record update date: Sep. 5, 2014 08:46 PM | NP_001177903.1, GI: 300794860, record update date: Sep. 5, 2014 08:46 PM |
| B | NM_001190975.1, GI: 300794883, record update date: Sep. 5, 2014 08:46 PM | NP_001177904.1, GI: 300794884, record update date: Sep. 5, 2014 08:46 PM |
| C | NM_009465.4, GI: 300794836, record update date: Sep. 5, 2014 08:46 PM | NP_033491.2, GI: 31542164, record update date: Sep. 5, 2014 08:46 PM (SEQ ID NO: 22) |

In some embodiments, the murine Axl polypeptide corresponds to Isoform "A", shown above. In some embodiments, the murine Axl polypeptide corresponds to Isoform "B", shown above.

In preferred embodiments, the murine Axl polypeptide corresponds to Isoform "C", shown above.

Human Tyro3

As used herein, 'human Tyro3' refers to the Tyro3 member of the human TAM family of receptor tyrosine kinases. In some embodiments, the human Tyro3 polypeptide corresponds to NCBI accession no. NP_006284.2, GI:27597078, record update date: Nov. 28, 2014 12:30 AM (SEQ ID NO:

23). In one embodiment, the nucleic acid encoding the human Tyro3 polypeptide corresponds to NCBI accession no. NM_006293.3, GI:295842183, record update date: Nov. 28, 2014 12:30 AM.

Human Mer

As used herein, 'human Mer' refers to the Mer member of the human TAM family of receptor tyrosine kinases. In some embodiments, the human Mer polypeptide corresponds to NCBI accession no. NP_006334.2, GI:66932918, record update date: Sep. 6, 2014 04:03 AM (SEQ ID NO: 24). In one embodiment, the nucleic acid encoding the human Mer polypeptide corresponds to NCBI accession no. NM_006343, version no. NM_006343.2 GI:66932917, record update date: Sep. 6, 2014 04:03 AM.

Human Akt3

As used herein, 'human Akt3' refers to the Akt3 member of the human AKT subfamily of serine/threonine protein kinases. Human Akt3 occurs in the following isoforms:

| Akt 3 Isoform | mRNA: NCBI reference | Polypeptide: NCBI reference |
|---|---|---|
| A | NM_001206729.1, GI: 332078558, record update date: Sep. 6, 2014 02:43 AM | NP_001193658.1, GI: 332078559, record update date: Sep. 6, 2014 02:43 AM (SEQ ID NO: 25) |
| B | NM_005465.4, GI: 332078467, record update date: Sep. 6, 2014 02:43 AM | NP_005456.1, GI: 4885549, record update date: Sep. 6, 2014 02:43 AM |
| C | NM_181690.2, GI: 332078557, record update date: Sep. 6, 2014 02:43 AM | NP_859029.1, GI: 32307163, record update date: Sep. 6, 2014 02:43 AM |

In some embodiments, the human Akt polypeptide corresponds to Isoform "A", shown above. In some embodiments, the human Akt polypeptide corresponds to Isoform "B", shown above. In some embodiments, the human Akt polypeptide corresponds to Isoform "C", shown above.

Human Gas6

As used herein, 'human Gas6' (Growth Arrest Specific 6) refers to a ligand of the TAM family of receptor tyrosine kinases. In some embodiments, the human Gas6 polypeptide corresponds to NCBI accession no. NP_000811.1, GI:4557617, record update date: Sep. 6, 2014 02:44 AM (SEQ ID NO: 26). In one embodiment, the nucleic acid encoding the human Gas6 polypeptide corresponds to NCBI accession no. NM_000820.3, GI:673038877, record update date: Sep. 6, 2014 02:44 AM,

BSA

As used herein, 'BSA' refers to Bovine Serum Albumin. In some embodiments BSA corresponds to 'A9647—Bovine Serum Albumin' (Sigma Aldrich). In some embodiments BSA corresponds to Genbank accession no. CAA76847, version no. CAA76847.1 GI:3336842, record update date: Jan. 7, 2011 02:30 PM.

Comprise

This is generally used in the sense of "include", that is to say permitting the presence of one or more features or components.

Isolated

This refers to the state in which antibodies of the invention, or nucleic acid encoding such antibody, will generally be in accordance with the present invention. Antibody and nucleic acid will be free or substantially free of material with which they are naturally associated such as other polypeptides or nucleic acids with which they are found in their natural environment, or the environment in which they are prepared (e.g. cell culture) when such preparation is by recombinant DNA technology practiced in vitro or in vivo. Antibodies and nucleic acid may be formulated with diluents or adjuvants and still for practical purposes be isolated—for example the antibody will normally be mixed with gelatin or other carriers if used to coat microtitre plates for use in immunoassays, or will be mixed with pharmaceutically acceptable carriers or diluents when used in diagnosis or therapy. Antibodies may be glycosylated, either naturally or by systems of heterologous eukaryotic cells (e.g. CHO or NSO (ECACC 85110503) cells), or they may be (for example, if produced by expression in a prokaryotic cell) non-glycosylated.

Substantially as Set Out

By "substantially as set out" it is meant that the relevant CDR or VH or VL domain of the invention will be either identical or highly similar to the specified regions of which the sequence is set out herein. By "highly similar" it is contemplated that from 1 to 5, preferably from 1 to 4 such as 1 to 3 or 1 or 2, or 3 or 4, amino acid substitutions may be made in the CDR and/or VH or VL domain.

Antibodies of the present invention may further comprise antibody constant regions or parts thereof. For example, an antibody of the present invention may comprise a CL, CH1, CH2, and/or a CH3 domain (or any combination thereof). A VL domain may be attached at its C-terminal end to antibody light chain constant domains including human CK or CA chains, preferably CK chains. Similarly, an antibody based on a VH domain may be attached at its C-terminal end to all or part of an immunoglobulin heavy chain derived from any antibody isotype, e.g. IgG, IgA, IgE and IgM and any of the isotype sub-classes. Fc regions such as Δnab and Δnac as disclosed in WO99/58572 may be employed.

Chimeric, Humanised and CDR-Grafted Antibodies

As used herein "chimeric" antibodies or "humanised" antibodies or "CDR-grafted" include any combination of the herein described anti-Axl antibodies, or any CDR derived therefrom combined with one or more proteins or peptides derived from a non-murine, preferably, human antibody.

Chimeric or humanised antibodies include those wherein the CDR's are derived from one or more of the herein described anti-Axl antibodies and at least a portion, or the remainder of the antibody is derived from one or more human antibodies. Thus, the human part of the antibody may include the frameworks, CL (e.g. CK or CA), CH domains (e.g., CH1, CH2, CH3), hinge regions that are substantially non-immunogenic in humans.

The regions of the antibody that are derived from human antibodies need not have 100% identity with human antibodies. In a preferred embodiment, as few of the mouse amino acid residues as possible are retained in order for the immunogenicity to be negligible, but the mouse residues may be retained as necessary to support the antigen binding site formed by the CDR's while simultaneously maximizing the humanization of the antibody. Such changes or variations optionally and preferably retain or reduce the immunogenicity in humans or other species relative to non-modified antibodies.

It should be noted that a humanised antibody can be produced by a non-human animal or prokaryotic or eukaryotic cell that is capable of expressing functionally rearranged human immunoglobulin (e.g., heavy chain and/or light chain) genes. Further, when the antibody is a single chain antibody, it can comprise a linker peptide that is not found in native human antibodies. For example, an scFv can comprise a linker peptide, such as two to about twenty glycine or other amino acid residues (preferably glycine and serine residues (e.g., Gly$_4$Ser or Gly$_2$Ser repeats)), that connects the variable region of the heavy chain and the variable region of the light chain. Such linker peptides are considered to be non-immunogenic in humans. In some embodiments the linker is of at least 12 amino acids in length.

Antibody humanisation can be performed by, for example, synthesizing a combinatorial library comprising all six CDRs of a non-human target monoclonal antibody fused in frame to a pool of individual human frameworks. A human framework library that contains genes representative of all known heavy and light chain human germline sequences can be utilized. The resulting combinatorial libraries can then be screened for binding to antigens of interest. This approach can allow for the selection of the most favourable combinations of fully human frameworks in terms of maintaining the binding activity to the parental antibody. Humanised antibodies can then be further optimized by a variety of techniques.

For full-length antibody molecules, the immunoglobulin genes can be obtained from genomic DNA or mRNA of hybridoma cell lines. The antibody heavy and light chains are cloned in a mammalian vector system. Assembly is confirmed by sequencing using methods known in the art. The antibody construct can be expressed in other human or mammalian host cell lines. The construct can then be validated by transient transfection assays and Western blot analysis of the expressed antibody of interest. Stable cell lines with the highest productivity can be isolated and screened using rapid assay methods.

Human genes that encode the constant (C) regions of the humanized antibodies, fragments and regions can be derived from a human fetal liver library by known methods. Human C region genes can be derived from any human cell including those that express and produce human immunoglobulins. The human CH region can be derived from any of the known classes or isotypes of human heavy chains, including γ, μ, α, δ, ε, and subclasses thereof, such as G1, G2, G3 and G4. Since the heavy chain isotype is responsible for the various effector functions of an antibody, the choice of CH domain will be guided by the desired effector functions, such as complement fixation, or activity in antibody-dependent cellular cytotoxicity (ADCC). Preferably, the CH domain are derived from the gamma 1 (IgG1).

The human CL region can be derived from either human L chain isotype, kappa or lambda, preferably kappa.

Genes encoding human immunoglobulin C regions are obtained from human cells by standard cloning techniques (Sambrook, et al. Molecular Cloning: A Laboratory Manual, 2nd Edition, Cold Spring Harbor Press, Cold Spring Harbor, N.Y. (1989) and Ausubel et al., eds. Current Protocols in Molecular Biology (1987-1993)). Human C region genes are readily available from known clones containing genes representing the two types of light chains, the five classes of heavy chains and subclasses thereof.

Chimeric antibody fragments, such as Fab and F(ab')$_2$, can be prepared by designing a chimeric heavy chain gene that is appropriately truncated. For example, a chimeric gene encoding a heavy chain portion of an F(ab')$_2$ fragment would include DNA sequences encoding the CH1 domain and hinge region of the heavy chain, followed by a translational stop codon to yield the truncated molecule.

Methods for engineering or humanizing non-human or human antibodies can be used and are well known in the art. Generally, a humanized or engineered antibody has one or more amino acid residues from a source that is non-human, e.g., but not limited to mouse, rat, rabbit, non-human primate or other mammal. These human amino acid residues are often referred to as "import" residues, which are typically taken from an "import" variable, constant or other domain of a known human sequence. Known human Ig sequences are disclosed, e.g., www.ncbi.nlm.nih.gov/entrez/query.fcgi; www.atcc.org/phage/hdb.html; www.sciquest.com/; www.abcam.com/; www.antibodyresource.com/onlinecomp.html; www.public.iastate.edu/.about.pedro/research_tools.html; www.mgen.uni-heidelberg.de/SD/IT/IT.html; www.whfreeman.com/immunology/CH05/kuby05.htm; www.library.thinkquest.org/12429/Immune/Antibody.html; www.hhmi.org/grants/lectures/1996/vlab/; www.path.cam.ac.uk/.about.mrc7/mikeimages.html; www.antibodyresource.corril; mcb.harvard.edu/BioLinks/Immunology.html. www.immunologylink.com/; pathbox.wustl.edu/.about.hcenter/index.html; www.biotech.ufteduI.about.hcl/; www.pebio.com/pa/340913/340913.html; www.nal.usda.gov/awic/pubs/antibody/; www.m.ehime-u.ac.jp/.about.yasuhito/Elisa.html; www.biodesign.com/table.asp; www.icnet.uk/axp/facs/davies/links.html; www.biotech.ufl.edu/.about.fccl/protocol.html; www.isac-net.org/sites_geo.html; aximt1.imt.uni-marburg.deI.about.rek/AEP-Start.html; baserv.uci.kun.nl/.about.jraats/links1.html; www.recab.uni-hd.de/immuno.bme.nwvu.edu/; www.mrc-cpe.cam.ac.uk/imt-doc/public/INTRO.html; www.ibt.unam.mx/vir/V_mice.html; imgt.cnusc.fr:8104/; www.biochem.ucl.ac.uk/.about.martin/abs/index.html; antibody.bath.ac.uk/; abgen.cvm.tamu.edu/lab/wwwabgen.html; www.unizh.ch/.about.honegger/AHOseminar/Slide01.html; www.cryst.bbk.ac.uk/.about.ubcg07s/; www.nimr.mrc.ac.uk/CC/ccaewg/ccaewg.htm; www.path.cam.ac.uk/.about.mrc7/humanisation/TAHHP.html; www.ibt.unam.mx/vir/structure/stat_aim.html; www.biosci.missouri.edu/smithgp/index.html; www.cryst.bioc.cam.ac.uk/.about.fmolina/Webpages/Pept/spottech.html; www.jerini.de/fr_products.htm; www.patents.ibm.con/ibm.html. Kabat et al. Sequences of Proteins of Immunological Interest, U.S. Dept. Health (1983), each entirely incorporated herein by reference.

Such imported sequences can be used to reduce immunogenicity or reduce, enhance or modify binding, affinity, on-rate, off-rate, avidity, specificity, half-life, or any other suitable characteristic, as known in the art. Generally, part or all of the non-human or human CDR sequences are maintained while the non-human sequences of the variable and constant regions are replaced with human or other amino acids.

Antibodies can also optionally be humanized with retention of high affinity for the antigen and other favorable biological properties. To achieve this goal, humanized antibodies can be optionally prepared by a process of analysis of the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the consensus and import sequences so that the desired antibody characteristic, such as increased affinity for the target antigen(s), is achieved.

In general, the CDR residues are directly and most substantially involved in influencing antigen binding. Humanization or engineering the antibody can be performed using any known method, such as but not limited to those described in Winter et al., Nature 321:522 (1986); Riechmann et al., Nature 332:323 (1988); Verhoeyen et al., Science 239:1534 (1988)), Sims et al., J. Immunol. 151: 2296 (1993); Chothia and Lesk, J. Mol. Biol. 196:901 (1987), Carter et al., Proc. Natl. Acad. Sci. U.S.A. 89:4285 (1992); Presta et al., J. Immunol. 151:2623 (1993), U.S. Pat. Nos. 5,723,323, 5,976,862, 5,824,514, 5,817,483, 5,814, 476, 5,763,192, 5,723,323, 5,766,886, 5,714,352, 6,204,023, 6,180,370, 5,693,762, 5,530,101, 5,585,089, 5,225,539; 4,816,567, PCT/: US98/16280, US96/18978, US91/09630, US91/05939, US94/01234, GB89/01334, GB91/01134, GB92/01755; WO90/14443, WO90/14424, WO90/14430, EP 229246.

The human constant region of the humanized antibody can be of any class or isotype (IgG, IgA, IgM, IgE, IgD, etc.) and can comprise a kappa or lambda light chain. In one embodiment, the human constant region comprises an IgG heavy chain or defined fragment, for example, at least one of the IgG subclasses, IgG1, IgG2, IgG3 or IgG4.

Labelled Antibodies

Antibodies of the invention may be labelled with a detectable or functional label. Detectable labels include radiolabels such as [$^{131}$I] or [$^{99}$Tc], which may be attached to antibodies of the invention using conventional chemistry known in the art of radioimmunoconjugates. Labels also include enzyme labels such as horseradish peroxidase. Labels further include chemical moieties, such as biotin, which may be detected via binding to a specific cognate detectable moiety, e.g. labelled avidin or streptavidin. Preferably, the labels include fluorescent labels such as FITC.

Organic Moiety

The modified antibodies and antigen-binding fragments can comprise one or more organic moieties that are covalently bonded, directly or indirectly, to the antibody. Each organic moiety that is bonded to an antibody or antigen-binding fragment described herein can independently be a hydrophilic polymeric group, a fatty acid group or a fatty acid ester group. As used herein, the term "fatty acid" encompasses mono-carboxylic acids and di-carboxylic acids. A "hydrophilic polymeric group," as the term is used herein, refers to an organic polymer that is more soluble in water than in octane. For example, poly-lysine is more soluble in water than in octane. Thus, an antibody modified by the covalent attachment of poly-lysine is encompassed by the present disclosure. Hydrophilic polymers suitable for modifying antibodies described herein can be linear or branched and include, for example, poly-alkane glycols, e.g., polyethylene glycol (PEG), monomethoxy-polyethylene glycol (mPEG), PPG and the like, carbohydrates (e.g., dextran, cellulose, oligosaccharides, polysaccharides and the like), polymers of hydrophilic amino acids (e.g., poly-lysine, poly-arginine, poly-aspartate and the like), poly-alkane oxides (e.g., polyethylene oxide, polypropylene oxide and the like) and polyvinyl pyrolidone. Preferably, the hydrophilic polymer that modifies the antibody described herein has a molecular weight of about 800 to about 150,000 Daltons as a separate molecular entity. For example PEG5000 and PEG20,000, wherein the subscript is the average molecular weight of the polymer in Daltons, can be used. The hydrophilic polymeric group can be substituted with one to about six alkyl, fatty acid or fatty acid ester groups. Hydrophilic polymers that are substituted with a fatty acid or fatty acid ester group can be prepared by employing suitable methods. For example, a polymer comprising an amine group can be coupled to a carboxylate of the fatty acid or fatty acid ester, and an activated carboxylate (e.g., activated with N,N-carbonyl di-imidazole) on a fatty acid or fatty acid ester can be coupled to a hydroxyl group on a polymer.

Fatty acids and fatty acid esters suitable for modifying antibodies described herein can be saturated or can contain one or more units of unsaturation. Fatty acids that are suitable for modifying antibodies described herein include, for example, n-dodecanoate (C12, laurate), n-tetradecanoate (C14, myristate), n-octadecanoate (C18, stearate), n-eicosanoate (C20, arachidate), n-docosanoate (C22, behenate), n-triacontanoate (C30), n-tetracontanoate (C40), cis-δ 9-octadecanoate (C18, oleate), all cis-δ 5,8,11,14-eicosatetraenoate (C20, arachidonate), octanedioic acid, tetradecanedioic acid, octadecanedioic acid, docosanedioic acid, and the like. Suitable fatty acid esters include mono-esters of dicarboxylic acids that comprise a linear or branched lower alkyl group. The lower alkyl group can comprise from one to about twelve, preferably one to about six, carbon atoms.

The modified human antibodies and antigen-binding fragments can be prepared using suitable methods, such as by reaction with one or more modifying agents. A "modifying agent" as the term is used herein, refers to a suitable organic group (e.g., hydrophilic polymer, a fatty acid, a fatty acid ester) that comprises an activating group. An "activating group" is a chemical moiety or functional group that can, under appropriate conditions, react with a second chemical group thereby forming a covalent bond between the modifying agent and the second chemical group. For example, amine-reactive activating groups include electrophilic groups such as tosylate, mesylate, halo (chloro, bromo, fluoro, iodo), N-hydroxysuccinimidyl esters (NHS), and the like. Activating groups that can react with thiols include, for example, maleimide, iodoacetyl, acrylolyl, pyridyl disulfides, 5-thiol-2-nitrobenzoic acid thiol (TNB-thiol), and the like. An aldehyde functional group can be coupled to amine- or hydrazide-containing molecules, and an azide group can react with a trivalent phosphorous group to form phosphoramidate or phosphorimide linkages. Suitable methods to introduce activating groups into molecules are known in the art (see for example, Hernanson, G. T., Bioconjugate Techniques, Academic Press: San Diego, Calif. (1996)). An activating group can be bonded directly to the organic group (e.g., hydrophilic polymer, fatty acid, fatty acid ester), or through a linker moiety, for example a divalent C1-C12 group wherein one or more carbon atoms can be replaced by a heteroatom such as oxygen, nitrogen or sulfur. Suitable linker moieties include, for example, tetra-ethylene glycol, —(CH$_2$)$_3$—, —NH—(CH$_2$)$_6$—NH—, —(CH$_2$)$_2$—NH— and —CH$_2$—O—CH$_2$—CH$_2$—O—CH$_2$—CH$_2$—O—CH—NH—. Modifying agents that comprise a linker moiety can be produced, for example, by reacting a mono-Boc-alkyldiamine (e.g., mono-Boc-ethylenediamine, mono-Boc-diaminohexane) with a fatty acid in the presence of 1-ethyl-3-(3-dimethylaminopropyl) carbodiimide (EDC) to form an amide bond between the free amine and the fatty acid carboxylate. The Boc protecting group can be removed from the product by treatment with trifluoroacetic acid (TFA) to expose a primary amine that can be coupled to another carboxylate as described, or can be reacted with maleic anhydride and the resulting product cyclized to produce an activated maleimido derivative of the fatty acid. (See, for example, Thompson, et al., WO 92/16221).

The modified antibodies can be produced by reacting a human antibody or antigen-binding fragment with a modifying agent. For example, the organic moieties can be bonded to the antibody in a non-site specific manner by employing an amine-reactive modifying agent, for example, an NHS ester of PEG. Modified human antibodies or antigen-binding fragments can also be prepared by reducing disulfide bonds (e.g., intra-chain disulfide bonds) of an antibody or antigen-binding fragment. The reduced antibody or antigen-binding fragment can then be reacted with a thiol-reactive modifying agent to produce the modified antibody described herein. Modified human antibodies and antigen-binding fragments comprising an organic moiety that is bonded to specific sites of an antibody described herein can be prepared using suitable methods, such as reverse proteolysis (Fisch et al., Bioconjugate Chem., 3:147-153 (1992); Werlen et al., Bioconjugate Chem., 5:411-417 (1994); Kumaran et al., Protein Sci. 6(10):2233-2241 (1997); Itoh et al., Bioorg. Chem., 24(1): 59-68 (1996); Capellas et al., Biotechnol. Bioeng., 56(4):456-463 (1997)), and the methods described in Hermanson, G. T., Bioconjugate Techniques, Academic Press: San Diego, Calif. (1996).

Immunoconjugates

The invention also provides immunoconjugates comprising an anti-Axl antibody herein conjugated to one or more cytotoxic agents, such as chemotherapeutic agents or drugs, growth inhibitory agents, toxins (e.g., protein toxins, enzymatically active toxins of bacterial, fungal, plant, or animal origin, or fragments thereof), or radioactive isotopes.

In one embodiment, an immunoconjugate is an antibody-drug conjugate (ADC) in which an antibody is conjugated to one or more drugs, including but not limited to a maytansinoid (see U.S. Pat. Nos. 5,208,020, 5,416,064 and European Patent EP 0 425 235 B1); an auristatin such as monomethylauristatin drug moieties DE and DF (MMAE and MMAF) (see U.S. Pat. Nos. 5,635,483 and 5,780,588, and 7,498, 298); a dolastatin; a calicheamicin or derivative thereof (see U.S. Pat. Nos. 5,712,374, 5,714,586, 5,739,116, 5,767,285, 5,770,701, 5,770,710, 5,773,001, and 5,877,296; Hinman et al., Cancer Res. 53:3336-3342 (1993); and Lode et al., Cancer Res. 58:2925-2928 (1998)); an anthracycline such as daunomycin or doxorubicin (see Kratz et al., Current Med. Chem. 13:477-523 (2006); Jeffrey et al., Bioorganic & Med. Chem. Letters 16:358-362 (2006); Torgov et al., Bioconj. Chem. 16:717-721 (2005); Nagy et al., Proc. Natl. Acad. Sci. USA 97:829-834 (2000); Dubowchik et al., Bioorg. & Med. Chem. Letters 12:1529-1532 (2002); King et al., J. Med. Chem. 45:4336-4343 (2002); and U.S. Pat. No. 6,630, 579); methotrexate; vindesine; a taxane such as docetaxel, paclitaxel, larotaxel, tesetaxel, and ortataxel; a trichothecene; and CC1065.

In another embodiment, an immunoconjugate comprises an antibody as described herein conjugated to an enzymatically active toxin or fragment thereof, including but not limited to diphtheria toxin A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (P API, P APII, and PAP-S), *Momordica charantia* inhibitor, curcin, crotin, *Sapaonaria officinalis* inhibitor, gelonin, mitogellin, restrictocin, phenomycin, enomycin, and the tricothecenes.

In another embodiment, an immunoconjugate comprises an antibody as described herein conjugated to a radioactive atom to form a radioimmunoconjugate. A variety of radioactive isotopes are available for the production of radioimmunoconjugates. Examples include [$^{211}$At], [$^{131}$I], [$^{125}$I], [$^{90}$Y], [$^{186}$Re], [$^{188}$Re], [$^{153}$Sm], [$^{212}$Bi], [$^{32}$P], [$^{212}$Pb] and radioactive isotopes of Lu. When the radioimmunoconjugate is used for detection, it may comprise a radioactive atom for scintigraphic studies, for example [$^{99}$Tc] or [$^{123}$I], or a spin label for nuclear magnetic resonance (NMR) imaging (also known as magnetic resonance imaging, MRI), such as iodine-123 again, iodine-131, indium-111, fluorine-19, carbon-13, nitrogen-15, oxygen-17, gadolinium, manganese or iron.

Conjugates of an antibody and cytotoxic agent may be made using a variety of bifunctional protein coupling agents such as N-succinimidyl-3-(2-pyridyldithio) propionate (SPDP), succinimidyl-4-(N-maleimidomethyl) cyclohexane-1-carboxylate (SMCC), iminothiolane (IT), bifunctional derivatives of imidoesters (such as dimethyl adipimidate HCl), active esters (such as disuccinimidyl suberate), aldehydes (such as glutaraldehyde), bis-azido compounds (such as bis (p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). For example, a ricin immunotoxin can be prepared as described in Vitetta et al., Science 238:1098 (1987). Carbon-14-labeled 1-isothiocyanatobenzyl-3-methyldiethylene triaminepentaacetic acid (MXDTPA) is an exemplary chelating agent for conjugation of radionucleotide to the antibody. See WO94/11026. The linker may be a "cleavable linker" facilitating release of a cytotoxic drug in the cell. For example, an acid-labile linker, peptidase-sensitive linker, photo-labile linker, dimethyl linker or disulfide-containing linker (Chari et al., Cancer Res. 52: 127-131 (1992); U.S. Pat. No. 5,208,020) may be used.

The immunoconjugates or ADCs herein expressly contemplate, but are not limited to such conjugates prepared with cross-linker reagents including, but not limited to, BMPS, EMCS, GMBS, HBVS, LC-SMCC, MBS, MPBH, SBAP, SIA, SIAB, SMCC, SMPB, SMPH, sulfo-EMCS, sulfo-GMBS, sulfo-KMUS, sulfo-MBS, sulfo-SIAB, sulfo-SMCC, and sulfo-SMPB, and SVSB (succinimidyl-(4-vinylsulfone)benzoate) which are commercially available (e.g., from Pierce Biotechnology, Inc., Rockford, Ill., U.S.A).

Glycosylation Variants

In certain embodiments, an antibody provided herein is altered to increase or decrease the extent to which the antibody is glycosylated. Addition or deletion of glycosylation sites to an antibody may be conveniently accomplished by altering the amino acid sequence such that one or more glycosylation sites is created or removed.

Where the antibody comprises an Fc region, the carbohydrate attached thereto may be altered. Native antibodies produced by mammalian cells typically comprise a branched, biantennary oligosaccharide that is generally attached by an N-linkage to Asn297 of the CH2 domain of the Fc region. See, e.g., Wright et al. TIBTECH 15:26-32 (1997). The oligosaccharide may include various carbohydrates, e.g., mannose, N-acetyl glucosamine (GlcNAc), galactose, and sialic acid, as well as a fucose attached to a GlcNAc in the "stem" of the biantennary oligosaccharide structure. In some embodiments, modifications of the oligosaccharide in an antibody of the invention may be made in order to create antibody variants with certain improved properties.

In one embodiment, antibody variants are provided having a carbohydrate structure that lacks fucose attached (directly or indirectly) to an Fc region. For example, the amount of fucose in such antibody may be from 1% to 80%, from 1% to 65%, from 5% to 65% or from 20% to 40%. The amount of fucose is determined by calculating the average amount of fucose within the sugar chain at Asn297, relative to the sum of all glycostructures attached to Asn297 (e. g., complex, hybrid and high mannose structures) as measured by MALDI-TOF mass spectrometry, as described in WO 2008/077546, for example. Asn297 refers to the asparagine residue located at about position 297 in the Fc region (Eu numbering of Fc region residues); however, Asn297 may also be located about ±3 amino acids upstream or downstream of position 297, i.e., between positions 294 and 300, due to minor sequence variations in antibodies. Such fucosylation variants may have improved ADCC function. See, e.g., US Patent Publication Nos. US 2003/0157108 (Presta, L.); US 2004/0093621 (Kyowa Haklw Kogyo Co., Ltd). Examples of publications related to "defucosylated" or "fucose-deficient" antibody variants include: US2003/01571; WO2000/61739; WO2001/29246; US2003/0115614; US2002/0164328; US2004/0093621; US2004/0132140; US2004/0110704; US2004/0110282; US2004/0109865; WO2003/085119; WO2003/084570; WO2005/035586; WO2005/035778; WO2005/053742; WO2002/031140; Okazaki et al. J. Mol. Biol. 336:1239-1249 (2004); Yamane-Ohnuki et al. Biotech. Bioeng. 87: 614 (2004).

Examples of cell lines capable of producing defucosylated antibodies include Lec13 CHO cells deficient in protein fucosylation (Ripka et al. Arch. Biochem. Biophys. 249: 533-545 (1986); US Pat Appl No US 2003/0157108 A1, Presta, L; and WO 2004/056312 A1, Adams et al., especially at Example 11), and knockout cell lines, such as alpha-1,6-fucosyltransferase gene, FUT8, knockout CHO cells (see, e.g., Yamane-Ohnuki et al. Biotech. Bioeng. 87: 614 (2004); Kanda, Y. et al., Biotechnol. Bioeng., 94(4):680-688 (2006); and WO2003/085107).

Antibodies variants are further provided with bisected oligosaccharides, e.g., in which a biantennary oligosaccharide attached to the Fc region of the antibody is bisected by GlcNAc. Such antibody variants may have reduced fucosylation and/or improved ADCC function. Examples of such antibody variants are described, e.g., in WO 2003/011878 (Jean-Mairet et al.); U.S. Pat. No. 6,602,684 (Umana et al.); and US2005/0123546 (Umana et al.). Antibody variants with at least one galactose residue in the oligosaccharide attached to the Fe region are also provided. Such antibody variants may have improved CDC function. Such antibody variants are described, e.g., in WO 1997/30087 (Patel et al.); WO 1998/58964 (Raju, S.); and WO 1999/22764 (Raju, S.).

Fc Region Variants

In certain embodiments, one or more amino acid modifications may be introduced into the Fc region of an antibody provided herein, thereby generating an Fc region variant. The Fc region variant may comprise a human Fc region sequence (e.g., a human IgG1, IgG2, IgG3 or IgG4 Fc region) comprising an amino acid modification (e.g. a substitution) at one or more amino acid positions.

In certain embodiments, the invention contemplates an antibody variant that possesses some but not all effector functions, which make it a desirable candidate for applications in which the half-life of the antibody in vivo is important yet certain effector functions (such as complement fixation and ADCC) are unnecessary or deleterious. In vitro and/or in vivo cytotoxicity assays can be conducted to confirm the reduction/depletion of CDC and/or ADCC activities. For example, Fc receptor (FcR) binding assays can be conducted to ensure that the antibody lacks Fcγ binding (hence likely lacking ADCC activity), but retains FcRn binding ability. The primary cells for mediating ADCC, NK cells, express FcγRIII only, whereas monocytes express FcγRI, FcγRII and FcγRIII. FcR expression on hematopoietic cells is summarized in Table 3 on page 464 of Ravetch and Kinet, Annu. Rev. Immunol. 9:457-492 (1991). Non-limiting examples of in vitro assays to assess ADCC activity of a molecule of interest is described in U.S. Pat. No. 5,500,362 (see, e.g. Hellstrom, I. et al. Proc. Nat'l Acad. Sci. USA 83:7059-7063 (1986)) and Hellstrom, I et al., Proc. Nat'l Acad. Sci. USA 82:1499-1502 (1985); U.S. Pat. No. 5,821,337 (see Bruggemann, M. et al., J. Exp. Med. 166: 1351-1361 (1987)). Alternatively, non-radioactive assay methods may be employed (see, for example, ACTI™ non-radioactive cytotoxicity assay for flow cytometry (CellTechnology, Inc. Mountain View, Calif.; and CytoTox 96® non-radioactive cytotoxicity assay (Promega, Madison, Wis.). Useful effector cells for such assays include peripheral blood mononuclear cells (PBMC) and Natural Killer (NK) cells. Alternatively, or additionally, ADCC activity of the molecule of interest may be assessed in vivo, e.g., in an animal model such as that disclosed in Clynes et al. Proc. Nat'l Acad. Sci. USA 95:652-656 (1998). C1q binding assays may also be carried out to confirm that the antibody is unable to bind C1q and hence lacks complement-dependent cytotoxicity (CDC) activity. See, e.g., C1q and C3c binding ELISA in WO2006/029879 and WO2005/100402. To assess complement activation, a CDC assay may be performed (see, for example, Gazzano-Santoro et al., J. Immunol. Methods 202:163 (1996); Cragg, M. S. et al., Blood 101:1045-1052 (2003); and Cragg, M. S. and M. J. Glennie, Blood 103:2738-2743 (2004)). FcRn binding and in vivo clearance/half-life Fc determinations can also be performed using methods known in the art (see, e.g., Petkova, S. B. et al., Int'l. Immunol. 18(12): 1759-1769 (2006)).

Antibodies with reduced effector function include those with substitution of one or more of Fc region residues 238, 265, 269, 270, 297, 327 and 329 (U.S. Pat. No. 6,737,056). Such Fc mutants include Fc mutants with substitutions at two or more of amino acid positions 265, 269, 270, 297 and 327, including the so-called "DANA" Fc mutant with substitution of residues 265 and 297 to alanine (U.S. Pat. No. 7,332,581).

Certain antibody variants with improved or diminished binding to FcRs are described (see, e.g., U.S. Pat. No. 6,737,056; WO 2004/056312, and Shields et al., J. Biol. Chem. 9(2): 6591-6604 (2001)).

In certain embodiments, an antibody variant comprises an Fc region with one or more amino acid substitutions, that improve ADCC activity, e.g., substitutions at positions 298, 333, and/or of the Fc region (EU numbering of residues).

In some embodiments, alterations are made in the Fc region that result in altered (i.e., either improved or diminished) C1q binding and/or CDC activity, e.g., as described in U.S. Pat. No. 6,194,551, WO 99/51642, and Idusogie et al. J. Immunol. 164: 4178-4184 (2000).

Antibodies with increased half-lives and improved binding to the neonatal Fc receptor (FcRn), that is responsible for the transfer of maternal IgGs to the fetus (Guyer et al., J. Immunol. 117:587 (1976) and Kim et al., J. Immunol.

24:249 (1994)), are described in US2005/0014934A1 (Hinton et al.). Those antibodies comprise an Fc region with one or more substitutions therein that improve binding of the Fc region to FcRn. Such Fc variants include those with substitutions at one or more of Fc region residues: 238, 256, 265, 272, 286, 303, 305, 307, 311, 312, 317, 340, 356, 360, 362, 376, 378, 380, 382, 413, 424 or 434, e.g., substitution of Fc region residue 434 (U.S. Pat. No. 7,371,826). See also Duncan & Winter, Nature 322:738-40 (1988); U.S. Pat. Nos. 5,648,260; 5,624,821; and WO 94/29351 concerning other examples of Fc region variants.

Cysteine Engineered Antibody Variants

In certain embodiments, it may be desirable to create cysteine engineered antibodies, e.g., "thioMAbs," in which one or more residues of an antibody are substituted with cysteine residues.

In particular embodiments, the substituted residues occur at accessible sites of the antibody. By substituting those residues with cysteine, reactive thiol groups are thereby positioned at accessible sites of the antibody and may be used to conjugate the antibody to other moieties, such as drug moieties or linker-drug moieties, to create an immunoconjugate, as described further herein. In certain embodiments, any one or more of the following residues may be substituted with cysteine: V205 (Kabat numbering) of the light chain; A118 (EU numbering) of the heavy chain; and S400 (EU numbering) of the heavy chain Fc region. Cysteine engineered antibodies may be generated as described, e.g., in U.S. Pat. No. 7,521,541.

Methods of Diagnosis and Treatment

Antibodies of the present invention are designed to be used in methods of diagnosis or treatment in human or animal subjects, preferably human.

Accordingly, further aspects of the invention provide methods of diagnosis comprising administration of an antibody as provided, with one or more reagents e.g. conjugated to a detectable label such as FITC. The antibody as provided may be used in the development of a rapid and reliable test for cancer cells derived from biopsied tissue. For example, the antibody may be used as a test for metastatic cancer cells, such as circulating tumour cells, that may be found circulating in body fluids such as blood or lymph. Other cancers of interest include breast, lung, gastric, head and neck, colorectal, renal, pancreatic, uterine, hepatic, bladder, endometrial and prostate cancers as well as lymphomas (e.g., non-Hodgkin's lymphoma, NHL) and leukemia (particularly acute myeloid leukemia, AML).

Further aspects of the invention provide methods of treatment comprising administration of an antibody as provided, pharmaceutical compositions comprising such an antibody, the antibody as described herein for use in a method of treatment, the antibody as described herein for use in a method of treatment of particular clinical indications described herein, and use of such an antibody in the manufacture of a medicament for administration, for example in a method of making a medicament or pharmaceutical composition comprising formulating the antibody with a pharmaceutically acceptable excipient.

Clinical Indications

Clinical indications in which an antibody with high specificity for human Axl may be used to provide therapeutic benefit include any condition in which Axl is overexpressed, or wherein Axl antagonism will provide a clinical benefit. These include immune disorders, cardiovascular disorders, thrombosis, diabetes, immune checkpoint disorders, fibrotic disorders (fibrosis), or proliferative diseases such as cancer, particularly metastatic cancer. Furthermore, Axl is known to play a role in many cancers of epithelial origin.

Fibrotic disorders of interest include strabmisus, scleroderma, keloid, Nephrogenic systemic fibrosis, pulmonary fibrosis, idiopathic pulmonary fibrosis (IPF), cystic fibrosis (CF), systemic sclerosis, cardiac fibrosis, non-alcoholic steatohepatitis (NASH), other types of liver fibrosis, primary biliary cirrhosis, renal fibrosis, cancer, and atherosclerosis. In these diseases, the chronic development of fibrosis in tissue leads to marked alterations in the architecture of the affected organs and subsequently cause defective organ function. As a result of this process of sustained attrition to organs, many diseases that involve fibrosis are often progressive conditions and have a poor long-term prognosis (see Rockey, D.C., Bell, P. D. and Hill, J. A. (2015), N. Engl. Med., Vol. 372, pp. 1138-1149).

Immune checkpoint disorders of interest include: Chronic viral infections, Melanoma, Colorectal cancer, Breast cancer, Ovarian cancer, Non-small cell lung cancer (NSCLC), Prostate cancer, Renal cell cancer, Pancreatic cancer, Esophagus cancer, Bladder cancer, Myeloma, Kidney cancer, Bladder cancer, Brain tumor, and Lymphoma.

Cancers of interest include: leukaemias such as but not limited to, acute leukemia, acute lymphocytic leukemia, acute myelocytic leukaemias such as myeloblastic, promyelocytic, myelomonocytic, monocytic, erythroleukaemia leukaemias and myelodysplastic syndrome, chronic leukaemias such as but not limited to, chronic myelocytic (granulocytic) leukemia, chronic lymphocytic leukemia, hairy cell leukemia; polycythemia vera; lymphomas such as but not limited to Hodgkin's disease, non-Hodgkin's disease; multiple myelomas such as but not limited to smoldering multiple myeloma, nonsecretory myeloma, osteosclerotic myeloma, plasma cell leukemia, solitary plasmacytoma and extramedullary plasmacytoma; Waldenstrom's macroglobulinemia; monoclonal gammopathy of undetermined significance; benign monoclonal gammopathy; heavy chain disease; bone and connective tissue sarcomas such as but not limited to bone sarcoma, osteosarcoma, chondrosarcoma, Ewing's sarcoma, malignant giant cell tumor, fibrosarcoma of bone, chordoma, periosteal sarcoma, soft-tissue sarcomas, angiosarcoma (hemangiosarcoma), fibrosarcoma, Kaposi's sarcoma, leiomyosarcoma, liposarcoma, lymphangiosarcoma, metastatic cancers, neurilemmoma, rhabdomyosarcoma, synovial sarcoma; brain tumors such as but not limited to, glioma, glioblastoma, astrocytoma, brain stem glioma, ependymoma, oligodendroglioma, nonglial tumor, acoustic neurinoma, craniopharyngioma, medulloblastoma, meningioma, pineocytoma, pineoblastoma, primary brain lymphoma; breast cancer, including, but not limited to, adenocarcinoma, lobular (small cell) carcinoma, intraductal carcinoma, medullary breast cancer, mucinous breast cancer, tubular breast cancer, papillary breast cancer, primary cancers, Paget's disease, and inflammatory breast cancer; adrenal cancer such as but not limited to pheochromocytoma, and adrenocortical carcinoma; thyroid cancer such as but not limited to papillary or follicular thyroid cancer, Medullary thyroid carcinoma, medullary thyroid cancer and anaplastic thyroid cancer; GIST—gastrointestinal stromal tumor; pancreatic cancer such as but not limited to, insulinoma, gastrinoma, glucagonoma, vipoma, somatostatin-secreting tumor, and carcinoid or islet cell tumor; pituitary cancers such as but limited to Cushing's disease, prolactin-secreting tumor, acromegaly, and diabetes insipius; eye cancers such as but not limited to ocular melanoma such as iris melanoma, choroidal melanoma, and cilliary body melanoma, and retinoblastoma; vaginal cancers such as squamous cell carcinoma, adenocarcinoma, and melanoma; vulvar cancer such as squamous cell carcinoma, melanoma, adenocarcinoma, basal cell carcinoma, sarcoma, and Paget's disease; cervical cancers such as but not limited to, squamous cell carcinoma, and adenocarcinoma; uterine cancers such as but not limited to endometrial carcinoma and uterine sarcoma; ovarian cancers such as but not limited to, ovarian epithelial carcinoma, borderline tumor, germ cell tumor, and stromal tumor; esophageal cancers such as but not limited to, squamous cancer, adenocarcinoma, adenoid cyctic carcinoma, mucoepidermoid carcinoma, adenosquamous carcinoma, sarcoma, melanoma, plasmacytoma, verrucous carcinoma, and oat cell (small cell) carcinoma; stomach cancers such as but not limited to, adenocarcinoma, fungating (polypoid), ulcerating, superficial spreading, diffusely spreading, malignant lymphoma, liposarcoma, fibrosarcoma, and carcinosarcoma; colon cancers; rectal cancers; liver cancers such as but not limited to hepatocellular carcinoma and hepatoblastoma, gallbladder cancers such as adenocarcinoma; cholangiocarcinomas such as but not limited to pappillary, nodular, and diffuse; lung cancers such as non-small cell lung cancer (NSCLC), squamous cell carcinoma (epidermoid carcinoma), adenocarcinoma, large-cell carcinoma and small-cell lung cancer (SCLC); testicular cancers such as but not limited to germinal tumor, seminoma, anaplastic, classic (typical), spermatocytic, nonseminoma, embryonal carcinoma, teratoma carcinoma, choriocarcinoma (yolk-sac tumor), prostate cancers such as but not limited to, adenocarcinoma, leiomyosarcoma, and rhabdomyosarcoma; genital cancers such as penile cancer; oral cancers such as but not limited to squamous cell carcinoma; basal cancers; salivary gland cancers such as but not limited to adenocarcinoma, mucoepidermoid carcinoma, and adenoidcystic carcinoma; pharynx cancers such as but not limited to squamous cell cancer, and verrucous; skin cancers such as but not limited to, basal cell carcinoma, squamous cell carcinoma and melanoma, superficial spreading melanoma, nodular melanoma, lentigo malignant melanoma, acral lentiginous melanoma; kidney cancers such as but not limited to renal cell cancer, Clear cell renal cell carcinoma, adenocarcinoma, hypernephroma, fibrosarcoma, transitional cell cancer (renal pelvis and/or ureter); Wilms' tumor; bladder cancers such as but not limited to transitional cell carcinoma, squamous cell cancer, adenocarcinoma, carcinosarcoma. In addition, cancers include myxosarcoma, osteogenic sarcoma, endotheliosarcoma, lymphangioendotheliosarcoma, mesothelioma, synovioma, hemangioblastoma, epithelial carcinoma, cystadenocarcinoma, bronchogenic carcinoma, sweat gland carcinoma, sebaceous gland carcinoma, papillary carcinoma and papillary adenocarcinomas. Preferably, the cancer is selected from breast, melanoma, prostate, ovarian, colorectal, lung or glioma cancer. More preferably, the cancer is metastatic breast or lung cancer. The targeting and treatment of circulating tumour cells is envisaged.

The treatment of metastatic cancer depends on where the primary tumour is located. When breast cancer spreads to the lungs, for example, it remains a breast cancer and the treatment is determined by the metastatic cancer origin within the breast, not by the fact that it is now in the lung. About 5 percent of the time, metastatic cancer is discovered but the primary tumour cannot be identified. The treatment of these metastatic cancers is dictated by their location rather than their origin. Metastatic cancers are named by the tissue of the original tumour (if known). For example, a breast cancer that has spread to the brain is called metastatic breast cancer to the brain.

Anti-Axl treatment in accordance with the present invention may be used to provide clear benefit for patients with conditions where Axl is overexpressed, or wherein Axl antagonism will provide a clinical benefit. Treatment may be given by injection (e.g. intravenously) or by local delivery methods. The antibody as provided may be used to direct the delivery of pharmaceutical compositions to the target tissue, or systemically in order to target, for example, Circulating Tumour Cells (CTCs) or other metastatic cells.

In a further aspect of the invention, there is provided a method of inhibiting Cancer Stem Cells in a subject, the method comprising of contacting the subject with an antibody (or conjugate thereof) as described herein. Antibodies and conjugates for use in such a method are also envisaged.

EGFR Antagonism

The invention also provides methods of inhibiting constitutive Axl activation comprising administering to the individual an effective amount of any of the anti-Axl antibodies disclosed herein to inhibit constitutive Axl.

In one aspect, the invention provides methods for treating a subject suffering from a cancer associated with an EGFR activating mutation or an EGFR gene amplification, wherein the subject has developed a resistance to treatment with an EGFR antagonist, comprising determining whether the subject has Axl expression, an Axl activating mutation or an Axl gene amplification, and administering to those subjects having an Axl activating mutation or an Axl gene amplification an EGFR antagonist and any of the anti-Axl antibodies described herein.

In one aspect, the invention provides methods for treating a subject suffering from a cancer associated with an EGFR activating mutation or an EGFR gene amplification, comprising: (i) monitoring a subject being treated with an EGFR antagonist to determine if the subject develops Axl expression, an Axl activating mutation or an Axl gene amplification, and (ii) modifying the treatment regimen of the subject to include any of the anti-Axl antibodies described herein in addition to the EGFR antagonist where the subject has developed an Axl activating mutation or an Axl gene amplification.

In one aspect, the invention provides methods for treating a subject suffering from a cancer associated with an EGFR activating mutation or an EGFR gene amplification, comprising: (i) monitoring a subject being treated with EGFR antagonist to determine if the subject develops a resistance to the inhibitor, (ii) testing the subject to determine whether the subject has Axl expression, an Axl activating mutation or an Axl gene amplification, and (iii) modifying the treatment regimen of the subject to include any of the anti-Axl antibodies described herein in addition to the EGFR antagonist where the subject has an Axl activating mutation or an Axl gene amplification.

In one aspect, the invention provides methods for evaluating an EGFR antagonist, comprising: (i) monitoring a population of subjects being treated with an EGFR antagonist to identify those subjects that develop a resistance to the therapeutic, (ii) testing the resistant subjects to determine whether the subjects have Axl expression, an Axl activating mutation or an Axl gene amplification, and (iii) modifying the treatment regimen of the subjects to include any of the anti-Axl antibodies described herein in addition to the EGFR antagonist where the subjects have Axl expression, an Axl activating mutation or an Axl gene amplification.

In one aspect, the invention provides methods for reducing EGFR phosphorylation in a cancer cell, wherein said cancer cell has acquired resistance to an EGFR antagonist, and wherein said cell comprises an Axl activating mutation or an Axl gene amplification, comprising the step of contacting the cell with any of the anti-Axl antibodies described herein and an EGFR antagonist.

In one aspect, the invention provides methods for reducing PBK mediated signaling in a cancer cell, wherein said cancer cell has acquired resistance to an EGFR antagonist, and wherein said cell comprises Axl expression, an Axl activating mutation or an Axl gene amplification, comprising the step of contacting the cell with any of the anti-Axl antibodies described herein and an EGFR antagonist.

In one aspect, the invention provides methods for reducing EGFR-mediated signaling in a cancer cell, wherein said cancer cell has acquired resistance to an EGFR antagonist, and wherein said cell comprises Axl expression, an Axl activating mutation or an Axl gene amplification, comprising contacting the cell with any of the anti-Axl antibodies described herein and an EGFR antagonist.

In one aspect, the invention provides methods for restoring sensitivity of a cancer cell to an EGFR antagonist, wherein said cancer cell has acquired resistance to an EGFR antagonist, and wherein said cell comprises Axl expression, an Axl activating mutation or an Axl gene amplification, comprising contacting the cell with any of the anti-Axl antibodies described herein and an EGFR antagonist.

In one aspect, the invention provides methods for reducing growth or proliferation of a cancer cell, wherein said cancer cell has acquired resistance to an EGFR antagonist, and wherein said cell comprises Axl expression, an Axl activating mutation or an Axl gene amplification, comprising the step of contacting the cell with any of the anti-Axl antibodies described herein and an EGFR antagonist.

In one aspect, the invention provides methods for increasing apoptosis of a cancer cell, wherein said cancer cell has acquired resistance to an EGFR antagonist, and wherein said cell comprises Axl expression, an Axl activating mutation or an Axl gene amplification, comprising the step of contacting the cell with any of the anti-Axl antibodies described herein and an EGFR antagonist.

In one aspect, the invention provides methods for reducing resistance of a cancer cell to an EGFR antagonist, wherein said cancer cell has acquired resistance to an EGFR antagonist, and wherein said cell comprises an Axl activating mutation or an Axl gene amplification, comprising the step of contacting the cell with any of the anti-Axl antibodies described herein and an EGFR antagonist.

In one aspect, the invention provides methods for treating acquired EGFR antagonist resistance in a cancer cell, wherein said cell comprises an Axl activating mutation or an Axl gene amplification, comprising contacting the cell with any of the anti-Axl antibodies described herein and an EGFR antagonist.

In some embodiments, the cancer cell is any EGFR-driven cancer. In some embodiments, the cancer cell comprises an EGFR activating mutation. In some embodiments, the cancer cell comprises an EGFR gene amplification. In some embodiments, the EGFR gene amplification is at least 2-fold. In some embodiments, the Axl amplification is at least 2-fold. In some embodiments, the cancer cell comprises an EGFR gene mutation associated with increased resistance to an EGFR antagonist. In some embodiments, the EGFR gene mutation associated with increased resistance to an EGFR antagonist is a T790M mutation of EGFR.

In some embodiments, the EGFR antagonist is a small molecule therapeutic, a nucleic acid therapeutic, or a protein therapeutic. In some embodiments, the EGFR antagonist is an antibody, an antisense molecule, or a small molecule kinase inhibitor. In some embodiments, the EGFR antagonist is an EGFR kinase inhibitor selected from the group consisting of: gefitinib, erlotinib, cetuximab, panitumumab. In some embodiments, the EGFR antagonist is an anti-EGFR antibody selected from the group consisting of: cetuximab, panitumumab. In some embodiments, the nucleic acid therapeutic is a siRNA molecule.

In one aspect, the invention provides methods for identifying a subject as a candidate for treatment with an EGFR antagonist and any of the anti-Axl antibodies described herein, wherein said subject has been treated with an EGFR antagonist and suffers from cancer that has acquired resistance to said EGFR antagonist, comprising detecting Axl expression, an Axl activating mutation or Axl gene amplification in a cancer cell from said subject.

In one aspect, the invention provides methods for identifying a subject who is being treated with an EGFR antagonist and who is at risk for acquiring resistance to said EGFR antagonist, comprising detecting the presence of Axl expression, an Axl activating mutation or an Axl gene amplification in a cancer cell from said subject, wherein the presence of said Axl expression, Axl activating mutation or Axl gene amplification indicates a risk for acquiring said resistance.

In one aspect, the invention provides methods for treating a subject suffering from a cancer that is resistant to treatment with an EGFR antagonist, comprising administering to the subject an EGFR antagonist and any of the anti-Axl antibodies described herein.

In one aspect, the invention provides methods for treating a subject suffering from a cancer associated with an EGFR activating mutation or an EGFR gene amplification, wherein the subject has developed a resistance to treatment with an EGFR antagonist, comprising determining whether the subject has Axl expression, such as elevated Axl levels and/or activity, and administering to those subjects having Axl expression, such as elevated Axl activity an EGFR antagonist and any of the anti-Axl antibodies described herein.

In one aspect, the invention provides methods for treating a subject suffering from a cancer associated with an EGFR activating mutation or an EGFR gene amplification, comprising: (i) monitoring a subject being treated with an EGFR antagonist to determine if the subject develops Axl expression, such as elevated levels and/or Axl activity, and (ii) modifying the treatment regimen of the subject to include any of the anti-Axl antibodies described herein in addition to the EGFR antagonist where the subject has developed Axl expression, such as elevated Axl levels and/or activity.

In one aspect, the invention provides methods for treating a subject suffering from a cancer associated with an EGFR activating mutation or an EGFR gene amplification, comprising: (i) monitoring a subject being treated with EGFR antagonist to determine if the subject develops a resistance to the inhibitor, (ii) testing the subject to determine whether the subject has Axl expression, such as elevated Axl levels and/or activity, and (iii) modifying the treatment regimen of the subject to include any of the anti-Axl antibodies described herein in addition to the EGFR antagonist where the subject has elevated Axl levels and/or activity.

In another aspect, the invention provides a method for (i) restoring the sensitivity of a cancer cell to an EGFR antagonist, (ii) reducing resistance of a cancer cell to an EGFR antagonist, and/or (iii) treating acquired EGFR antagonist resistance in a cancer cell, by contacting the cell with an EGFR antagonist and any of the anti-Axl antibodies described herein.

In exemplary embodiments, the cancer cell has acquired a resistance to an EGFR antagonist and comprises elevated levels of Axl activity and/or expression, e.g., associated with an activating mutation in the Axl gene, an Axl gene amplification, or Gas6 mediated Axl activation. The methods disclosed herein may be used to restore the sensitivity, reduce the resistance, and/or treat an acquired resistance, of a cancer cell.

In another aspect, the invention provides a method for reducing growth and/or proliferation of a cancer cell, or increasing apoptosis of a cancer cell, by contacting the cell with an EGFR antagonist and any of the anti-Axl antibodies described herein. In exemplary embodiments, the cancer cell has acquired a resistance to an EGFR antagonist and comprises elevated Axl activity and/or expression, e.g., associated with an activating mutation in the Axl gene, an Axl gene amplification, or Gas6 mediated Axl activation.

Pharmaceutical Compositions

Antibodies of the present invention will usually be administered in the form of a pharmaceutical composition, that may comprise at least one component in addition to the antibody.

Thus pharmaceutical compositions according to the present invention, and for use in accordance with the present invention, may comprise, in addition to active ingredient, a pharmaceutically acceptable excipient, carrier, buffer, stabiliser or other materials well known to those skilled in the art. Such materials should be non-toxic and should not interfere with the efficacy of the active ingredient. The precise nature of the carrier or other material will depend on the route of administration, which may be oral, or by injection, e.g. intravenous. The pharmaceutical compositions may be for human or animal usage in human and veterinary medicine.

Examples of such suitable excipients for the various different forms of pharmaceutical compositions described herein may be found in the "Handbook of Pharmaceutical Excipients", 2nd Edition, (1994), Edited by A Wade and P J Weller.

Acceptable carriers or diluents for therapeutic use are well known in the pharmaceutical art, and are described, for example, in Remington's Pharmaceutical Sciences, Mack Publishing Co. (A. R. Gennaro edit. 1985). Examples of suitable carriers include lactose, starch, glucose, methylcellulose, magnesium stearate, mannitol, sorbitol and the like. Examples of suitable diluents include ethanol, glycerol, water and buffered saline.

The choice of pharmaceutical carrier, excipient or diluent can be selected with regard to the intended route of administration and standard pharmaceutical practice. The pharmaceutical compositions may comprise as, or in addition to, the carrier, excipient or diluent any suitable binder(s), lubricant(s), suspending agent(s), coating agent(s), solubilising agent(s), buffer(s), flavouring agent(s), surface active agent(s), thickener(s), preservative(s) (including anti-oxidants) and the like, and substances included for the purpose of rendering the formulation isotonic with the blood of the intended recipient.

Examples of suitable binders include starch, gelatine, natural sugars such as glucose, anhydrous lactose, free-flow lactose, beta-lactose, corn sweeteners, natural and synthetic gums, such as acacia, tragacanth or sodium alginate, carboxymethyl cellulose and polyethylene glycol.

Examples of suitable lubricants include sodium oleate, sodium stearate, magnesium stearate, sodium benzoate, sodium acetate, sodium chloride and the like.

Preservatives, stabilizers, dyes and even flavouring agents may be provided in the pharmaceutical composition. Examples of preservatives include sodium benzoate, sorbic acid and esters of p hydroxybenzoic acid. Antioxidants and suspending agents may be also used.

Pharmaceutical formulations include those suitable for oral, topical (including dermal, buccal and sublingual), rectal or parenteral (including subcutaneous, intradermal, intramuscular and intravenous), nasal and pulmonary administration, e.g., by inhalation. The formulation may, where appropriate, be conveniently presented in discrete dosage units and may be prepared by any of the methods well known in the art of pharmacy. All methods include the step of bringing into association an active compound with liquid carriers or finely divided solid carriers or both and then, if necessary, shaping the product into the desired formulation. Pharmaceutical formulations suitable for oral administration wherein the carrier is a solid are most preferably presented as unit dose formulations such as boluses, capsules or tablets each containing a predetermined amount of active agent. A tablet may be made by compression or moulding, optionally with one or more accessory ingredients. Compressed tablets may be prepared by compressing in a suitable machine an active agent in a free-flowing form such as a powder or granules optionally mixed with a binder, lubricant, inert diluent, lubricating agent, surface-active agent or dispersing agent. Moulded tablets may be made by moulding an active agent with an inert liquid diluent. Tablets may be optionally coated and, if uncoated, may optionally be scored. Capsules may be prepared by filling an active agent, either alone or in admixture with one or more accessory ingredients, into the capsule shells and then sealing them in the usual manner. Cachets are analogous to capsules wherein an active agent together with any accessory ingredient(s) is sealed in a rice paper envelope. An active agent may also be formulated as dispersible granules, which may for example be suspended in water before administration, or sprinkled on food. The granules may be packaged, e.g., in a sachet. Formulations suitable for oral administration wherein the carrier is a liquid may be presented as a solution or a suspension in an aqueous or non-aqueous liquid, or as an oil-in-water liquid emulsion.

Formulations for oral administration include controlled release dosage forms, e.g., tablets wherein an active agent is formulated in an appropriate release—controlling matrix, or is coated with a suitable release—controlling film. Such formulations may be particularly convenient for prophylactic use.

Pharmaceutical formulations suitable for rectal administration wherein the carrier is a solid are most preferably presented as unit dose suppositories. Suitable carriers include cocoa butter and other materials commonly used in the art. The suppositories may be conveniently formed by admixture of an active agent with the softened or melted carrier(s) followed by chilling and shaping in moulds.

Pharmaceutical formulations suitable for parenteral administration include sterile solutions or suspensions of an active agent in aqueous or oleaginous vehicles.

Injectable preparations may be adapted for bolus injection or continuous infusion. Such preparations are conveniently presented in unit dose or multi-dose containers that are sealed after introduction of the formulation until required for use. Alternatively, an active agent may be in powder form which is constituted with a suitable vehicle, such as sterile, pyrogen-free water, before use.

An active compound may also be formulated as long-acting depot preparations, which may be administered by intramuscular injection or by implantation, e.g., subcutaneously or intramuscularly. Depot preparations may include, for example, suitable polymeric or hydrophobic materials, or ion-exchange resins. Such long-acting formulations are particularly convenient for prophylactic use.

Formulations suitable for pulmonary administration via the buccal cavity are presented such that particles containing an active compound and desirably having a diameter in the range of 0.5 to 7 microns are delivered in the bronchial tree of the recipient. As one possibility such formulations are in the form of finely comminuted powders which may conveniently be presented either in a pierceable capsule, suitably of, for example, gelatin, for use in an inhalation device, or alternatively as a self-propelling formulation comprising an active agent, a suitable liquid or gaseous propellant and optionally other ingredients such as a surfactant and/or a solid diluent. Suitable liquid propellants include propane and the chlorofluorocarbons, and suitable gaseous propellants include carbon dioxide. Self-propelling formulations may also be employed wherein an active agent is dispensed in the form of droplets of solution or suspension.

Such self-propelling formulations are analogous to those known in the art and may be prepared by established procedures. Suitably they are presented in a container provided with either a manually-operable or automatically functioning valve having the desired spray characteristics; advantageously the valve is of a metered type delivering a fixed volume, for example, 25 to 100 microliters, upon each operation thereof.

As a further possibility, an active agent may be in the form of a solution or suspension for use in an atomizer or nebuliser whereby an accelerated airstream or ultrasonic agitation is employed to produce a fine droplet mist for inhalation.

Formulations suitable for nasal administration include preparations generally similar to those described above for pulmonary administration. When dispensed such formulations should desirably have a particle diameter in the range 10 to 200 microns to enable retention in the nasal cavity; this may be achieved by, as appropriate, use of a powder of a suitable particle size or choice of an appropriate valve. Other suitable formulations include coarse powders having a particle diameter in the range 20 to 500 microns, for administration by rapid inhalation through the nasal passage from a container held close up to the nose, and nasal drops comprising 0.2 to 5% w/v of an active agent in aqueous or oily solution or suspension.

Pharmaceutically acceptable carriers are well known to those skilled in the art and include, but are not limited to, 0.1 M and preferably 0.05 M phosphate buffer or 0.8% saline.

Additionally, such pharmaceutically acceptable carriers may be aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's or fixed oils. Preservatives and other additives may also be present, such as, for example, antimicrobials, antioxidants, chelating agents, inert gases and the like.

Formulations suitable for topical formulation may be provided for example as gels, creams or ointments. Such preparations may be applied e.g. to a wound or ulcer either directly spread upon the surface of the wound or ulcer or carried on a suitable support such as a bandage, gauze, mesh or the like which may be applied to and over the area to be treated.

Liquid or powder formulations may also be provided which can be sprayed or sprinkled directly onto the site to be treated, e.g. a wound or ulcer. Alternatively, a carrier such as a bandage, gauze, mesh or the like can be sprayed or sprinkle with the formulation and then applied to the site to be treated.

According to a further aspect of the invention, there is provided a process for the preparation of a pharmaceutical or veterinary composition as described above, the process comprising bringing the active compound(s) into association with the carrier, for example by admixture. In general, the formulations are prepared by uniformly and intimately bringing into association the active agent with liquid carriers or finely divided solid carriers or both, and then if necessary shaping the product. The invention extends to methods for preparing a pharmaceutical composition comprising bringing an agent into association with a pharmaceutically or veterinary acceptable carrier or vehicle.

Administration

The pharmaceutical compositions of the present invention may be adapted for oral, rectal, nasal, intrabronchial, topical (including buccal and sublingual), vaginal or parenteral (including subcutaneous, intramuscular, intravenous, intraarterial and intradermal), intraperitoneal or intrathecal administration. Preferably, the formulation is an intravenously or subcutaneously administered formulation.

The formulations may conveniently be presented in unit dosage form, i.e., in the form of discrete portions containing a unit dose, or a multiple or sub-unit of a unit dose. By way of example, the formulations may be in the form of tablets and sustained release capsules, and may be prepared by any method well known in the art of pharmacy.

Formulations for oral administration in the present invention may be presented as: discrete units such as capsules, gellules, drops, cachets, pills or tablets each containing a predetermined amount of the active agent; as a powder or granules; as a solution, emulsion or a suspension of the active agent in an aqueous liquid or a non-aqueous liquid; or as an oil-in-water liquid emulsion or a water-in-oil liquid emulsion; or as a bolus etc. Preferably, these compositions contain from 1 to 250 mg and more preferably from 10-100 mg, of active ingredient per dose.

For compositions for oral administration (e.g. tablets and capsules), the term "acceptable carrier" includes vehicles such as common excipients e.g. binding agents, for example syrup, acacia, gelatine, sorbitol, tragacanth, polyvinylpyrrolidone (Povidone), methylcellulose, ethylcellulose, sodium carboxymethylcellulose, hydroxypropyl-methylcellulose, sucrose and starch; fillers and carriers, for example corn starch, gelatine, lactose, sucrose, microcrystalline cellulose, kaolin, mannitol, dicalcium phosphate, sodium chloride and alginic acid; and lubricants such as magnesium stearate, sodium stearate and other metallic stearates, glycerol stearate stearic acid, silicone fluid, talc waxes, oils and colloidal silica. Flavouring agents such as peppermint, oil of wintergreen, cherry flavouring and the like can also be used. It may be desirable to add a colouring agent to make the dosage form readily identifiable. Tablets may also be coated by methods well known in the art.

A tablet may be made by compression or moulding, optionally with one or more accessory ingredients. Compressed tablets may be prepared by compressing in a suitable machine the active agent in a free flowing form such as a powder or granules, optionally mixed with a binder, lubricant, inert diluent, preservative, surface-active or dispersing agent. Moulded tablets may be made by moulding in a suitable machine a mixture of the powdered compound moistened with an inert liquid diluent. The tablets may be optionally be coated or scored and may be formulated so as to provide slow or controlled release of the active agent.

Other formulations suitable for oral administration include lozenges comprising the active agent in a flavoured base, usually sucrose and acacia or tragacanth; pastilles comprising the active agent in an inert base such as gelatine and glycerine, or sucrose and acacia; and mouthwashes comprising the active agent in a suitable liquid carrier.

Other forms of administration comprise solutions or emulsions which may be injected intravenously, intra-arterially, intrathecally, subcutaneously, intradermally, intraperitoneally or intramuscularly, and which are prepared from sterile or sterilisable solutions. Injectable forms typically contain between 10-1000 mg, preferably between 10-250 mg, of active ingredient per dose.

The pharmaceutical compositions of the present invention may also be in form of suppositories, pessaries, suspensions, emulsions, lotions, ointments, creams, gels, sprays, solutions or dusting powders.

An alternative means of transdermal administration is by use of a skin patch. For example, the active ingredient can be incorporated into a cream consisting of an aqueous emulsion of polyethylene glycols or liquid paraffin. The active ingredient can also be incorporated, at a concentration of between 1 and 10% by weight, into an ointment consisting of a white wax or white soft paraffin base together with such stabilisers and preservatives as may be required.

Alternative formulation strategies may provide preparations suitable for oral or suppository route. The route of administration may be determined by the physicochemical characteristics of the treatment, by special considerations for the disease, to optimise efficacy or to minimise side-effects.

A further mode of administration employs pre-coating of, or otherwise incorporation into, indwelling devices, for which the optimal amount of antibody will be determined by means of appropriate experiments.

An antibody molecule in some preferred embodiments of the invention is a monomeric fragment, such as Fab or scFv. Such antibody fragments may have the feature of a relatively short half-life.

Dosage

A person of ordinary skill in the art can easily determine an appropriate dose of one of the instant compositions to administer to a subject without undue experimentation. Typically, a physician will determine the actual dosage which will be most suitable for an individual patient and it will depend on a variety of factors including the activity of the specific agent employed, the metabolic stability and length of action of that agent, the age, body weight, general health, sex, diet, mode and time of administration, rate of excretion, drug combination, the severity of the particular condition, and the individual undergoing therapy.

In accordance with the present invention, compositions provided may be administered to individual patients. Administration is preferably in a "therapeutically effective amount", this being sufficient to show benefit to a patient. Such benefit may be at least amelioration of at least one symptom. The actual amount administered, and the rate and time-course of administration, will depend on the nature and severity of what is being treated. Prescription of treatment, e.g., decisions on dosage etc., is within the responsibility of general practitioners and other medical doctors. Appropriate doses of antibody are well known in the art; see Ledermann J. A. et al. (1991) Int. J. Cancer 47: 659-664; Bagshawe, K. D. et al. (1991) Antibody, Immunoconjugates and Radiopharmaceuticals 4: 915-922.

The precise dose will depend upon a number of factors, including whether the antibody is for diagnosis or for treatment, the size and location of the area to be treated, the precise nature of the antibody (e.g. whole antibody, antibody fragment or diabody), and the nature of any detectable label or other molecule attached to the antibody. A typical antibody dose may be administered as a bolus intravenously. Other modes of administration include intravenous infusion over several hours, to achieve a similar total cumulative dose. This is a dose for a single treatment of an adult patient, which may be proportionally adjusted for children and infants, and also adjusted for other antibody formats in proportion to molecular weight. Treatments may be repeated at daily, twice-weekly, weekly or monthly intervals, at the discretion of the physician.

The dosages disclosed herein are exemplary of the average case. There can of course be individual instances where higher or lower dosage ranges are merited, and such are within the scope of this invention.

In accordance with this invention, an effective amount of agent may be administered to inhibit Axl. Of course, this dosage amount will further be modified according to the type of administration of the agent. For example, to achieve an "effective amount" for acute therapy, parenteral administration is preferred. An intravenous infusion of the compound in 5% dextrose in water or normal saline, or a similar formulation with suitable excipients, is most effective, although an intramuscular bolus injection is also useful. Typically, the parenteral dose will be about 0.01 to about 100 mg/kg; preferably between 0.1 and 20 mg/kg, in a manner to maintain the concentration of drug in the plasma at a concentration effective to inhibit a kinase or saturate the target receptor. The agents may be administered one to four times daily at a level to achieve a total daily dose of about 0.4 to about 400 mg/kg/day. The precise amount of an active agent that is therapeutically effective, and the route by which such agent is best administered, is readily determined by one of ordinary skill in the art by comparing the blood level of the agent to the concentration required to have a therapeutic effect.

The agents of this invention may also be administered orally to the patient, in a manner such that the concentration of drug is sufficient to achieve one or more of the therapeutic indications disclosed herein. Typically, a pharmaceutical composition containing the agent is administered at an oral dose of between about 0.1 to about 50 mg/kg in a manner consistent with the condition of the patient. Preferably, the oral dose would be about 0.5 to about 20 mg/kg.

The agents of this invention may be tested in one of several biological assays to determine the concentration of an agent that is required to have a given pharmacological effect.

Combination Therapy

The anti-Axl antibodies of the invention may be administered alone or in combination with other treatments, either simultaneously or sequentially dependent upon the condition to be treated. For example, the antibodies of the invention or conjugates thereof may be used as an anti-cancer monotherapy or in combination therapy with other cancer treatments as mentioned below. Other treatments may include the administration of suitable doses of pain relief drugs such as non-steroidal anti-inflammatory drugs (e.g. aspirin, ibuprofen or ketoprofen) or opiates such as morphine, or anti-emetics.

Suitable Agents for Use in Combination Therapy

These include alkylating agents, e.g., alkyl sulfonates such as busulfan;

nitrogen mustards such as chlorambucil, cyclophosphamide, estramustine, ifosfamide, mechlorethamine, melphalan, and uramustine, ethyleneimine derivatives such as thiotepa;

nitrosoureas such as carmustine, lomustine, and streptozocin, triazenes such as dacarbazine, procarbazine, and temozolamide;

platinum compounds such as cisplatin, carboplatin, oxaliplatin, satraplatin, and picoplatin onnaplatin, tetraplatin, sprioplatin, iproplatin, chloro(diethylenediamino)-platinum (II) chloride, dichloro(ethylenediamino)-platinum (II), diamino(2-ethylmalonato)platinum (II), (1,2-diaminocyclohexane)malonatoplatinum (II), (4-carboxyphthalo)-(1,2-diaminocyclohexane)platinum (II), (1,2-diaminocyclohexane)-(isocitrato)platinum (II), and (1,2-diaminocyclohexane)-cis-(pyruvato)platinum (II);

anti-metabolites, including antifolates such as methotrexate, permetrexed, raltitrexed, and trimetrexate;

pyrimidine analogs such as azacitidine, capecitabine, cytarabine, edatrexate, floxuridine, fluorouracil, gemcitabine, and troxacitabine;

purine analogs such as cladribine, chlorodeoxyadenosine, clofarabine, fludarabine, mercaptopurine, pentostatin, and thioguanine;

natural products, including antitumor antibiotics such as bleomycin, dactinomycin, mithramycin, mitomycin, mitoxantrone, porfiromycin, and anthracyclines such as daunorubicin, doxorubicin, epirubicin, idarubicin, and valrubicin;

mitotic inhibitors such as the vinca alkaloids vinblastine, vinvesir, vincristine, vindesine, and vinorelbine;

enzymes such as L-asparaginase and PEG-L-asparaginase;

microtubule polymer stabilizers such as the taxanes paclitaxel and docetaxel;

topoisomerase I inhibitors such as the camptothecins irinotecan and topotecan; topoisomerase II inhibitors such as podophyllotoxin, amsacrine, etoposide, teniposide, losoxantrone and actinomycin;

hormones and hormone antagonists, including androgens such as fluoxymesterone and testolactone, anti-androgens such as bicalutamide, cyproterone, flutamide, and nilutamide; corticosteroids such as dexamethasone and prednisone;

aromatase inhibitors such as aminoglutethimide, anastrozole, exemestane, formestane, and letrozole;

estrogens such as diethylstilbestrol;

anti-estrogens such as fulvestrant, raloxifene, tamoxifen, and toremifine;

luteinising hormone-releasing hormone (LHRH) agonists and antagonists such as abarelix, buserelin, goserelin, leuprolide, histrelin, desorelin, nafarelin acetate and triptorelin;

progestins such as medroxyprogesterone acetate and megestrol acetate, and thyroid hormones such as levothyroxine and liothyronine;

PKB pathway inhibitors, including perifosine, enzastaurin hydrochloride, and triciribine;

PI3K inhibitors such as semaphore and SF1126;

mTOR inhibitors such as rapamycin and analogues;

CDK inhibitors, including seliciclib, alvocidib, and 7-hydroxystaurosporine;

COX-2 inhibitors, including celecoxib;

HDAC inhibitors, including trichostatin A, suberoylanilide hydroxamic acid, and chlamydocin;

DNA methylase inhibitors, including temozolomide; and miscellaneous agents, including altretamine, arsenic trioxide, thalidomide, lenalidomide, gallium nitrate, levamisole, mitotane, hydroxyurea, octreotide, procarbazine, suramin, photodynamic compounds such as methoxsalen and sodium porfimer, and proteasome inhibitors such as bortezomib.

Molecular targeted therapy agents including:

functional therapeutic agents, e.g., gene therapy agents; antisense therapy agents;

tyrosine kinase inhibitors such as erlotinib hydrochloride, gefitinib, imatinib mesylate, and semaxanib;

RAF inhibitors such as sorafenib;

gene expression modulators such as the retinoids and rexinoids, for example adapalene, bexarotene, trans-retinoic acid, 9-cis-retinoic acid, and N-(4-hydroxyphenyl)retinamide;

phenotype-directed therapy agents, including monoclonal antibodies such as alemtuzumab, bevacizumab, cetuximab, ibritumomab tiuxetan, rituximab, and trastuzumab;

immunotoxins such as emtansine, radioimmunoconjugates such as 1-tositumobab, and cancer vaccines.

Biologic therapy agents including:

interferons such as interferon-[alpha]2a and interferon-[alpha]2b, and interleukins such as aldesleukin, denileukin diftitox, and oprelvekin. Axl inhibiting agents including 1-(6,7-dihydro-5H-benzo[6,7]cyclohepta[1,2-c]pyridazin-3-yl)-N3-((7-(S)-pyrrolidin-1-yl)-6,7,8,9-tetrahydro-5H-benzo[7]annulene-2-yl)-1H-1,2,4-triazole-3,5-diamine (BGB324/R428), CH5451098 (Roche) and Axl inhibitors described in PCT/US07/089177, PCT/US2010/021275 and PCT/EP2011/004451, incorporated herein by reference.

In addition to these agents intended to act against cancer cells, anticancer therapies include the use of protective or adjunctive agents, including:

cytoprotective agents such as amifostine, and dexrazoxane;

phosphonates such as pamidronate and zoledronic acid; and stimulating factors such as epoetin, darbeopetin, filgrastim, PEG-filgrastim, and sargramostim.

Many combination chemotherapeutic regimens are known to the art, such as combinations of carboplatin/paclitaxel, capecitabine/docetaxel, fluorauracil/levamisole, fluorauracil/leucovorin, methotrexate/leucovorin, and trastuzumab/paclitaxel, alone or in further combination with carboplatin, and the like.

Immune Checkpoint Modulators

A particularly preferred class of agent for use in combination with the anti-Axl antibodies disclosed herein are Immune Checkpoint Modulators (ICMs) such as Immune Checkpoint Inhibitors (ICIs).

Immune checkpoints, which are inhibitory pathways in the immune system, may be co-opted by tumours to induce immune resistance. The use of antibodies to block or modulate immune checkpoints, including T-cell stimulatory and inhibitory receptors and dendritic cell stimulatory receptors, and thus to reduce or reverse the immune resistance of the cancer, is thus an important avenue in cancer research.

T-cell stimulatory receptors that may be modulated through the use of immune checkpoint modulating antibodies include CD28, ICOS, 4-1BB, OX40, GITR, CD27, TWEAKR, HVEM and TIM-1. T-cell inhibitory receptors that maybe modulated through the use of immune checkpoint modulating antibodies include PD-L1, CTLA-4, PD-1, BTLA, TIM-3, VISTA, LAG-3 and TIGIT. Dendritic cell stimulatory receptors that may be modulated through the use of immune checkpoint modulating antibodies include CD40 and 4-1BB.

Thus ICMs suitable for use in combination with the anti-Axl antibodies disclosed herein include the immune checkpoint modulating, or inhibiting, antibodies of which there are many known in the art. Particularly suitable immune checkpoint modulating antibodies include:

CTLA-4 targeting antibodies, including Ipilimumab and Tremelimumab.

PD-1 targeting antibodies, including Pembrolizumab, Mivolumab and AMP-514/MED10680.

BD-L1 targeting antibodies, including MPDL3280A, MED14736, MSB0010718C and BMS-936559.

4-1BB targeting antibodies, including Urelumab and PF-05082566.

OX-40 targeting antibodies, including MED16469, MED16383 (rOX40L) and MOXR0916.

GITR targeting antibodies, including TRX518.

CD27 targeting antibodies, including CDX-1127.

CD40 targeting antibodies, including CP-870,893.

LAG3 targeting antibodies, including BMS-986016.

Where a combination of ICM antibodies are used in conjunction with an anti-AXL antibody of the invention, all of the ICM antibodies used may target inhibitory receptors, all of the ICM antibodies used may target stimulatory receptors, or a combination of inhibitory receptor and stimulatory receptor targeting ICM antibodies may be used.

The disclosure therefore provides an antibody that binds Axl, as described herein, for use in treatment (of, for example, a proliferative disease such as cancer), wherein the treatment further comprises one or more immune checkpoint modulating antibodies. Likewise, there is provided an antibody that binds Axl, as described herein, in the manufacture of a medicament for the treatment of a proliferative disease (such as cancer), wherein the treatment further comprises one or more immune checkpoint modulating antibodies. The antibodies may be selected from Ipilimumab, Tremelimumab, Pembrolizumab, Mivolumab, AMP-514/MED10680, MPDL3280A, MED14736, MSB0010718C, BMS-936559, Urelumab, PF-05082566, MED16469, MED16383 (rOX40L), MOXR0916, TRX518, CDX-1127, CP-870,893 and BMS-986016. The cancer may be selected from lung cancer, melanoma, breast cancer, ovarian cancer or carcinoma.

The compound of the invention may be administered before the one or more immune checkpoint modulating antibodies, simultaneously with the one or more immune checkpoint modulating antibodies, or after the one or more immune checkpoint modulating antibodies.

Anti-Tumour Antibodies

Another particularly preferred class of agent for use in combination with the anti-Axl antibodies of the present invention are anti-tumour antibodies specific for a target other than Axl. Such antibodies suitable for use in combination with the anti-Axl antibodies of the present invention are set out in the table below:

| Antigen category | Examples of antigens | Examples of therapeutic mAbs raised against these targets | Tumor types expressing antigen |
| --- | --- | --- | --- |
| Haematopoietic differentiation antigens | CD20 | Rituximab | Non-Hodgkin's lymphoma |
| | | Ibritumomab tiuxetan and tositumomab | Lymphoma |
| | CD30 | Brentuximab vedotin | Hodgkin's lymphoma |
| | CD33 | Gemtuzumab ozogamicin | Acute myelogenous leukaemia |
| | CD52 | Alemtuzumab | Chronic lymphocytic leukaemia |
| Glycoproteins expressed by solid tumours | EpCAM | IGN101 and adecatumumab | Epithelial tumours (breast, colon and lung) |
| | CEA | Labetuzumab | Breast, colon and lung tumours |
| | gpA33 | huA33 | Colorectal carcinoma |
| | Mucins | Pemtumomab and oregovomab | Breast, colon, lung and ovarian tumours |
| | TAG-72 | CC49 (minretumomab) | Breast, colon and lung tumours |
| | CAIX | cG250 | Renal cell carcinoma |
| | PSMA | J591 | Prostate carcinoma |
| | Folate-binding protein | MOv18 and MORAb-003 (farletuzumab) | Ovarian tumours |
| Glycolipids | Gangliosides (such as GD2, GD3 and GM2) | 3F8, ch14.18 and KW-2871 | Neuroectodermal tumours and some epithelial tumours |
| Carbohydrates | Le$^y$ | hu3S193 and IgN311 | Breast, colon, lung and prostate tumours |
| Targets of anti-angiogenic mAbs | VEGF | Bevacizumab | Tumour vasculature |
| | VEGFR | IM-2C6 and CDP791 | Epithelium-derived solid tumours |
| | Integrin αVβ3 | Etaracizumab | Tumour vasculature |
| | Integrin α5β1 | Volociximab | Tumour vasculature |
| Growth and differentiation signalling | EGFR | Cetuximab, panitumumab, nimotuzumab and 806 | Glioma, lung, breast, colon, and head and neck tumours |
| | ERBB2 | Trastuzumab and pertuzumab | Breast, colon, lung, ovarian and prostate tumours |
| | ERBB3 | MM-121 | Breast, colon, lung, ovarian and prostate, tumours |
| | MET | AMG 102, METMAB and SCH 900105 | Breast, ovary and lung tumours |

-continued

| Antigen category | Examples of antigens | Examples of therapeutic mAbs raised against these targets | Tumor types expressing antigen |
|---|---|---|---|
| | IGF1R | AVE1642, IMC-A12, MK-0646, R1507 and CP 751871 | Glioma, lung, breast, head and neck, prostate and thyroid cancer |
| | EPHA3 | KB004 and IIIA4 | Lung, kidney and colon tumours, melanoma, glioma and haematological malignancies |
| | TRAILR1 | Mapatumumab (HGS-ETR1) | Colon, lung and pancreas tumours and haematological malignancies |
| | TRAILR2 | HGS-ETR2 and CS-1008 | |
| | RANKL | Denosumab | Prostate cancer and bone metastases |
| Stromal and extracellular matrix antigens | FAP | Sibrotuzumab and F19 | Colon, breast, lung, pancreas, and head and neck tumours |
| | Tenascin | 81C6 | Glioma, breast and prostate tumours |

Throughout the specification, preferably the methods described herein are performed in vitro or ex vivo. Methods can also be performed in vivo.

Reporters and Assays

The present invention provides a method comprising causing or allowing binding of an antibody as provided herein to Axl. As noted, such binding may take place in vivo, e.g. following administration of an antibody, or nucleic acid encoding an antibody, or it may take place in vitro, for example in ELISA, Western blot analysis, immunocytochemistry, immunohistochemistry, immunoprecipitation or affinity chromatography.

The amount of antibody bound to Axl receptor may be determined. Quantitation may be related to the amount of the antigen in a test sample, which may be of diagnostic interest.

The reactivity of antibody in a sample may be determined by any appropriate means. Radioimmunoassay (RIA) is one possibility. Radioactively labelled antigen is mixed with unlabelled antigen (the test sample) and allowed to bind to the antibody. Bound antigen is physically separated from unbound antigen and the amount of radioactive antigen bound to the antibody determined. The more antigen there is in the test sample the less radioactive antigen will bind to the antibody. A competitive binding assay may also be used with non-radioactive antigen, using antigen or an analogue linked to a reporter molecule. The reporter molecule may be a fluorochrome, phosphor or laser dye with spectrally isolated absorption or emission characteristics. Suitable fluorochromes include fluorescein, rhodamine, phycoerythrin and Texas Red. Suitable chromogenic dyes include diaminobenzidine.

Other reporters include macromolecular colloidal particles or particulate material such as latex beads that are coloured, magnetic or paramagnetic, and biologically or chemically active agents that can directly or indirectly cause detectable signals to be visually observed, electronically detected or otherwise recorded. These molecules may be enzymes which catalyse reactions that develop or change colours or cause changes in electrical properties, for example. They may be molecularly excitable, such that electronic transitions between energy states result in characteristic spectral absorptions or emissions. They may include chemical entities used in conjunction with biosensors. Biotin/avidin or biotin/streptavidin and alkaline phosphatase detection systems may be employed.

The signals generated by individual antibody-reporter conjugates may be used to derive quantifiable absolute or relative data of the relevant antibody binding in samples (normal and test).

The present invention also provides the use of an antibody as above for measuring antigen levels in a competition assay, that is to say a method of measuring the level of antigen in a sample by employing an antibody as provided by the present invention in a competition assay. This may be where the physical separation of bound from unbound antigen is not required. Linking a reporter molecule to the antibody so that a physical or optical change occurs on binding is one possibility. The reporter molecule may directly or indirectly generate detectable, and preferably measurable, signals. The linkage of reporter molecules may be directly or indirectly, covalently, e.g. via a peptide bond or non-covalently. Linkage via a peptide bond may be as a result of recombinant expression of a gene fusion encoding antibody and reporter molecule.

The present invention also provides for measuring levels of antigen directly, by employing an antibody according to the invention for example in a biosensor system.

The mode of determining binding is not a feature of the present invention and those skilled in the art are able to choose a suitable mode according to their preference and general knowledge.

Competing Antibodies

The present invention further extends to an antibody that competes for binding to Axl with any antibody that both binds the antigen and comprises an antibody variable domain (either VH or VL or both) including a CDR with amino acid substantially as set out herein or a variable domain with amino acid sequence substantially as set out herein. Competition between the antibodies may be assayed easily in vitro, for example by tagging a specific reporter molecule to one binding member that can be detected in the presence of other untagged binding member(s), to enable identification of antibodies that bind the same epitope or an overlapping epitope. Competition may be determined for example using ELISA or flow cytometry. Alternatively, competing antibodies may be identified via surface plasmon resonase (SPR) technique using Biacore instrument, as described in Example 6.

In another method, to screen for antibodies that bind to the epitope on Axl bound by an antibody of interest (e.g., those that block binding of the 10G5 antibody to Axl), a routine cross-blocking assay such as that described in Antibodies. A Laboratory Manual. Cold Spring Harbor Laboratory. Ed Harlow and David Lane (1988), can be performed.

In testing for competition, a peptide fragment of the antigen may be employed, especially a peptide including an epitope of interest. A peptide having the epitope sequence plus one or more amino acids at either end may be used. Such a peptide may be said to "consist essentially" of the specified sequence. Antibodies according to the present invention may be such that their binding for antigen is inhibited by a peptide with or including the sequence given. In testing for this, a peptide with either sequence plus one or more amino acids may be used.

Antibodies that bind a specific peptide may be isolated for example from a phage display library by panning with the peptide(s).

Nucleic Acids, Constructs, and Expression

The present invention further provides an isolated nucleic acid encoding an antibody of the present invention. Nucleic acid includes DNA and RNA. In a preferred aspect, the present invention provides a nucleic acid that codes for a CDR, VH or VL domain of the invention as defined above.

The present invention also provides constructs in the form of plasmids, vectors, transcription or expression cassettes that comprise at least one polynucleotide as above.

The present invention also provides a recombinant host cell that comprises one or more constructs as above. A nucleic acid encoding any CDR, VH or VL domain, or antibody as provided, itself forms an aspect of the present invention, as does a method of production of the encoded product, which method comprises expression from encoding nucleic acid therefor. Expression may conveniently be achieved by culturing under appropriate conditions recombinant host cells containing the nucleic acid. Following production by expression, a VH or VL domain, or antibody may be isolated and/or purified using any suitable technique known in the art.

Antibodies, VH and/or VL domains, and encoding nucleic acid molecules and vectors according to the present invention may be provided isolated and/or purified, e.g. from their natural environment, in substantially pure or homogeneous form, or, in the case of nucleic acid, free or substantially free of nucleic acid or genes of an origin other than the sequence encoding a polypeptide with the required function. Nucleic acid according to the present invention may comprise DNA or RNA and may be wholly or partially synthetic. Reference to a nucleotide sequence as set out herein encompasses a DNA molecule with the specified sequence, and encompasses a RNA molecule with the specified sequence in which U is substituted for T, unless context requires otherwise.

Systems for cloning and expression of a polypeptide in a variety of different host cells are well known. Suitable host cells include bacteria, mammalian cells, yeast, baculovirus, and insect cell systems. Mammalian cell lines available in the art for expression of a heterologous polypeptide include Chinese hamster ovary cells (CHO), HeLa cells, baby hamster kidney (BHK) cells, NSO and SP2/0 mouse myeloma cells, YB2/0 rat myeloma cells, human cell lines HEK-293 and PER.C6 and many others. A common, preferred bacterial host is E. coli.

The expression of antibodies and antibody fragments in prokaryotic cells such as E. coli is well established in the art. For a review, see for example Plückthun, A. Bio/Technology 9: 545-551 (1991). Expression in eukaryotic cells in culture is also available to those skilled in the art as an option for production of an antibody, see for reviews, for example Ref, M. E. (1993) Curr. Opinion Biotech. 4: 573-576; Trill J. J. et al. (1995) Curr. Opinion Biotech 6: 553-560.

Suitable vectors can be chosen or constructed, containing appropriate regulatory sequences, including promoter sequences, terminator sequences, polyadenylation sequences, enhancer sequences, marker genes and other sequences as appropriate. Vectors may be plasmids, viral e.g. phage, or phagemid, as appropriate (Sambrook and Russell, 2001, Molecular Cloning: a Laboratory Manual: $3^{rd}$ edition, Cold Spring Harbor Laboratory Press). Many known techniques and protocols for manipulation of nucleic acid, for example in preparation of nucleic acid constructs, mutagenesis, sequencing, introduction of DNA into cells and gene expression, and analysis of proteins, are described in detail in Current Protocols in Molecular Biology, Second Edition, Ausubel et al. eds., John Wiley & Sons, 1992.

Thus, a further aspect of the present invention provides a host cell containing nucleic acid as disclosed herein. A still further aspect provides a method comprising introducing such nucleic acid into a host cell. The introduction may employ any available technique. For eukaryotic cells, suitable techniques may include calcium phosphate transfection, DEAE-Dextran, electroporation, liposome-mediated transfection and transduction using retrovirus or other virus, e.g. vaccinia or, for insect cells, baculovirus. For bacterial cells, suitable techniques may include calcium chloride transformation, electroporation and transfection using bacteriophage.

The introduction may be followed by causing or allowing expression from the nucleic acid, e.g. by culturing host cells under conditions for expression of the gene.

In one embodiment, the nucleic acid of the invention is integrated into the genome (e.g. chromosome) of the host cell. Integration may be promoted by inclusion of sequences that promote recombination with the genome, in accordance with standard techniques.

The present invention also provides a method that comprises using a construct as stated above in an expression system in order to express an antibody or polypeptide as above.

Aspects and embodiments of the present invention will now be illustrated by way of example with reference to the following experimentation.

All documents cited anywhere in this specification are incorporated by reference.

STATEMENTS OF INVENTION

The following paragraphs describe a number of specifically envisioned embodiments and combinations of the present invention.

1. An antibody that binds Axl and which comprises:
a VH domain comprising a VH CDR3 with the amino acid sequence of SEQ ID NO: 32 and optionally one or more VH CDR's with an amino acid sequence selected from SEQ ID NO: 31 and SEQ ID NO: 30; and/or a VL domain comprising one or more VL CDR's with an amino acid sequence selected from SEQ ID NO: 33, SEQ ID NO: 34 and SEQ ID NO: 35.

2. The antibody according to paragraph 1 which comprises:
a VH domain comprising the VH CDR's with the amino acid sequences of SEQ ID NO: 30, SEQ ID NO: 31 and SEQ ID NO: 32.

3. The antibody according to either one of statements 1 or 2 which comprises:
a VL domain comprising the VL CDR's with the amino acid sequences of SEQ ID NO: 33, SEQ ID NO: 34 and SEQ ID NO: 35.

4. The antibody according to any preceding statement which comprises:
an antibody VH domain selected from the group consisting of the 10G5 VH(GH1) domain (SEQ ID NO: 1) and the 10G5 VH(GH2) domain (SEQ ID NO: 2); and/or
an antibody VL domain selected from the group consisting of the 10G5 VL(GL1) domain (SEQ ID NO: 3) and the 10G5 VL(GL2) domain (SEQ ID NO: 4)

5. An antibody according to any preceding paragraph comprising the 10G5 VH(GH1) domain (SEQ ID NO: 1).

6. An antibody according to any preceding paragraph comprising the 10G5 VH(GH2) domain (SEQ ID NO: 2).

7. An antibody according to any preceding paragraph comprising the 10G5 VL(GL1) domain (SEQ ID NO: 3).

8. An antibody according to any preceding paragraph comprising the 10G5 VL(GL2) domain (SEQ ID NO: 4).

9. An antibody according to any preceding paragraph that comprises a scFv antibody molecule.

10 An antibody according to any preceding paragraph that comprises an antibody constant region.

11. An antibody according to paragraph 10 wherein the heavy chain constant region has the sequence set out in SEQ ID NO: 5.

12. An antibody according to any preceding paragraph that comprises the 10G5 GH1 Heavy chain (SEQ ID NO: 6).

13. An antibody according to any preceding paragraph that comprises the 10G5 GH2 Heavy chain (SEQ ID NO: 7).

14. An antibody according to any preceding paragraph that comprises a light chain constant region.

15. An antibody according to paragraph 14 wherein the light chain constant region has the sequence set out in SEQ ID NO: 8.

16. An antibody according to any preceding paragraph that comprises the 10G5 GL1 Light chain (SEQ ID NO: 9).

17. An antibody according to any preceding paragraph that comprises the 10G5 GL2 Light chain (SEQ ID NO: 10).

18. An antibody according to paragraph 17 that comprises a whole antibody.

19. An antibody according to any one of paragraphs 1 to 18 that comprises additional amino acids providing a further functional characteristic in addition to the ability to bind antigen.

20. An antibody according to any one of paragraphs 1 to 19 that binds Axl with a $K_D$ at least 15% lower than a chimeric antibody comprising the VH of SEQ ID NO: 12 and the VL of SEQ ID NO: 13.

21. An antibody according to any one of paragraphs 1 to 20 that binds Axl with a $K_D$ no greater than $10^{-9}$ M.

22. An antibody according to any one of paragraphs 1 to 21 that has an $EC_{50}$ at least 15% lower than a chimeric antibody comprising the VH of SEQ ID NO: 12 and the VL of SEQ ID NO: 13.

23. An antibody according to any one of paragraphs 1 to 22 that has been defucosylated.

24. An antibody according to any one of paragraphs 1 to 23 wherein the Axl is human Axl.

25. An antibody according to any one of paragraphs 1 to 24 that specifically binds primate Axl.

26. An antibody according to any one of paragraphs 1 to 25 that:
(i) binds murine Axl with a $K_D$ greater than $10^{-3}$ M;
(ii) binds human Mer with a $K_D$ greater than $10^{-3}$ M; and/or
(iii) binds human Tyro3 with a $K_D$ greater than $10^{-3}$ M.

27. An antibody according to any one of paragraphs 1 to 26 that inhibits the binding of Axl to Gas6.

28. An antibody according to any one of paragraphs 1 to 27 that down-regulates expression of the Axl receptor.

29. An antibody according to paragraph 28, wherein the antibody reduces Axl receptor expression to less than 50% of the level observed in an otherwise identically treated sample that is not contacted with to the antibody.

30. An antibody according to either one of paragraphs 28 or 29, wherein the downregulation of Axl receptor expression is observed within 12 hours of contacting the sample with the antibody.

31. An antibody according to any one of paragraphs 28 to 30, wherein the down regulation of Axl receptor expression persists for at least 24 hours following contacting the sample with the antibody.

32. An antibody according to any one of paragraphs 1 to 31 that increases the rate of Axl receptor internalization.

33. An antibody according to any one of paragraphs 1 to 32 that inhibits Axl activity.

34. An antibody according to any preceding paragraph, wherein the antibody inhibits Axl autophosphorylation.

35. An antibody according to either one of paragraphs 33 or 34, wherein the antibody inhibits Axl receptor downstream signalling.

36. An antibody according to any one of paragraphs 33 to 35, wherein the phosphorylation of Akt at Serine 473 in a sample contacted with the antibody of the invention is less than 50% of the level observed in an otherwise identically treated sample that is not contacted with the antibody 37. An antibody according to any one of paragraphs 1 to 36 that increases the rate of cell death.

38. An antibody according to any one of paragraphs 1 to 37 that inhibits tumour growth.

39. An antibody according to any one of paragraphs 1 to 38 that reduces the expression of fibrotic markers, such as alpha-SMA, Col1A1, MCP1 and/or TGF-beta.

40. An antibody according to any one of paragraphs 1 to 39 that is conjugated to a detectable label, enzyme, or toxin, optionally via a peptidyl bond or linker.

41. An antibody according to paragraph 40 wherein the toxin is selected from the group comprising MMAE and MMAF.

42. An antibody according to paragraph 40 wherein the detectable label is FITC.

43. An antibody according to any one of paragraphs 1 to 42 binds to the epitope bound by the 10G5 antibody obtainable from the hybridoma WR-10G5-E5.

44. An isolated nucleic acid that comprises a nucleotide sequence encoding an antibody or antibody VH or VL domain of an antibody according to any one of paragraphs 1 to 39.

45. A host cell transformed with nucleic acid according to paragraph 44.

46. A method of producing an antibody or antibody VH or VL domain, the method comprising culturing host cells according to paragraph 40 under conditions for production of said antibody or antibody VH or VL domain.

47. A method according to paragraph 46 further comprising isolating and/or purifying said antibody or antibody VH or VL variable domain.

48. A method according to paragraph 46 or paragraph 47 further comprising formulating the antibody or antibody VH or VL variable domain into a composition including at least one additional component.

49. A composition comprising an antibody according to any one of paragraphs 1 to 39, or an immunoconjugate thereof, in conjunction with a pharmaceutically acceptable excipient.

50. The composition according to paragraph 49, further comprising an Immune Checkpoint Modulator, and/or an anti-tumour antibody specific for a target other than Axl.

51. The composition according to paragraph 49, further comprising a second anti-Axl antibody, wherein the second anti-Axl antibody does not compete with the 10G5 antibody obtainable from the hybridoma WR-10G5-E5 for Axl binding.

52. The composition according to paragraph 50, wherein the Immune Checkpoint Modulator is an antibody, such as Ipilimumab, Tremelimumab, Pembrolizumab, Mivolumab, AMP-514/MED10680, MPDL3280A, MED14736, MSB0010718C, BMS-936559, Urelumab, PF-05082566, MED16469, MED16383 (rOX40L), MOXR0916, TRX518, CDX-1127, CP-870,893 or BMS-986016.

53. The composition according to paragraph 50, wherein the anti-tumour antibody specific for a target other than Axl is selected from the group consisting of Rituximab, Ibritumomab tiuxetan, tositumomab, Brentuximab vedotin, Gemtuzumab ozogamicin, Alemtuzumab, IGN101, adecatumumab, Labetuzumab, huA33, Pemtumomab, oregovomab, CC49 (minretumomab), cG250, J591, MOv18, MORAb-003 (farletuzumab), 3F8, ch14.18, KW-2871, hu3S193, IgN311, Bevacizumab, IM-2C6, CDP791, Etaracizumab, Volociximab, Cetuximab, panitumumab, nimotuzumab 806, Trastuzumab, pertuzumab, MM-121, AMG 102, METMAB, SCH 900105, AVE1642, IMC-A12, MK-0646, R1507, CP 751871, KB004, IIIA4, Mapatumumab (HGS-ETR1), HGS-ETR2, CS-1008, Denosumab, Sibrotuzumab, F19, 8106.

54. An antibody according to any one of paragraphs 1 to 42, or the composition according to any one of paragraphs 49 to 53, for use in a method of treatment.

55. An antibody or composition according to paragraph 54 for use in a method of treating a fibrotic disorder.

56. An antibody or composition according to paragraph 54 for use in a method of treating a proliferative disease.

57. An antibody or composition according to paragraph 56 where the proliferative disease is cancer.

58. An antibody or composition according to paragraph 57 where the cancer is metastatic cancer.

59. Use of an antibody according to any one of paragraphs 1 to 42, or the composition according to any one of paragraphs 49 to 53, in the manufacture of a medicament for treatment of a disease or disorder characterised by increased expression or activity of Axl.

60. A method of treatment of a disease or disorder characterised by increased expression or activity of Axl, the method comprising administering an antibody according to any one of paragraphs 1 to 43, or the composition according to any one of paragraphs 49 to 53, to a patient with the disease or disorder or at risk of developing the disease or disorder.

61. An antibody according to any one of paragraphs 54 to 58, or method of claim 60, wherein the method of treatment comprises administering the antibody according to any one of paragraphs 1 to 41, or the composition according to any one of paragraphs 49 to 53, in combination with an Immune Checkpoint Modulator and/or an anti-tumour antibody specific for a target other than Axl.

62. A method according to paragraph 60 wherein the antibody directs the delivery of a pharmaceutical composition to target metastatic cancer cells.

63. Use of an antibody according to any one of paragraphs 1 to 41 and one or more reagents that allow determination of the binding of said antibody to metastatic cancer cells, in the manufacture of a diagnostic agent for the detection of a disease or disorder characterised by overexpression of Axl.

64. A method of diagnosis of a disease or disorder characterised by overexpression of Axl, the method comprising administering an antibody according to any one of paragraphs 1 to 32, or the composition according to any one of paragraphs 49 to 53, and one or more reagents that allow determination of the binding of said antibody to metastatic cancer cells, to a patient with the disease or disorder or at risk of developing the disease or disorder.

65. A diagnostic kit comprising an antibody according to any one of paragraphs 1 to 41 and one or more reagents that allow determination of the binding of said member to metastatic cancer cells.

66. A kit comprising an antibody according to any one of paragraphs 1 to 41, or the composition according to any one of paragraphs 49 to 53.

67. A pharmaceutical composition comprising as active principle an antibody according to paragraphs 1 to 41 in an effective amount, in conjunction with a pharmaceutically acceptable excipient.

EXAMPLES

Example 1: Generation of Mouse Anti-Axl Monoclonal Antibodies

Monoclonal antibodies (MAb) against human Axl receptor were generated by DNA immunization of immunocompetent NMRI mice (Charles River) with a plasmid encoding a full-length human Axl fused to C-terminal Myc epitope.

Spleen cells from mice showing presence of rhAxl-specific antibodies in the blood were used for fusion with mouse myeloma cells according to standard protocols. The cells were cultured in plates ($10^5$ cells per well) with hypoxanthine-aminopterin-thymidine (HAT) medium for hybridoma selection. After twelve days of selection, the supernatants of 14 generated hybridomas were harvested and tested for Axl binding in enzyme-linked immunosorbent assay (ELISA) and flow cytometry. Three positive clones, showing the highest antigen-binding activity after the second round of subcloning by limited dilution, were expanded for large scale antibody production in vitro. The MAbs were purified from the cell culture supernatants by Protein G affinity chromatography.

The antibody clone 10G5 showing specific binding to Axl+ cells in flow cytometry was selected for further characterization.

For flow cytometry, the adherent cells in culture were washed with PBS, detached by trypsin (0.25%) treatment for 1 min and hitting culture dish for full detachment. Trypsin was quenched by adding into the tissue flask the complete medium followed by washing the cells with PBS. During the washing steps, the cells were collected by centrifugation at 200 g for 5 min. The antibody was diluted for total concentration in PBS containing 0.02% bovine serum albumin (BSA).

Cell staining was performed using 200 μL of cell suspension comprising $10^5$ cells for 20 min at room temperature. After two washing steps with PBS/0.02% BSA, the cells were resuspended in 200 μL incubated with an APC-conjugated donkey anti-mouse IgG (H+L) secondary antibody (Jackson Laboratories, Cat. no. 715-136-150) at concentration 2 μg/mL for 20 min at room temperature. The stained cells were washed twice with PBS/0.02% BSA and kept on ice before analysis using a BD LSR Fortessa cell analyzer (BD Biosciences).

Example 2: Mouse Monoclonal Antibody 10G5 does not Cross-React with Other Members of Human TAM Receptor Family All binding experiments were performed using Biacore 3000 instrument (GE Healthcare) at 25° C. Soluble recombinant antigens corresponding to the extracellular domains of members of the human TAM receptor family, Axl (rhAxl-Fc chimera; R&D Systems, Cat. no. 154-AL), Mer (rhMer-Fc chimera; R&D Systems, Cat. no. 891-MR) and Tyro3 (rhTyro3/Dtk-Fc chimera; R&D Systems, Cat. no. 859-DK) were immobilized on the surface of CM5 sensor chip using amine coupling at the surface density of 393.0, 303.6 and 364.0 resonance units (RU), respectively. The Biacore run was performed in an automatic mode using Binding analysis wizard. Samples containing MAb 10G5 at concentration 10 μg/mL in HBS-EP buffer (GE Healthcare) were injected over the surfaces with immobilized antigens at flow rate of 30 μL/min for 3 min (association) followed by 5 min dissociation.

The results shown in FIG. 1 demonstrate specific binding of the mouse monoclonal antibody 10G5 to human Axl and no binding to recombinant human Mer and Tyro3 antigens.

Example 3: Mouse Monoclonal Antibody 10G5 does not Cross-React with Mouse Axl The binding experiments were performed using Biacore 3000 instrument (GE Healthcare) at 25° C. The soluble recombinant antigens corresponding to human Axl (rhAxl-Fc chimera; R&D Systems, Cat. no. 154-AL), mouse Axl (rmAxl-Fc chimera; R&D Systems, R&D Systems; Cat. no. 854-AX) and human Tyro3 (rhTyro3/Dtk-Fc chimera; R&D Systems, Cat. no. 859-DK) were immobilized on the surface of CM5 sensor chip using amine coupling at the surface density of 1,308.0, 2,115.9 and 1,429.0 RU, respectively. The Biacore runs were performed in an automatic mode using Binding analysis wizard.

The sample containing MAb 10G5 or recombinant mouse (rm) Axl-ligand Gas6 (R&D Systems, Cat. no. 986-GS/CF) at concentration 10 μg/mL in HBS-EP buffer (GE Healthcare) was injected over the surfaces with immobilized antigens at flow rate of 30 μL/min for 3 min (association) followed by 5 min dissociation.

Figure 2:
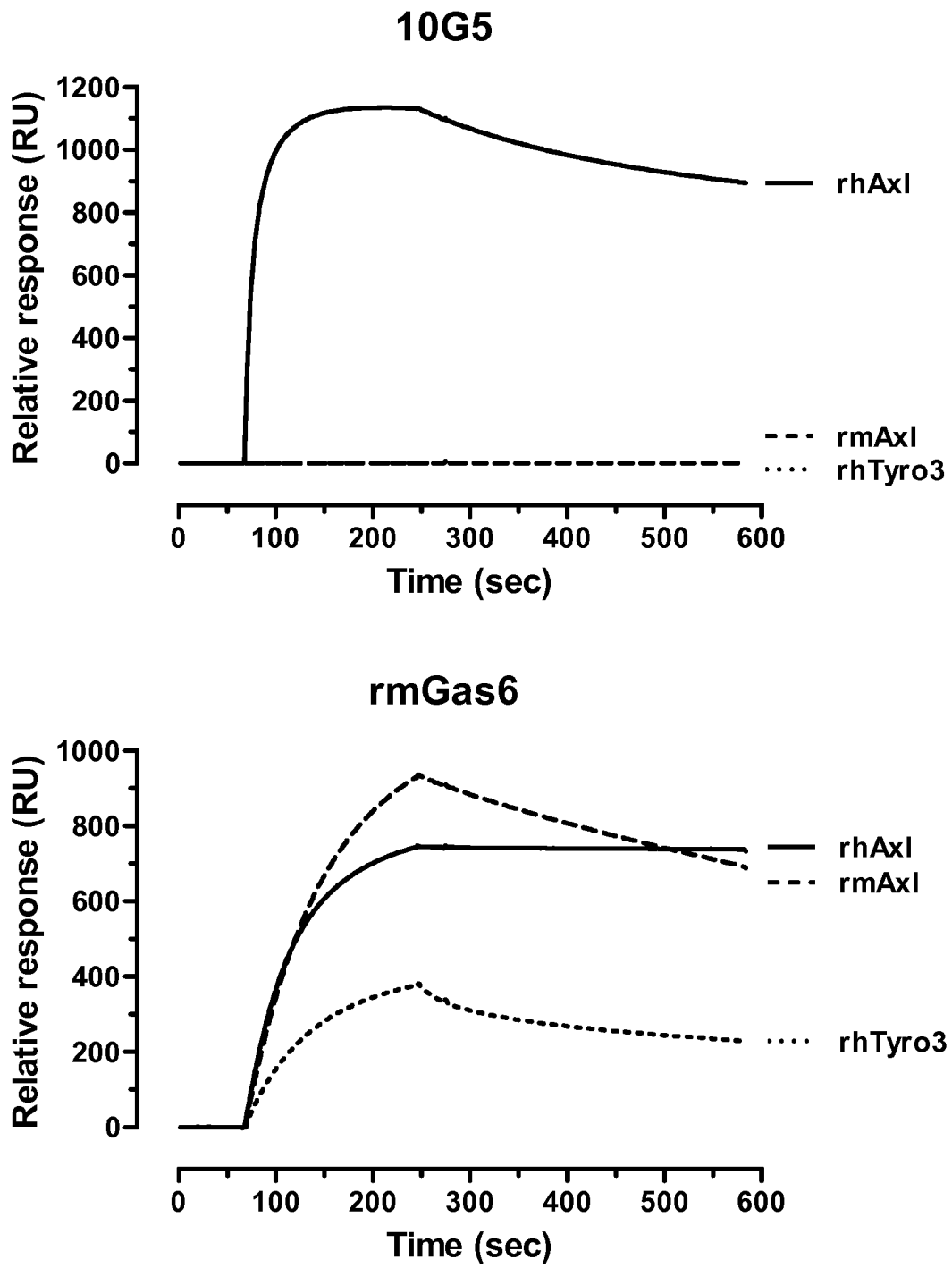

The results shown in FIG. 2 demonstrate specific interaction of MAbs 10G5 with human Axl and no binding to recombinant mouse Axl and human Mer antigens (FIG. 2, upper and middle panel, respectively). In contrast, mouse Gas6, used as a control, demonstrated strong binding to both human and mouse Axl and somewhat weaker binding to human Tyro3 (FIG. 2, lower panel).

Example 4: Mouse Monoclonal Antibody 10G5 Specifically Binds to Axl Receptor from Non-Human Primates The sequence of Axl receptor from cynomolgus monkey (*Macaca fascicularis*; SEQ ID NO: 27) was retrieved from WO2009062690A1. Based on the sequence, recombinant extracellular domain of cyno-Axl was generated by transient expression in CHO cells as a fusion protein with human Fc. The recombinant cyno-Axl-Fc was purified to homogeneity using Protein A-Sepharose (GE Healthcare). The binding experiments were performed using Biacore 3000 instrument (GE Healthcare) at 25° C. The soluble recombinant antigens corresponding to human Axl (rhAxl-Fc chimera; R&D Systems, Cat. no. 154-AL) and cyno-Axl were immobilized on the surface of CM5 sensor chip using amine coupling at the surface density of 775 and 880 RU, respectively. The Biacore runs were performed in an automatic mode using Binding analysis wizard.

The sample containing MAb 10G5 or human Axl-specific MAb 5F11 (control) at concentration 10 μg/mL in HBS-EP buffer (GE Healthcare) was injected over the surfaces with immobilized antigens at flow rate of 30 μL/min for 3 min (association) followed by 5 min dissociation.

Figure 3:
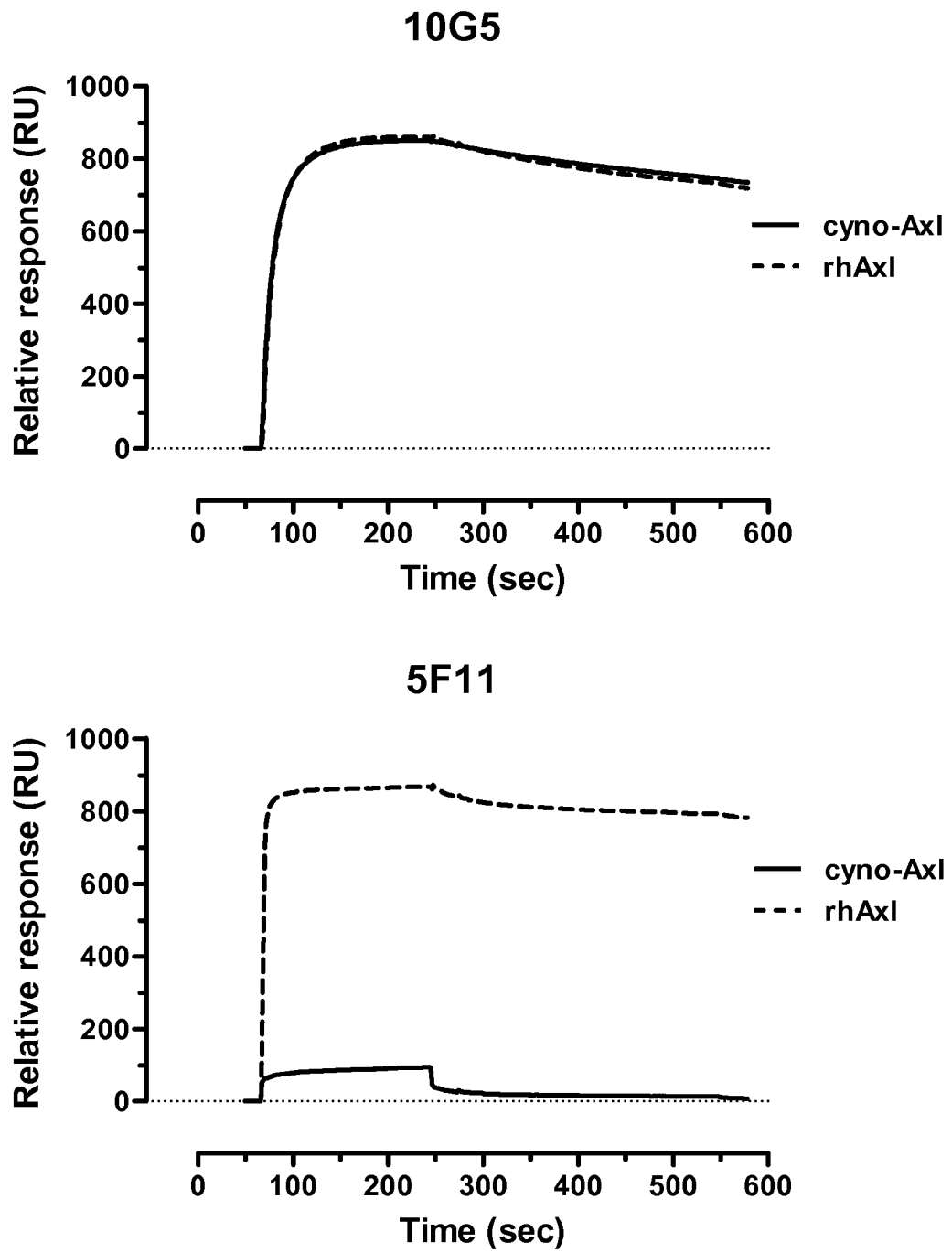

The results shown in FIG. 3 demonstrate strong and specific interaction of MAbs 10G5 with Axl antigens from both human and cynomolgus monkey. In contrast, the control antibody 5F11 showed strong binding to human Axl and lack of cross-reactivity with Axl from cynomolgus monkey.

Example 5: Affinity Determination of Mouse Monoclonal Antibody 10G5

Affinity determination of anti-Axl antibody 10G5 was performed at 25° C. by surface plasmon resonance measurements using Biacore 3000 instrument (GE Healthcare). As a solid antigen-coated surface, a sensor chip CM5 with immobilized rhAxl-Fc chimera (R&D Systems, Cat. no. 154-AL) at density 190 RU was used.

For the kinetics measurements, different concentrations of anti-Axl antibodies (from 0.3 to 666.7 nM) in HBS-EP buffer (Biacore, Cat. no. BR-1001-88) were injected at flow rate of 30 μL/min with 3 min injection time followed by 5 min dissociation (buffer alone). After each cycle, the surface was regenerated by 30 sec injection of a regeneration solution (10 mM HCl, 1 M NaCl) at flow rate 50 μL/min.

The mass transfer control experiments demonstrated absence of significant mass transfer limitations for MAb 10G5. An additional, linked reactions control experiment did not reveal linked reactions for the antibody, since the dissociation phases were practically identical after injection for 1, 3 or 20 min of one analyte concentration (160 nM for MAb 10G5).

The kinetic association (on-rate, $k_{on}$) and dissociation (off-rate, $k_{off}$) rates were calculated using BIAevaluation software and 1:1 Langmuir binding model. The equilibrium dissociation constant ($K_D$) was calculated as the $k_{off}/k_{on}$ ratio. The half-life ($t_{1/2}$) of the formed antibody-antigen complexes was calculated as the $\ln 2/k_{off}$ ratio.

Figure 4:
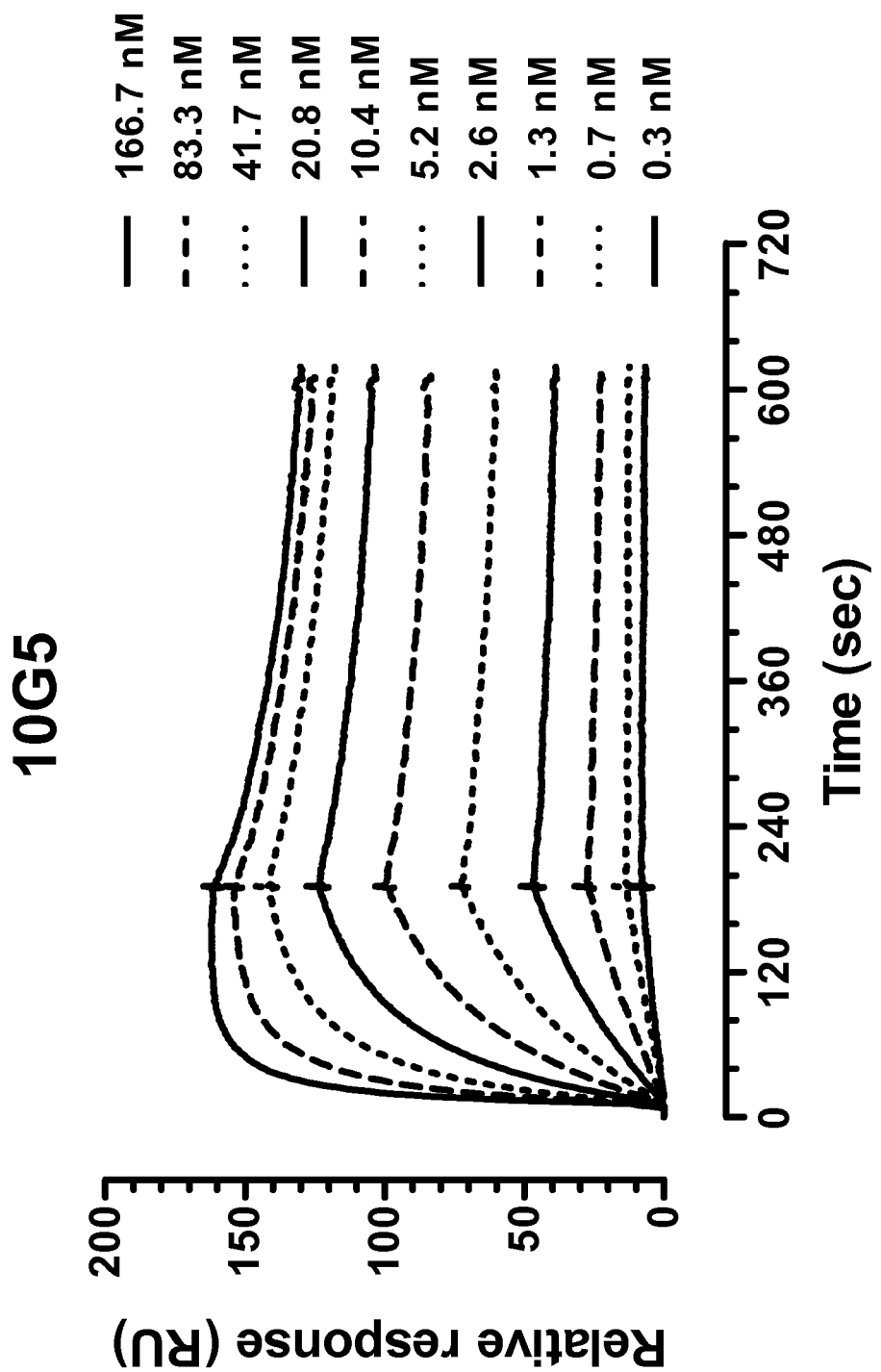

As shown in FIG. 4, the mouse MAb 10G5 demonstrated high affinity in subnanomolar range, with a $K_D$ value of 0.53 nM.

Example 6: Mouse Monoclonal Antibody 10G5 Blocks Binding of Gas6 to Axl

A competitive binding study was performed using Biacore 3000 instrument (GE Healthcare) and Binding Analysis wizard with several cycles of two samples injection. As a first sample, a saturating concentration of MAb 10G5 (160 nM or 24 µg/mL) was injected over the surface of a CM5 sensor chip coated with rhAxl-Fc (using amine coupling) for 3 min at flow rate of 30 µL/min followed by 2.5 min stabilization (HBS-EP buffer alone) before the injection of the second sample. The following second samples were used: recombinant human (rh) Gas6 (R&D Systems, Cat. no. 885-GS), recombinant mouse (rm) Gas6 (R&D Systems, Cat. no. 986-GS/CF) and a panel of anti-Axl antibodies, such as MAB154 (R&D Systems, Cat. no. MAB154), and 10G5; all at concentration 25 µg/mL. The second sample was injected for 3 min, followed by 2.5 min stabilization (buffer alone) and regeneration of the surface by 30 sec injection of a regeneration solution (10 mM HCl, 1 M NaCl) at flow rate 50 µL/min.

The results shown in FIG. 5 demonstrated MAb 10G5 did not compete for Axl binding with the commercial control antibody MAB154 (R&D Systems). However, the antibody 10G5 inhibited Axl binding by its ligand Gas6, both of human and murine origin.

Example 7: Mouse Monoclonal Antibody 10G5 Inhibits Growth of Highly Aggressive Breast Carcinoma Cells in Tree-Dimensional (3D) Organotypic Models A highly aggressive triple-negative human breast cancer cell line MDA-MB-231 (ATCC® HTB-26TH) was cultured according to recommended conditions in Dulbecco's Modified Eagle's Medium/Nutrient Mixture F-12 Ham medium supplemented with 10% foetal bovine serum (FBS), glutamine and penicillin and streptomycin. The cells were pretreated in suspension for at least 1 hour at 37° C., to ensure proper binding of antibodies on the cell surface before they were placed in extracellular matrix. The cells cultures were observed every day and fresh treatments were done every other day. The antibodies were used at concentrations 50-100 µg/mL. Imaging of coverslip 3D assay (35 mm dish) was done on a NIKON light microscopy using both Phase contrast and Hoffman optics. Already at day 3, difference in growth of cells treated with MAb10G5 and cells treated with a control irrelevant IgG was observed. At day 6, it became evident that cells treated with antibody 10G5 had significantly inhibited growth and tumour mass development in the extracellular matrix, as compared to the control-treated cells (FIG. 6). Nuclei staining revealed that the cells treated with MAb 10G5, despite the inhibited growth, are still viable. This experiment demonstrated that anti-Axl antibody 10G5 has the potential to inhibit development of organotypic tumour masses.

Example 8: Antibody 10G5 Induce Changes in Morphology of 3D Tumour Colonies In Vitro MDA-MB-231 cells were grown on extracellular matrix and allowed to form the highly aggressive stellate shaped morphology. Stellate-shaped tumour masses were then treated with the control IgG and antibody 10G5, as described in EXAMPLE 7. Antibody 10G5 caused degradation of stellate patterns (FIG. 7) accompanied by cell death and DNA fragmentation. These results demonstrated that blocking Axl using specific monoclonal antibody 10G5 has strong anti-tumour effect in 3D models in vitro.

Example 9: Antibody 10G5 Induces Axl Receptor Internalization

The expression of Axl receptor protein in MBA-MD-231 cells treated with different antibodies was examined by Western blot analysis. The cells were seeded in a 6-well plate at density of $5\times10^5$ cells per well and cultured overnight before treatment initiation. The cells were treated for 20 hrs in the presence of isotype control (mouse IgG2b), anti-Axl antibodies (10G5 and MAb #3) at concentrations of 100 µg/mL or multikinase inhibitor Foretinib (targets Met, Ron, Axl, Tie-2, and VEGFR2) at a concentration of 0.5 µM followed by harvesting by centrifugation at 1,200 rpm for 5 min and washing with sterile PBS. The cells were collected by centrifugation and resuspended in NP40-lysis buffer followed by 30 min incubation on ice. The cell lysates were cleared by centrifugation (12,000 rpm, 4° C., 5 min) and the protein concentrations were determined using BCA protein assay. The cell lysate samples comprising 35 µg of total protein were denatured in presence of the reducing agent (Life Technologies) and loaded into the wells of NuPAGE 10% Bis-Tris polyacrylamide (PAA) gel, 1.0 mm×12 well (Invitrogen). The electrophoresis was performed using Bis-Tris SDS running buffer under the recommended conditions (Life Technologies) and the proteins were transfer on PVDF membrane, as described for 2 gels in a manual for XCell II™ Blot Module (Invitrogen) using the transfer buffer with 20% methanol. The membrane was incubated in 10 mL of blocking buffer, TBS/0.1% Tween20 (TBST) with 5% skimmed milk, for 1 hr at room temperature followed by overnight incubation in 5 mL of incubation buffer (TBST with 3% skimmed milk) containing 1:1000 dilution of anti-Axl MAb154 (R&D Systems) at 4° C. The membrane was washed three times for 5 min each with 10 mL of TBST followed by 1 hr incubation with goat-anti mouse IgG (H+L) HRP-conjugated secondary antibody (1:2000) in 5 mL of incubation buffer with gentle rolling at room temperature. Afterwards, the membrane was washed three times for 5 min in 10 mL of TBST and twice with 10 mL of TBS buffer. The membrane was incubated with 1 mL ECL substrate for 1 min at room temperature. Excess substrate solution was aspirated and the blot was visualised using a ChemiDoc™ XRS+ imager (Bio Rad) and Image lab software. As loading control, detection using anti-mouse actin antibody (1:10, 000; Sigma) was used under the same conditions.

The results shown in FIG. 8 demonstrated significant reduction of Axl protein in cells treated with MAb 10G5 compared to the cells treated with either irrelevant IgG or MAb #3. The results indicate that MAb 10G5 induces internalization and intracellular degradation of Axl receptor.

Example 10: Antibody 10G5 Block Ligand-Induced Axl Downstream Signaling

The experiments were performed using human cervical cancer derived cell line HeLa (ATCC® CCL-2™). The cells were grown in T175 flasks to 80% confluency in MEM culture medium (Sigma) supplemented with 10% FBS, penicillin-streptomycin and L-glutamine. The cells were washed with PBS and detached by treatment with 0.25% Trypsin/EDTA (Sigma) followed by centrifugation and resuspension in fresh medium (MEM/0.5% FBS). The cells were seeded in Petri dishes ($3\times10^6$ cells per dish) in MEM medium supplemented with 10% FBS. After three hrs incubation at 37° C., the cells were washed with PBS and kept in starvation medium (MEM/0.5% FBS) overnight. The cells were pre-incubated with anti-Axl antibody 10G5 at concentration 1 µg/mL for 1 hr followed by stimulation with Axl ligand, recombinant mouse Gas6 (R&D Systems), at concentration 10 µg/mL for 20 min. The cell lysates were prepared, as described in EXAMPLE 9, the Western blot analysis was performed using anti-phospho-Akt (Ser$^{473}$)

antibody (Cell Signaling) followed by goat anti-rabbit horseradish peroxidase (Jackson ImmunoResearch); the anti-phospho-Akt does not distinguish between AKT1, AKT2, and AKT3, hence the total level of 'phospho-Akt' is shown in the blot. Detection with anti-GAPDH antibody (Millipore) was used as loading control.

Figure 9:
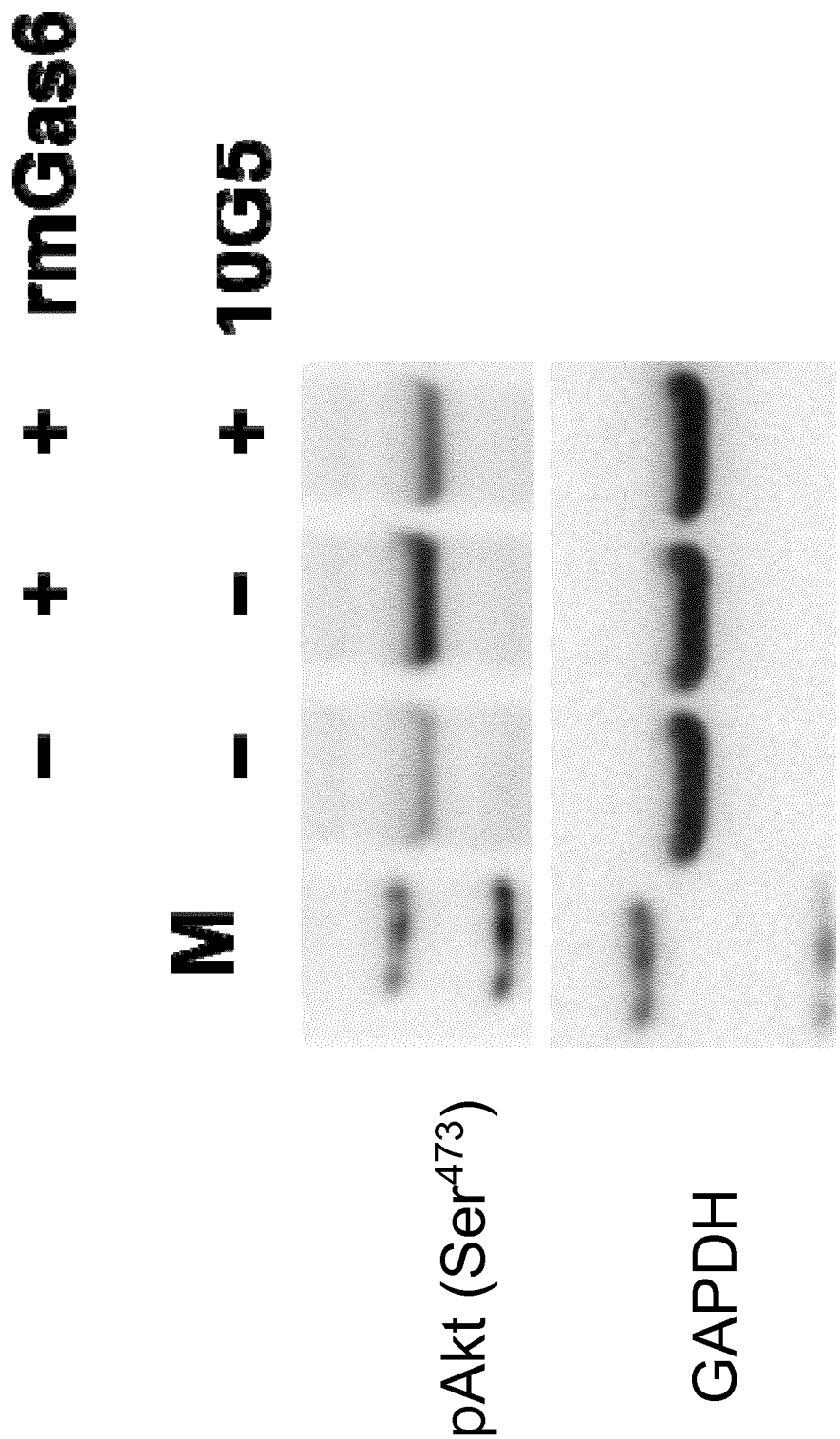

The results shown in FIG. 9 demonstrated that Axl-specific ligand Gas6 induced strong Axl signalling in HeLa cells that used downstream phosphorylation of Akt on $Ser^{473}$ as the readout. This signalling could significantly be reduced in the presence of antibody 10G5.

Example 11: Sequencing of Mouse Monoclonal Antibody 10G5

The hybridoma cells were propagated under standard conditions; $5 \times 10^6$ hybridoma cells were used for mRNA isolation and cDNA synthesis according to standard protocols. For PCR amplification of the genes encoding heavy and light chain variable regions (VH and VL, respectively), Mouse IgG Library Primer Set (Progen, Heidelberg, Germany, Cat. no. F2010) was used.

For the hybridoma 10G5, PCR amplification using different primer combinations resulted in 12 sequences from PCR using 6 different primer combinations for the VH gene and in 5 sequences from PCR using 2 different primer combinations for the VL gene. The sequences of the clones VH1 (B6-4) and VK1 (F1-3) were selected for further work on the basis of highest homology with the corresponding germline sequences, as determined by nucleotide alignment with IMGT database.

The deduced amino acid sequences of the VH and VL domains for antibody 10G5 are shown in FIG. 10.

Example 12: Generation and Testing Chimeric Monoclonal Antibody 10G5

The VH and VL sequences retrieved from the murine hybridoma 10G5 was used for generation of the synthetic genes with codon optimization for expression in mammalian cells (GeneArt). These mouse VH and VL genes were ligated in frame with the genetic elements encoding constant domains of the human IgG1 heavy and light (C-kappa) chains, respectively, in an expression vector suitable for antibody production in mammalian cells. Production of the chimeric (mouse variable/human constant) IgG1 antibodies was achieved by transient expression in Chinese Hamster Ovary (CHO) cells followed by purification using Protein A affinity chromatography.

Figure 11:
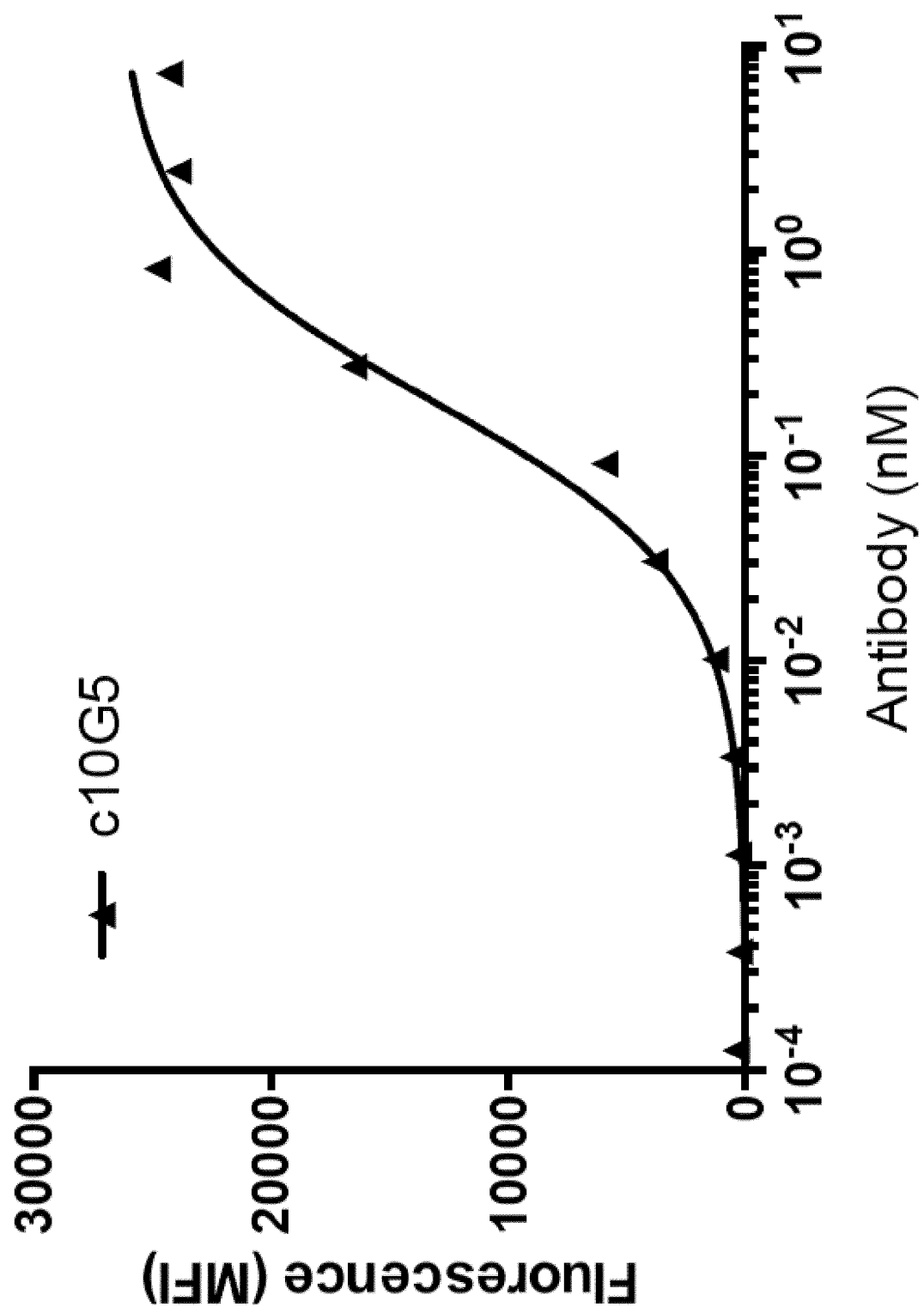

The purified chimeric antibodies (>95% purity) were analysed for binding to Axl-positive breast cancer cell line MDA-MB-231 in flow cytometry. For comparison, the parental mouse MAb 10G5 were used. For flow cytometry, the adherent cells in culture were washed with PBS, detached by treatment with trypsin (0.25%) for 1 min and hitting culture dish for full detachment. Trypsin was quenched by adding into the tissue flask the complete medium followed by washing the cells with PBS. During the washing steps, the cells were collected by centrifugation at 200 g for 5 min. The antibody was diluted for total concentration in PBS containing 0.02% bovine serum albumin (BSA). Cell staining was performed using 200 μL of cell suspension comprising $10^5$ cells for 20 min at room temperature. The cell-bound antibodies were detected with APC-conjugated donkey anti-human or anti-mouse, respectively, IgG (H+L) F(ab')$_2$ fragments (Jackson ImmunoResearch). After two washing steps with PBS/0.02% BSA, the cells were resuspended in 200 μL and kept on ice before analysis on Accuri C6 flow cytometer (BD Biosciences). The results shown in FIG. 11 demonstrated strong binding of the chimeric antibodies to the Axl-positive MDA-MB-231 cells in flow cytometry.

In addition, the Axl-binding properties of the chimeric antibody c10G5 was tested using Biacore 3000 instrument (GE Healthcare) and a sensor chip CM5 coated with human Axl (rhAxl-Fc chimera; R&D Systems, Cat. no. 154-AL) at the surface density of 1,308.0 RU. The Biacore runs were performed in an automatic mode using Binding analysis wizard. The samples comprising either the chimeric antibody c10G5 or their murine counterparts at concentration 10 μg/mL in HBS-EP buffer (GE Healthcare) were injected over the surfaces with immobilized antigens at flow rate of 30 μL/min for 3 min (association) followed by 5 min dissociation.

Figure 12:
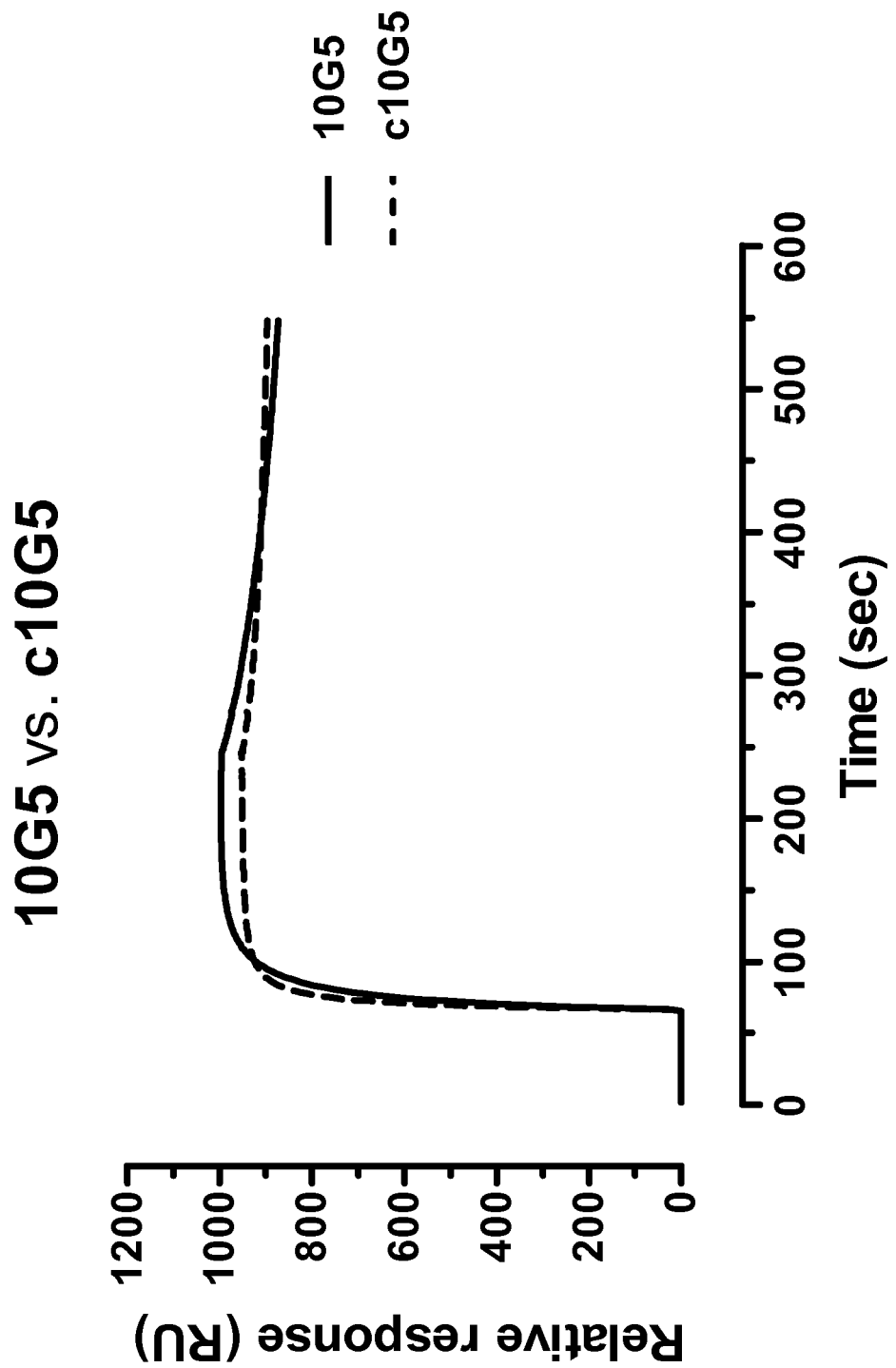

The results shown in FIG. 12 demonstrate that the chimeric antibody c10G5 binds immobilized Axl with profiles very similar to the binding profiles of the corresponding mouse antibody from the hybridoma 10G5y.

Example 13: Chimeric Antibody 10G5 Bind Axl with the Same Affinities as the Parental Mouse Antibodies Affinity determination of the chimeric anti-Axl antibody c10G5 was performed at 25° C. by surface plasmon resonance measurements using Biacore 3000 instrument (GE Healthcare). As a solid antigen-coated surface, a sensor chip CM5 with immobilized rhAxl-Fc chimera (R&D Systems, Cat. no. 154-AL) at density 190 RU was used.

For the kinetics measurements, different concentrations of anti-Axl antibodies (from 0.3 to 333.3 nM) in HBS-EP buffer (Biacore, Cat. no. BR-1001-88) were injected at flow rate of 30 μL/min with 3 min injection time followed by 5 min dissociation (buffer alone). After each cycle, the surface was regenerated by 30 sec injection of a regeneration solution (10 mM HCl, 1 M NaCl) at flow rate 50 μL/min.

The mass transfer control experiments demonstrated absence of significant mass transfer limitations for chimeric MAb c10G5.

The kinetic association (on-rate, $k_{on}$) and dissociation (off-rate, $k_{off}$) rates were calculated using BIAevaluation software and 1:1 Langmuir binding model. The equilibrium dissociation constant ($K_D$) was calculated as the $k_{off}/k_{on}$ ratio. The half-life ($t_{1/2}$) of the formed antibody-antigen complexes was calculated as the ln $2/k_{off}$ ratio.

Figure 13:
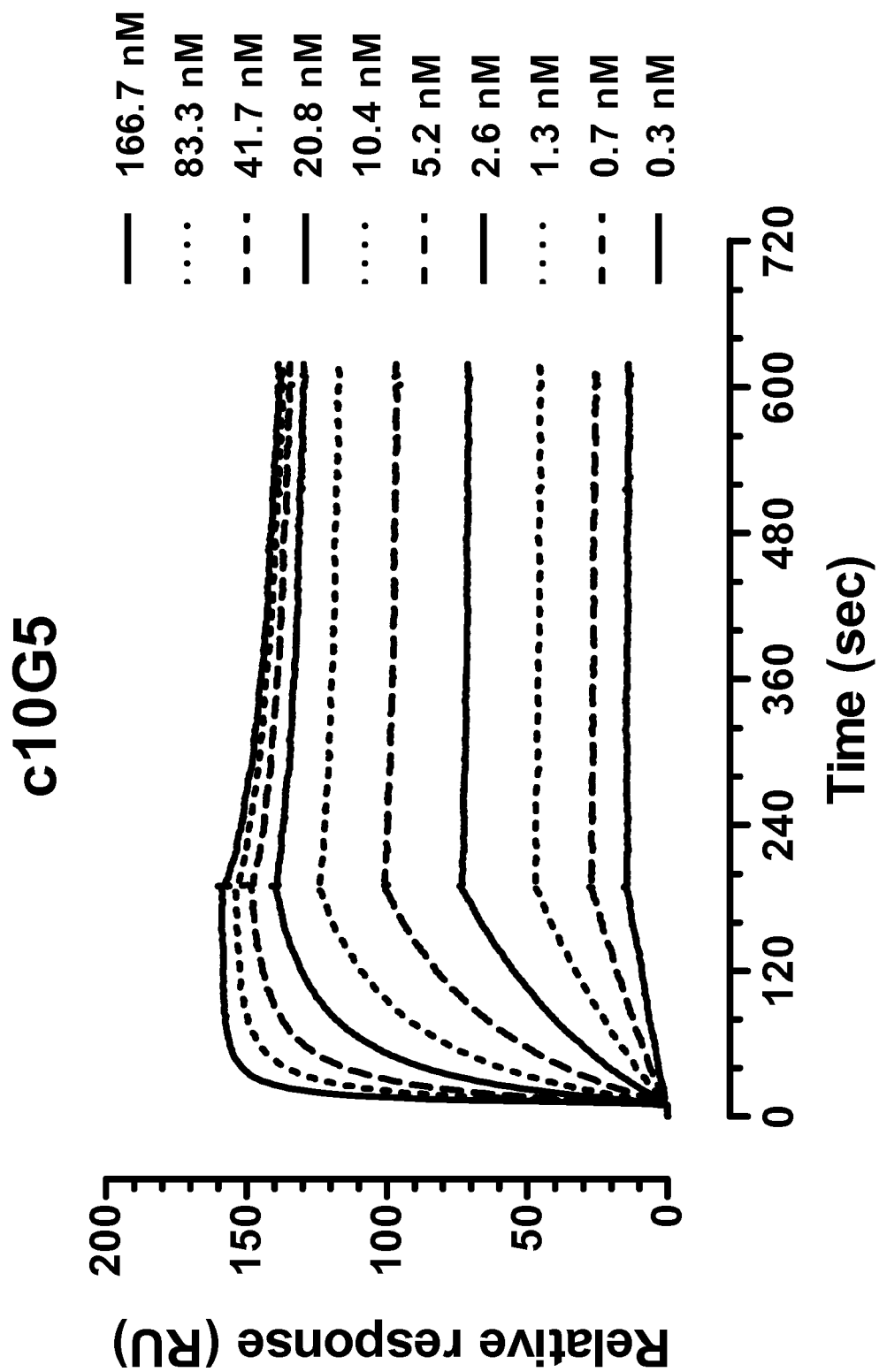

As shown in FIG. 13, the chimeric MAb c10G5 demonstrated high affinity in subnanomolar range, with a $K_D$ value of 0.10 nM, somewhat better than the affinities of the parental murine antibody (see EXAMPLE 5).

Example 14: Chimeric Antibody 10G5 Inhibits Tumor Growth in a Mouse Model of Human Non-Small Cell Lung Cancer To evaluate the anti-tumour activity of anti-Axl chimeric antibodies in vivo, we used a mouse xenograft model of human non-small cell lung cancer (NSCLC). The human NSCLC A549 cells (ATCC #CCL-185) A549 cells were propagated in vitro as a monolayer culture in DMEM medium supplemented with 10% FBS, 2 mM L-Glutamine, 100 U/ml penicillin and 100 μg/ml streptomycin, 0.01M HEPES buffer, 0.45% D-(+)-glucose, 1 mM sodium pyruvate. Nude mice were implanted subcutaneously (s.c.) into the flank with $5 \times 10^6$ A549 cells resuspended in serum-free medium/Matrigel (1:1). When the tumour size reached 100 mm³ (Day 0 in FIG. 14), the animals were randomized and treated with either vehicle (sterile PBS) or anti-Axl chimeric antibody 10G5 at 20 mg/kg, by intraperitoneal (i.p.) injections twice weekly for 4 weeks.

As shown in FIG. 14, the chimeric antibody 10G5 significantly attenuated growth of A549 tumours compared with the control (P<0.01, as determined by two-way ANOVA); around 40% inhibition was observed after four weeks of treatment.

Example 15: Chimeric Antibody 10G5 Inhibits Tumor Growth in a Mouse Xenograft Model of Human Acute Myeloid Leukaemia To evaluate the anti-tumour activity of anti-Axl chimeric antibodies in a model of haematological cancer, we used a mouse xenograft model of human acute myeloid leukaemia (AML). The human AML Mv4-11 cells (ATCC #CRL-9591) cells were propagated in suspension in IMDM medium supplemented with 10% FBS, 2 mM L-Glutamine, 100 U/ml penicillin and 100 µg/ml streptomycin. Nude mice were implanted s.c. into the flank with 5×10⁶ Mv4-11 cells resuspended in the mixture of serum-free IMDM medium and Matrigel (1:1). When the tumour size reached 200 mm³ (Day 0 in FIG. 15), the animals were randomized and treated with either vehicle (sterile PBS) or anti-Axl chimeric antibody 10G5 at 30 mg/kg, by i.p. injections twice weekly for 4 weeks.

As shown in FIG. 15, the chimeric antibody 10G5 extremely significantly attenuated growth of Mv4-11 tumours compared with the control (P<0.0001, as determined by two-way ANOVA); around 75% inhibition was observed after three weeks of treatment.

Example 16: Defucosylated Glycoengineered C10G5 (Glymax) Shows Enhanced Anti-Tumor Effect Compared to C10G5 in a Mouse Model of Human Non-Small Cell Lung Cancer The naked anti-Axl antibodies can prevent tumor growth both by inhibiting the specific signaling pathway of the target receptor and/or through tumor cell killing via its effector functions, such as antibody-dependent cellular cytotoxicity (ADCC), complement-dependent cytotoxicity (CDC) and/or antibody-dependent cellular phagocytosis (ADCP). Antibodies lacking core fucosylation show a significantly enhanced antibody-dependent cell-mediated cytotoxicity (ADCC) and an increased efficacy of anti-tumor activity.

To compare the anti-tumor effects of two variants of the chimeric antibody c10G5—wt and defucosylated—we used a mouse xenograft model of human non-small cell lung cancer (NSCLC). The human NSCLC A549 cells (ATCC #CCL-185) A549 cells were propagated in vitro as a monolayer culture in DMEM medium supplemented with 10% FBS, 2 mM L-Glutamine, 100 U/ml penicillin and 100 µg/ml streptomycin, 0.01M HEPES buffer, 0.45% D-(+)-glucose, 1 mM sodium pyruvate. SCID mice were implanted subcutaneously (s.c.) into the flank with 5×10⁶ A549 cells resuspended in serum-free medium/Matrigel (1:1). When the tumour size reached 130 mm³ (Day 0 in FIG. 15), the animals were randomized and treated with either anti-Axl c10G5 or Glymax-c10G5 at 30 mg/kg, by intraperitoneal (i.p.) injections twice weekly for 4 weeks.

Figure 16:
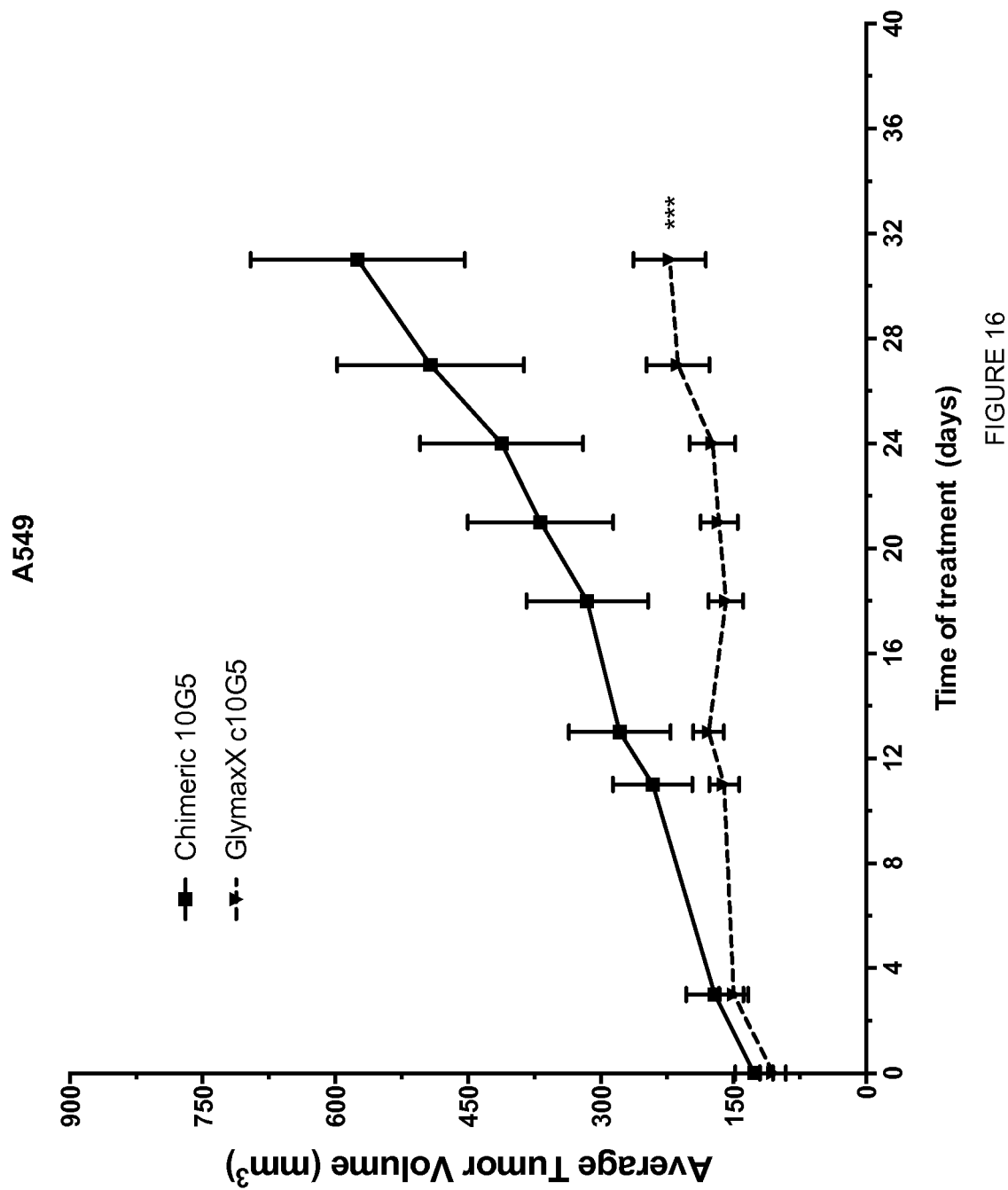

As shown in FIG. 16, the antibody Glymax-c10G5 significantly attenuated growth of A549 tumours compared with the c10G5 (P<0.0001, as determined by two-way ANOVA). The significant difference in activity of wt and defucosylated versions of the chimeric 10G5 indicates importance of antibody-dependent cellular cytotoxicity (ADCC) in inhibition of tumor growth.

Example 17: hu10G5 H2L1 Inhibits Tumor Growth in a Mouse Model of Human Non-Small Cell Lung Cancer hu10G5 H2L1 is a humnaised variant of 10G5; the antibody has the CDRs and binding specificity of murine 10G5, but with multiple substitutions in the V-domain framework regions. To evaluate the anti-tumour activity of hu10G5 H2L1 in vivo, we used a mouse xenograft model of human non-small cell lung cancer (NSCLC). The human NSCLC A549 cells (ATCC #CCL-185) A549 cells were propagated in vitro as a monolayer culture in DMEM medium supplemented with 10% FBS, 2 mM L-Glutamine, 100 U/ml penicillin and 100 µg/ml streptomycin, 0.01M HEPES buffer, 0.45% D-(+)-glucose, 1 mM sodium pyruvate. SCID mice were implanted subcutaneously (s.c.) into the flank with 5×10⁶ A549 cells resuspended in serum-free medium/Matrigel (1:1). When the tumour size reached 100 mm³ (Day 18 in FIG. 16), the animals were randomized and treated with either vehicle (SYNAGIS) or anti-Axl hu10G5 H2L1 at 30 mg/kg, by intraperitoneal (i.p.) injections twice weekly for 2 weeks.

Figure 17:
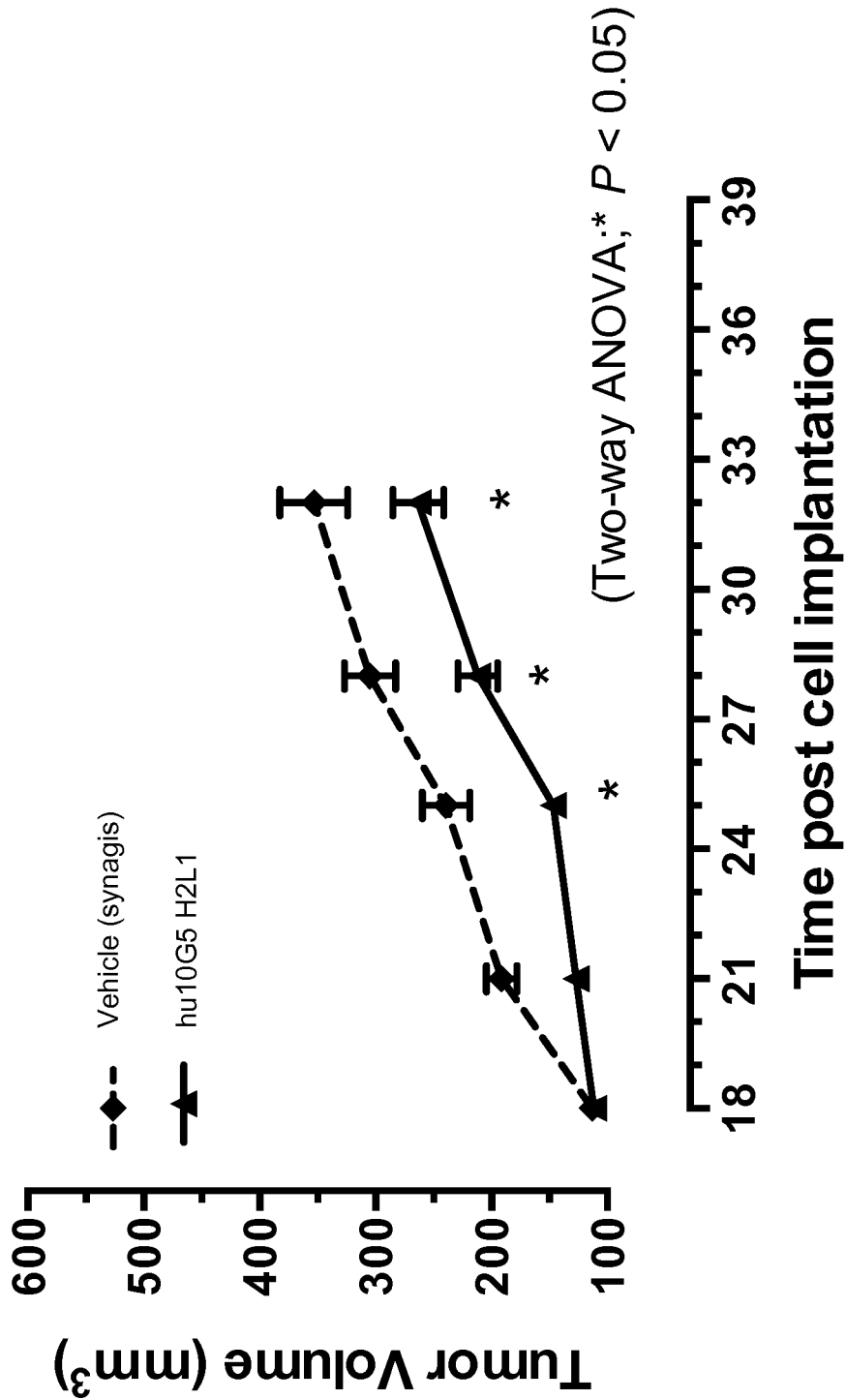

As shown in FIG. 17, the antibody hu10G5 H2L1 significantly attenuated growth of A549 tumours compared with the control (P<0.051, as determined by two-way ANOVA); around 25% inhibition was observed after two weeks of treatment.

Example 18: Glycoengineered hu10G5 (H1L1-GLYMAXX) Potentiates the Effect of Anti-EGFR Treatment on Tumor Growth in a Mouse Model of Human Non-Small Cell Lung Cancer hu10G5 (H1L1-GLYMAXX) is a humanized and defucosylated antibody with the CDRs and binding specificity of 10G5. To evaluate the anti-tumour activity of hu10G5 (H1L1-GLYMAXX) in vivo, we used a mouse xenograft model of human non-small cell lung cancer (NSCLC). The human NSCLC A549 cells (ATCC #CCL-185) A549 cells were propagated in vitro as a monolayer culture in DMEM medium supplemented with 10% FBS, 2 mM L-Glutamine, 100 U/ml penicillin and 100 µg/ml streptomycin, 0.01M HEPES buffer, 0.45% D-(+)-glucose, 1 mM sodium pyruvate. NUDE mice were implanted subcutaneously (s.c.) into the flank with 5×10⁶ A549 cells resuspended in serum-free medium/Matrigel (1:1). When the tumour size reached 100 mm³ (Day 0 in FIG. 18), the animals were randomized and treated either with vehicle (SYNAGIS), Erbitux (20 mg/kg) or hu10G5 (H1L1-GLYMAXX) (15 or 30 mg/kg either alone or in combination. Antibodies were administered by intraperitoneal (i.p.) injections twice weekly for 3 weeks.

Figure 18:
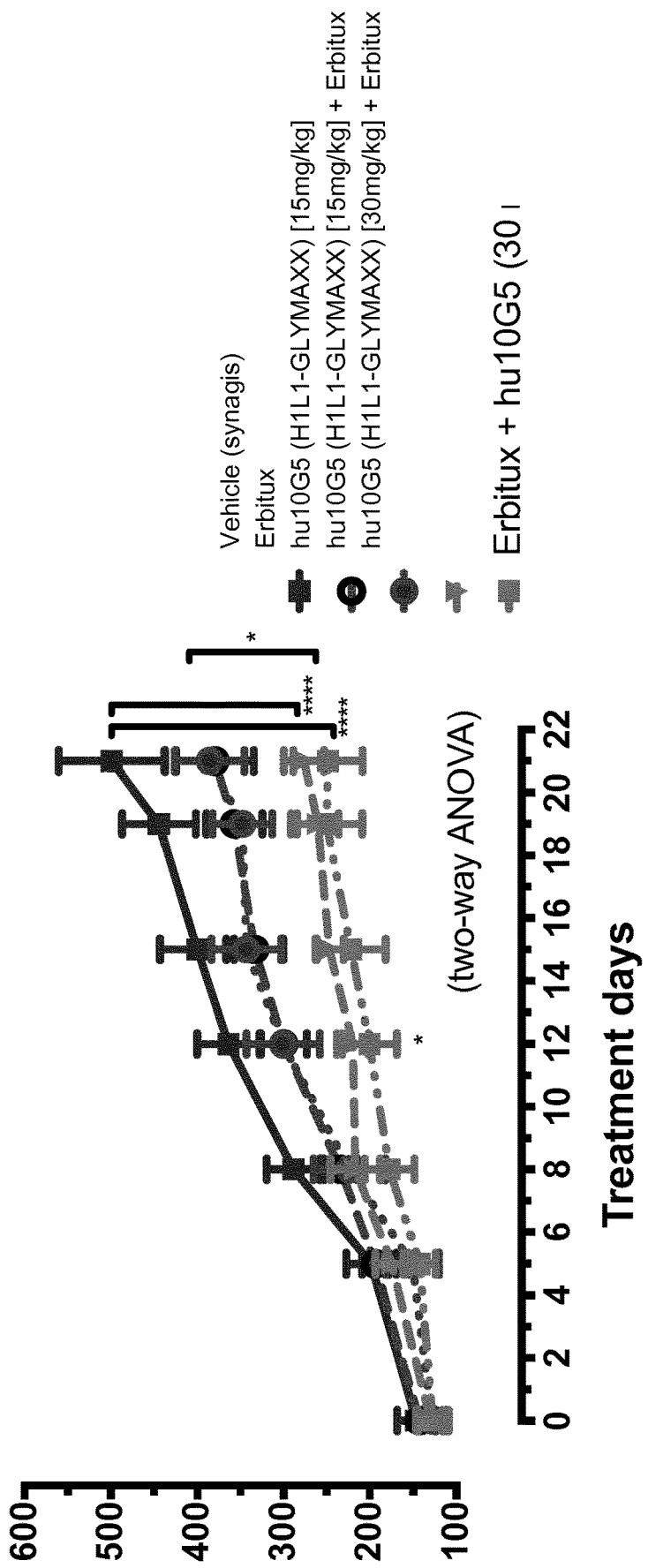

As shown in FIG. 18, hu10G5 (H1L1-GLYMAXX) showed moderate anti-tumor activity very similar to the anti-tumor effect of the Anti-EGFR therapeutic antibody cetuximab (Erbitux). For both antibodies used as the single agents, the observed effect was however statistically not significant when compared to the mouse cohort treated with the isotype control antibody (Synagis). Combination of both antibodies resulted in significant tumor growth retardation (P<0.0001; as determined by two-way ANOVA) when compared to isotype control treated animals. The effect was also significant when compared to the groups treated with either hu10G5 (H1L1-GLYMAXX) antibody or Erbitux alone (P<0.05; as determined by two-way ANOVA).

Example 19: Affinity Determination of Humanized H2L1 and H1L1 10G5 Antibodies Binding analysis of c10G5 versus humanized 10G5 variants on flow cytometry. Titration of IgG on AXL+ and AXL− cells.

For flow cytometry, the adherent cells in culture were washed with PBS, detached by treatment with trypsin (0.25%) for 1 min. The cells were collected by centrifugation at 200 g for 5 min. The antibody was diluted for total concentration in PBS containing 0.2% bovine serum albumin (BSA). Cell staining was performed using 200 μL of cell suspension comprising 200 000 cells for 30 min at room temperature. The cell-bound antibodies were detected with APC-conjugated donkey anti-human IgG (H+L) F(ab')2 fragments (Jackson ImmunoResearch Laboratories #709-136-149, 1:400 dilution). After two washing steps with PBS/0.2% BSA, the cells were resuspended in 200 μL PBS and kept on ice before analysis on Fortessa flow cytometer (BD Biosciences).

As shown below in Table 3 and also in FIGS. 19A & B, the humanised 10G5 antibodies demonstrated high affinities in subnanomolar range.

TABLE 3

| MAb | On-rate $(k_{on}; M^{-1}s^{-1})$ | Off-rate $(k_{off}; s^{-1})$ | $K_D$ (M) | Half-life $(t_{1/2}; \text{min})$ |
|---|---|---|---|---|
| murine 10G5 | $8.29 \times 10^5$ | $4.39 \times 10^{-4}$ | $5.30 \times 10^{-10}$ | 26.32 min |
| H1L1 | $1.54 \times 10^6$ | $1.61 \times 10^{-4}$ | $1.05 \times 10^{-10}$ | 71.72 min |
| H2L1 | $2.07 \times 10^6$ | $1.42 \times 10^{-4}$ | $6.86 \times 10^{-11}$ | 81.36 min |

Example 20: Cell Killing Activity of Humanized H2L1 and H1L1 10G5 Antibodies Tumour cell killing using antibody-Saporin conjugates. Comparison of chimeric 10G5 and two humanized 10G5 variants.

For generation of immunotoxin, the chimeric MAb was non-covalently coupled to a plant toxin Saporin using FabFc-ZAP human conjugate (4.5 nM final concentration) (Advanced Targeting Systems, Cat. no. IT-65). The effect of chAb-Saporin internalization on tumour cell viability was tested using Axl-positive tumour cell line MDA-MB-231 (human triple negative breast carcinoma). Eight hundred cells were seeded per well in 96-well plates in DMEM/F-12 media supplied with 10% FBS, L-glutamine (4 mM), streptomycin (5 μg/ml) and penicillin (5 U/ml) and allowed to attach for 16 hours. The cells were incubated with different dilutions of immunotoxin chAb-Saporin for 72 hrs. The viability of the cells was determined by performing an XTT/PMS assay using a CLARIOstar® microplate reader (BMG LABTECH)

Figure 20:
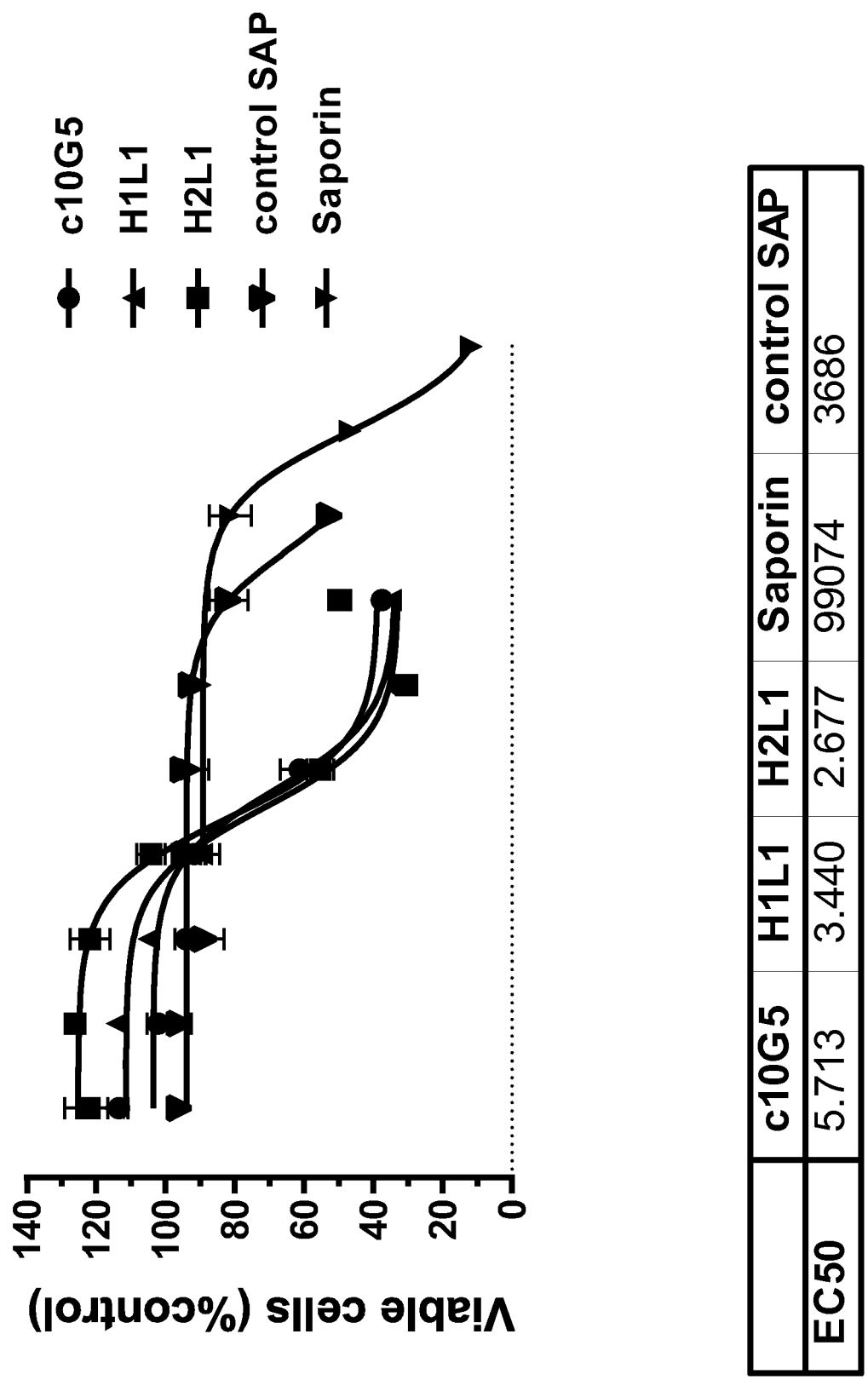

The results shown in FIG. 20 demonstrated good internalization and very strong cell killing potency of 10G5-based immunotoxins with EC50 value (effective concentration leading to killing of 50% cells) in picomolar range.

Unconjugated Saporin and an isotype control antibody (human IgG1) coupled to Saporin (control SAP) were used as negative controls. Effective concentrations leading to 50% cell killing (EC50, pM) are shown in Table 4, below.

TABLE 4

| | ch10G5 | H1L1 | H2L1 | Saporin | Control SAP |
|---|---|---|---|---|---|
| EC50 (pM) | 5.713 | 3.440 | 2.677 | 99074 | 3686 |

Example 21: Comparison of 10G5 with Prior Art Anti-Axl Antibodies

Genentech antibody YW327.652: bound epitope

Direct BiaCore competition binding analysis demonstrates that 10G5 does not compete with the Genentech antibody YW327.652 for binding to Axl. This shows that the two antibodies bind to different epitopes.

Materials/Equipment

| | |
|---|---|
| 1. Anti-AXL monoclonal antibodies (all in PBS): | |
| 1) c10G5 (126, MAB-G, Evitria, Lot # 3439) | 4.6 mg/mL |
| 2) YW327.652-var (153, CONTR-1, Evitria, Lot # 3537) | 4.5 mg/mL |
| 2. Sensor Chip CM5 # 5 with immobilized Hu-Axl-Fc (661.9 RU), hu-EGFR-Fc (548.5 RU), mono-AXL (776.6 RU) | |
| 3. Running buffer (HBS-EP) | Biacore; Cat. # BR-1001-88; Lot. # 10213176 |
| 4. Plastic vials 7 mm (0.8 mL) | Biacore; Cat. # BR-1002-12 |
| 5. Regeneration solution: | 10 mM HCl, 1M NaCl |
| 6. Biacore 3000 | GE Healthcare |

Methods

| | |
|---|---|
| 1. Dilute all antibodies in HBS-EP to 100 μg/mL (666.7 nM): | |
| 1) c10G5 | 25 μL + 1 mL |
| 2) YW327.6S2-var | 37.5 μL + 1.5 mL |

2. In the instrument control software, use the following template:

Assay Principle: Direct Binding Injections:

Use Flow Cell(s): 2 with 1 as reference
Flow Rate: 30 (μL/min)
Number of Injections: 2
First Sample:

Injection Time: 3 (min)
Wait After Injection: 2.5 (min)
Second Sample:

Injection Time: 3 (min)
Wait After Injection: 2.5 (min)

Cycles:
Run Order: As Entered

| No. | Repl. | First sample | Second sample |
|---|---|---|---|
| 2 | 1 | MAb c10G5 (666.7 nM) | MAb YW327.652-var (666.7 nM) |
| 5 | 1 | MAb YW327.652-var (666.7 nM) | MAb YW327.652-var (666.7 nM) |
| 7 | 1 | MAb YW327.652-var (666.7 nM) | MAb c10G5 (666.7 nM) |

Regeneration:

Single Injection

Regeneration Flow Rate: 50 (μL/min)

Solution: 10 mM HCl, 1 M NaCl

Injection Time: 30 (s)

Predip. Needle: No

Stabilization Time After Regenerations: 2 (min)

3. At the end of the day: Desorb (3 mL BIAdesorb solution 1, 3 mL BIAdesorb solution 2).
4. At the end of the week: Sanitize (0.525 mL BIAdisinfectant solution+6.475 mL ddH20, 0.005% surfactant P20).
5. Export curves as text files. Open and analyze the sensograms using software Prism (GraphPad, San Diego, Calif.).

Results

The competitive binding analysis was performed by injecting a first sample (MAbs c10G5 or YW327.6S2-var) at a concentration sufficient to reach plateau within 1-2 min followed by injection of MAb YW327.6S2-var as a second sample (FIG. 21A).

In a second part of the of experiment, the antibody YW327.6S2-var was injected as a first sample followed by injection of either antibody YW327.6S2-var or c10G5 as a second sample (FIG. 21B).

Conclusions

The results demonstrated that the Genentech's antibody YW327.6S2 can bind human AXL in the presence of the c10G5 antibody. Therefore the YW327.6S2 and 10G5 antibodies recognise different epitopes.

Consistent with their binding different epitopes, 10G5 and YW327.6S2 show different species cross reactivity: YW327.6S2 cross-reacts with both human and murine Axl (see Oncogene (2010) 29, 5254-5264, page 5255, left column), whereas 10G5 shows no significant binding to murine Axl (see Example 3).

Genentech Antibody YW327.6S2: Cell Killing

Tumour cell killing using antibody-Saporin conjugates performed as described in Example 20. A comparison of two variants of humanised 10G5 and YW327.6S2 was performed. The results are shown below in Table 5.

TABLE 5

|  | H1L1 | H2L1 | YW327.6S2 | Saporin | Control SAP |
|---|---|---|---|---|---|
| EC50 (pM) | 17.13 | 2.664 | 33.25 | 246564 | 8.981 |

INSERM Antibodies D9 and E8

Unlike 10G5, the 'D9' and 'E8' antibodies described in Oncogene 33, 5405-5414 (20 Nov. 2014, doi:10.1038/onc.2013.487) do not inhibit the binding of GAS6 to Axl. This indicates the D9 and E8 antibodies do not bind the same epitope as 10G5.

U3 Pharma 11B7 Antibody

The 11B7 antibody described in WO 2009062690 A1 has not been shown to inhibit the binding of the GAS6 ligand to the receptor Axl. This indicates that the 11B7 antibody does not bind the same epitope as 10G5.

Example 22: Further Comparison of 10G5 with Prior Art Anti-Axl Antibodies

Compared Antibodies

Some of the anti-Axl antibodies described in Example 21 were subjected to further testing. The tested antibodies were:

Hu10G5 (H2L1)*†

*same antibody sequence, different preparation

†same CDR sequences

Hu10G5 (H2L1-prep2)*†

Chimeric 10G5†, WO2016/097370

YW327.652 [Genentech]

Chugai Pharmaceutical 'H9-L0' anti-Axl, US2012/0121587 (SEQ ID NOs.3 and 65)

INSERM anti-Axl D4, WO2016/091891 (VH=SEQ ID NO: 1, VL=SEQ ID NO: 2)

U3 Pharma '11D5' anti-Axl, WO2009/062690A1

Chimeric 1H12, WO2015/193428

Binding Competition Assays

Goal

To determine if the above antibodies:

(1) bind the same or overlapping epitopes; and (2) compete with the Gas6 for binding to Axl.

Materials

Antibodies as above.

rhGas6 ligand

Sensor chip with immobilised Axl: Hs-Axl-Fc (638.2 RU), Mm-Axl-Fc (334.5 RU), Rhe-Axl-Fc (350.2 RU)

Buffers, solution, and Biacore equipment as Example 21.

Method

General

In this experiment, a first antibody was allowed to bind to saturation. A second antibody was then applied and its ability to bind was monitored.

If the second antibody recognizes the same (or overlapping) epitope as the first antibody then binding will be blocked. If the second antibody recognizes a different epitope then binding will be detected at the same level as if no first antibody was present.

The ability of Gas6 to block antibody binding was also tested, using Gas6 at 10 μg/mL in HBS-EP.

All tests were performed in parallel on Hs-Axl-Fc, Mm-Axl-Fc and Rhe-Axl-Fc surfaces.

See FIG. 1 for a list of the pairs that were tested (in this list Contr-1 is incorrectly labeled YW367 instead of YW327.6S2var). All antibodies were at 25 μg/mL in HBS-EP.

Steps

1. Preparation of solutions:

| Ab/Ligand | Target conc. |
|---|---|
| H2L1 | 25 μg/mL |
| YW327.6S2 | 25 μg/mL |
| INSERM | 25 μg/mL |
| Chugai | 25 μg/mL |
| U3 | 25 μg/mL |
| Gas6 | 10 μg/mL |
| H2L1-prep2 | 25 μg/mL |
| 1H12 | 25 μg/mL |
| 10G5 | 25 μg/mL |

2. Perform Biacore experiments at 25° C.
3. In the instrument control software choose Direct Binding, and select settings for two injections as shown below.

4. Place the solutions in the appropriate reagent rack positions, matching the sample content and recommended volumes with the indicated rack positions suggested by the BIAcore software.
5. Store the template & the result file, start the analysis.

Assay Principle

| Assay Principle: Direct Binding |
|---|

Injections

| Use Flow Cell(s): | 2, 3, 4 with 1 as reference |
|---|---|
| Flow Rate: | 20 (µl/min) |
| Number of Injections: | 2 |
| First Sample | |
| Injection Time: | 3 (min) |
| Wait After Injection: | 2.5 (min) |
| Second Sample | |
| Injection Time: | 4 (min) |
| Wait After Injection: | 2.5 (min) |

Cycles

| Run Order: As Entered | | |
|---|---|---|
| Repl. | First Sample | Second Sample |
| As required, with each Ab pair tested in both configurations i.e. $1^{st}$ A, $2^{nd}$ B and $1^{st}$ B, $2^{nd}$ A | | |

Results

Figure 21:
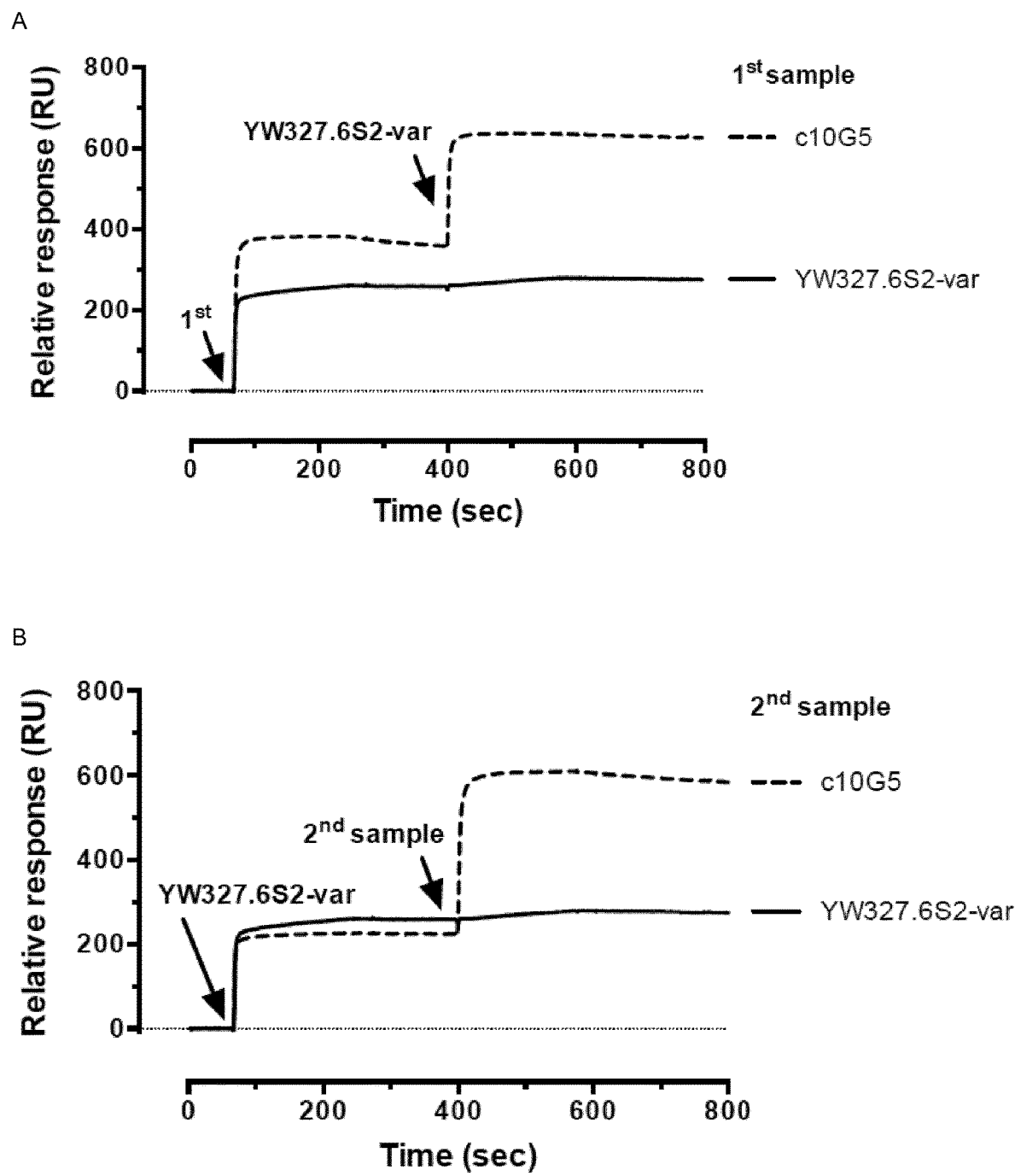

A typical Biacore response graph is shown in FIG. 21. The start of each injection is indicated, with their corresponding responses. The proteins used at each injection are also indicated. The regeneration phase was successfully conducted after each test, but the trace is trimmed from FIG. 21 for clarity.

Consistent with previous results, only the YW327.652 bound to Mouse Axl-Fc. Binding of all antibodies to Human Axl-Fc and Rhesus Axl-Fc gave qualitatively similar results.

Chugai and INSERM showed weaker binding under all conditions, with INSERM showing no detectable binding (suggesting a defective batch of Ab). The Chugai binding was sufficiently strong to assess the bound epitope. The table below summarizes the ability of a second protein to bind when another protein is already bound to the immobilized Axl-Fc. If the binding of the second protein is unaffected by the presence of the first, then they have independent epitopes, whereas if the first protein blocks binding of the second then the epitopes must be overlapping or close together.

| Addition order $1^{st}/2^{nd}$ | $1^{st}$ Response | $2^{nd}$ Response | Expected response if independent | Conclusion regarding epitopes |
|---|---|---|---|---|
| H2L1/H2L1 | 318 | 11.64 | 318 | overlap |
| H2L1/H2L1-prep2 | 320 | 8.9 | 323 | overlap |
| H2L1/YW327.6S2 | 308 | 299 | 291 | independent |
| H2L1/Chugai | 319 | 33.5 | 50 | independent |
| H2L1/INSERM | 319 | 13 | −1 | INSERM does not bind |
| H2L1/U3 | 319 | 321 | 322 | independent |
| YW327.6S2/H2L1 | 291 | 323 | 318 | independent |
| YW327.6S2/1H12 | ~220 | ~400 | ~400 | independent |
| 1H12/YW327.6S2 | ~400 | ~300 | ~220 | independent |
| 10G5/1H12 | ~170 | ~180 | ~220 | independent |
| 1H12/10G5 | ~220 | ~170 | ~170 | independent |
| Chugai/H2L1 | 50 | 317 | 318 | independent |
| Inserm/H2L1 | −1 | 319 | 318 | INSERM does not bind |
| U3/H2L1 | 322 | 320 | 318 | independent |
| H2L1-prep2/H2L1 | 323 | 13.8 | 318 | overlap |
| Gas6/H2L1 | 37 | 281 | 318 | overlap |
| Gas6/YW327.6S2 | 28 | 265 | 291 | overlap |
| Gas6/Chugai | 24 | 52 | 50 | independent |
| Gas6/INSERM | 21 | −3 | −1 | INSERM does not bind |
| Gas6/U3 | 18 | 333 | 322 | independent |
| Gas6/H2L1-prep2 | 14 | 301 | 318 | overlap |

As expected, as they are different preparations of the same antibody sequence, H2L1 and H2L1-prep2 have overlapping epitopes.

No competition was observed between binding of H2L1 and YW327.6S2 or U3 indicating that they have distinct epitopes. Although binding of Chugai was weak, the data suggest that it too does not share an epitope with H2L1.

When the first protein was Gas6, the data indicate that Gas6 blocks binding of H2L1, H2L1-prep2, and YW327.6S2. Gas6 does not block binding of Chugai or U3.

No competition was observed between binding of 1H12 and either YW327.6S2 or 10G5 indicating that they bind distinct epitopes.

Conclusions

Binding of H2L1 to immobilized Axl-Fc has no effect on binding of YW327.6S2, U3, or Chugai.

No binding of INSERM was observed under any conditions, suggesting a defective batch of Ab.

Binding of Gas6 to immobilized AxlFc inhibited the subsequent binding of H2L1, H2L1-prep2, and YW327.6S2. Gas 6 binding did not inhibit binding of Chugai or U3.

The epitope bound by H2L1 is therefore different from the epitopes bound by YW327.6S2, Chugai, and U3.

No results were obtained for the INSERM antibody in this assay. However, as noted above, the INSERM 'D9' and 'E8' antibodies described in Oncogene 33, 5405-5414 (20 Nov. 2014, doi:10.1038/onc.2013.487) do not inhibit the binding of GAS6 to Axl. This indicates the D9 and E8 antibodies do not bind the same epitope as H2L1 or YW327.6S2.

Thus, this assay in combination with published binding data demonstrates that the H2L1 antibody binds an epitope novel amongst those tested and, further, is one of only two antibodies (with YW327.6S2) which inhibits the binding of the Axl-ligand Gas6 to Axl.

Inhibition of Axl Activation

Goal

To assess the level to which various Axl inhibitors reduce activation of Axl, as assessed through on of inhibition of Tyrosine 866 (Y866), one of Axl's known autophosphorylation sites (others include Y779 and Y821—see Oncotarget. 2014 October; 5(20): 9546-9563; doi: 10.18632/oncotarget.2542 and references cited therein).

Lysate preparation

1. Seed out HeLa cells in 14 10-cm dishes
    a. 3 million cells per dish
2. Incubate cells until attached
3. Remove medium and wash cells with PBS 4. Serum-starve the cells in 0.5% FBS media
   a. 0.5% MEM for HeLa
   b. O/N at least 24 hour starvation
5. Incubate cells with anti-Axl antibodies for 1 hour in 6 ml fresh 0.5% MEM.
   a. BGB324 (CAS=1037624-75-1, UNII=0ICW2LX8AS): 0.2 uM
   b. H2L1-Evitra*: 50 ug/ml
      *same sequence, different preparation
   c. H2L1-Catalent*: 50 ug/ml
   d. YW327.652: 50 ug/ml
6. Stimulate designated plates with 0.01 ug/ml rhGas6 in 6 ml of total media per 10-cm dish.
   a. rhGas6 stimulation 0.01 ug/ml
7. Set-up: Make each in 26 ml of 0.5% MEM
   #1. Starvation
   #2. rhGas6 stimulation (0.01 ug/ml)
   #3. rhGas6 stimulation+pre-incubation with BGB324 0.2 uM
   #4. rhGas6 stimulation+pre-incubation with H2L1-Evitra: 50 ug/ml
   #5. rhGas6 stimulation+pre-incubation with H2L1-Catalent: 50 ug/ml
   #6. rhGas6 stimulation+pre-incubation with YW327.652 50 ug/ml
   #7. BGB324 0.2 uM alone
   #8. H2L1-Evitra: 50 ug/ml alone
   #9. H2L1-Catalent: 50 ug/ml alone
   #10. YW327.652 50 ug/ml alone
8. Stop reaction by lysing cells on ice
9. Wash with cold PBS
10. Add RIPA buffer (plus phosphatase inhibitors)
    a. 100 ul/dish
11. Scrape cells from dish
12. Incubate 5-10 min on ice
13. Spin down 13,000 rpm 5-10 min (cold)
14. Supernatant transferred to fresh tube
15. Measure phospho-protein by ELISA ELISA Measurement Axl protein using BerGenBio's monoclonal mouse anti-HsAxl antibody 5F11 as the capture antibody, and the affinity selected polyclonal rabbit anti-phospho-Axl antibodies (pAxl-Y866-16) as the detection antibody.

Materials
Nunc MaxiSorp 96C plates
Tris-buffered saline (TBS) pH7.6
Tween 20 (Sigma)
Wash buffer (TBS+0.05% Tween 20)
Fetal bovine serum (FBS) (Sigma)
Monoclonal mouse anti-HsAxl antibody 5F11, 3.6 mg/ml stock (BerGenBio).
Polyclonal rabbit anti-Hs-phospho-Y866 Axl antibody pAxl-Y866-16, 1.0 mg/ml (BerGenBio). Use diluted 1:1000 in TBS+10% FBS
HRP-conjugated Goat anti-Rabbit secondary antibody (Jackson Labs 111-035-144). Use at 1:2000 in TBS+10% FBS
Recombinant Human AxlFc chimera (AxlFc standard) (R&D Systems, 154-AL-100)
Recombinant Human AxlFc chimera conjugated to phospho-Axl peptides (pAxlFc standard) (BerGenBio)
0.2M Sodium carbonate buffer pH9.4
TMB stock solution (10 mg/ml 3,3',5,5'-Tetramethylbenzidine, Sigma T2885 in DMSO)
100 mM Sodium acetate pH6
1M $H_2SO_4$
30% Hydrogen peroxide solution Lysates: prepared as above. For HeLa cells total protein concentration 1.5 mg/ml gives a strong signal.
Microplate reader with 450 nm absorbance. Absorbance at 595 nm (if available) should be subtracted to reduce background, but the effect is marginal.
Optional: Thermo Multidrop Combi for rapid filling of 96-well plates with wash solution.

Protocol
Prepare Plates
Add 100 μl per well of 3.6 μg/ml capture antibody 5F11 diluted in 0.2M sodium carbonate bicarbonate pH 9.4 to a 96-well MaxiSorp C plate and incubate at 4° C. overnight.
Fill wells completely with 10% Fetal Bovine Serum in Tris-buffered saline, seal plates with foil and block for 4-5 hrs at 37° C.
Prepare and add samples
Prepare a series of AxlFc standards and pAxlFc standards (approx. range 60 ng/ml to 2 μg/ml, with 3-fold dilutions) and in the same buffer as your lysates.
Discard the blocking solution from the plates, wash twice with wash buffer (fill wells completely, then discard by flicking plate)
Add standards and lysate (minimum 50 μl/well. 100 μl/well preferred) to wells as appropriate
Seal plates and incubate for overnight at 4° C.
Add Detection antibody
Wash the plate twice with wash buffer
Add 100 μl/well of detection antibody (pAxl-Y866-16)
Incubate for 2-3 hours at room temperature in a humidified chamber
Add secondary antibody
Wash the plate twice with wash buffer
Add 100 μl/well HRP-conjugated Goat anti-rabbit antibody.
Incubate for 2 hours at room temperature in a humidified chamber.
Develop
Prepare fresh substrate solution:
   100 μl 10 mg/ml TMB stock solution
   10 μl 30% Hydrogen peroxide solution
   9.9 ml 100 mM Sodium acetate pH6
   Optional: test a small volume of the substrate solution by adding 1 μl leftover HRP-conjugated detection antibody mixture (step 12). The colour should change very rapidly to dark blue.
1. Wash the plate 3 times with wash buffer
2. Add 100 μl substrate solution to each well
3. Develop for 30 mins and stop reaction with 50 μl/well 1M $H_2SO_4$.
4. Read plate on microplate reader with absorbance of 450 nm. Subtract absorbance at 595 nm if available Results

| Lysate | Absorbance @ 450 nm |
| --- | --- |
| Starved | 0.044 |
| rhGas6 (0.01ug/ml) | 0.077 |
| rhGas6 + BGB324 | 0.045 |
| rhGas6 + H2L1(Evitria) | 0.04 |
| rhGas6 + H2L1 (Catalent) | 0.055 |
| rhGas6 + YW327.6S2var | 0.092 |
| BGB324 | 0.039 |
| H2L1 (Evitria) | 0.047 |
| H2L1 (Catalent) | 0.059 |
| YW327.6S2var | 0.092 |

Discussion

Lysates from cells stimulated with Gas6 in the presence of either H2L1 preparation or BGB324 gave pAXL readings (0.040, 0.055, 0.045) which were significantly lower than that of the Gas6 stimulated control cells (0.077); H2L1-Evitria and BGB324 were particularly low, with reading comparable to the starved control (0.44).

In contrast, the pAxl results indicate that the YW327.6S2var antibody strongly activates Axl auto-phosphorylation, with YW327.6S2var alone giving a pAxl reading of 0.092—higher than the Gas6 stimulated control cells (0.077).

The similar reading observed with the antibodies alone, or with Gas6, is consistent with the competition studies showing that both H2L1 and YW327.6S2var compete with Gas6 for Axl binding.

Activity in Fibrosis Assay

Goal

To assess the level to which various Axl inhibitors reduce the activity of pro-fibrotic markers in a fibrosis model. The model utilises LX2 cells—a hepatic stellate cell line of human origin—and monitors expression of extracellular matrix proteins alpha-SMA and Col1A1 (see, for example, *Matrix Biology*, Volume 34, February 2014, Pages 170-178; doi.org/10.1016/j.matbio.2013.11.002), pro-inflammatory MCP1 (*J Interferon Cytokine Res.* 2009 June; 29(6): 313-326; doi: 10.1089/jir.2008.0027), and the cytokine TGF-beta (implicated in excessive tissue damage in inflammatory contexts—see *Curr Opin Pharmacol.* 2009 August; 9(4): 447-53; doi: 10.1016/j.coph.2009.04.008).

Material and Methods

Cell Line and Treatments:

LX2 cells were used; this is a cell line of hepatic stellate cells of human origin, as first described in Gut (2005) 54(1):142-51. doi: 10.1136/gut.2004.042127. LX2 cells were routinely cultured in DMEM/10% FBS.

Viability Assay:

the tetrazolium based MTT assay was used to determine cell death. Briefly, approximately $2 \times 10^4$ cells per well were plated in 96-well tissue culture plates and after the o/n appropriate o/n treatments with BGB324, chimeric 1H12 Ab (see WO2015/193428), H2L1-prep2, and YW327.6S2var Ab at different concentrations, 10 μl of MTT reagent (5 mg/ml in PBS) were added and the plates were incubated for approximately 2 h. The media was removed afterwards and the formazan was solubilized with 100 ul 1-propanol and quantified with a spectrophotometer at a wavelength of 570 and 630 nm.

Effect of Axl Blocking Antibodies in Blocking Axl-Dependent AKT Activation in LX2 Cells:

Cells were seeded in 12-well/plate ($2 \times 10^5$ cells/well) in DMEM/10% FBS and allowed to attach and grow for >24h. Before experiments cells were left overnight in DMEM w/o FBS, pre-treated with BGB324, H2L1-prep2, or YW327.6S2var blocking antibodies at different concentrations (10-50 μg/ml) for 1 hour and then stimulated with a pre-clustered anti-Axl activating antibody (1H12 Ab, 1 μg/mL) for 15 minutes. Axl activation was read out via phosphorylation of Akt on serine 473 (Western blot).

Protein Analysis:

Cells were lysed in RIPA buffer (150 mM NaCl, 1.0% IGEPAL® CA-630, 0.5% sodium deoxycholate, 0.1% SDS, 50 mM Tris, pH 8.0, SIGMA-ALDRICH) supplemented with antiproteases and anti-phosphatases (PMSF, sodium orthovanadate, protease inhibitor cocktail, and sodium fluoride), adjusted to 1× Laemmli loading buffer, sonicated, and centrifuged. 20-30 μl of the samples were subjected to 8% sodium dodecyl sulphate-polyacrylamide gel electrophoresis and then transferred to nitrocellulose membranes. Membranes were blocked in 5% BSA-FAF and washed in TBS Tween buffer and then developed with Pierce-ECL western blotting Substrate.

The antibodies used were p-AKT (p-Akt1/2/3 (C-11)), 1:200 in 5% BSA/TBS-T, o/n at 4° C.; AKT (1:200), followed by anti-mouse m-IgGK BP-HRP (1:2000, 1h, RT); anti-AKT (Akt1/2/3 (H-136)), 1:400, 1h, RT followed by anti-rabbit-IgG-HRP (1:20000, 1h, RT).

Effect of Axl Blocking Antibodies in LX2 Cell Activation Features:

Cells were seeded in 12-well/plate ($2 \times 10^5$ cells/well) in DMEM/10% FBS and allowed to attach and grow for >24h.

Before experiments cells were left overnight in DMEM w/o FBS, pre-treated with BGB324, H2L1-prep2, or YW327.6S2var blocking antibodies (50 μg/ml) for 1 hour and then stimulated with a pre-clustered anti-Axl activating antibody (chimeric 1H12 Ab, 1 μg/mL).

Total RNA was isolated with TRIzol reagent. Total RNA was reverse transcribed to complementary DNA (cDNA) using the iScript cDNA Synthesis Kit (Bio-Rad), following the manufacturer's instructions. The housekeeping gene 18S and RPM were used as reference genes for normalization and $H_2O$ was used as a negative control.

To analyse LX2 activation features the mRNA expression of α-SMA; TGF-β, COL1A1, and MCP1 were analysed.

Activation of Axl Using the 1H12 Clustering Antibody

Activation of Axl is often achieved by treating Axl with its ligand, Gas6. However, as an alternative to Gas6, Axl may be strongly and consistently activated by treatment with the 1H12 clustering antibody.

Figure 22:
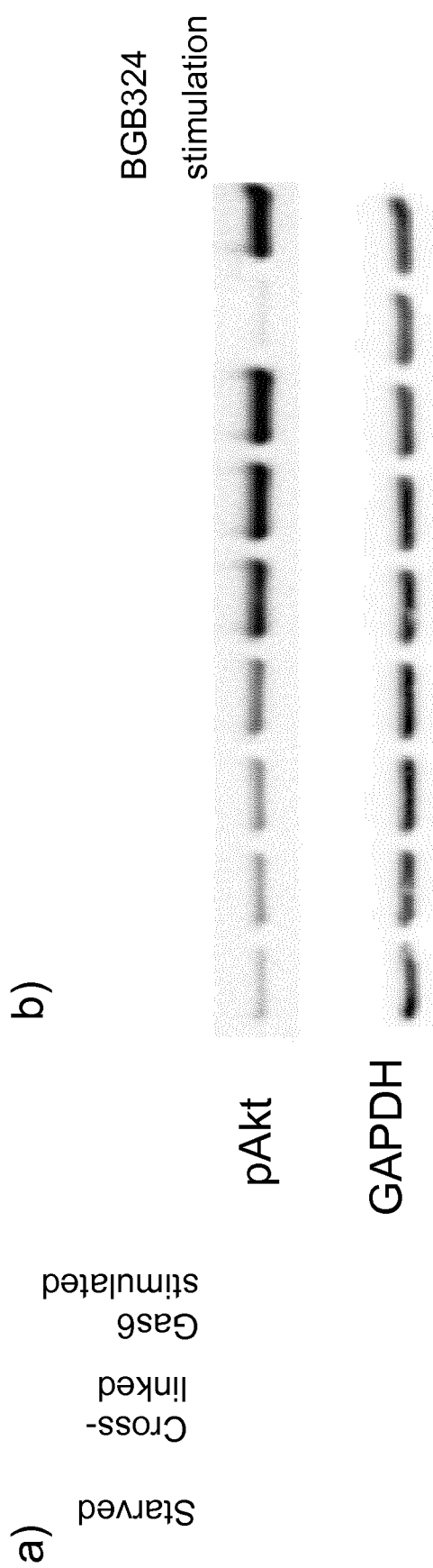

Comparing Gas6 and 1H12, stimulation of Akt phosphorylation was weaker with Gas6 than with 1H12 (see FIG. 22A). Stimulation with 1H12 showed good performance on pAkt activity on western blot analysis, with a clear response to BGB324 (FIG. 22B).

As described in Example 21, the 1H12 antibody binds a different epitope from either the YW327.6S2var or H2L1-prep2 antibodies. Accordingly, Axl may be activated using 1H12 without impeding YW327.6S2var or H2L1-prep2 Axl binding.

Results

Figure 23:
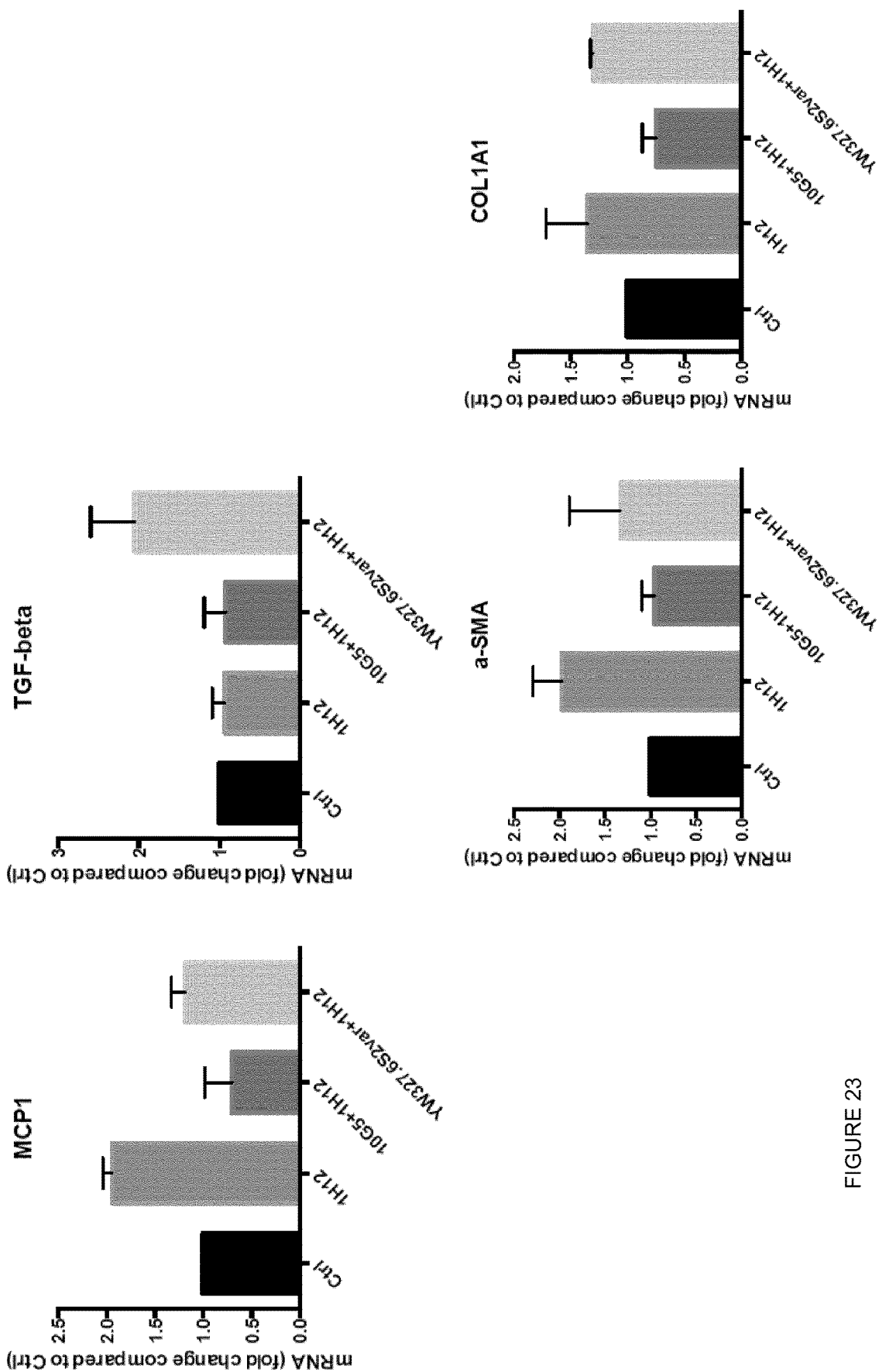

The results obtained are displayed in FIG. 23.

Discussion

Cells treated with H2L1-prep2 prior to exposure to the activating 1H12 antibody consistently exhibited expression levels for all four assayed markers which were similar to the unstimulated control cells.

In contrast, following pre-treatment with the YW327.6S2var antibody, raised expression levels were observed for all four assayed markers.

Activity in NSCLC Xenograft Model

Goal

To compare the anti-tumor activities of anti-Axl function-blocking antibodies defucosylated chimeric 10G5 (GlymaxX-c10G5) and the variant of anti-Axl human antibody from Genentech (YW327.6S2var) in A549 human non-small cell lung carcinoma (NSCLC) xenograft model in nude mice.

Experimental Procedures

Materials

Experimental Animals

Species/Strain: Mus musculus/Hsd: Athymic Nude-Foxn1nu

Source: Harlan Laboratories

Sex: Female

Weight: 20-30 grams on the day of implantation

Age: at least 6 weeks old on the day of randomization

Animal Identification: Cage number and ear notching

Cells and Cell Culture

A549 cells from ATCC (CCL-185).

DMEM medium supplemented with 10% FBS, 2 mM L-Glutamine, 100 U/ml penicillin and 100 µg/ml streptomycin, 0.01M HEPES buffer, 0.45% D-(+)-glucose, 1 mM sodium pyruvate.

0.25% Trypsin-EDTA, Sigma, Cat #SLBD8049.

BD Matrigel™ Basement Membrane Matrix Growth Factor Reduced, BD Bioscience, Cat #354230, Lot #2229975.

Drugs

Isotype control: Xolair™ omalizumab (Novartis Europharm Ltd, UK; Lot No. S2085), 150 mg/mL.

Anti-AXL Antibodies:
1. Chimeric (murine variable/human constant) defucosylated IgG1 c10G5 (MAb-GGlymaxX; Evitria, Lot No. 3556), 6.4 mg/mL.
2. Human YW327.6S2var (CONTR-1; Evitria, Lot No. 3537), 4.5 mg/mL.

Drug Preparation:

Need drugs for a total of 9 mice per group: Make drugs for 10 mice per group 250 µL per mouse×10=2.5 mL made in total GlymaxX-c10G5: dilute 1172 µL of 6.4 mg/mL GlymaxX stock solution by mixing with 1328 µL of sterile PBS to result in 2.5 mL of 3 mg/ml dosing solution. Antibody stocks will be kept at −80° C. Upon withdrawal, the antibodies will be thawed at room temperature and immediately put on ice. Antibody drugging solutions will be kept on ice until administration. Any leftover antibody drugging solutions will be kept at 4° C.

Human MAb YW327.6S2var: mix 1667 µL of 4.5 mg/ml CONTR-1 stock solution with 833 µL of sterile PBS to result in 2.5 mL of 3 mg/mL dosing solution. Antibody stocks will be kept at −80° C. Upon withdrawal, the antibodies will be thawed at room temperature and immediately put on ice. Antibody drugging solutions will be kept on ice until administration. Any leftover antibody drugging solutions will be kept at 4° C.

Xolair™ omalizumab: to obtain 2.5 mL of a drugging solution of 3 mg/mL, dilute 50 µL of antibody stock in 2490 µL of sterile PBS. Antibody stock solution is kept at 4° C. as advised by the manufacturer.

Methods

Cell Culture

A549 cells were maintained in vitro as a monolayer culture in DMEM medium supplemented with 10% FBS, 2 mM L-Glutamine, 100 U/ml penicillin and 100 µg/ml streptomycin, 0.01M HEPES buffer, 0.45% D-(+)-glucose, 1 mM sodium pyruvate.

While in an exponential growth phase, the cells were harvested and counted before tumor inoculation. In brief, sub-confluent cultured A549 cells were washed with sterile PBS and detached from flask with 0.25% (w/v) trypsin solution. The detached cells were washed once and resuspended at $4 \times 10^7$ cells per ml in serum-free DMEM medium and diluted 1:1 in BD Matrigel™ Basement Membrane Matrix Growth Factor Reduced. A total of $4 \times 10^6$ cells were injected per tumor. Cell viability was determined using trypan blue exclusion.

Subcutaneous Tumor Inoculation

Each mouse was inoculated subcutaneously into the right flank with 0.1 ml of approximately $4 \times 10^7$ cells/ml A549 cells in serum-free DMEM medium with 50% matrigel (Annex 1). Treatment was initiated for mice inoculated with A549 cells 24 days after tumor cell inoculation when the tumors had reached average volume of 125 mm$^3$. Each treatment group comprised nine tumorbearing mice.

Assignment of Experimental Groups

Before commencement of treatment, animals were weighted and the tumor volume was measured twice a week. Since the tumor volume could affect the effectiveness of any given treatment, mice were assigned into groups using a Latin square method. Randomization was based on the tumor volume and it ensures that each animal had the same probability of being assigned to a given treatment and, therefore, systematic error was reduced and the treatment groups were comparable at the baseline. 45 animals were randomized into 5 treatment groups.

Dosing

On the appropriate days, each animal received a specific amount of isotype control antibody (Xolair™) or an anti-Axl antibody in the following dose: 30 mg/kg, 3 mg/ml, bi-weekly administration×5 weeks, Euthanased on day 38. Dosing administration was IP and dosing volume was 10 ml/kg by 30-gauge needle.

Clinical Observations

At the time of routine monitoring, the animals were checked for any effects of tumor growth or treatments on normal behavior, such as mobility, dehydration, body weight gain/loss, eye matting and any other abnormal effect. Death and observed clinical signs were recorded. Non-fasted body weights were recorded every day.

Tumor Measurements and the Endpoints

Tumor measurements: Tumor size was measured twice a week in two dimensions using a caliper, and the tumor volume was calculated using the formula: $V=0.5\ a \times b^2$ [mm$^3$], where a and b are the long and short diameter of the tumor, respectively.

Endpoint:

Mice were sacrificed by cervical dislocation while in deep anesthesia. For each animal, each tumor divided in two equal parts, one was snap frozen in liquid nitrogen and stored in −80° C. freezer, and the other part was fixed at 4% formaldehyde, transferred to 70% ethanol after 24 h and stored at 4° C. for further evaluation.

Statistical Analysis

The tumor growth curves were compared by two-way (time and treatment) ANOVA with Bonferroni post-tests to compare replicate means using software PRISM (GraphPad, San Diego, Calif.). Differences between the groups were considered significant when P<0.05. The outliers were detected by comparison of individual tumor volumes using Grubbs' test with online Outlier calculator (QuickCalcs, GraphPad; http://graphpad.com/quickcalcs/Grubbs1.cfm). Figures were generated using software PRISM (GraphPad).

Results

Body Weight Change

Body weight changes because of vehicle or anti-AXL antibody treatment over the course of 38 days was monitored. Treatment was initiated at day 0 and was performed twice a week for 5 weeks. In general, a drop in body weight >20% indicates treatment toxicity and should lead to the euthanization of the animal. No group showed a reduction in body weight indicative of toxicity.

Tumour Volume Changes

Figure 24:
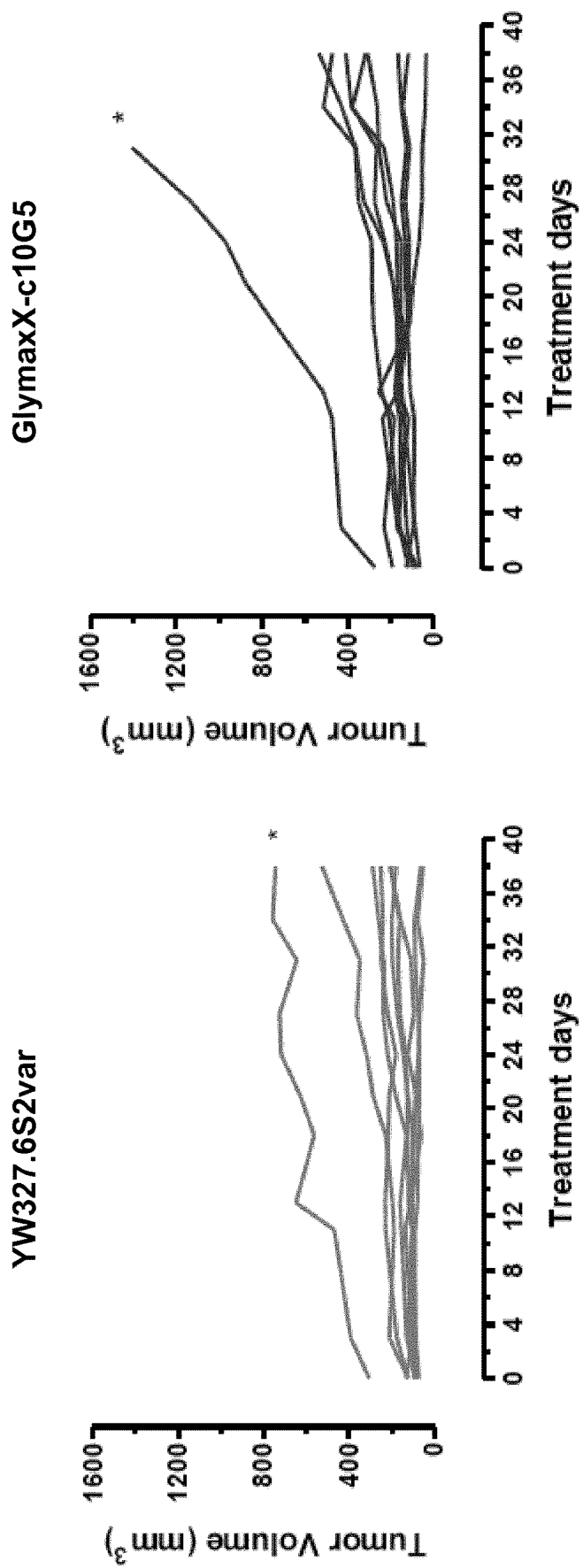

A plot showing the tumor growth of individual tumors in mice treated with either GlymaxX-c10G5) and the variant of anti-Axl human antibody from Genentech (YW327.6S2var) is shown in FIG. 24.

Tumor growth retardation was observed in both the animal groups treated with defucosylated chimeric antibody c10G5 (GlymaxX-c10G5) and Genentech's antibody YW327.6S2var.

There were also single outliers in both the YW327.6S2var and GlymaxX-c10G5 groups which have been excluded from further analyses (indicated with asterisks in FIG. 24).

Comparison of the tumor growth curves for different groups until day 31 of treatment indicated significant difference for the YW327.6S2var and GlymaxX-c10G5 groups from the group treated with the isotype control—see table below).

| | Significance of difference between isotype control group and anti-Axl group | |
|---|---|---|
| Day | YW327.652var | GlymaxX-c10G5 |
| 0 | Not significant (P >0.05) | Not significant (P >0.05) |
| 3 | Not significant (P >0.05) | Not significant (P >0.05) |
| 11 | Not significant (P >0.05) | Not significant (P >0.05) |
| 13 | Not significant (P >0.05) | Not significant (P >0.05) |
| 18 | P <0.05 | Not significant (P >0.05) |
| 21 | P <0.05 | P <0.05 |
| 24 | P <0.01 | P <0.01 |
| 27 | P <0.001 | P <0.01 |
| 31 | P <0.0001 | P <0.001 |

Discussion

Defucosylated chimeric antibody c10G5 has similar anti-tumor activity as the Genentech's fully human MAb YW327.6S2 in this murine Xenograft NSCLC xenograft model.

The above observation suggests H2L1, a humanized antibody with the binding specificity of 10G5 may be more efficacious than YW327.6S2 in a human subject. The reason for this is that, as reported in examples 21 and 22, YW327.6S2 binds to murine Axl whereas 10G5 does not. Accordingly, the effects reported for YW327.6S2 are a result of antibody action on both the human xenograft cells and the host murine tissue. In contrast, the effects reported for 10G5 arise solely from antibody action on the human xenograft cells

```
SEQUENCES

SEQ ID NO. 1 [hu10G5 VH(GH1)]
EVQLVQSGAGLVQPGGSVRLSCAASGYSFTDFYINWVRQAPGKGLEWIARIFPGGDNTYY
NEKFKGRFTLSADTSSSTAYLQLNSLRAEDTAVYYCARRGLYYAMDYWGQGTLVTVSS

SEQ ID NO. 2 [hu10G5 VH(GH2)]
EVQLVESGGGLVQPGGSLRLSCAASGYSFTDFYINWVRQAPGKGLEWVARIFPGGDNTYY
NEKFKGRFTLSADTSKSTAYLQMNSLRAEDTAVYYCARRGLYYAMDYWGQGTLVTVSS

SEQ ID NO. 3 [hu10G5 VL(GL1)]
DIQMTQSPSSLSASVGDRVTITCRSSQSLVHSNGIPYLHWYQQKPGKAPKLLIYRVSNRFS
GVPSRFSGSGSGTDFTLTISSLQPEDFATYYCSQGTHVPPTFGQGTKVEIK

SEQ ID NO. 4 [hu10G5 VL(GL2)]
DIQMTQSPSSLSASVGDRVTITCRSSQSLVHSNGIPYLHWYQQKPGKAPKLLIYRVSNRFS
GVPSRFSGSRSGTDFTLTISSLQPEDFATYYCSQGTHVPPTFGQGTKVEIK

SEQ ID NO. 5 [example heavy chain constant region]
ASTKGPSVFPLAPSSKSTSGGTAALGCLVKDYFPEPVTVSWNSGALTSGVHTFPAVLQSSG
LYSLSSVVTVPSSSLGTQTYICNVNHKPSNTKVDKKVEPKSCDKTHTCPPCPAPELLGGPS
VFLFPPKPKDTLMISRTPEVTCVVVDVSHEDPEVKFNWYVDGVEVHNAKTKPREEQYNSTY
RVVSVLTVLHQDWLNGKEYKCKVSNKALPAPIEKTISKAKGQPREPQVYTLPPSREEMTKN
QVSLTCLVKGFYPSDIAVEWESNGQPENNYKTTPPVLDSDGSFFLYSKLTVDKSRWQQGN
VFSCSVMHEALHNHYTQKSLSLSPGK SEQ ID NO. 6 [10G5 GH1 Heavy chain]
EVQLVQSGAGLVQPGGSVRLSCAASGYSFTDFYINWVRQAPGKGLEWIARIFPGGDNTYY
NEKFKGRFTLSADTSSSTAYLQLNSLRAEDTAVYYCARRGLYYAMDYWGQGTLVTVSSAS
TKGPSVFPLAPSSKSTSGGTAALGCLVKDYFPEPVTVSWNSGALTSGVHTFPAVLQSSGLY
SLSSVVTVPSSSLGTQTYICNVNHKPSNTKVDKKVEPKSCDKTHTCPPCPAPELLGGPSVF
LFPPKPKDTLMISRTPEVTCVVVDVSHEDPEVKFNWYVDGVEVHNAKTKPREEQYNSTYR
VVSVLTVLHQDWLNGKEYKCKVSNKALPAPIEKTISKAKGQPREPQVYTLPPSREEMTKNQ
VSLTCLVKGFYPSDIAVEWESNGQPENNYKTTPPVLDSDGSFFLYSKLTVDKSRWQQGNV
FSCSVMHEALHNHYTQKSLSLSPGK SEQ ID NO. 7 [10G5 GH2 Heavy chain]
EVQLVESGGGLVQPGGSLRLSCAASGYSFTDFYINWVRQAPGKGLEWVARIFPGGDNTYY
NEKFKGRFTLSADTSKSTAYLQMNSLRAEDTAVYYCARRGLYYAMDYWGQGTLVTVSSAS
TKGPSVFPLAPSSKSTSGGTAALGCLVKDYFPEPVTVSWNSGALTSGVHTFPAVLQSSGLY
```

| SEQUENCES |
| --- |
| SLSSVVTVPSSSLGTQTYICNVNHKPSNTKVDKKVEPKSCDKTHTCPPCPAPELLGGPSVF<br>LFPPKPKDTLMISRTPEVTCVVVDVSHEDPEVKFNWYVDGVEVHNAKTKPREEQYNSTYR<br>VVSVLTVLHQDWLNGKEYKCKVSNKALPAPIEKTISKAKGQPREPQVYTLPPSREEMTKNQ<br>VSLTCLVKGFYPSDIAVEWESNGQPENNYKTTPPVLDSDGSFFLYSKLTVDKSRWQQGNV<br>FSCSVMHEALHNHYTQKSLSLSPGK<br><br>SEQ ID NO. 8 [example light chain constant region]<br>RTVAAPSVFIFPPSDEQLKSGTASVVCLLNNFYPREAKVQWKVDNALQSGNSQESVTEQD<br>SKDSTYSLSSTLTLSKADYEKHKVYACEVTHQGLSSPVTKSFNRGEC<br><br>SEQ ID NO. 9 [10G5 GL1 Light chain]<br>DIQMTQSPSSLSASVGDRVTITCRSSQSLVHSNGIPYLHWYQQKPGKAPKLLIYRVSNRFS<br>GVPSRFSGSGSGTDFTLTISSLQPEDFATYYCSQGTHVPPTFGQGTKVEIKRTVAAPSVFIF<br>PPSDEQLKSGTASVVCLLNNFYPREAKVQWKVDNALQSGNSQESVTEQDSKDSTYSLSST<br>LTLSKADYEKHKVYACEVTHQGLSSPVTKSFNRGEC<br><br>SEQ ID NO. 10 [10G5 GL2 Light chain]<br>DIQMTQSPSSLSASVGDRVTITCRSSQSLVHSNGIPYLHWYQQKPGKAPKLLIYRVSNRFS<br>GVPSRFSGSRSGTDFTLTISSLQPEDFATYYCSQGTHVPPTFGQGTKVEIKRTVAAPSVFIF<br>PPSDEQLKSGTASVVCLLNNFYPREAKVQWKVDNALQSGNSQESVTEQDSKDSTYSLSST<br>LTLSKADYEKHKVYACEVTHQGLSSPVTKSFNRGEC<br><br>SEQ ID NO. 11 [hu10G5 VH(GH1), nucleic acid]<br>gaggtgcagctggtccagtccggagctggactggtgcagccaggcggatctgtcagactgagttgcgccgcttccggctacagc<br>ttcaccgactttatatcaactgggtcagacaggcccccggcaagggtctggagtggatcgctcgcattttccctgggggtgacaa<br>cacatactacaacgaaaagttcaaaggcaggttcaccctgtccgccgatacttccagctctaccgcatacctgcaactgaactcc<br>ctgagggcagaagacacagccgtgtactattgtgccaggcggggcctgtactatgctatggattattggggccagggaaccctg<br>gtgacagtctcgagc<br><br>SEQ ID NO. 12 [hu10G5 VH(GH2), nucleic acid]<br>gaggtgcagctggtggaatccggcggagggctggtgcagccaggtggcagcctgagactgtcttgcgccgcttcaggatactc<br>cttcaccgactttatatcaactgggtcagacaggcccccggcaagggcctggagtgggtcgctcgcattttccctggaggggac<br>aacacatactacaacgaaaagttcaaaggcaggttcaccctgagtgctgatacttctaaaagtaccgcatacctgcaaatgaat<br>agcctgagggcagaggacacagccgtgtactattgtgccaggcggggcctgtactatgctatggattattgggggacaggggacc<br>ctggtgacagtctcgagc<br><br>SEQ ID NO. 13 [hu10G5 VL(GL1), nucleic acid]<br>gacatccagatgacacagtctccctccagcctgagcgcctctgtgggagatagagtcaccatcacatgcaggtctagtcagagc<br>ctggtgcactctaacggcatccccctacctgcattggtatcagcagaagcagggaaagctcccaagctgctgatctacagagtc<br>agtaatcggttctctggtgtcccttcgaggtttagtggctcaggctccgggacagacttcactctgaccatttcatccctgcaaccag<br>aggattttgcaacttactattgtagcagggcacacacgtgcccctactttcggtcagggcaccaaagtcgaaattaag<br><br>SEQ ID NO. 14 [hu10G5 VL(GL2), nucleic acid]<br>gacatccagatgacacagtctccctccagcctgagcgcctctgtgggcgatcgagtcaccatcacatgcaggtctagtcagagc<br>ctggtgcactctaacggcattcctacctgcattggtatcagcagaagcaggaaaagctcccaagctgctgatctacagagtca<br>gtaatcggttctctggcgtgccctccaggttctccgggtcacgctccggaacagactccactctgaccatttcatccctgcaaccag<br>aggattttgcaacttactattgtagcagggaacacacgtgcccctactttcggccagggaaccaaagtcgaaattaag<br><br>SEQ ID NO. 15 [example heavy chain constant region, nucleic acid]<br>gctagcacaaagggcccctagtgtgtttcctctggctccctcttccaaatccacttctggtggcactgctgctctgggatgcctggtgaa<br>ggattactttcctgaacctgtgactgtctcatggaactctggtgctctgacttctggtgtccacactttccctgctgtgctgcagtctagtg<br>gactgtactctctgtcatctgtggtcactgtgccctcttcatctctgggaacccagacctacatttgtaatgtgaaccacaaaccatcc<br>aacactaaagtggacaaaaaagtggaaccaaatcctgtgacaaaacccacacctgcccacctgtcctgcccctgaactgct<br>gggaggaccttctgtgtttctgttccccccaaaccaaaggtaccctgatgatctctagaaccctgaggtgacatgtgtggtggt<br>ggatgtgtctcatgaggaccctgaggtcaaattcaactggtacgtggatggagtggaagtccacaatgccaaaaccaagcctag<br>agaggaacagtacaattcaacctacagagtggtcagtgtgctgactgtgctgcatcaggattggctgaatggcaaggaatacaa<br>gtgtaaagtctcaaacaaggcctgcctgctccaattgagaaaacaatctcaaaggccaagggacagcctagggaacccag<br>gtctacaccctgccaccttcaagagaggaaatgaccaaaaaccaggtgtccctgacatgcctggtcaaaggcttctacccttctg<br>acattgctgtggagtgggagtcaaatggacagcctgagaacaactacaaaacaacccccctgtgctggattctgatggctctttt<br>ctttctgtactccaaactgactgtggacaagtctagatggcagcaggggaatgtcttttcttgctctgtcatgcatgaggctctgcata<br>accactacactcagaaatccctgtctctgtctcccgggaaa<br><br>SEQ ID NO. 16 [10G5 GH1 Heavy chain, nucleic acid]<br>gaggtgcagctggtccagtccggagctggactggtgcagccaggcggatctgtcagactgagttgcgccgcttccggctacagc<br>ttcaccgactttatatcaactgggtcagacaggcccccggcaagggtctggagtggatcgctcgcattttccctgggggtgacaa<br>cacatactacaacgaaaagttcaaaggcaggttcaccctgtccgccgatacttccagctctaccgcatacctgcaactgaactcc<br>ctgagggcagaagacacagccgtgtactattgtgccaggcggggcctgtactatgctatggattattggggccagggaaccctg<br>gtgacagtctcgagcgctagcacaaagggcccctagtgtgtttcctctggctccctcttccaaatccacttctggtggcactgctgctct<br>gggatgcctggtgaaggattactttcctgaacctgtgactgtctcatggaactctggtgctctgacttctggtgtccacactttccctgct<br>gtgctgcagtctagtggactgtactctctgtcatctgtggtcactgtgccctcttcatctctgggaacccagacctacatttgtaatgtga<br>accacaaaccatccaacactaaagtggacaaaaaagtggaacccaatcctgtgacaaaacccacacctgcccaccttgtcc<br>tgcccctgaactgctgggaggaccttctgtgtttctgttccccccaaaccaaaggtaccctgatgatctctagaacccctgaggt<br>gacatgtgtggtggatgtgtctcatgaggaccctgaggtcaaattcaactggtacgtggatggagtggaagtccacaatgcc<br>aaaaccaagcctagagaggaacagtacaattcaacctacagagtggtcagtgtgctgactgtgctgcatcaggattggctgaat<br>ggcaaggaatacaagtgtaaagtctcaaacaaggcctgcctgctccaattgagaaaacaatctcaaaggccaagggacag<br>cctagggaacccaggtctacaccctgccaccttcaagagaggaaatgaccaaaaaccaggtgtccctgacatgcctggtcaa<br>aggcttctacccttctgacattgctgtggagtgggagtcaaatggacagcctgagaacaactacaaaacaacccccctgtgctg |

SEQUENCES gattctgatggctctttctttctgtactccaaactgactgtggacaagtctagatggcagcaggggaatgtcttttcttgctctgtcatgc
atgaggctctgcataaccactacactcagaaatccctgtctctgtctcccgggaaa SEQ ID NO. 17 [10G5 GH2 Heavy chain, nucleic acid]
gaggtgcagctggtggaatccggcggagggctggtgcagccaggtggcagcctgagactgtcttgcgccgcttcaggatactc
cttcaccgacttttatatcaactgggtcagacaggcccccggcaagggcctggagtgggtcgctcgcattttccctggaggggac
aacacatactacaacgaaaagttcaaaggcaggttcacctctgagtgctgatacttctaaaagtaccgcatacctgcaaatgaat
agcctgagggcagaggacacagccgtgtactattgtgccaggcggggcctgtactatgctatggattattggggacaggggacc
ctggtgacagtctcgagcgctagcacaaagggcccatcggtcttccccctggcaccctcctccaagagcacctctgggggcacagcggcc
ctgggctgcctggtcaaggactacttccccgaaccggtgacggtgtcgtggaactcaggcgccctgaccagcggcgtgcacacc
ttcccggctgtcctacagtcctcaggactctactccctcagcagcgtggtgaccgtgccctccagcagcttgggcacccagacctacatc
tgcaacgtgaatcacaagcccagcaacaccaaggtggacaagaaagttgagcccaaatcttgtgacaaaactcacacatgcccaccgt
gcccagcacctgaactcctggggggaccgtcagtcttcctcttccccccaaaacccaaggacaccctcatgatctcccggacccctg
aggtcacatgcgtggtggtggacgtgagccacgaagaccctgaggtcaagttcaactggtacgtggacggcgtggaggtgcataat
gccaagacaaagccgcgggaggagcagtacaacagcacgtaccgtgtggtcagcgtcctcaccgtcctgcaccaggactggctg
aatggcaaggagtacaagtgcaaggtctccaacaaagccctcccagcccccatcgagaaaaccatctccaaagccaaaggg
cagccccgagaaccacaggtgtacaccctgcccccatcccgggatgagctgaccaagaaccaggtcagcctgacctgcctggtc
aaaggcttctaccccagcgacatcgccgtggagtgggagagcaatgggcagccggagaacaactacaagaccacgcctcccgtg
ctggactccgacggctccttcttcctctacagcaagctcaccgtggacaagagcaggtggcagcaggggaacgtcttctcatgctccgtgatg
catgaggctctgcataaccactacactcagaaatccctgtctctgtctcccgggaaa SEQ ID NO. 18 [light constant region, nucleic acid]
Cgtacggtcgcggcgccttctgtgttcattttccccccatctgatgaacagctgaaatctggcactgcttctgtggtctgtctgctgaac
aacttctaccctagagaggccaaagtccagtggaaagtggacaatgctctgcagagtgggaattcccaggaatctgtcactgag
caggactctaaggatagcacatactccctgtcctctactctgacactgagcaaggctgattacgagaaacacaaagtgtacgcc
tgtgaagtcacacatcagggcctgtctagtcctgtgaccaaatccttcaatagggagagtgc SEQ ID NO. 19 [10G5 GL1 Light chain, nucleic acid]
gacatccagatgacacagtctccctcccagcctgagcgcctctgtgggagatagagtcaccatcacatgcaggtctagtcagagc
ctggtgcactctaacggcatccctacctgcattggtatcagcagaagcagggaaagctcccaagctgctgatctacagagtc
agtaatcggttctctggtgtcccttcgaggtttagtggctcaggctccgggacagacttcactctgaccattcatcccgcaaccag
aggattttgcaacttactattgtagccagggcacacacgtgccccctacttcggtcagggcaccaaagtcgaattaagcgtacg
gtcgcggcgccttctgtgttcattttccccccatctgatgaacagctgaaatctggcactgcttctgtggtctgtctgctgaacaacttct
accctagagaggccaaagtccagtggaaagtggacaatgctctgcagagtgggaattcccaggaatctgtcactgagcagga
ctctaaggatagcacatactccctgtcctctactctgacactgagcaaggctgattacgagaaacacaaagtgtacgcctgtgaa
gtcacacatcagggcctgtctagtcctgtgaccaaatccttcaatagggagagtgc SEQ ID NO. 20 [10G5 GL2 Light chain, nucleic acid]
gacatccagatgacacagtctccctcccagcctgagcgcctctgtgggcgatcgagtcaccatcacatgcaggtctagtcagagc
ctggtgcactctaacggcattccttacctgcattggtatcagcagaagcaggaaaagctcccaagctgctgatctacagagtca
gtaatcggttctctggcgtgccctccaggttctccgggtcacgctccggaacagacttcactctgaccattcatccctgcaaccag
aggattttgcaacttactattgtagccagggaacacacgtgcccctactttcggcagggaaccaaagtcgaattaagcgtac
ggtcgcggcgccttctgtgttcattttccccccatctgatgaacagctgaaatctggcactgcttctgtggtctgtctgctgaacaacttc
taccctagagaggccaaagtccagtggaaagtggacaatgctctgcagagtgggaattcccaggaatctgtcactgagcagga
ctctaaggatagcacatactccctgtcctctactctgacactgagcaaggctgattacgagaaacacaaagtgtacgcctgtgaa
gtcacacatcagggcctgtctagtcctgtgaccaaatccttcaatagggagagtgc SEQ ID NO. 21 [Human Axl]
MAWRCPRMGRVPLAWCLALCGWACMAPRGTQAEESPFVGNPGNITGARGLTGTLRCQL
QVQGEPPEVHWLRDGQILELADSTQTQVPLGEDEQDDWIVVSQLRITSLQLSDTGQYQCL
VFLGHQTFVSQPGYVGLEGLPYFLEEPEDRTVAANTPFNLSCQAQGPPEPVDLLWLQDAV
PLATAPGHGPQRSLHVPGLNKTSSFSCEAHNAKGVTTSRTATITVLPQQPRNLHLVSRQPT
ELEVAWTPGLSGIYPLTHCTLQAVLSDDGMGIQAGEPDPPEEPLTSQASVPPHQLRLGSLH
PHTPYHIRVACTSSQGPSSVVTHWLPVETPEGVPLGPPENISATRNGSQAFVHWQEPRAPL
QGTLLGYRLAYQGQDTPEVLMDIGLRQEVTLELQGDGSVSNLTVCVAAYTAAGDGPWSLP
VPLEAWRPGQAQPVHQLVKEPSTPAFSWPWWYVLLGAVVAAACVLILALFLVHRRKKETR
YGEVFEPTVERGELVVRYRVRKSYSRRTTEATLNSLGISEELKEKLRDVMVDRHKVALGKT
LGEGEFGAVMEGQLNQDDSILKVAVKTMKIAICTRSELEDFLSEAVCMKEFDHPNVMRLIGV
CFQGSERESFPAPVVILPFMKHGDLHSFLLYSRLGDQPVYLPTQMLVKFMADIASGMEYLS
TKRFIHRDLAARNCMLNENMSVCADFGLSKKIYNGDYYRQGRIAKMPVKWIAIESLADRVY
TSKSDVWSFGVTMWEIATRGQTPYPGVENSEIYDYLRQGNRLKQPADCLDGLYALMSRC
WELNPQDRPSFTELREDLENTLKALPPAQEPDEILYVNMDEGGGYPEPPGAAGGADPPTQ
PDPKDSCSCLTAAEVHPAGRYVLCPSTTPSPAQPADRGSPAAPGQEDGA SEQ ID NO. 22 [Murine Axl]
MGRVPLAWWLALCCWGCAAHKDTQTEAGSPFVGNPGNITGARGLTGTLRCELQVQGEPP
EVVWLRDGQILELADNTQTQVPLGEDWQDEWKVVSQLRISALQLSDAGEYQCMVHLEGRT
FVSQPGFVGLEGLPYFLEEPEDKAVPANTPFNLSCQAQGPPEPVTLLWLQDAVPLAPVTGH
SSQHSLQTPGLNKTSSFSCEAHNAKGVTTSRTATITVLPQRPHHLHVVSRQPTELEVAWTP
GLSGIYPLTHCNLQAVLSDDGVGIWLGKSDPPEDPLTLQVSVPPHQLRLEKLLPHTPYHIRIS
CSSSQGPSPVVTHWLPVETTEGVPLGPPENVSAMRNGSQVLVRWQEPRVPLQGTLLGYRL
AYRGQDTPEVLMDIGLTREVTLELRGDRPVANLTVSVTAYTSAGDGPWSLPVPLEPWRPG
QGQPLHHLVSEPPPRAFSWPWWYVLLGALVAAACVLILALFLVHRRKKETRYGEVFEPTVE
RGELVVRYRVRKSYSRRTTEATLNSLGISEELKEKLRDVMVDRHKVALGKTLGEGEFGAVM
EGQLNQDDSILKVAVKTMKIAICTRSELEDFLSEAVCMKEFDHPNVMRLIGVCFQGSDREGF
PEPVVILPFMKHGDLHSFLLYSRLGDQPVFLPTQMLVKFMADIASGMEYLSTKRFIHRDLAA
RNCMLNENMSVCADFGLSKKIYNGDYYRQGRIAKMPVKWIAIESLADRVYTSKSDVWSFG -continued

SEQUENCES

VTMWEIATRGQTPYPGVENSEIYDYLRQGNRLKQPVDCLDGLYALMSRCWELNPRDRPSF
AELREDLENTLKALPPAQEPDEILYVNMDEGGSHLEPRGAAGGADPPTQPDPKDSCSCLTA
ADVHSAGRYVLCPSTAPGPTLSADRGCPAPPGQEDGA

SEQ ID NO. 23 [Human Tyro3]
malrrsmgrpglpplplpppprlglllaalaslllpesaaaglklmgapvkltvsqgqpvklncsvegmeepdiqwvkdgavvqnl
dqlyipvseqhwigflslksversdagrywcqvedggeteisqpvwltvegvpfftvepkdlavppnapfqlsceavgppepvtiv
wwrgttkiggpapspsvlnvtgvtqstmfsceahnlkglassrtatvhlqalpaapfnitvtklsssnasvawmpgadgrallqsct
vqvtqapggwevlavvvpvppftcllrdlvpatnyslrvrcanalgpspyadwvpfqtkglapasapqnlhairtdsglileweevi
peaplegplgpyklswvqdngtqdeltvegtranltgwdpqkdlivrvcvsnavgcgpwsqplvvsshdragqqgpphsrtsw
vpvvlgvltalvtaaalalillrkrrketrfgqafdsvmargepavhfraarsfnrerperieatldslgisdelkekledvlipeqqftlgrm
lgkgefgsvreaqlkqedgsfvkvavkmlkadiiassdieeflreaacmkefdhphvaklvgvslrsrakgrlpipmvilpfmkhg
dlhafllasrigenpfnlplqtlirfmvdiacgmeylssrnfihrdlaarncmlaedmtvcvadfglsrkiysgdyyrqgcasklpvkwl
alesladnlytvqsdvwafgvtmweimtrgqtpyagienaelynyliggnrlkqppecmedvydlmyqcwsadpkqrpsftclr
melenilgqlsvlsasqdplyinieraeeptaggslelpgrdqpysgagdgsgmgavggtpsdcryiltpggllaeqpgqaehqp
esplnetqrllllqqgllphssc SEQ ID NO. 24 [Human Mer]
mgpaplplllglflpalwrraiteareeakpyplfpgpfpgslqtdhtpllslphasgyqpalmfsptqpgrphtgnvaipqvtsvesk
plpplafkhtvghiilsehkgvkfncsisvpniyqdttiswwkdgkellgahhaitqfypddevtaiiasfsitsvqrsdngsyickmki
nneeivsdpiyievqglphftkqpesmnvtrntafnltcqavgppepvnifwvqnssrvneqpekspsvltvpgltemavfscea
hndkgltvskgvqinikaipspptevsirnstahsiliswvpgfdgyspfrncsiqvkeadplsngsvmifntsalphlyqikqlqala
nysigvscmneigwsavspwilastttegapsvaplnvtvflnessdnvdirwmkpptkqqdgelvgyrishvwqsagiskelle
evgqngsrarisvqvhnatctvriaavtrggvgpfsdpvkifipahgwvdyapsstpapgnadpvliifgcfcgfililglilyislairkrv
qetkfgnafteedselvvnyiakksfcrraieltlhslgvseelqnkledvvidrnlllilgkilgegefgsvmegnlkqedgtslkvavkt
mkldnssqreieeflseaacmkdfshpnvirllgvciemssqgipkpmvilpfmkygdlhtyllysrletgpkhiplqtllkfmvdial
gmeylsnrnflhrdlaarncmlrddmtvcvadfglskkiysgdyyrqgriakmpvkwiaiesladrvytsksdvwafgvtmweia
trgmtpypgvqnhemydyllhghrlkqpedcldelyeimyscwrtdpldrptfsvlrlqlelleslpdvrnqadviyvntqllesseg
laqgstlapldlnidpdsiiasctpraaisvvtaevhdskphegryilnggseewedltsapsaavtaeknsvlpgerlvrngvsws
hssmlplgsslpdellfaddssegsevlm SEQ ID NO. 25 [Human Akt3]
msdvtivkegwvqkrgeyiknwrpryfllktdgsfigykekpqdvdlpyplnnfsvakcqlmkterpkpntfiirclqwttviertfhvd
tpeereewteaiqavadrlqrqeeermncsptsqidnigeeemdastthhkrktmndfdylkllgkgtfgkvilvrekasgkyya
mkilkkeviiakdevahtltesrvlkntrhpfltslkysfqtkdrlcfvmeyvnggelffhlsrervfsedrtrfygaeivsaldylhsgkivy
rdlklenlmldkdghikitdfglckegitdaatmktfcgtpeylapevlednydygravdwwglgvvmyemmcgrlpfynqdhekl
felilmedikfprtlssdaksllsgllikdpnkrlgggpddakeimrhsffsgvnwqdyydkklvppfkpqvtsetdtryfdeeftaqtiti
tppekcqqsdcgmlgnwkk SEQ ID NO. 26 [Human Gas6]
mapslspgpaalrrapqllllllaaecalaallpareatqflrprqrrafqvfeeakqghlerecveelcsreearevfendpetdyfyp
ryldcinkygspytknsgfatcyqnlpdqctpnpcdrkgtqacqdlmgnffclckagwggrlcdkdynecsqenggclqichnkp
gsfhcschsgfelssdgrtcqdidecadseacgearcknlpgsysclcdegfayssqekacrdvdeclqgrceqvcvnspgsyt
chcdgrgglklsqdmdtcedilpcvpfsvaksvkslylgrmfsgtpvirlrfkrlqptrlvaefdfrtfdpegillfagghqdstwivlalra
grlelqlryngygrvtssgpvinhgmwqtisveelarnlvikvnrdavmkiavagdlfqperglyhlnltvggipfhekdlvqpinprl
dgcmrswnwlngedttiqetvkvntrmqcfsvtergsfypgsgfafysldymrtpldvgtestwevevvahirpaadtgvlfalwa
pdlravplsvalvdyhstkklkkqlvvlavehtalalmeikvcdgqehvvtvslrdgeatlevdgtrgqsevsaaqlqerlavlerhlr
spvltfagglpdvpvtsapvtafyrgcmtlevnrrllldldeaaykhsditahscppvepaaa SEQ ID NO.27 [Axl from Macaca fascicularis; also called herein "Cyno Axl"]
MAWRCPRMGRVPLAWCLALCGWVCMAPRGTQAEESPFVGNPGNITGARGLTGTLRCQL
QVQGEPPEVHWLRDGQILELADSTQTQVPLGEDEQDDWIVVSQLRIASLQLSDAGQYQCL
VFLGHQNFVSQPGYVGLEGLPYFLEEPEDRTVAANTPFNLSCQAQGPPEPVDLLWLQDAV
PLATAPGHGPQRNLHVPGLNKTSSFSCEAHNAKGVTTSRTATITVLPQQPRNLHLVSRQPT
ELEVAWTPGLSGIYPLTHCTLQAVLSDDGMGIQAGEPDPPEEPLTLQASVPPHQLRLGSLH
PHTPYHIRVACTSSQGPSSWTHWLPVETPEGVPLGPPENISATRNGSQAFVHWQEPRAPL
QGTLLGYRLAYQGQDTPEVLMDIGLRQEVTLELQGDGSVSNLTVCVAAYTAAGDGPWSLP
VPLEAWRPGQAQPVHQLVKETSAPAFSWPWWYILLGAVVAAACVLILALFLVHRRKKETRY
GEVFEPTVERGELVVRYRVRKSYSRRTTEATLNSLGISEELKEKLRDVMVDRHKVALGKTL
GEGEFGAVMEGQLNQDDSILKVAVKTMKIAICTRSELEDFLSEAVCMKEFDHPNVMRLIGV
CFQGSERESFPAPVVILPFMKHGDLHSFLLYSRLGDQPVYLPTQMLVKFMADIASGMEYLS
TKRFIHRDLAARNCMLNENMSVCVADFGLSKKIYNGDYYRQGRIAKMPVKWIAIESLADRVY
TSKSDVWSFGVTMWEIATRGQTPYPGVENSEIYDYLRQGNRLKQPADCLDGLYALMSRC
WELNPQDRPSFTELREDLENTLKALPPAQEPDEILYVNMDEGGGYPEPPGAAGGADPPTQ
LDPKDSCSCLTSAEVHPAGRYVLCPSTAPSPAQPADRGSPAAPGQEDGA SEQ ID NO. 28 [murine 10G5 VH domain]
QVQLQQSGAELVRPGASVKLSCKASGYSFTDFYINWVRQRPGQGLEWIARIFPGGDNTYY
NEKFKGKATLTAEESSSTAYIQLSSLTSEDSAVYFCARRGLYYAMDYWGQGISVTVSS SEQ ID NO. 29 [murine 10G5 VL domain]
DVLMTQTPLSLPVSLGDQASISCRSSQSLVHSNGIYLHWYLQKPGQSPKLLIYRVSNRFSG
VPDRFSGSGSGTDFTLKISRVEAEDLGVYFCSQGTHVPPTFGGGTKLEIK

SEQUENCES

SEQ ID NO. 30 [10G5 VH CDR1]
GYSFTDFYIN

SEQ ID NO. 31 [10G5 VH CDR2]
RIFPGGDNTYYNEKFKG

SEQ ID NO. 32 [10G5 VH CDR3]
RGLYYAMDY

SEQ ID NO. 33 [10G5 VL CDR1]
RSSQSLVHSNGIPYLH

SEQ ID NO. 34 [10G5 VL CDR2]
RVSNRFS

SEQ ID NO. 35 [10G5 VL CDR3]
SQGTHVPPT

Biological Deposits

The present disclosure refers to two the hybridoma cell line WR-10G5-E5. This cell line has been deposited in accordance with the 'Budapest Treaty on the International Recognition of the Deposit of Microorganisms for the Purposes of Patent Procedure'. Additional details of the WR-10G5-E5 deposit are set out below, and also disclosed in WO2016/097370.

WR-10G5-E5

| | |
|---|---|
| Depositary Institution → | European Collection of Cell Cultures (ECACC) Public Health England Porton Down Salisbury Wiltshire SP4 OJG United Kingdom |
| Date of deposit → | 16 Dec. 2015 |
| Accession number → | 15121602 |
| Characteristics → | Hybridoma—B-Lymphocyte; Species-*M.musculus* (mouse); Morphology-lymphoblast; Immunogen—human Axl extracellular domain; Immunocyte donor—NMRI mice; Immortal partner X63.Ag8.653; product Ig class/sub-class-IgG1 |

The invention claimed is:

1. An antibody that binds Axl and which comprises:
an antibody VH domain selected from the group consisting of a VH domain comprising the amino acid sequence of SEQ ID NO: 2 and a VH domain comprising the amino acid sequence of SEQ ID NO: 1; and
an antibody VL domain selected from the group consisting of a VL domain comprising the amino acid sequence of SEQ ID NO: 3 and a VL domain comprising the amino acid sequence of SEQ ID No: 4.

2. The antibody of claim 1, comprising the VH domain comprising the amino acid sequence of SEQ ID NO: 2 and VL domain comprising the amino acid sequence of SEQ ID NO: 3.

3. The antibody of claim 1, comprising the VH domain comprising the amino acid sequence of SEQ ID NO: 1 and the VL domain comprising the amino acid sequence of SEQ ID NO: 4.

4. The antibody of claim 1, wherein:
(i) the antibody comprises all or a portion of an antibody heavy chain constant region and/or all or a portion of an antibody light chain constant region;
(ii) the antibody is a whole antibody; or
(iii) the antibody is an antigen-binding antibody fragment.

5. The antibody of claim 4, wherein the whole antibody is an IgG antibody; or wherein the antigen-binding antibody fragment is a single domain antibody, Fv, scFv, dsFv, Fd, Fab, F(ab')$_2$, minibody, diabody, single-chain diabody, tandem scFv, TandAb, bi-body, tri-body, kappa(lambda)-body, SIP, or SMIP.

6. The antibody of claim 1, wherein the antibody inhibits the binding of Axl to Gash.

7. The antibody of claim 1, wherein the antibody reduces the expression of fibrotic markers.

8. An immunoconjugate comprising the antibody of claim 1 conjugated to a detectable label, enzyme, or toxin, optionally via a peptidyl bond or linker.

9. An isolated nucleic acid that comprises a nucleotide sequence encoding a VH domain or a VL domain or both a VH domain and a VL domain of the antibody of claim 1.

10. A host cell transformed with nucleic acid of claim 9.

11. A method of producing an antibody a antibody VH and VL domains, the method comprising culturing the host cell of claim 10 under conditions for production of said antibody or antibody VH and VL domains.

12. A composition comprising an antibody of claim 1, or an immunoconjugate thereof, in conjunction with a pharmaceutically acceptable excipient.

13. The composition of claim 12, further comprising an Immune Checkpoint Modulator, and/or an anti-tumour antibody specific for a target other than Axl.

14. A method of treating a fibrotic disorder in a subject, comprising administering an effective amount of the antibody of claim 1 or an immunoconjugate thereof to the subject.

15. A method of treating a proliferative disease in a subject, comprising administering an effective amount of the antibody of claim 1 or an immunoconjugate thereof to the subject.

16. The method of claim 15, wherein the proliferative disease is cancer.

17. The method of claim 16, wherein the cancer is metastatic cancer.

18. A method of treating a disease or disorder characterised by overexpression of Axl in a subject, comprising administering an effective amount of the antibody of claim 1 or an immunoconjugate thereof to the subject.

19. A diagnostic kit comprising the antibody of claim 1 and one or more reagents that allow determination of the binding of said antibody to metastatic cancer cells.

20. A kit comprising the antibody of claim 1 or an immunoconjugate thereof.

21. The antibody of claim 7, wherein the fibrotic markers comprise alpha-SMA, Col1A1, MCP1, and/or TGF-beta.

22. The antibody of claim 2, comprising a heavy chain comprising the amino acid sequence of SEQ ID NO:7 and a light chain comprising the amino acid sequence of SEQ ID NO: 9.

23. An isolated nucleic acid that comprises a nucleotide sequence encoding the VH domain and the VL domain of the antibody of claim 2.

24. A host cell transformed with nucleic acid of claim 23.

25. A method of producing an antibody or antibody VH and VL domains, the method comprising culturing the host cell of claim 24 under conditions for production of said antibody or antibody VH and VL domains.

26. A composition comprising an antibody of claim 2, and a pharmaceutically acceptable excipient.

27. A method of treating a fibrotic disorder in a subject, comprising administering an effective amount of the antibody of claim 2 to the subject.

28. A method of treating a proliferative disease in a subject, comprising administering an effective amount of the antibody of claim 2 to the subject.

29. The method of claim 28, wherein the proliferative disease is cancer.

30. A method of treating a disease or disorder characterised by overexpression of Axl in a subject, comprising administering an effective amount of the antibody of claim 2 to the subject.

31. A diagnostic kit comprising the antibody of claim 2 and one or more reagents that allow determination of the building of said antibody to metastatic cancer cells.

* * * * *

UNITED STATES PATENT AND TRADEMARK OFFICE
CERTIFICATE OF CORRECTION

PATENT NO. : 11,198,734 B2  
APPLICATION NO. : 16/098933  
DATED : December 14, 2021  
INVENTOR(S) : Micklem et al.

Page 1 of 1

It is certified that error appears in the above-identified patent and that said Letters Patent is hereby corrected as shown below:

In the Claims

In Claim 2, at Column 135, Line 45, after "and" insert --the--;

In Claim 6, at Column 135, Line 65, "Gash" should read --Gas6--;

In Claim 9, at Column 136, Line 38, delete "a VH domain or a VL domain or both";

In Claim 11, at Column 36, Line 41, "antibody a antibody VH" should read --antibody or antibody VH--.

Signed and Sealed this  
Fifteenth Day of March, 2022

Drew Hirshfeld  
*Performing the Functions and Duties of the*  
*Under Secretary of Commerce for Intellectual Property and*  
*Director of the United States Patent and Trademark Office*